United States Patent
Wollerton et al.

(10) Patent No.: US 12,247,074 B2
(45) Date of Patent: Mar. 11, 2025

(54) ANTIBODY MOLECULES

(71) Applicant: F-star Beta Limited, Cambridge (GB)

(72) Inventors: Francisca Wollerton, Cambridge (GB); Matthew Lakins, Cambridge (GB); Mateusz Wydro, Cambridge (GB); Sachin Surade, Cambridge (GB); Michael Dyson, Sawston Cambridgeshire (GB)

(73) Assignee: INVOX PHARMA LIMITED, London (GB)

( * ) Notice: Subject to any disclaimer, the term of this patent is extended or adjusted under 35 U.S.C. 154(b) by 1091 days.

(21) Appl. No.: 17/259,642

(22) PCT Filed: Jul. 12, 2019

(86) PCT No.: PCT/EP2019/068804
§ 371 (c)(1),
(2) Date: Jan. 12, 2021

(87) PCT Pub. No.: WO2020/011973
PCT Pub. Date: Jan. 16, 2020

(65) Prior Publication Data
US 2021/0301022 A1 Sep. 30, 2021

(30) Foreign Application Priority Data
Jul. 12, 2018 (GB) .................................. 1811403

(51) Int. Cl.
*C07K 16/28* (2006.01)
*A61K 39/00* (2006.01)

(52) U.S. Cl.
CPC .... *C07K 16/2827* (2013.01); *A61K 2039/505* (2013.01); *C07K 2317/31* (2013.01); *C07K 2317/526* (2013.01); *C07K 2317/565* (2013.01); *C07K 2317/71* (2013.01)

(58) Field of Classification Search
CPC ............ C07K 16/2827; C07K 2317/31; C07K 2317/526; C07K 2317/565; C07K 2317/71; C07K 2317/622; C07K 2317/72; A61K 2039/505; A61P 35/00
See application file for complete search history.

(56) References Cited

U.S. PATENT DOCUMENTS

| | | | |
|---|---|---|---|
| 3,909,459 A | 9/1975 | Friese et al. | |
| 3,967,230 A | 6/1976 | Kamigaito et al. | |
| 4,004,183 A | 1/1977 | Oki et al. | |
| 5,595,756 A | 1/1997 | Bally et al. | |
| 6,380,664 B1 | 4/2002 | Pollner | |
| 7,288,638 B2 | 10/2007 | Jure-Kunkel et al. | |
| 7,592,426 B2 | 9/2009 | Ebel et al. | |
| 8,217,149 B2 | 7/2012 | Irving et al. | |
| 8,383,796 B2 | 2/2013 | Korman et al. | |
| 8,911,732 B2 | 12/2014 | Dennis et al. | |
| 9,567,399 B1* | 2/2017 | Campbell | C07K 16/468 |
| 9,617,338 B1 | 4/2017 | Campbell et al. | |
| 10,090,646 B2 | 10/2018 | Takaoka et al. | |
| 10,205,305 B2 | 2/2019 | Uegaki et al. | |
| 10,233,258 B2 | 3/2019 | Akamatsu et al. | |
| 10,604,576 B2 | 3/2020 | Campbell et al. | |
| 11,214,618 B2 | 1/2022 | Tuna et al. | |
| 11,214,620 B2 | 1/2022 | Campbell et al. | |
| 11,548,948 B2 | 1/2023 | Tuna et al. | |
| 11,629,193 B2 | 4/2023 | Tuna et al. | |
| 2003/0030355 A1 | 2/2003 | Honda | |
| 2007/0071675 A1 | 3/2007 | Wu et al. | |
| 2009/0055944 A1 | 2/2009 | Korman et al. | |
| 2012/0237498 A1 | 9/2012 | Ahrens et al. | |
| 2012/0276104 A1 | 11/2012 | Woisetschlager | |
| 2013/0034559 A1 | 2/2013 | Queva et al. | |
| 2014/0004121 A1 | 1/2014 | Fanslow, III et al. | |
| 2014/0341917 A1 | 11/2014 | Nastri et al. | |
| 2015/0214697 A1 | 7/2015 | Yoshida et al. | |
| 2015/0259420 A1 | 9/2015 | Triebel et al. | |
| 2016/0043531 A1 | 2/2016 | Firstenberg et al. | |
| 2016/0137740 A1 | 5/2016 | Hammond et al. | |
| 2016/0244528 A1 | 8/2016 | Gray et al. | |
| 2017/0198050 A1 | 7/2017 | Eckelman et al. | |

(Continued)

FOREIGN PATENT DOCUMENTS

| | | |
|---|---|---|
| CN | 101802006 A | 8/2010 |
| CN | 104955845 A | 9/2015 |

(Continued)

OTHER PUBLICATIONS

Lo, M et al. "Effector-attenuating Substitutions That Maintain Antibody Stability and Reduce Toxicity in Mice", 2017, Journal of Biological Chemistry, 292(2), 3900-3908. (Year: 2017).*
[No Author Listed], FS118 First in Human Study in Patients With Advanced Malignancies. Sponsored by F-star Therapeutics Limited. Clinical Trial. Retrieved from https://clinicaltrials.gov/ct2/show/NCT03440437. Feb. 22, 2018. 7 pages.
[No Author Listed], Molecular biological basis of immunotherapy. New and Orphan Drugs for Leukemia Therapeutics. Sep. 30, 2016. 387-390. Retrieved on Dec. 18, 2023. 7 pages.
Asgarov et al., A new anti-mesothelin antibody targets selectively the membrane-associated form. MAbs. Apr. 2017;9(3):Supplementary Data. doi: 10.1080/19420862.2017.1288770. 6 pages.
Awuah et al., Reduced Shedding of Surface Mesothelin Improves Efficacy of Mesothelin-Targeting Recombinant Immunotoxins. Mol Cancer Ther. Jul. 2016;15(7):1648-55. doi: 10.1158/1535-7163.MCT-15-0863. Epub May 18, 2016.

(Continued)

*Primary Examiner* — Nelson B Moseley, II
*Assistant Examiner* — Alyssa Rae Stonebraker
(74) *Attorney, Agent, or Firm* — Wolf, Greenfield & Sacks, P.C.

(57) ABSTRACT

The present disclosure, in some aspects, provides antibody molecules, or antigen-binding fragments thereof capable of binding specifically to PD-L1. The present disclosure further provides antibody molecules, or antigen-binding fragments thereof capable of binding specifically to PD-L1 and a second antigen-binding site. Methods of making and/or using such antibody molecules or antigen bending fragments are also provided.

Figure 1:
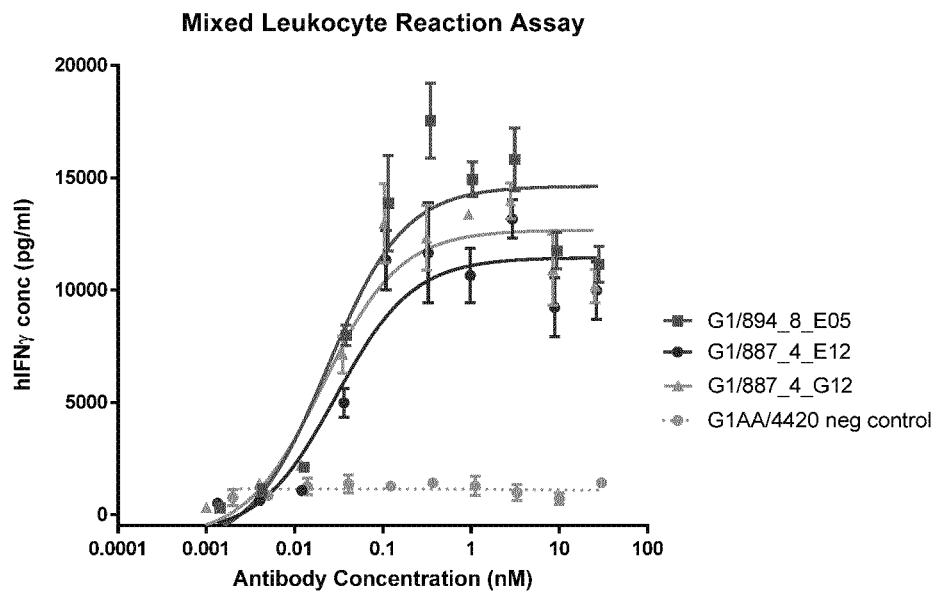

21 Claims, 2 Drawing Sheets
Specification includes a Sequence Listing.

(56) References Cited

U.S. PATENT DOCUMENTS

| | | |
|---|---|---|
| 2017/0355756 A1 | 12/2017 | Julien et al. |
| 2017/0362321 A1 | 12/2017 | Campbell et al. |
| 2018/0118841 A1 | 5/2018 | Ellmark et al. |
| 2018/0175592 A1 | 6/2018 | Uegaki et al. |
| 2018/0194862 A1 | 7/2018 | Akamatsu et al. |
| 2018/0339031 A1 | 11/2018 | Masternak et al. |
| 2019/0106494 A1 | 4/2019 | Wang et al. |
| 2019/0202920 A1 | 7/2019 | Tuna et al. |
| 2019/0256602 A1 | 8/2019 | Campbell et al. |
| 2019/0330344 A1 | 10/2019 | Tuna et al. |
| 2019/0330351 A1 | 10/2019 | Campbell et al. |
| 2019/0338032 A1 | 11/2019 | Campbell et al. |
| 2019/0338049 A1 | 11/2019 | Tuna et al. |
| 2020/0407446 A1 | 12/2020 | McCourt et al. |
| 2021/0139590 A1 | 5/2021 | Tuna et al. |
| 2021/0237498 A1 | 8/2021 | Yoda et al. |
| 2021/0238299 A1 | 8/2021 | Pechouckova et al. |
| 2021/0277134 A1 | 9/2021 | Lakins et al. |
| 2021/0309753 A1 | 10/2021 | Tuna et al. |
| 2021/0355228 A1 | 11/2021 | Lakins et al. |
| 2022/0048996 A1 | 2/2022 | Tuna et al. |
| 2022/0049007 A1 | 2/2022 | Lakins et al. |
| 2022/0185890 A1 | 6/2022 | Tuna et al. |
| 2022/0185894 A1 | 6/2022 | Campbell et al. |
| 2022/0267421 A1 | 8/2022 | Munoz-Olaya et al. |
| 2022/0275092 A1 | 9/2022 | Morrow et al. |
| 2023/0357413 A1 | 11/2023 | Tuna et al. |
| 2023/0406935 A1 | 12/2023 | Tuna et al. |

FOREIGN PATENT DOCUMENTS

| | | |
|---|---|---|
| CN | 104968364 A | 10/2015 |
| CN | 107523546 A | 12/2017 |
| CN | 109563171 A | 4/2019 |
| EP | 1025230 B1 | 2/2006 |
| EP | 1180123 B1 | 7/2008 |
| EP | 2407487 A1 | 1/2012 |
| EP | 2546268 A1 | 1/2013 |
| EP | 2242771 B1 | 7/2013 |
| EP | 2905030 A1 | 8/2015 |
| EP | 2215121 B1 | 2/2016 |
| EP | 3354661 A1 | 8/2018 |
| EP | 3470426 A1 | 4/2019 |
| JP | S51-046628 A | 4/1976 |
| JP | 2003-022886 A | 1/2003 |
| JP | 2011-521905 A | 7/2011 |
| JP | 2012-500006 A | 1/2012 |
| JP | 2016-513467 A | 5/2016 |
| JP | 2016-533395 A | 10/2016 |
| JP | 2017-010741 A | 1/2017 |
| JP | 2018-508475 A | 3/2018 |
| RU | 2017112379 A | 10/2018 |
| TW | 201642897 A | 12/2016 |
| WO | WO 2001/077342 A1 | 10/2001 |
| WO | WO 2005/035584 A1 | 4/2005 |
| WO | WO 2006/072620 A1 | 7/2006 |
| WO | WO 2006/088447 A1 | 8/2006 |
| WO | WO 2006/099141 A2 | 9/2006 |
| WO | WO 2008/003103 A2 | 1/2008 |
| WO | WO 2008/068048 A2 | 6/2008 |
| WO | WO 2009/000006 A1 | 12/2008 |
| WO | WO 2009/068204 A1 | 6/2009 |
| WO | WO 2009/126944 A1 | 10/2009 |
| WO | WO 2009/132876 A1 | 11/2009 |
| WO | WO 2010/019570 A2 | 2/2010 |
| WO | WO 2010/057047 A1 | 5/2010 |
| WO | WO 2010/111282 A1 | 9/2010 |
| WO | WO 2010/124797 A1 | 11/2010 |
| WO | WO 2012/130831 A1 | 10/2012 |
| WO | WO 2013/181634 A2 | 12/2013 |
| WO | WO 2014/004549 A2 | 1/2014 |
| WO | WO 2014/008218 A1 | 1/2014 |
| WO | WO 2014/052064 A1 | 4/2014 |
| WO | WO 2014/089113 A1 | 6/2014 |
| WO | WO 2014/140180 A1 | 9/2014 |
| WO | WO 2014/151910 A1 | 9/2014 |
| WO | WO 2015/048312 A1 | 4/2015 |
| WO | WO 2015/049537 A1 | 4/2015 |
| WO | WO 2015/119923 A1 | 8/2015 |
| WO | WO 2015/138920 A1 | 9/2015 |
| WO | WO 2015/198312 A1 | 12/2015 |
| WO | WO 2015/200119 A1 | 12/2015 |
| WO | WO 2016/028672 A1 | 2/2016 |
| WO | WO 2016/040880 A1 | 3/2016 |
| WO | WO 2016/111645 A1 | 7/2016 |
| WO | WO 2016/162505 A1 | 10/2016 |
| WO | WO 2016/177802 A1 | 11/2016 |
| WO | WO 2016/185016 A1 | 11/2016 |
| WO | WO 2016/200782 A1 | 12/2016 |
| WO | WO 2017/009456 A1 | 1/2017 |
| WO | WO 2017/015560 A2 | 1/2017 |
| WO | WO 2017/019846 A8 | 2/2017 |
| WO | WO 2017/025498 A1 | 2/2017 |
| WO | WO 2017/049452 A1 | 3/2017 |
| WO | WO 2017/052241 A1 | 3/2017 |
| WO | WO 2017/055398 A2 | 4/2017 |
| WO | WO 2017/062888 A1 | 4/2017 |
| WO | WO 2017/077085 A2 | 5/2017 |
| WO | WO 2017/087589 A2 | 5/2017 |
| WO | WO 2017/087901 A2 | 5/2017 |
| WO | WO 2017/123650 A2 | 7/2017 |
| WO | WO 2017/182672 A1 | 10/2017 |
| WO | WO 2017/193032 A2 | 11/2017 |
| WO | WO 2017/205738 A1 | 11/2017 |
| WO | WO 2017/220555 A1 | 12/2017 |
| WO | WO 2017/220569 A1 | 12/2017 |
| WO | WO 2017/220990 A9 | 12/2017 |
| WO | WO 2018/017673 A1 | 1/2018 |
| WO | WO 2018/056821 A1 | 3/2018 |
| WO | WO 2018/060480 A1 | 4/2018 |
| WO | WO 2018/091740 A2 | 5/2018 |
| WO | WO 2018/115859 A1 | 6/2018 |
| WO | WO 2018/127610 A1 | 7/2018 |
| WO | WO 2018/222711 A2 | 12/2018 |
| WO | WO 2019/025545 A1 | 2/2019 |

OTHER PUBLICATIONS

Callahan et al., Targeting T Cell Co-receptors for Cancer Therapy. Immunity. May 17, 2016;44(5):1069-78. doi: 10.1016/j.immuni.2016.04.023.

Chatterjee et al., Noninvasive Imaging of Immune Checkpoint Ligand PD-L1 in Tumors and Metastases for Guiding Immunotherapy. Mol Imaging. Jan.-Dec. 2017;16:1536012117718459. doi: 10.1177/1536012117718459. 5 pages.

Chen et al., Enhancement and destruction of antibody function by somatic mutation: unequal occurrence is controlled by V gene combinatorial associations. EMBO J. Jun. 15, 1995;14(12):2784-94. doi: 10.1002/j.1460-2075.1995.tb07278.x.

Chu et al., An Update on Anti-CD137 Antibodies in Immunotherapies for Cancer. Int J Mol Sci. Apr. 12, 2019;20(8):1822. doi: 10.3390/ijms20081822. 17 pages.

Dahlén et al., Bispecific antibodies in cancer immunotherapy. Ther Adv Vaccines Immunother. Feb. 2018;6(1):3-17. doi: 10.1177/2515135518763280. Epub Mar. 28, 2018.

Del Bano et al., A Bispecific Antibody-Based Approach for Targeting Mesothelin in Triple Negative Breast Cancer. Front Immunol. Jul. 10, 2019;10:1593. doi: 10.3389/fimmu.2019.01593.

Edwards et al., The remarkable flexibility of the human antibody repertoire; isolation of over one thousand different antibodies to a single protein, BLyS. J Mol Biol. Nov. 14, 2003;334(1):103-18. doi: 10.1016/j.jmb.2003.09.054.

El-Khoueiry et al., The relationship of pharmacodynamics (PD) and pharmacokinetics (PK) to clinical outcomes in a phase I study of OX40 agonistic monoclonal antibody (mAb) PF-04518600 (PF-8600). J Clin Oncol. May 20, 2017. 35(15_suppl):3027-3027. Meeting Abstract. 2017 ASCO Annual Meeting I. doi: 10.1200/JCO.2017.35.15_suppl.3027. 4 pages.

Faroudi et al., Abstract 2399: LAG-3/PD-L1 mAb2 can overcome PD-L1-mediated compensatory upregulation of LAG-3 induced by

(56) References Cited

OTHER PUBLICATIONS single-agent checkpoint blockade. Proceedings: AACR Annual Meeting 2019; Mar. 29-Apr. 3, 2019. Atlanta, GA. Doi: 10.1158/1538-7445.AM2019-2399. Published Jul. 2019.

Faroudi et al., Abstract B009: FS118, a LAG-3/PD-L1 bispecific antibody, capable of driving potent anti-tumour immune responses and overcome PD-(L)1-mediated compensatory. Sep. 25-28, 2019. Fifth CRI-CIMT-EATI-AACR International Cancer Immunotherapy Conference (2019): Translating Science into Survival. Paris. 1 page.

Faroudi et al., FS118, a LAG-3/PD-L1 bispecific antibody, capable of driving potent anti-tumour immune responses and overcome PD-(L)1-mediated compensatory. Sep. 25-28, 2019. Poster. Fifth CRI-CIMT-EATI-AACR International Cancer Immunotherapy Conference (2019): Translating Science into Survival. Paris. 1 page.

Frenzel et al., Phage display-derived human antibodies in clinical development and therapy. MAbs. Oct. 2016;8(7):1177-1194. doi: 10.1080/19420862.2016.1212149. Epub Jul. 14, 2016.

F-STAR, Next-Generation Bispecifics for Cancer Immunotherapy. Feb. 2020. Presented on Mar. 11, 2020 at Immuno-Oncology Summit Europe 2020. London. 46 pages.

F-STAR, Redirecting T Cells. Overcoming Cancer. Improving Lives. Oct. 2019 Presentation in Investor Meeting. 36 pages.

F-STAR, Redirecting T Cells. Overcoming Cancer. Improving Lives. Apr. 2020 Presentation in Investor Meeting. 43 pages.

F-STAR, Redirecting T Cells. Overcoming Cancer. Improving Lives. Jan. 2020 Presentation in Investor Meeting. 41 pages.

Gaspar et al., FS120 mAb2, a dual agonist bispecific antibody targeting OX40 and CD137, activates T cells in vitro and induces FcyR-independent anti-tumour activity. SITC 2018. Nov. 7, 2018. Poster. 10 pages.

Gaspar, FS120 mAb2, a dual agonist bispecific antibody targeting OX40 and CD137. Sitc 2018. Nov. 11, 2018. Presentation. 12 pages.

Geuijen et al., Abstract 541: An unbiased screen identifies a CD137xPD-L1 bispecific IgG1 antibody with unique T cell activation and binding properties. Cancer Res. 2019;79(13_Supplement):541. Poster Presentation AACR Conference 2019. Jul. 1, 2019. doi: 10.1158/1538-7445.AM2019-541. 4 pages.

Glisson et al., Phase 1 study of MEDI0562, a humanized OX40 agonist monoclonal antibody (mAb), in adult patients (pts) with advanced solid tumors. Annals Onocol. Oct. 1, 2016;27(6):vi361. doi: 10.1093/annonc/mdw378.07.

Golfier et al., Anetumab ravtansine: a novel mesothelin-targeting antibody-drug conjugate cures tumors with heterogeneous target expression favored by bystander effect. Mol Cancer Ther. Jun. 2014;13(6):1537-48. doi: 10.1158/1535-7163.MCT-13-0926. Epub Apr. 8, 2014.

Gunde et al., Abstract 1532: A novel, monovalent tri-specific antibody-based molecule that simultaneously modulates PD-L1 and 4-1BB exhibits potent anti-tumoral activity in vivo. Cancer Res. 2019;79(13_Supplement): 1532. AACR Conference 2019. Jul. 1, 2019. doi: 10.1158/1538-7445.AM2019-1532. 4 pages.

Han et al., Bispecific anti-CD3 x anti-HER2 antibody mediates T cell cytolytic activity to HER2-positive colorectal cancer in vitro and in vivo. Int J Oncol. Dec. 2014;45(6):2446-54. doi: 10.3892/ijo.2014.2663. Epub Sep. 18, 2014.

Hassan et al., Mesothelin Immunotherapy for Cancer: Ready for Prime Time? J Clin Oncol. Dec. 2016;34(34):4171-4179. doi: 10.1200/JCO.2016.68.3672. Epub Oct. 31, 2016.

Hassan et al., Phase II clinical trial of amatuximab, a chimeric antimesothelin antibody with pemetrexed and cisplatin in advanced unresectable pleural mesothelioma. Clin Cancer Res. Dec. 1, 2014;20(23):5927-36. doi: 10.1158/1078-0432.CCR-14-0804. Epub Sep. 17, 2014.

Hebb et al., Administration of low-dose combination anti-CTLA4, anti-CD137, and anti-OX40 into murine tumor or proximal to the tumor draining lymph node induces systemic tumor regression. Cancer Immunol Immunother. Jan. 2018;67(1):47-60. doi: 10.1007/s00262-017-2059-y. Epub Sep. 13, 2017. Author Manuscript. 20 pages.

Ho et al., A novel high-affinity human monoclonal antibody to mesothelin. Int J Cancer. May 1, 2011;128(9):2020-30. doi: 10.1002/ijc.25557.

Koenig et al., Mutational landscape of antibody variable domains reveals a switch modulating the interdomain conformational dynamics and antigen binding. Proc Natl Acad Sci U S A. Jan. 24, 2017;114(4):E486-E495. doi: 10.1073/pnas.1613231114. Epub Jan. 5, 2017.

Kraman et al., Dual blockade of PD-L1 and LAG-3 with FS118, a unique bispecific antibody, induces CD8+ T-cell activation and modulates the tumour microenvironment to promote anti-tumour immune responses. Apr. 14-18, 2018. Poster 2719. Proceedings of the American Association for Cancer Research Annual Meeting 2018. Chicago, IL. 2 pages.

Kraman et al., Dual blockade of PD-L1 and LAG-3 with FS118, a unique bispecific antibody, induces T-cell activation with the potential to drive potent anti-tumour immune responses. Nov. 7, 2017;5 Suppl 2 (87):Abstract P348. 32nd Annual Meeting and Pre-Conference Programs of the Society for Immunotherapy of Cancer (SITC). Part II. Nov. 8-12, 2017. National Harbor, MD. 2 pages.

Kraman et al., Dual blockade of PD-L1 and LAG-3 with FS118, a unique bispecific antibody, induces T-cell activation with the potential to drive potent anti-tumour immune responses. Apr. 14-18, 2018;78(13 Suppl);Abstract 2719. Proceedings of the American Association for Cancer Research Annual Meeting 2018. Chicago, IL. 5 pages.

Kraman et al., Dual blockade of PD-L1 and LAG-3 with FS118, a unique bispecific antibody, induces T-cell activation with the potential to drive potent anti-tumour immune responses. Poster P348. 32nd Annual Meeting and Pre-Conference Programs of the Society for Immunotherapy of Cancer (SITC). Part II. Nov. 8-12, 2017. National Harbor, MD. 1 page.

Kraman et al., FS118, a Bispecific Antibody Targeting LAG-3 and PD-L1, Enhances T-Cell Activation Resulting in Potent Antitumor Activity. Clin Cancer Res. Jul. 1, 2020;26(13):3333-3344. doi: 10.1158/1078-0432.CCR-19-3548. Epub Apr. 16, 2020.

Kunik et al., Structural consensus among antibodies defines the antigen binding site. PLoS Comput Biol. 2012;8(2):e1002388. doi: 10.1371/journal.pcbi.1002388. Epub Feb. 23, 2012. 12 pages.

Kussie et al., A single engineered amino acid substitution changes antibody fine specificity. J Immunol. Jan. 1, 1994;152(1):146-52.

Kvarnhammar et al., The CTLA-4 x OX40 bispecific antibody ATOR-1015 induces anti-tumor effects through tumor-directed immune activation. J Immunother Cancer. Apr. 11, 2019;7(1):103. doi: 10.1186/s40425-019-0570-8.

Lakins et al., FS222 mAb2, a bispecific conditional agonist antibody targeting CD137 and PD-L1, induces potent lymphocyte activation and has a favourable safety profile. F-star, Cambridge, UK. Poster Presentation. AACR Annual Meeting Mar. 29-Apr. 3, 2019, Atlanta, GA. Poster No. 1540. 1 page.

Lakins et al., Optimising TNFRSF agonism and checkpoint blockade with a novel CD137/PD-L1 bispecific antibody. Abstracts Therapeutic Development. Dec. 1, 2018;29(Supplement 10):X30. doi: 10.1093/annonc/mdy487.014. 1 page.

Lamberts et al., ImmunoPET with Anti-Mesothelin Antibody in Patients with Pancreatic and Ovarian Cancer before Anti-Mesothelin Antibody-Drug Conjugate Treatment. Clin Cancer Res. Apr. 1, 2016;22(7):1642-52. doi: 10.1158/1078-0432.CCR-15-1272. Epub Nov. 20, 2015.

Levitan, Amgen Halts Rilotumumab Development Due to Increased Death Signal. Cancer Network. Nov. 26, 2014. Retrieved from www.cancernetwork.com/view/amgen-halts-rilotumumab-development-due-increased-death-signal. 3 pages.

Li et al., Discovery and preclinical characterization of the antagonist anti-PD-L1 monoclonal antibody LY3300054. J Immunother Cancer. Apr. 30, 2018;6(1):31. doi: 10.1186/s40425-018-0329-7. Erratum in: J Immunother Cancer. Jun. 4, 2018;6(1):45.

Lin et al., Fc-dependent expression of CD137 on human NK cells: insights into "agonistic" effects of anti-CD137 monoclonal antibodies. Blood. Aug. 1, 2008;112(3):699-707. doi: 10.1182/blood-2007-11-122465. Epub Jun. 2, 2008.

(56) References Cited

OTHER PUBLICATIONS

Link et al., Abstract 3752: Preclinical pharmacology of MP0310: A 4-1BB/FAP bispecific DARPin drug candidate promoting tumor-restricted T-cell costimulation. Cancer Res. Jul. 1, 2018;78(13_Supplement):3752.

Liu et al., Abstract 3642: Tumor-antigen expression-dependent activation of the CD137 costimulatory pathway by bispecific DART® proteins. Cancer Res. Jul. 1, 2017;77(13_Supplement):3642.

Ma et al., Recognition of mesothelin by the therapeutic antibody MORAb-009: structural and mechanistic insights. J Biol Chem. Sep. 28, 2012;287(40):33123-31. doi: 10.1074/jbc.M112.381756. Epub Jul. 11, 2012.

Mayes et al., Abstract 539: A bispecific Fc-silenced IgG1 antibody (MCLA-145) requires PD-L1 binding to activate CD137. Cancer Res. 2019;79(13_Supplement):539. AACR Presentation 2019. Jul. 1, 2019. doi: 10.1158/1538-7445.AM2019-539. 4 pages.

Mccourt, Development of an ICOS/PD-L1 Bispecific, Mar. 18-22, 2019. Abstract. Cambridge Healthtech Institute's 4th Annual Immuno-Oncology Summit Europe 2019 (London).

Melero et al., Clinical development of immunostimulatory monoclonal antibodies and opportunities for combination. Clin Cancer Res. Mar. 1, 2013;19(5):997-1008. doi: 10.1158/1078-0432.CCR-12-2214.

Perez-Ruiz et al., Anti-CD137 and PD-1/PD-L1 Antibodies En Route toward Clinical Synergy. Clin Cancer Res. Sep. 15, 2017;23(18):5326-5328. doi: 10.1158/1078-0432.CCR-17-1799. Epub Aug. 8, 2017.

Poon et al., Dual agonist bispecific antibody targeting OX40 and DC137 mediates anti-tumour immunity and synergises with PD-1/PD-L1 blockade to improve survival in a syngeneic mouse model. AACR 2019. Mar. 29, 2019. Poster. 9 pages.

Reichen et al., Abstract 3029: FAP-mediated tumor accumulation of a T-cell agonistic FAP/4-1BB DARPin drug candidate analyzed by SPECT/CT and quantitative biodistribution. Cancer Res. Jul. 1, 2018;78(13_Supplement):3029.

Ryan et al., A novel biologic platform elicits profound T cell costimulatory activity and antitumor immunity in mice. Cancer Immunol Immunother. Apr. 2018;67(4):605-613. doi: 10.1007/s00262-018-2116-1. Epub Jan. 11, 2018.

Schroeder, Chapter 13: Immunoglobulins and Their Genes. From Arthritis and Allied Conditions: A Textbook of Rheumatology. 15th Ed. vol. 1. Eds Koopman et al.Lippincot Williams & Wilkins. pp. 289-304. Supplied by the British Library Jul. 31, 2023.

Segal et al., Results from an Integrated Safety Analysis of Urelumab, an Agonist Anti-CD137 Monoclonal Antibody. Clin Cancer Res. Apr. 15, 2017;23(8):1929-1936. doi: 10.1158/1078- 0432.CCR-16-1272. Epub Oct. 18, 2016.

Tang et al., A human single-domain antibody elicits potent antitumor activity by targeting an epitope in mesothelin close to the cancer cell surface. Mol Cancer Ther. Apr. 2013;12(4):416-26. doi: 10.1158/1535-7163.MCT-12-0731. Epub Jan. 31, 2013.

Tuna, Delivering the next immuno-oncology breakthrough. PEGS Europe 2018. Nov. 11, 2018. Presentation. 24 pages.

Wang et al., Retargeting T cells for HER2-positive tumor killing by a bispecific Fv-Fc antibody. PLoS One. Sep. 23, 2013;8(9):e75589. doi: 10.1371/journal.pone.0075589. eCollection 2013.

Yap et al., A first-in-human phase I study of FS118, an anti-LAG-3/PD-L1 bispecific antibody in patients with solid tumors that have progressed on prior PD-1/PD-L1 therapy. Journal of Clinical Oncology. Jun. 1, 2019. Poster TPS2652. 2019 ASCO Annual Meeting Proceedings. 20 pages.

Yap et al., A first-in-human phase I study of FS118, an anti-LAG-3/PD-L1 bispecific antibody in patients with solid tumors that have progressed on prior PD-1/PD-L1 therapy. Journal of Clinical Oncology. May 26, 2019;37(15_suppl). 3 pages.

Yonezawa et al., Boosting Cancer Immunotherapy with Anti-CD137 Antibody Therapy. Clin Cancer Res. Jul. 15, 2015;21(14):3113-20. doi: 10.1158/1078-0432.CCR-15-0263. Epub Apr. 23, 2015.

Zhao et al., Novel Antibody Therapeutics Targeting Mesothelin In Solid Tumors. Clin Cancer Drugs. Oct. 2016;3(2):76-86. doi: 10.2174/2212697X03666160218215744.

International Search Report and Written Opinion for Application No. PCT/EP2019/068804, mailed Oct. 17, 2019.

International Preliminary Report on Patentability for Application No. PCT/EP2019/068804, mailed Jan. 21, 2021.

[No Author Listed] F-star Alpha: A new asset centric company. Retrieved from http://www.onenucleus.com/media/Events/LSLS/11%20feb%202014/Jane%20Dancer.pdf on Jan. 8, 2015. 15 pages.

Asgarov et al., A new anti-mesothelin antibody targets selectively the membrane-associated form. MAbs. Apr. 2017;9(3):567-577. doi: 10.1080/19420862.2017.1288770.

Bacac et al., Abstract 1494: CEA TCB: A novel head-to-tail 2:1 T cell bispecific antibody for treatment of CEA-positive solid tumors. Oncoimmunology. Aug. 2016; 5(Abstract): e1203498. Epub Jun. 24, 2016. doi: 10.1080/2162402X.2016.1203498.

Chester et al., 4-1BB agonism: adding the accelerator to cancer immunotherapy. Cancer Immunol Immunother. Oct. 2016;65(10):1243-8. doi: 10.1007/s00262-016-1829-2. Epub Mar. 31, 2016.

Chester et al., Dual antibody therapy to harness the innate anti-tumor immune response to enhance antibody targeting of tumors. Curr Opin Immunol. Apr. 2015;33:1-8. doi: 10.1016/j.coi.2014.12.010. Epub Jan. 7, 2015.

Goding et al., Combination of adoptive cell transfer, anti-PD-L1 and anti-LAG-3 antibodies for the treatment of recurrent tumors: better with more. OncoImmunology. Oct. 22, 2013;2(8):e25050-1-e25050-3.

Hasenhindl et al., Creating stable stem regions for loop elongation in Fcabs—insights from combining yeast surface display, in silico loop reconstruction and molecular dynamics simulations. Biochim Biophys Acta. 2014;1844(9):1530-1540. doi:10.1016/j.bbapap.2014.04.020.

Hasenhindl et al., Stability assessment on a library scale: a rapid method for the evaluation of the commutability and insertion of residues in C-terminal loops of the CH3 domains of IgG1-Fc. Protein Eng Des Sel. 2013;26(10):675-682.

Jing et al., Combined immune checkpoint protein blockade and low dose whole body irradiation as immunotherapy for myeloma. Journal of Immunotherapy of Cancer. doi: 10.1186/S40425-014-0043-Z. Jan. 20, 2015. 15 pages.

Kraman et al., A LAG-3/PD-L1 bispecific antibody inhibits tumor growth in two syngeneic colon carcinoma models. Journal of ImmunoTherapy of Cancer. 2016;4(Suppl 1):82(abstract P124).

Kraman et al., A LAG-3/PD-L1 bispecific antibody inhibits tumor growth in two syngeneic colon carcinoma models. Retrieved from http://www.f-star.com/media/73722/A-LAG-3-PD-L1-bispecific-antibody-inhibits-tumour-growth-in-two-syngeneic-colon-carcinoma-models.pdf. Nov. 9-13, 2016. 1 page.

Lakins et al., A Novel ICOS/PD-L1 Bispecific Antibody Modulates the Tumour Microenvironmentby Activating CD8+ T cells and Results in Tumour Growth Inhibition. F-Star Poster. Nov. 7, 2018. 1 page. Retrieved from https://www.f-star.com/media/87488/201811-SITC-2018-F-star-FS222-Poster-ONLINE.pdf.

Lee et al., 4-1BB and OX40 dual costimulation synergistically stimulate primary specific CD8 T cells for robust effector function. J Immunol. Sep. 1, 2004;173(5):3002-12. doi: 10.4049/jimmunol.173.5.3002.

Leung et al., A HER2-specific Modified Fc Fragment (Fcab) Induces Antitumor Effects Through Degradation of HER2 and Apoptosis. Mol Ther. Nov. 2015;23(11):1722-1733. doi: 10.1038/mt.2015.127. Epub Aug. 3, 2015. Erratum in: Mol Ther. Nov. 2015;23(11):1794.

Lobner et al., Engineered IgG1-Fc—one fragment to bind them all. Immunol Rev. Mar. 2016;270(1):113-31. doi: 10.1111/imr.12385.

Lobner et al., Two-faced Fcab prevents polymerization with VEGF and reveals thermodynamics and the 2.15 Å crystal structure of the complex. MAbs. Oct. 2017;9(7):1088-1104. doi: 10.1080/19420862.2017.1364825. Epub Aug. 17, 2017.

Lundqvist et al., 31st Annual Meeting and Associated Programs of the Society for Immunotherapy of Cancer (SITC 2016): Part One. Journal for Immunotherapy of Cancer. Nov. 16, 2016;4(1):74(abstract P124).

(56) References Cited

OTHER PUBLICATIONS

Qui et al., CD134 plus CD137 dual costimulation induces Eomesodermin in CD4 T cells to program cytotoxic Th1 differentiation. J Immunol. Oct. 1, 2011;187(7):3555-64. doi: 10.4049/jimmunol. 1101244. Epub Aug. 31, 2011.
Ramelet et al., Beneficial outcome of combination therapy with 4-1BB targeting antibody. Eur J Cancer. Nov. 29, 2016;69(Suppl 1):S96-S97.
Sallin et al., The anti-lymphoma activities of anti-CD137 monoclonal antibodies are enhanced in FcγRIII(-/-) mice. Cancer Immunol Immunother. Sep. 2014;63(9):947-58. doi: 10.1007/s00262-014-1567-2. Epub Jun. 14, 2014.
Schlothauer et al., Novel human IgG1 and IgG4 Fc-engineered antibodies with completely abolished immune effector functions. Protein Eng Des Sel. Oct. 2016;29(10):457-466. doi: 10.1093/protein/gzw040. Epub Aug. 29, 2016.
Shindo et al., Combination immunotherapy with 4-1BB activation and PD-1 blockade enhances antitumor efficacy in a mouse model of subcutaneous tumor. Anticancer Res. Jan. 2015;35(1):129-36.
Vilgelm et al., Combinatorial approach to cancer immunotherapy: strength in numbers. Journal of Leukocyte Biology. 2016;100(2):275-90. Epub Jun. 2, 2016.
Wozniak-Knopp et al., Designing Fcabs: well-expressed and stable high affinity antigen-binding Fc fragments. Protein Eng Des Sel. Sep. 1, 2017;30(9):657-671. doi: 10.1093/protein/gzx042.
Wozniak-Knopp et al., Introducing antigen-binding sites in structural loops of immunoglobulin constant domains: Fc fragments with engineered HER2/neu-binding sites and antibody properties. Protein Eng Des Sel. 2010;23(4):289-297. doi:10.1093/protein/gzq005.
Xu et al, In vitro characterization of five humanized OKT3 effector function variant antibodies. Cell Immunol. Feb. 25, 2000;200(1):16-26.
[No Author Listed] Abstract for CHI Immuno-Oncology Summit Europe. Mar. 18- 22, 2019. 1 page. PDR303.
[No Author Listed] F-Star Modular Bispecific Antibodies. Summary for ATLAS deck. Presented at JP Morgan. Jan. 2017. 1 page. PDR159.
[No Author Listed] First-in-Class bispecific antibodies for cancer immunotherapy. Presentation at Takeda. Dec. 13, 2016. 24 pages. PDR160.
[No Author Listed], Pipeline Overview: F-star is developing a pipeline of bispecific antibodies focused on oncology and immuno-oncology. F-Start website update. Sep. 2016. 2 pages. PDR126.
Ascierto et al., Initial efficacy of anti-lymphocyte activation gene-3 (anti-LAG-3:BMS-986016) in combination with nivolumab (nivo) in pts with melanoma (MEL) previously treated with anti-PD-1/PD-L1 therapy. J Clin Oncology. May 2, 20170;35(15):9520-9520. Abstract only. doi: 10.1200/JCO.2017.35.15_suppl.9520. EPub May 30, 2017.
Berg et al., Biochemistry. 5th ed. New York. 2002. Accessible at https://www.ncbi.nlm.nih.gov/books/NBK22358/section5.5. Accessed Jun. 9, 2021. 4 pages.
Bernett et al., Abstract P122: Multiple bispecific checkpoint combinations enhance T cell activity. J Immunother Cancer. 2016;4(Suppl 1):P122. 2 pages.
Bernett et al., Multiple bispecific checkpoint combinations enhance T cell activity. Xencor Poster Presentation. 2016. 1 page.
Bodhankar et al., PD-L1 Monoclonal Antibody Treats Ischemic Stroke by Controlling Central Nervous System Inflammation. Stroke. Oct. 2015;46(10):2926-34. doi: 10.1161/STROKEAHA.115. 010592. Epub Aug. 25, 2015.
Borlak et al., Immune-mediated liver injury of the cancer therapeutic antibody catumaxomab targeting EpCAM, CD3 and Fc? receptors. Oncotarget. May 10, 2016;7(19):28059-74. doi: 10.18632/oncotarget.8574.
Brewis, Development of an anti-PD-L1 Fcab. Presentation. Human Antibodies and Hybrodomas Conference. Oct. 2018. 22. PDR 312.
Brewis, Identification of a PD-L1 binding Fcab: a potent inhibitor of immunosuppressive signals. Abstract. Huamn Antibodies and Hybridomas 2018. Jun. 11, 2018. 1 page. PDR282.
Brewis, The use of bispecific antibodies to modulate anti-tumour immune responses. Oral Presentation at ELRIG—Research and Innovation. Mar. 29, 2017. 33 pages. PDR177.
Brewis, The use of bispecific antibodies to modulate anti-tumour immune responses. Oral Presentation at PEPtalk. Jan. 12, 2017. 26 pages. PDR163.
Burova et al., Abstract 1484: Combined treatment with anti-LAG-3 and anti-PD-1 fully human monoclonal antibodies inhibits tumor growth in immunocompetent double-humanized LAG-3/PD-1 mice. Proceedings: AACR 107th Annual Meeting 2016. Apr. 16-20, 2016. New Orleans, LA. doi: 10.1158/1538-7445.AM2016-1484. Published Jul. 2016. 8 pages.
Burova et al., Abstract P195: A novel anti-human LAG-3 antibody in combination with anti-human PD-1 (REGN2810) shows enhanced anti-tumor activity in PD-1 x LAG-3 dual-humanized mice and favorable pharmacokinetic and safety profiles in cynomolgus monkey. J Immunother Cancer. 2016;4(Suppl 1):P195. 2 pages.
Camisaschi et al., LAG-3 expression defines a subset of CD4(+)CD25(high)Foxp3(+) regulatory T cells that are expanded at tumor sites. J Immunol. Jun. 1, 2010;184(11):6545-51. doi: 10.4049/jimmunol.0903879. Epub Apr. 26, 2010.
Cemerski et al., T cell activation and anti-tumor efficacy of anti-LAG-3 antibodies is independent of LAG-3-MHCII blocking capacity. Poster Presentation. 30th Annual Meeting and Associated Programs of the Society for Immunotherapy of Cancer (SITC 2015). National Harbor, MD. Nov. 4-8, 2015. 1 page.
Chen et al., Molecular mechanisms of T cell co-stimulation and co-inhibition. Nat Rev Immunol. Apr. 2013;13(4):227-42. doi: 10.1038/nri3405. Epub Mar. 8, 2013. Erratum in: Nat Rev Immunol. Jul. 2013;13(7):542.
Chiu et al., Antibody Structure and Function: The Basis for Engineering Therapeutics. Antibodies (Basel). Dec. 3, 2019;8(4):55. doi: 10.3390/antib8040055.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80. doi: 10.1073/pnas.0915174107. Epub Feb. 16, 2010.
Davies, Analytical challenges for next generation biologics. Oral Presentation at Waters Biopharma Mini-Seminar. May 24, 2017. 20 pages. PDR191.
Davies, Bispecific Antibodies: New Opportunities for Novel Therapies. Oral Presentation at Bioprocess UK 2016. Nov. 26, 2016. 14 pages. PDR 135.
Davies, Overcoming the Manufacturing Challenges for Bisepcific mAbs. Oral Presentation at 5th Annual Cell Culture and Bioprocessing Congress. Nov. 6, 2016. 16 pages. PDR142.
Davies, Overcoming the Manufacturing Challenges for Bisepcific mAbs. Oral Presentation at Biopronet 3rd Annual Scientific Symposium. Oct. 20, 2016. 16 pages. PDR136.
Daxini et al., Vasculitis associated with immune checkpoint inhibitors—a systematic review. Clin Rheumatol. Sep. 2018;37(9):2579-2584. doi: 10.1007/s10067-018-4177-0. Epub Jun. 19, 2018.
Demeure et al., T Lymphocytes infiltrating various tumour types express the MHC class II ligand lymphocyte activation gene-3 (LAG-3): role of LAG-3/MHC class II interactions in cell-cell contacts. Eur J Cancer. Sep. 2001;37(13):1709-18. doi: 10.1016/s0959-8049(01)00184-8.
Deng et al., LAG-3 confers poor prognosis and its blockade reshapes antitumor response in head and neck squamous cell carcinoma. Oncoimmunology. Oct. 7, 2016;5(11):e1239005. doi: 10.1080/2162402X.2016.1239005.
Doody et al., Abstract B091: a LAG-3/PD-L1 bispecific antibody inhibits tumor growth in two syngeneic colon carcinoma models. Second CRI-CIMT-EATI-AACR International Cancer Immunotherapy Conference: Translating Science into Survival. Sep. 25-28, 2016. New York, NY. doi: 10.1158/23/26-6066.IMM2016-B091. Published Nov. 2016. 8 pages.
Doody, An anti-murine LAG-3/PD-L1 bispecific antibody which modulates T cell activity and inhibits tumour growth. Oral Presentation at 2nd Annual Advances in Immuno-Oncology Congress. May 16, 2017. 17 pages. PDR188.

(56) References Cited

OTHER PUBLICATIONS

Doody, In vivo Efficacy of bispecific antibodies targeting two immmune-modulatory receptors. Oral Presentation at PEGS Europe. Nov. 4, 2016. 16 pages. PDR144.

Everett et al., A LAG-3/PD-L1 bispecific antibody inhibits tumour growth in two syngeneic colon carcinoma models. Poster Presentation. AACR Tumor Immunology and Immunotherapy. Oct. 21, 2016. 1 page. PDR137.

Everett et al., Abstract PR06: a LAG-3/PD-L1 bispecific antibody inhibits tumour growth in two syngeneic colon carcinoma models. AACR Special Conference on Tumor Immunology and Immunotherapy. Oct. 20-23, 2016. Boston, MA. Doi: 10.1158/2326-6074.TUMIMM16-PR06. Published Mar. 2017. 8 pages.

Everett, A LAG-3/PD-L1 Bispecific Antibody Inhibits Tumour Growth in Two Syngeneic Colon Carcinoma Models. Oral Presentation at AACR Tumor Immunology and Immunotherapy. Boston, MA. Oct. 20-23, 2016. 5 pages. PDR141.

F-STAR, First-in-Class Bispecific Antibodies for Cance Immunotherapy. Jul. 2016. Presentation. 14 pages. PDR119.

Fiehler, Development of an anti-PD-L1 Fcab. Presentation. European Antibody Congress. Oct. 29, 2018. 26 pages. PDR312.

Foy et al., Poxvirus-Based Active Immunotherapy with PD-1 and LAG-3 Dual Immune Checkpoint Inhibition Overcomes Compensatory Immune Regulation, Yielding Complete Tumor Regression in Mice. PLoS One. Feb. 24, 2016;11(2):e0150084. doi: 10.1371/journal.pone.0150084.

Gandhi et al., Expression of LAG-3 by tumor-infiltrating lymphocytes is coincident with the suppression of latent membrane antigen-specific CD8+ T-cell function in Hodgkin lymphoma patients. Blood. Oct. 1, 2006;108(7):2280-9. doi: 10.1182/blood-2006-04-015164. Epub Jun. 6, 2006.

Gliddon, Pushing all the buttons: innovating in immuno-oncology with mAb. Oral Presentation at Phacilitate Immunotherapy World 2017. Jan. 18, 2017. 11 pages. PDR165.

Grosso et al., Programmed death-ligand 1 (PD-L1) expression in various tumor types. J Immunother Cancer. 2013;1(Suppl 1):P53. http://www.immunotherapyofcancer.org/content/1/S1/P53. 1 page.

Haines et al., Abstract 4714: Blockade of LAG-3 amplifies immune activation signatures and augments curative antitumor responses to anti-PD-1 therapy in immune competent mouse models of cancer. Proceedings: AACR Annual Meeting 2017. Apr. 1-5, 2017. Washington, DC. doi: 10.1158/1538-7445.AM2017-4714. Published Jul. 2017. 8 pages.

Herbst et al., Predictive correlates of response to the anti-PD-L1 antibody MPDL3280A in cancer patients. Nature. Nov. 27, 2014;515(7528):563-7. doi: 10.1038/nature14011. Author Manuscript.

Hid Cadena et al., Checks and Balances in Autoimmune Vasculitis. Front Immunol. Feb. 2, 20182;9:315. doi: 10.3389/fimmu.2018.00315.

Horn et al., CD3xPDL1 bi-specific T cell engager (BiTE) simultaneously activates T cells and NKT cells, kills PDL1+ tumor cells, and extends the survival of tumor-bearing humanized mice. Oncotarget. Aug. 3, 2017;8(35):57964-57980. doi: 10.18632/oncotarget.19865.

Huang et al., Abstract PR03: Combinatorial blockade of PD-1, CTLA-4, and LAG-3 pathways inhibits murine ovarian tumor growth. Abstracts: AACR Special Conference: Advances in Ovarian Cancer Research: Exploiting Vulnerabilites. Oct. 17-20, 2015. Orlando, FL. doi: 10.1158/1557-3265.OVCA15-PR03. Published Jan. 2016. 8 pages.

Iwai et al., Involvement of PD-L1 on tumor cells in the escape from host immune system and tumor immunotherapy by PD-L1 blockade. Proc Natl Acad Sci U S A. Sep. 17, 2002;99(19):12293-7. doi: 10.1073/pnas.192461099. Epub Sep. 6, 2002.

Jochems et al., Analyses of functions of an anti-PD-L1/TGF?R2 bispecific fusion protein (M7824). Oncotarget. Sep. 8, 2017;8(43):75217-75231. doi: 10.18632/oncotarget.20680.

Kehry et al., Abstract 271: Targeting PD-1, TIM-3 and LAG-3 in combination for improved immunotherapy combinations. AACR 106th Annual Meeting. Apr. 18-22, 2015. Philadelphia, PA. doi: 10.1158/1538-7445.AM2015-271. 8 pages.

Klooster et al., Abstract B088: Generation of immuno-modulatory receptor binding bispecific antibodies to modulate tumor immunity. Second CRI-CIMT-EATI-AACR International Cancer Immunotherapy Conference: Translating Science into Survival. Sep. 25-28, 2016. New York, NY. doi: 10.1158/2326-6066.IMM2016-B088. 4 pages.

Koopmans et al., A novel bispecific antibody for EGFR-directed blockade of the PD-1/PD-L1 immune checkpoint. Oncoimmunology. May 31, 2018;7(8):e1466016. doi: 10.1080/2162402X.2018.1466016.

Kraman et al., A LAG-3/PD-L1 bispecific antibody inhibits tmour growth in two syngeneic colon carcinoma models. Poster Presentation. BSI/NVVI Congress. Dec. 6, 2016. 1 page. PDR153.

Kraman et al., A LAG-3/PD-L1 bispecific antibody inhibits tumour growth in two syngeneic colon carcinoma models. Abstract B091. Poster Presentation. CRI-CIMT-EATI-AACR Cancer Immunotherapy Conference. Sep. 26, 2016. 1 page. PDR129.

Kraman et al., A LAG-3/PD-L1 bispecific antibody inhibits tumour growth in two syngeneic colon carcinoma models. Poster 003. Poster Presentation. 2nd Annual Advances in Immuno-Oncology Congress. May 15, 2017. 1 page. PDR185.

Kraman et al., A LAG-3/PD-L1 bispecific antibody inhibits tumour growth in two syngeneic colon carcinoma models. Poster 1103. Poster Presentation. Keystone Symposium—Cancer Immunology and Immunotherapy. Mar. 19, 2017. 1 page. PDR174.

Kraman et al., A LAG-3/PD-L1 bispecific antibody inhibits tumour growth in two syngeneic colon carcinoma models. Poster 128. Poster Presentation at SITC. Nov. 9, 2016. 1 page. PDR143.

Kraman et al., A LAG-3/PD-L1 bispecific antibody inhibits tumour growth in two syngeneic colon carcinoma models. Poster 5651. Poster Presentation. AACR Annual Meeting. Apr. 1, 2017. 1 page. PDR176.

Kraman et al., A Lag-3/PD-L1 bispecific antibody inhibits tumour growth in two syngeneic colon carcinoma models. Poster Presentation. International Conference on Human & Translational Immunology. Sep. 16, 2016. 1 page. PDR123.

Kraman et al., A LAG-3/PD-L1 bispecific antibody inhibits tumour growth in two syngeneic coon carcinoma models. Poster 3005. Poster Presentation. Keystome Symposium—Biobetters and Next-Generation Biologics. Jan. 22-26, 2017. 1 page. PDR164.

Kraman et al., Abstract 5651:A LAG-3/PD/L1 bispecific antibody inhibits tumor growth in two syngeneic colon carcinoma models. AACR Annual Meeting 2017. Apr. 1-5, 2017. Washington, DC. Doi: 10.1158/1538-7445.AM2017-5651. 8 pages.

La Motte-Mohs et al., Abstract 3217: MGD013, a bispecific PD-1 x LAG-3 Dual-Affinity Re-Targeting (DART®) protein with T-cell immunomodulatory activity for cancer treatment. AACR 107th Annual Meeting. Apr. 16-20, 2016. New Orleans, LA. Doi: 10.1158/1538-7445.AM2016-3217. 8 pages.

La Motte-Mohs et al., MGD013, a bispecific PD-1 x LAG-3 Dual-Affinity Re-Targeting (DART®) protein with T-cell immunomodulatory activity for cancer treatment. Poster Presentation. 2016. http://ir.macrogenics.com/events.cfm. 1 page.

Larkin et al., Combined Nivolumab and Ipilimumab or Monotherapy in Untreated Melanoma. N Engl J Med. Jul. 2, 2015;373(1):23-34. doi: 10.1056/NEJMoa1504030. Epub May 31, 2015. Erratum in: N Engl J Med. Nov. 29, 2018;379(22):2185.

Liu et al., Dual Targeting of Innate and Adaptive Checkpoints on Tumor Cells Limits Immune Evasion. Cell Rep. Aug. 21, 2018;24(8):2101-2111. doi: 10.1016/j.celrep.2018.07.062.

Mccourt et al., KY1055; a novel ICOS/PD-L1 bispecific antibody, enhance T cell activation and delivers potent monotherapy anti-tumour response in vivo. Abstract. CIMT 2018. Feb. 28, 2018. 1 page. PDR245.

Mccourt et al., KY1055; a novel ICOS/PD-L1 bispecific antibody, enhance T cell activation and delivers potent monotherapy anti-tumour response in vivo. Poster Presentation. CIMT Conference. May 9, 2018. 1 page. PDR 264.

Mccourt et al., KY1055; a novel ICOS/PD-L1 bispecific antibody, enhance T cell activation and delivers potent monotherapy anti-tumour response in vivo. Presentation. CIMT Conference. May 9, 2018. 13 pages. PDR265.

(56) References Cited

OTHER PUBLICATIONS

Michaelson et al., Anti-tumor activity of stability-engineered IgG-like bispecific antibodies targeting TRAIL-R2 and LTbetaR. MAbs. Mar.-Apr. 2009;1(2):128-41. doi: 10.4161/mabs.1.2.7631. Epub Mar. 11, 2009.

Munoz-Olaya, Development of an anti-PD-L1Fcab. Presentation. PEGS Lisbon. Nov. 16, 2018. 24 pages. PDR321.

Nalivaiko et al., A Recombinant Bispecific CD20xCD95 Antibody With Superior Activity Against Normal and Malignant B-cells. Mol Ther. Feb. 2016;24(2):298-305. doi: 10.1038/mt.2015.209. Epub Nov. 19, 2015.

Pavlidou et al., Simultaneous costimulatory T-cell engagement and checkpoint inhibition by PRS-344/ONC0055, a 4-1BB/PD-L1 bispecific compound for tumor localized activation of the immune system. SITC 2018. Poster Presentation. 2018. 1 page.

Powles et al., MPDL3280A (anti-PD-L1) treatment leads to clinical activity in metastatic bladder cancer. Nature. Nov. 27, 2014;515(7528):558-62. doi: 10.1038/nature13904.

Sainson et al., KY1055, a novel ICOS/PD-L1 bispecific antibody, efficiently enhances T cell activation and delivers a potent anti-tumour response in vivo. Abstract. AACR. Jan. 22, 2018. 1 page. PDR236.

Sainson et al., KY1055, a novel ICOS/PD-L1 bispecific antibody, efficiently enhances T cell activation and delivers a potent anti-tumour response in vivo. Poster Presentation. AACR 2018. Apr. 4, 2018. 1 page. PDR254.

Strauss et al., Phase I Trial of M7824 (MSB0011359C), a Bifunctional Fusion Protein Targeting PD-L1 and TGF?, in Advanced Solid Tumors. Clin Cancer Res. Mar. 15, 2018;24(6):1287-1295. doi: 10.1158/1078-0432.CCR-17-2653. Epub Jan. 3, 2018.

Tuna, Identification of a PD-L1 binding FCAB: a potent inhibitor of immunosuppressive signals. Abstract. European Antibody Congress. May 3, 2018. 1 page. PDR270.

Tuna, The use of bispecific antibodies to modulate anti-tumour immune responses. Oral Presentation at 10th Annual Proteins and Antibodies Congress. 2017 Ap 24. 26 pages. PDR183.

Vanamee et al., Structural principles of tumor necrosis factor superfamily signaling. Sci Signal. Jan. 2, 2018;11(511):eaao4910. doi: 10.1126/scisignal.aao4910. 12 pages.

Weismann, a LAG-3/PD-L1 Bispecific Antibody Inhibits Tumour Growth In Two Syngeneic Colon Carcinoma Models. International Conference on Human and Translational Immunology. Rhodes, Greece. 2016 Spe 16-21. Presentation. 6 pages. PDR128.

Wherry, T cell exhaustion. Nat Immunol. Jun. 2011;12(6):492-9. doi: 10.1038/ni.2035.

Wilton, KY1055, a bispecific mAb2 targeting ICOS and PD-L1. Presentation. Feb. 21, 2018. 17 pages. PDR238.

Wolchok et al., Nivolumab plus ipilimumab in advanced melanoma. N Engl J Med. Jul. 11, 2013;369(2):122-33. doi: 10.1056/NEJMoa1302369. Epub Jun. 2, 2013. Erratum in: N Engl J Med. Nov. 29, 2018;379(22):2185. Author Manuscript.

Woo et al., Immune inhibitory molecules LAG-3 and PD-1 synergistically regulate T-cell function to promote tumoral immune escape. Cancer Res. Feb. 15, 2012;72(4):917-27. doi: 10.1158/0008-5472.CAN-11-1620. Epub Dec. 20, 2011.

Workman et al., Negative regulation of T cell homeostasis by lymphocyte activation gene-3 (CD223). J Immunol. Jan. 15, 2005;174(2):688-95. doi: 10.4049/jimmunol.174.2.688.

Workman et al., The CD4-related molecule, LAG-3 (CD223), regulates the expansion of activated T cells. Eur J Immunol. Apr. 2003;33(4):970-9. doi: 10.1002/eji.200323382.

Wydro, Bispecific antibodies: new opportunities for novel therapies. Oral Presentation at 7th Annual Biologics Symposium. Mar. 1, 2017. 24 pages. PDR172.

Wykes et al., Immune checkpoint blockade in infectious diseases. Nat Rev Immunol. Feb. 2018;18(2):91-104. doi: 10.1038/nri.2017.112. Epub Oct. 9, 2017.

Zhang et al., Structural basis of a novel PD-L1 nanobody for immune checkpoint blockade. Cell Discov. Mar. 7, 2017;3:17004. doi: 10.1038/celldisc.2017.4.

U.S. Appl. No. 16/955,450, filed Jun. 18, 2020, Tuna et al.
U.S. Appl. No. 17/259,634, filed Jan. 12, 2021, Munoz-Olaya et al.
U.S. Appl. No. 17/259,680, filed Jan. 12, 2021, Pechouckova et al.
U.S. Appl. No. 17/259,677, filed Jan. 12, 2021, Munoz-Olaya et al.
U.S. Appl. No. 17/259,754, filed Jan. 12, 2021, Lakins et al.
U.S. Appl. No. 17/259,714, filed Jan. 12, 2021, Tuna et al.
U.S. Appl. No. 17/259,791, filed Jan. 12, 2021, Lakins et al.
U.S. Appl. No. 17/259,796, filed Jan. 12, 2021, Tuna et al.
PCT/EP2019/068804, Oct. 17, 2019, International Search Report and Written Opinion.
PCT/EP2019/068804, Jan. 21, 2021, International Preliminary Report on Patentability.

[No Author Listed], mesothelin isoform 1 preproprotein [Homo sapiens]. NCBI Reference Sequence: NP_001170826.1. May 2, 2024. Retrieved from https://www.ncbi.nlm.nih.gov/protein/NP_001170826.1/. 4 pages.

[No Author Listed], mesothelin isoform 1 preproprotein [Mus musculus]. NCBI Reference Sequence: NP_001343215.1. Jun. 18, 2024. Retrieved from https://www.ncbi.nlm.nih.gov/protein/NP_001343215.1. 3 pages.

[No Author Listed], Predicted: mesothelin isoform X4 [Macaca fascicularis]. NCBI Reference Sequence: XP_005590874.2. Jan. 25, 2016. Retrieved from https://www.ncbi.nlm.nih.gov/protein/XP_005590874.2. 2 pages.

[No Author Listed], tumor necrosis factor receptor superfamily member 9 precursor [Homo sapiens]. NCBI Reference Sequence: NP_001552.2. Jun. 9, 2024. Retrieved from https://www.ncbi.nlm.nih.gov/protein/NP_001552.2. 4 pages.

Badri et al., Optimization of radiation dosing schedules for proneural glioblastoma. J Math Biol. Apr. 2016;72(5):1301-36. doi: 10.1007/s00285-015-0908-x.

Baylot et al., TCTP Has a Crucial Role in the Different Stages of Prostate Cancer Malignant Progression. Results Probl Cell Differ. 2017;64:255-261. doi: 10.1007/978-3-319-67591-6_13.

Brinkmann et al., The making of bispecific antibodies. MAbs. Feb./Mar. 2017;9(2):182-212. doi: 10.1080/19420862.2016.1268307.

Cooper, The Development and Causes of Cancer. From The Cell: Molecular Approach. 2nd Ed. Sunderland, MA. Sinauer Associates. 2000. 9 pages.

Durham et al., Lymphocyte Activation Gene 3 (LAG-3) modulates the ability of CD4 T-cells to be suppressed in vivo. PLoS One. Nov. 5, 2014;9(11):e109080. doi: 10.1371/journal.pone.0109080. 13 pages.

Gide et al., Distinct Immune Cell Populations Define Response to Anti-PD-1 Monotherapy and Anti-PD-1/Anti-CTLA-4 Combined Therapy. Cancer Cell. Feb. 11, 2019;35(2):238-255.e6. doi: 10.1016/j.ccell.2019.01.003.

Heppner et al., Tumor heterogeneity: biological implications and therapeutic consequences. Cancer Metastasis Rev. 1983;2(1):5-23. doi: 10.1007/BF00046903.

Koyama et al., Adaptive resistance to therapeutic PD-1 blockade is associated with upregulation of alternative immune checkpoints. Nat Commun. Feb. 17, 2016;7:10501. doi: 10.1038/ncomms10501. 9 pages.

Matsuzaki et al., Tumor-infiltrating NY-ESO-1-specific CD8+ T cells are negatively regulated by LAG-3 and PD-1 in human ovarian cancer. Proc Natl Acad Sci U S A. Apr. 27, 2010;107(17):7875-80. doi: 10.1073/pnas.1003345107. Epub Apr. 12, 2010.

Muller et al., Spliceosomal peptide P140 for immunotherapy of systemic lupus erythematosus: results of an early phase II clinical trial. Arthritis Rheum. Dec. 2008;58(12):3873-83. doi: 10.1002/art.24027.

Seckinger et al., Development and characterization of NILK-2301, a novel CEACAM5xCD3 κλ bispecific antibody for immunotherapy of CEACAM5-expressing cancers. J Hematol Oncol. Dec. 12, 2023;16(1):117. doi: 10.1186/s13045-023-01516-3.

Shen, et al. Single variable domain-IgG fusion. A novel recombinant approach to Fc domain-containing bispecific antibodies. J Biol Chem. Apr. 21, 2006;281(16):10706-14. doi: 10.1074/jbc.M513415200. Epub Feb. 15, 2006.

Torres et al., The immunoglobulin constant region contributes to affinity and specificity. Trends Immunol. Feb. 2008;29(2):91-7. doi: 10.1016/j.it.2007.11.004. Epub Jan. 10, 2008.

(56) References Cited

OTHER PUBLICATIONS

Yap et al., Abstract TPS2652: A first-in-human phase I study of FS118, an anti-LAG-3/PD-L1 bispecific antibody in patients with solid tumors that have progressed on prior PD-1/PD-L1 therapy. Journal of Clinical Oncology. May 15, 2019;37(15_suppl). 2019 ASCO Annual Meeting Proceedings. 4 pages.

* cited by examiner

SEQUENCE LISTING

<160> NUMBER OF SEQ ID NOS: 184

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ser Tyr Gly Ile Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (6)..(6)
<223> OTHER INFORMATION: Xaa is Ser, Asn, or Gly
<220> FEATURE:
<221> NAME/KEY: SITE
<222> LOCATION: (7)..(7)
<223> OTHER INFORMATION: Xaa is is Gly or Ser
<220> FEATURE:
<221> NAME/KEY: SITE
<222> LOCATION: (8)..(8)
<223> OTHER INFORMATION: Xaa is or Gly, Asn or Ser
<220> FEATURE:
<221> NAME/KEY: SITE
<222> LOCATION: (9)..(9)
<223> OTHER INFORMATION: Xaa is Thr or Ala

<400> SEQUENCE: 2

Trp Ile Ser Ala Tyr Xaa Xaa Xaa Xaa Asn Tyr Ala Gln Lys Leu Gln
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: Synthetic

<400> SEQUENCE: 3

Asp Leu Phe Pro Thr Ile Phe Gly Val Ser Tyr Tyr Tyr Tyr
1               5                   10

<210> SEQ ID NO 4
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(1)
<223> OTHER INFORMATION: Xaa selected from Ser, Asn and Gly
<220> FEATURE:
<221> NAME/KEY: SITE
<222> LOCATION: (2)..(2)
<223> OTHER INFORMATION: Xaa selected from Gly and Ser
<220> FEATURE:
<221> NAME/KEY: SITE
<222> LOCATION: (3)..(3)
<223> OTHER INFORMATION: Xaa selected from Gly, Asn and Ser
<220> FEATURE:

```
<221> NAME/KEY: SITE
<222> LOCATION: (4)..(4)
<223> OTHER INFORMATION: Xaa selected from Thr and Ala

<400> SEQUENCE: 4

Xaa Xaa Xaa Xaa
1

<210> SEQ ID NO 5
<211> LENGTH: 4
<212> TYPE: PRT
<213> ORGANISM: Artificial Sequence
<220> FEATURE:
<223> OTHER INFORMATION: Synthetic

<400> SEQUENCE: 5

Ser Gly Gly Thr
1

<210> SEQ ID NO 6
<211> LENGTH: 4
<212> TYPE: PRT
<213> ORGANISM: Artificial Sequence
<220> FEATURE:
<223> OTHER INFORMATION: Synthetic

<400> SEQUENCE: 6

Asn Ser Asn Thr
1

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Gly Gly Ser Thr
1

<210> SEQ ID NO 8
<211> LENGTH: 4
<212> TYPE: PRT
<213> ORGANISM: Artificial Sequence
<220> FEATURE:
<223> OTHER INFORMATION: Synthetic

<400> SEQUENCE: 8

Ser Gly Asn Ala
1

<210> SEQ ID NO 9
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (7)..(7)
<223> OTHER INFORMATION: Xaa is Gly or Ser
<220> FEATURE:
<221> NAME/KEY: SITE
<222> LOCATION: (8)..(8)
<223> OTHER INFORMATION: Xaa is Asn or Gly

<400> SEQUENCE: 9
```

```
Arg Ala Ser Gln Ser Ile Xaa Xaa Arg Leu Ala
1               5                   10
```

<210> SEQ ID NO 10
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (4)..(4)
<223> OTHER INFORMATION: Xaa is Thr or Asn
<220> FEATURE:
<221> NAME/KEY: SITE
<222> LOCATION: (5)..(5)
<223> OTHER INFORMATION: Xaa is Ser or Leu
<220> FEATURE:
<221> NAME/KEY: SITE
<222> LOCATION: (7)..(7)
<223> OTHER INFORMATION: Xaa is Thr or Ser

<400> SEQUENCE: 10

```
Glu Ala Ser Xaa Xaa Glu Xaa
1               5
```

<210> SEQ ID NO 11
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (3)..(3)
<223> OTHER INFORMATION: Xaa is Ser or Ala
<220> FEATURE:
<221> NAME/KEY: SITE
<222> LOCATION: (4)..(4)
<223> OTHER INFORMATION: Xaa is Tyr or Asn
<220> FEATURE:
<221> NAME/KEY: SITE
<222> LOCATION: (5)..(5)
<223> OTHER INFORMATION: Xaa is Ser or Thr
<220> FEATURE:
<221> NAME/KEY: SITE
<222> LOCATION: (6)..(6)
<223> OTHER INFORMATION: Xaa is Thr, Trp or Phe
<220> FEATURE:
<221> NAME/KEY: SITE
<222> LOCATION: (8)..(8)
<223> OTHER INFORMATION: Xaa is absent or Arg
<220> FEATURE:
<221> NAME/KEY: SITE
<222> LOCATION: (9)..(9)
<223> OTHER INFORMATION: Xaa is Tyr, Arg or Val
<220> FEATURE:
<221> NAME/KEY: SITE
<222> LOCATION: (10)..(10)
<223> OTHER INFORMATION: Xaa is Thr or Ser

<400> SEQUENCE: 11

```
Gln Gln Xaa Xaa Xaa Xaa Pro Xaa Xaa Xaa
1               5                   10
```

<210> SEQ ID NO 12
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (12)..(12)

```
<223> OTHER INFORMATION: Xaa is Tyr or Ser

<400> SEQUENCE: 12

Thr Gly Thr Ser Ser Asp Val Gly Gly Tyr Asn Xaa Val Ser
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Glu Val Thr Asn Arg Pro Ser
1               5

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

Ser Ser Phe Lys Arg Gly Ser Thr Leu Val Val
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic

<400> SEQUENCE: 15

Arg Ala Ser Gln Ser Ile Gly Asn Arg Leu Ala
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Glu Ala Ser Thr Ser Glu Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Gln Gln Ser Tyr Ser Thr Pro Tyr Thr
1               5

<210> SEQ ID NO 18
<211> LENGTH: 17
<212> TYPE: PRT
<213> ORGANISM: Artificial Sequence
<220> FEATURE:
<223> OTHER INFORMATION: Synthetic
```

```
<400> SEQUENCE: 18

Trp Ile Ser Ala Tyr Ser Gly Gly Thr Asn Tyr Ala Gln Lys Leu Gln
1               5                   10                  15

Gly

<210> SEQ ID NO 19
<211> LENGTH: 11
<212> TYPE: PRT
<213> ORGANISM: Artificial Sequence
<220> FEATURE:
<223> OTHER INFORMATION: Synthetic

<400> SEQUENCE: 19

Arg Ala Ser Gln Ser Ile Ser Gly Arg Leu Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Synthetic

<400> SEQUENCE: 20

Glu Ala Ser Asn Leu Glu Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Gln Gln Ser Tyr Ser Trp Pro Arg Thr
1               5

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Gln Gln Ser Tyr Ser Thr Pro Arg Val Thr
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Synthetic

<400> SEQUENCE: 23

Trp Ile Ser Ala Tyr Asn Ser Asn Thr Asn Tyr Ala Gln Lys Leu Gln
1               5                   10                  15

Gly

<210> SEQ ID NO 24
<211> LENGTH: 10
<212> TYPE: PRT
```

```
<213> ORGANISM: Artificial Sequence
<220> FEATURE:
<223> OTHER INFORMATION: Synthetic

<400> SEQUENCE: 24

Gln Gln Ala Asn Thr Phe Pro Arg Val Ser
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic

<400> SEQUENCE: 25

Thr Gly Thr Ser Ser Asp Val Gly Gly Tyr Asn Tyr Val Ser
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic

<400> SEQUENCE: 26

Thr Gly Thr Ser Ser Asp Val Gly Gly Tyr Asn Ser Val Ser
1               5                   10

<210> SEQ ID NO 27
<211> LENGTH: 123
<212> TYPE: PRT
<213> ORGANISM: Artificial Sequence
<220> FEATURE:
<223> OTHER INFORMATION: Synthetic

<400> SEQUENCE: 27

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120

<210> SEQ ID NO 28
<211> LENGTH: 107
<212> TYPE: PRT
<213> ORGANISM: Artificial Sequence
<220> FEATURE:
<223> OTHER INFORMATION: Synthetic

<400> SEQUENCE: 28
```

```
Asp Ile Gln Met Thr Gln Ser Pro Ser Thr Leu Ser Ala Ser Val Arg
1               5                   10                  15

Asp Arg Val Ile Ile Thr Cys Arg Ala Ser Gln Ser Ile Gly Asn Arg
            20                  25                  30

Leu Ala Trp Tyr Gln His Lys Pro Gly Lys Ala Pro Lys Leu Leu Ile
        35                  40                  45

Tyr Glu Ala Ser Thr Ser Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105
```

<210> SEQ ID NO 29
<211> LENGTH: 123
<212> TYPE: PRT
<213> ORGANISM: Artificial Sequence
<220> FEATURE:
<223> OTHER INFORMATION: Synthetic

<400> SEQUENCE: 29

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120
```

<210> SEQ ID NO 30
<211> LENGTH: 107
<212> TYPE: PRT
<213> ORGANISM: Artificial Sequence
<220> FEATURE:
<223> OTHER INFORMATION: Synthetic

<400> SEQUENCE: 30

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80
```

```
Glu Asp Phe Ala Thr Tyr Tyr Cys Gln Gln Ser Tyr Ser Trp Pro Arg
                85                  90                  95

Thr Phe Gly Gln Gly Thr Lys Val Glu Ile Lys
            100                 105
```

<210> SEQ ID NO 31
<211> LENGTH: 123
<212> TYPE: PRT
<213> ORGANISM: Artificial Sequence
<220> FEATURE:
<223> OTHER INFORMATION: Synthetic

<400> SEQUENCE: 31

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Ser Gly Gly Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120
```

<210> SEQ ID NO 32
<211> LENGTH: 108
<212> TYPE: PRT
<213> ORGANISM: Artificial Sequence
<220> FEATURE:
<223> OTHER INFORMATION: Synthetic

<400> SEQUENCE: 32

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
                20                  25                  30

Leu Ala Trp Tyr Gln Gln Lys Pro Gly Lys Ala Pro Asn Leu Leu Ile
            35                  40                  45

Tyr Glu Ala Ser Asn Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Val Thr Phe Gly Gln Gly Thr Lys Val Glu Ile Lys
            100                 105
```

<210> SEQ ID NO 33
<211> LENGTH: 123
<212> TYPE: PRT
<213> ORGANISM: Artificial Sequence
<220> FEATURE:
<223> OTHER INFORMATION: Synthetic

<400> SEQUENCE: 33

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Ser Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
            115                 120

<210> SEQ ID NO 34
<211> LENGTH: 107
<212> TYPE: PRT
<213> ORGANISM: Artificial Sequence
<220> FEATURE:
<223> OTHER INFORMATION: Synthetic

<400> SEQUENCE: 34

Asp Ile Gln Met Thr Gln Ser Pro Ser Thr Leu Ser Ala Ser Val Arg
1               5                   10                  15

Asp Arg Val Ile Ile Thr Cys Arg Ala Ser Gln Ser Ile Gly Asn Arg
            20                  25                  30

Leu Ala Trp Tyr Gln His Lys Pro Gly Lys Ala Pro Lys Leu Leu Ile
        35                  40                  45

Tyr Glu Ala Ser Thr Ser Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 35
<211> LENGTH: 123
<212> TYPE: PRT
<213> ORGANISM: Artificial Sequence
<220> FEATURE:
<223> OTHER INFORMATION: Synthetic

<400> SEQUENCE: 35

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Ser Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120

<210> SEQ ID NO 36
<211> LENGTH: 107
<212> TYPE: PRT
<213> ORGANISM: Artificial Sequence
<220> FEATURE:
<223> OTHER INFORMATION: Synthetic

<400> SEQUENCE: 36

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Trp Pro Arg
                85                  90                  95

Thr Phe Gly Gln Gly Thr Lys Val Glu Ile Lys
            100                 105

<210> SEQ ID NO 37
<211> LENGTH: 123
<212> TYPE: PRT
<213> ORGANISM: Artificial Sequence
<220> FEATURE:
<223> OTHER INFORMATION: Synthetic

<400> SEQUENCE: 37

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Ser Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120

```
<210> SEQ ID NO 38
<211> LENGTH: 108
<212> TYPE: PRT
<213> ORGANISM: Artificial Sequence
<220> FEATURE:
<223> OTHER INFORMATION: Synthetic

<400> SEQUENCE: 38
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Val Thr Phe Gly Gln Gly Thr Lys Val Glu Ile Lys
            100                 105

```
<210> SEQ ID NO 39
<211> LENGTH: 123
<212> TYPE: PRT
<213> ORGANISM: Artificial Sequence
<220> FEATURE:
<223> OTHER INFORMATION: Synthetic

<400> SEQUENCE: 39
```

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Ser Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120

```
<210> SEQ ID NO 40
<211> LENGTH: 108
<212> TYPE: PRT
<213> ORGANISM: Artificial Sequence
<220> FEATURE:
<223> OTHER INFORMATION: Synthetic

<400> SEQUENCE: 40
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
 50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Gln Ala Asn Thr Phe Pro Arg
                85                  90                  95

Val Ser Phe Gly Gly Gly Thr Lys Val Glu Ile Lys
                100                 105

<210> SEQ ID NO 41
<211> LENGTH: 123
<212> TYPE: PRT
<213> ORGANISM: Artificial Sequence
<220> FEATURE:
<223> OTHER INFORMATION: Synthetic

<400> SEQUENCE: 41

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Ser Gly Gly Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
                100                 105                 110

Trp Gly Gln Gly Thr Leu Val Thr Val Ser Ser
            115                 120

<210> SEQ ID NO 42
<211> LENGTH: 111
<212> TYPE: PRT
<213> ORGANISM: Artificial Sequence
<220> FEATURE:
<223> OTHER INFORMATION: Synthetic

<400> SEQUENCE: 42

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln Phe Pro Gly Lys Ala Pro Lys Leu
            35                  40                  45

Met Ile Phe Glu Val Thr Asn Arg Pro Ser Gly Val Ser Asp Arg Phe
        50                  55                  60

Ser Gly Ser Lys Ser Asp Asn Thr Ala Ser Leu Thr Ile Ser Gly Leu
65                  70                  75                  80

Gln Ala Glu Asp Glu Ala Glu Tyr Tyr Cys Ser Ser Phe Lys Arg Gly
                85                  90                  95

Ser Thr Leu Val Val Phe Gly Gly Gly Thr Lys Leu Thr Val Leu

<210> SEQ ID NO 43
<211> LENGTH: 123
<212> TYPE: PRT
<213> ORGANISM: Artificial Sequence
<220> FEATURE:
<223> OTHER INFORMATION: Synthetic

<400> SEQUENCE: 43

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Ser Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120
```

<210> SEQ ID NO 44
<211> LENGTH: 111
<212> TYPE: PRT
<213> ORGANISM: Artificial Sequence
<220> FEATURE:
<223> OTHER INFORMATION: Synthetic

<400> SEQUENCE: 44

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln Phe Pro Gly Lys Ala Pro Lys Leu
        35                  40                  45

Met Ile Phe Glu Val Thr Asn Arg Pro Ser Gly Val Ser Asp Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Glu Tyr Tyr Cys Ser Ser Phe Lys Arg Gly
                85                  90                  95

Ser Thr Leu Val Val Phe Gly Gly Gly Thr Lys Leu Thr Val Leu
            100                 105                 110
```

<210> SEQ ID NO 45
<211> LENGTH: 123
<212> TYPE: PRT
<213> ORGANISM: Artificial Sequence
<220> FEATURE:
<223> OTHER INFORMATION: Synthetic

<400> SEQUENCE: 45

```
Glu Val Gln Leu Val Gln Ser Gly Ala Glu Val Lys Arg Pro Gly Ala
1               5                   10                  15
```

```
Ser Val Lys Val Ser Cys Lys Ala Ser Gly Tyr Thr Phe Thr Ser Tyr
        20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
 50                      55                  60

Gln Gly Arg Val Thr Met Thr Thr Asp Thr Ser Thr Ser Thr Ala Tyr
65                   70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr
            100                 105                 110

Trp Gly Gln Gly Thr Leu Val Thr Val Ser Ser
            115                 120
```

<210> SEQ ID NO 46
<211> LENGTH: 111
<212> TYPE: PRT
<213> ORGANISM: Artificial Sequence
<220> FEATURE:
<223> OTHER INFORMATION: Synthetic

<400> SEQUENCE: 46

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln Phe Pro Gly Lys Ala Pro Lys Leu
            35                  40                  45

Met Ile Phe Glu Val Thr Asn Arg Pro Ser Gly Val Ser Asp Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Glu Tyr Tyr Cys Ser Ser Phe Lys Arg Gly
                85                  90                  95

Ser Thr Leu Val Val Phe Gly Gly Gly Thr Lys Leu Thr Val Leu
            100                 105                 110
```

<210> SEQ ID NO 47
<211> LENGTH: 452
<212> TYPE: PRT
<213> ORGANISM: Artificial Sequence
<220> FEATURE:
<223> OTHER INFORMATION: Synthetic

<400> SEQUENCE: 47

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
```

```
                    85                  90                  95
Ala Arg Asp Leu Phe Pro Thr Ile Phe Gly Val Ser Tyr Tyr Tyr Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Leu Gly Thr Gln Thr Tyr Ile Cys Asn Val
    195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
    435                 440                 445

Leu Ser Pro Gly
    450

<210> SEQ ID NO 48
<211> LENGTH: 214
<212> TYPE: PRT
<213> ORGANISM: Artificial Sequence
<220> FEATURE:
<223> OTHER INFORMATION: Synthetic
```

<400> SEQUENCE: 48

```
Asp Ile Gln Met Thr Gln Ser Pro Ser Thr Leu Ser Ala Ser Val Arg
1               5                   10                  15

Asp Arg Val Ile Ile Thr Cys Arg Ala Ser Gln Ser Ile Gly Asn Arg
            20                  25                  30

Leu Ala Trp Tyr Gln His Lys Pro Gly Lys Ala Pro Lys Leu Leu Ile
        35                  40                  45

Tyr Glu Ala Ser Thr Ser Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 49
<211> LENGTH: 452
<212> TYPE: PRT
<213> ORGANISM: Artificial Sequence
<220> FEATURE:
<223> OTHER INFORMATION: Synthetic
```

<400> SEQUENCE: 49

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
```

```
            130                 135                 140
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 50
<211> LENGTH: 214
<212> TYPE: PRT
<213> ORGANISM: Artificial Sequence
<220> FEATURE:
<223> OTHER INFORMATION: Synthetic

<400> SEQUENCE: 50

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
```

```
                35                  40                  45
Tyr Glu Ala Ser Asn Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Ser Tyr Ser Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 452
<212> TYPE: PRT
<213> ORGANISM: Artificial Sequence
<220> FEATURE:
<223> OTHER INFORMATION: Synthetic

<400> SEQUENCE: 51

Glu Val Gln Leu Val Gln Ser Gly Ala Glu Val Lys Arg Pro Gly Ala
 1               5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Ser Gly Gly Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
```

```
                180             185             190
Thr Val Pro Ser Ser Leu Gly Thr Gln Thr Tyr Ile Cys Asn Val
            195                 200             205
Asn His Lys Pro Ser Asn Thr Lys Val Asp Lys Val Glu Pro Lys
        210                 215                 220
Ser Cys Asp Lys Thr His Thr Cys Pro Pro Cys Pro Ala Pro Glu Ala
225                 230                 235                 240
Ala Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
        290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly
    450

<210> SEQ ID NO 52
<211> LENGTH: 215
<212> TYPE: PRT
<213> ORGANISM: Artificial Sequence
<220> FEATURE:
<223> OTHER INFORMATION: Synthetic

<400> SEQUENCE: 52

Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Ser Ile Ser Gly Arg
            20                  25                  30
Leu Ala Trp Tyr Gln Gln Lys Pro Gly Lys Ala Pro Asn Leu Leu Ile
        35                  40                  45
Tyr Glu Ala Ser Asn Leu Glu Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Arg
```

```
                        85                  90                  95
Val Thr Phe Gly Gln Gly Thr Lys Val Glu Ile Lys Arg Thr Val Ala
                    100                 105                 110

Ala Pro Ser Val Phe Ile Phe Pro Pro Ser Asp Glu Gln Leu Lys Ser
                    115                 120                 125

Gly Thr Ala Ser Val Val Cys Leu Leu Asn Asn Phe Tyr Pro Arg Glu
                130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
                210                 215

<210> SEQ ID NO 53
<211> LENGTH: 452
<212> TYPE: PRT
<213> ORGANISM: Artificial Sequence
<220> FEATURE:
<223> OTHER INFORMATION: Synthetic

<400> SEQUENCE: 53

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Ser Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
                210                 215                 220

Ser Cys Asp Lys Thr His Thr Cys Pro Pro Cys Pro Ala Pro Glu Leu
```

```
            225                 230                 235                 240

Leu Gly Gly Pro Ser Val Phe Leu Phe Pro Lys Pro Lys Asp Thr
                245                 250                 255

Leu Met Ile Ser Arg Thr Pro Glu Val Thr Cys Val Val Asp Val
                260                 265                 270

Ser His Glu Asp Pro Glu Val Lys Phe Asn Trp Tyr Val Asp Gly
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly
            450

<210> SEQ ID NO 54
<211> LENGTH: 215
<212> TYPE: PRT
<213> ORGANISM: Artificial Sequence
<220> FEATURE:
<223> OTHER INFORMATION: Synthetic

<400> SEQUENCE: 54

Asp Ile Gln Met Thr Gln Ser Pro Ser Thr Leu Ser Ala Ser Val Arg
1               5                   10                  15

Asp Arg Val Ile Ile Thr Cys Arg Ala Ser Gln Ser Ile Gly Asn Arg
                20                  25                  30

Leu Ala Trp Tyr Gln His Lys Pro Gly Lys Ala Pro Lys Leu Leu Ile
                35                  40                  45

Tyr Glu Ala Ser Thr Ser Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg Thr Ala Ala Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
```

```
            130                 135                 140
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 55
<211> LENGTH: 452
<212> TYPE: PRT
<213> ORGANISM: Artificial Sequence
<220> FEATURE:
<223> OTHER INFORMATION: Synthetic

<400> SEQUENCE: 55

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Ser Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
```

```
            275                 280                 285
Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 56
<211> LENGTH: 215
<212> TYPE: PRT
<213> ORGANISM: Artificial Sequence
<220> FEATURE:
<223> OTHER INFORMATION: Synthetic

<400> SEQUENCE: 56

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Trp Pro Arg
                85                  90                  95

Thr Phe Gly Gln Gly Thr Lys Val Glu Ile Lys Arg Thr Ala Ala Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
```

```
            180                 185                 190
Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 57
<211> LENGTH: 452
<212> TYPE: PRT
<213> ORGANISM: Artificial Sequence
<220> FEATURE:
<223> OTHER INFORMATION: Synthetic

<400> SEQUENCE: 57

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Ser Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
```

```
                    325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Asp Glu Leu Thr Lys Asn Gln
            355                 360                 365
Val Ser Leu Thr Cys Leu Val Lys Gly Phe Tyr Pro Ser Asp Ile Ala
        370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly
    450

<210> SEQ ID NO 58
<211> LENGTH: 216
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Ser Ile Ser Gly Arg
            20                  25                  30
Leu Ala Trp Tyr Gln Gln Lys Pro Gly Lys Ala Pro Asn Leu Leu Ile
        35                  40                  45
Tyr Glu Ala Ser Asn Leu Glu Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Arg
                85                  90                  95
Val Thr Phe Gly Gln Gly Thr Lys Val Glu Ile Lys Arg Thr Ala Ala
            100                 105                 110
Ala Ala Pro Ser Val Phe Ile Phe Pro Pro Ser Asp Glu Gln Leu Lys
        115                 120                 125
Ser Gly Thr Ala Ser Val Val Cys Leu Leu Asn Asn Phe Tyr Pro Arg
    130                 135                 140
Glu Ala Lys Val Gln Trp Lys Val Asp Asn Ala Leu Gln Ser Gly Asn
145                 150                 155                 160
Ser Gln Glu Ser Val Thr Glu Gln Asp Ser Lys Asp Ser Thr Tyr Ser
                165                 170                 175
Leu Ser Ser Thr Leu Thr Leu Ser Lys Ala Asp Tyr Glu Lys His Lys
            180                 185                 190
Leu Tyr Ala Cys Glu Val Thr His Gln Gly Leu Ser Ser Pro Val Thr
        195                 200                 205
Lys Ser Phe Asn Arg Gly Glu Cys
    210                 215
```

<210> SEQ ID NO 59
<211> LENGTH: 452
<212> TYPE: PRT
<213> ORGANISM: Artificial Sequence
<220> FEATURE:
<223> OTHER INFORMATION: Synthetic

<400> SEQUENCE: 59

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Ser Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
```

```
                     370                 375                 380
Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 60
<211> LENGTH: 216
<212> TYPE: PRT
<213> ORGANISM: Artificial Sequence
<220> FEATURE:
<223> OTHER INFORMATION: Synthetic

<400> SEQUENCE: 60

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Gln Ala Asn Thr Phe Pro Arg
                85                  90                  95

Val Ser Phe Gly Gly Gly Thr Lys Val Glu Ile Lys Arg Thr Ala Ala
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 61
<211> LENGTH: 452
<212> TYPE: PRT
<213> ORGANISM: Artificial Sequence
<220> FEATURE:
<223> OTHER INFORMATION: Synthetic

<400> SEQUENCE: 61
```

-continued

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
```

-continued

```
                420                 425                 430
Val Met His Glu Ala Leu His Asn His Tyr Thr Gln Lys Ser Leu Ser
            435                 440                 445

Leu Ser Pro Gly
        450

<210> SEQ ID NO 62
<211> LENGTH: 217
<212> TYPE: PRT
<213> ORGANISM: Artificial Sequence
<220> FEATURE:
<223> OTHER INFORMATION: Synthetic

<400> SEQUENCE: 62

Gln Ser Ala Leu Thr Gln Pro Ala Ser Val Ser Gly Ser Pro Gly Gln
1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln Phe Pro Gly Lys Ala Pro Lys Leu
        35                  40                  45

Met Ile Phe Glu Val Thr Asn Arg Pro Ser Gly Val Ser Asp Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Glu Tyr Tyr Cys Ser Ser Phe Lys Arg Gly
                85                  90                  95

Ser Thr Leu Val Val Phe Gly Gly Gly Thr Lys Leu Thr Val Leu Gly
            100                 105                 110

Gln Pro Ala Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 63
<211> LENGTH: 452
<212> TYPE: PRT
<213> ORGANISM: Artificial Sequence
<220> FEATURE:
<223> OTHER INFORMATION: Synthetic

<400> SEQUENCE: 63

Glu Val Gln Leu Val Gln Ser Gly Ala Glu Val Lys Arg Pro Gly Ala
1               5                  10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45
```

```
Gly Trp Ile Ser Ala Tyr Asn Ser Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
450
```

```
<210> SEQ ID NO 64
<211> LENGTH: 217
<212> TYPE: PRT
<213> ORGANISM: Artificial Sequence
<220> FEATURE:
<223> OTHER INFORMATION: Synthetic

<400> SEQUENCE: 64
```

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln Phe Pro Gly Lys Ala Pro Lys Leu
        35                  40                  45

Met Ile Phe Glu Val Thr Asn Arg Pro Ser Gly Val Ser Asp Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Glu Tyr Tyr Cys Ser Ser Phe Lys Arg Gly
                85                  90                  95

Ser Thr Leu Val Val Phe Gly Gly Gly Thr Lys Leu Thr Val Leu Gly
            100                 105                 110

Gln Pro Ala Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

```
<210> SEQ ID NO 65
<211> LENGTH: 452
<212> TYPE: PRT
<213> ORGANISM: Artificial Sequence
<220> FEATURE:
<223> OTHER INFORMATION: Synthetic

<400> SEQUENCE: 65
```

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 66
<211> LENGTH: 217
<212> TYPE: PRT
<213> ORGANISM: Artificial Sequence
<220> FEATURE:
<223> OTHER INFORMATION: Synthetic

<400> SEQUENCE: 66

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln Phe Pro Gly Lys Ala Pro Lys Leu
        35                  40                  45

Met Ile Phe Glu Val Thr Asn Arg Pro Ser Gly Val Ser Asp Arg Phe
    50                  55                  60

Ser Gly Ser Lys Ser Asp Asn Thr Ala Ser Leu Thr Ile Ser Gly Leu
65                  70                  75                  80

Gln Ala Glu Asp Glu Ala Glu Tyr Tyr Cys Ser Ser Phe Lys Arg Gly
                85                  90                  95

Ser Thr Leu Val Val Phe Gly Gly Gly Thr Lys Leu Thr Val Leu Gly
            100                 105                 110

Gln Pro Ala Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
210                 215

<210> SEQ ID NO 67
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (3)..(3)
<223> OTHER INFORMATION: Xaa is Pro or Thr

<400> SEQUENCE: 67

Gly Tyr Xaa Phe Thr Ser Tyr Gly
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (5)..(5)
<223> OTHER INFORMATION: Xaa is Ser, Asn or Gly
<220> FEATURE:
<221> NAME/KEY: SITE
<222> LOCATION: (6)..(6)
<223> OTHER INFORMATION: Xaa is Gly or Ser
<220> FEATURE:
<221> NAME/KEY: SITE
<222> LOCATION: (7)..(7)
<223> OTHER INFORMATION: Xaa is Gly, Asn or Ser
<220> FEATURE:
```

```
<221> NAME/KEY: SITE
<222> LOCATION: (8)..(8)
<223> OTHER INFORMATION: Xaa is Thr or Ala

<400> SEQUENCE: 68

Ile Ser Ala Tyr Xaa Xaa Xaa Xaa
1               5

<210> SEQ ID NO 69
<211> LENGTH: 16
<212> TYPE: PRT
<213> ORGANISM: Artificial Sequence
<220> FEATURE:
<223> OTHER INFORMATION: Synthetic

<400> SEQUENCE: 69

Ala Arg Asp Leu Phe Pro Thr Ile Phe Gly Val Ser Tyr Tyr Tyr Tyr
1               5                   10                  15

<210> SEQ ID NO 70
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (4)..(4)
<223> OTHER INFORMATION: Xaa is Gly or Ser
<220> FEATURE:
<221> NAME/KEY: SITE
<222> LOCATION: (5)..(5)
<223> OTHER INFORMATION: Xaa is Asn or Gly

<400> SEQUENCE: 70

Gln Ser Ile Xaa Xaa Arg
1               5

<210> SEQ ID NO 71
<211> LENGTH: 3
<212> TYPE: PRT
<213> ORGANISM: Artificial Sequence
<220> FEATURE:
<223> OTHER INFORMATION: Synthetic

<400> SEQUENCE: 71

Glu Ala Ser
1

<210> SEQ ID NO 72
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (3)..(3)
<223> OTHER INFORMATION: Xaa is Ser or Ala
<220> FEATURE:
<221> NAME/KEY: SITE
<222> LOCATION: (4)..(4)
<223> OTHER INFORMATION: Xaa is Tyr or Asn
<220> FEATURE:
<221> NAME/KEY: SITE
<222> LOCATION: (5)..(5)
<223> OTHER INFORMATION: Xaa is Ser or Thr

<400> SEQUENCE: 72

Gln Gln Xaa Xaa Xaa Thr Pro Tyr Thr
```

<210> SEQ ID NO 73
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (3)..(3)
<223> OTHER INFORMATION: Xaa is Ser or Ala
<220> FEATURE:
<221> NAME/KEY: SITE
<222> LOCATION: (4)..(4)
<223> OTHER INFORMATION: Xaa is Tyr or Asn
<220> FEATURE:
<221> NAME/KEY: SITE
<222> LOCATION: (5)..(5)
<223> OTHER INFORMATION: Xaa is Ser or Thr

<400> SEQUENCE: 73

Gln Gln Xaa Xaa Xaa Thr Pro Arg Val Thr
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (3)..(3)
<223> OTHER INFORMATION: Xaa is Ser or Ala
<220> FEATURE:
<221> NAME/KEY: SITE
<222> LOCATION: (4)..(4)
<223> OTHER INFORMATION: Xaa is Tyr or Asn
<220> FEATURE:
<221> NAME/KEY: SITE
<222> LOCATION: (5)..(5)
<223> OTHER INFORMATION: Xaa is Ser or Thr

<400> SEQUENCE: 74

Gln Gln Xaa Xaa Xaa Phe Pro Arg Val Ser
1               5                   10

<210> SEQ ID NO 75
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (3)..(3)
<223> OTHER INFORMATION: Xaa is Ser or Ala
<220> FEATURE:
<221> NAME/KEY: SITE
<222> LOCATION: (4)..(4)
<223> OTHER INFORMATION: Xaa is Tyr or Asn
<220> FEATURE:
<221> NAME/KEY: SITE
<222> LOCATION: (5)..(5)
<223> OTHER INFORMATION: Xaa is Ser or Thr

<400> SEQUENCE: 75

Gln Gln Xaa Xaa Xaa Trp Pro Arg Thr
1               5

<210> SEQ ID NO 76

-continued

```
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (9)..(9)
<223> OTHER INFORMATION: Xaa is Tyr or Ser

<400> SEQUENCE: 76

Ser Ser Asp Val Gly Gly Tyr Asn Xaa
1               5

<210> SEQ ID NO 77
<211> LENGTH: 3
<212> TYPE: PRT
<213> ORGANISM: Artificial Sequence
<220> FEATURE:
<223> OTHER INFORMATION: Synthetic

<400> SEQUENCE: 77

Glu Val Thr
1

<210> SEQ ID NO 78
<211> LENGTH: 17
<212> TYPE: PRT
<213> ORGANISM: Artificial Sequence
<220> FEATURE:
<223> OTHER INFORMATION: Synthetic

<400> SEQUENCE: 78

Trp Ile Ser Ala Tyr Asn Gly Asn Thr Asn Tyr Ala Gln Lys Leu Gln
1               5                   10                  15

Gly

<210> SEQ ID NO 79
<211> LENGTH: 433
<212> TYPE: PRT
<213> ORGANISM: Artificial Sequence
<220> FEATURE:
<223> OTHER INFORMATION: Synthetic

<400> SEQUENCE: 79

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140
```

```
Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
            165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
            210                 215                 220

Val Ile Pro Glu Leu Pro Leu Ala His Pro Pro Asn Glu Arg Thr Ala
225                 230                 235                 240

Ala Ala Thr Ser Ile Thr Ala Tyr Lys Ser Glu Gly Glu Ser Ala Glu
            245                 250                 255

Phe Ser Phe Pro Leu Asn Leu Gly Glu Glu Ser Leu Gln Gly Glu Leu
            260                 265                 270

Arg Trp Lys Ala Glu Lys Ala Pro Ser Ser Gln Ser Trp Ile Thr Phe
            275                 280                 285

Ser Leu Lys Asn Gln Lys Val Ser Val Gln Lys Ser Thr Ser Asn Pro
            290                 295                 300

Lys Phe Gln Leu Ser Glu Thr Leu Pro Leu Thr Leu Gln Ile Pro Gln
305                 310                 315                 320

Val Ser Leu Gln Phe Ala Gly Ser Gly Asn Leu Thr Leu Thr Leu Asp
            325                 330                 335

Arg Gly Ile Leu Tyr Gln Glu Val Asn Leu Val Val Met Lys Val Thr
            340                 345                 350

Gln Pro Asp Ser Asn Thr Leu Thr Cys Glu Val Met Gly Pro Thr Ser
            355                 360                 365

Pro Lys Met Arg Leu Ile Leu Lys Gln Glu Asn Gln Glu Ala Arg Val
370                 375                 380

Ser Arg Gln Glu Lys Val Ile Gln Val Gln Ala Pro Glu Ala Gly Val
385                 390                 395                 400

Trp Gln Cys Leu Leu Ser Glu Gly Glu Glu Val Lys Met Asp Ser Lys
            405                 410                 415

Ile Gln Val Leu Ser Lys Gly Leu Asn Gly Ser His His His His
            420                 425                 430

His

<210> SEQ ID NO 80
<211> LENGTH: 477
<212> TYPE: PRT
<213> ORGANISM: Artificial Sequence
<220> FEATURE:
<223> OTHER INFORMATION: Synthetic

<400> SEQUENCE: 80

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
50                  55                  60
```

```
Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr Ala
225                 230                 235                 240

Ala Ala Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Lys Gly Ser His His His His His His
465                 470                 475
```

```
<210> SEQ ID NO 81
<211> LENGTH: 432
<212> TYPE: PRT
<213> ORGANISM: Artificial Sequence
<220> FEATURE:
<223> OTHER INFORMATION: Synthetic

<400> SEQUENCE: 81
```

| | | | | | | | | | | | | | | | |
|---|---|---|---|---|---|---|---|---|---|---|---|---|---|---|---|
| Met | Arg | Ile | Phe | Ala | Gly | Ile | Ile | Phe | Thr | Ala | Cys | Cys | His | Leu | Leu |
| 1 | | | | 5 | | | | | 10 | | | | | 15 | |
| Arg | Ala | Phe | Thr | Ile | Thr | Ala | Pro | Lys | Asp | Leu | Tyr | Val | Val | Glu | Tyr |
| | | | 20 | | | | | 25 | | | | | 30 | | |
| Gly | Ser | Asn | Val | Thr | Met | Glu | Cys | Arg | Phe | Pro | Val | Glu | Arg | Glu | Leu |
| | | | 35 | | | | | 40 | | | | | 45 | | |
| Asp | Leu | Leu | Ala | Leu | Val | Val | Tyr | Trp | Glu | Lys | Glu | Asp | Glu | Gln | Val |
| | 50 | | | | | 55 | | | | | 60 | | | | |
| Ile | Gln | Phe | Val | Ala | Gly | Glu | Glu | Asp | Leu | Lys | Pro | Gln | His | Ser | Asn |
| 65 | | | | | 70 | | | | | 75 | | | | | 80 |
| Phe | Arg | Gly | Arg | Ala | Ser | Leu | Pro | Lys | Asp | Gln | Leu | Leu | Lys | Gly | Asn |
| | | | | 85 | | | | | 90 | | | | | 95 | |
| Ala | Ala | Leu | Gln | Ile | Thr | Asp | Val | Lys | Leu | Gln | Asp | Ala | Gly | Val | Tyr |
| | | | 100 | | | | | 105 | | | | | 110 | | |
| Cys | Cys | Ile | Ile | Ser | Tyr | Gly | Gly | Ala | Asp | Tyr | Lys | Arg | Ile | Thr | Leu |
| | | | 115 | | | | | 120 | | | | | 125 | | |
| Lys | Val | Asn | Ala | Pro | Tyr | Arg | Lys | Ile | Asn | Gln | Arg | Ile | Ser | Val | Asp |
| | 130 | | | | | 135 | | | | | 140 | | | | |
| Pro | Ala | Thr | Ser | Glu | His | Glu | Leu | Ile | Cys | Gln | Ala | Glu | Gly | Tyr | Pro |
| 145 | | | | | 150 | | | | | 155 | | | | | 160 |
| Glu | Ala | Glu | Val | Ile | Trp | Thr | Asn | Ser | Asp | His | Gln | Pro | Val | Ser | Gly |
| | | | | 165 | | | | | 170 | | | | | 175 | |
| Lys | Arg | Ser | Val | Thr | Thr | Ser | Arg | Thr | Glu | Gly | Met | Leu | Leu | Asn | Val |
| | | | 180 | | | | | 185 | | | | | 190 | | |
| Thr | Ser | Ser | Leu | Arg | Val | Asn | Ala | Thr | Ala | Asn | Asp | Val | Phe | Tyr | Cys |
| | | | 195 | | | | | 200 | | | | | 205 | | |
| Thr | Phe | Trp | Arg | Ser | Gln | Pro | Gly | Gln | Asn | His | Thr | Ala | Glu | Leu | Ile |
| | 210 | | | | | 215 | | | | | 220 | | | | |
| Ile | Pro | Glu | Leu | Pro | Ala | Thr | His | Pro | Pro | Gln | Asn | Arg | Thr | Ala | Ala |
| 225 | | | | | 230 | | | | | 235 | | | | | 240 |
| Ala | Thr | Ser | Ile | Thr | Ala | Tyr | Lys | Ser | Glu | Gly | Ser | Ala | Glu | Phe |
| | | | | 245 | | | | | 250 | | | | | 255 | |
| Ser | Phe | Pro | Leu | Asn | Leu | Gly | Glu | Glu | Ser | Leu | Gln | Gly | Glu | Leu | Arg |
| | | | 260 | | | | | 265 | | | | | 270 | | |
| Trp | Lys | Ala | Glu | Lys | Ala | Pro | Ser | Ser | Gln | Ser | Trp | Ile | Thr | Phe | Ser |
| | | | | 275 | | | | | 280 | | | | | 285 | |
| Leu | Lys | Asn | Gln | Lys | Val | Ser | Val | Gln | Lys | Ser | Thr | Ser | Asn | Pro | Lys |
| | 290 | | | | | 295 | | | | | 300 | | | | |
| Phe | Gln | Leu | Ser | Glu | Thr | Leu | Pro | Leu | Thr | Leu | Gln | Ile | Pro | Gln | Val |
| 305 | | | | | 310 | | | | | 315 | | | | | 320 |
| Ser | Leu | Gln | Phe | Ala | Gly | Ser | Gly | Asn | Leu | Thr | Leu | Thr | Leu | Asp | Arg |
| | | | | 325 | | | | | 330 | | | | | 335 | |
| Gly | Ile | Leu | Tyr | Gln | Glu | Val | Asn | Leu | Val | Val | Met | Lys | Val | Thr | Gln |
| | | | 340 | | | | | 345 | | | | | 350 | | |
| Pro | Asp | Ser | Asn | Thr | Leu | Thr | Cys | Glu | Val | Met | Gly | Pro | Thr | Ser | Pro |
| | | | | 355 | | | | | 360 | | | | | 365 | |
| Lys | Met | Arg | Leu | Ile | Leu | Lys | Gln | Glu | Asn | Gln | Glu | Ala | Arg | Val | Ser |

```
            370                 375                 380
Arg Gln Glu Lys Val Ile Gln Val Gln Ala Pro Glu Ala Gly Val Trp
385                 390                 395                 400

Gln Cys Leu Leu Ser Glu Gly Glu Val Lys Met Asp Ser Lys Ile
                405                 410                 415

Gln Val Leu Ser Lys Gly Leu Asn Gly Ser His His His His His
                420                 425                 430
```

<210> SEQ ID NO 82
<211> LENGTH: 476
<212> TYPE: PRT
<213> ORGANISM: Artificial Sequence
<220> FEATURE:
<223> OTHER INFORMATION: Synthetic

<400> SEQUENCE: 82

```
Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
                20                  25                  30

Gly Ser Asn Val Thr Met Glu Cys Arg Phe Pro Val Glu Arg Glu Leu
            35                  40                  45

Asp Leu Leu Ala Leu Val Val Tyr Trp Glu Lys Glu Asp Glu Gln Val
        50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
                100                 105                 110

Cys Cys Ile Ile Ser Tyr Gly Gly Ala Asp Tyr Lys Arg Ile Thr Leu
            115                 120                 125

Lys Val Asn Ala Pro Tyr Arg Lys Ile Asn Gln Arg Ile Ser Val Asp
130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
                180                 185                 190

Thr Ser Ser Leu Arg Val Asn Ala Thr Ala Asn Asp Val Phe Tyr Cys
            195                 200                 205

Thr Phe Trp Arg Ser Gln Pro Gly Gln Asn His Thr Ala Glu Leu Ile
        210                 215                 220

Ile Pro Glu Leu Pro Ala Thr His Pro Pro Gln Asn Arg Thr Ala Ala
225                 230                 235                 240

Ala Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
```

```
            305                 310                 315                 320
Tyr Arg Val Val Ser Val Leu Thr Val Leu His Gln Asp Trp Leu Asn
                    325                 330                 335

Gly Lys Glu Tyr Lys Cys Lys Val Ser Asn Lys Ala Leu Pro Ala Pro
                    340                 345                 350

Ile Glu Lys Thr Ile Ser Lys Ala Lys Gly Gln Pro Arg Glu Pro Gln
                    355                 360                 365

Val Tyr Thr Leu Pro Pro Ser Arg Asp Glu Leu Thr Lys Asn Gln Val
                    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                    405                 410                 415

Pro Val Leu Asp Ser Asp Gly Ser Phe Phe Leu Tyr Ser Lys Leu Thr
                    420                 425                 430

Val Asp Lys Ser Arg Trp Gln Gln Gly Asn Val Phe Ser Cys Ser Val
                    435                 440                 445

Met His Glu Ala Leu His Asn His Tyr Thr Gln Lys Ser Leu Ser Leu
                    450                 455                 460

Ser Pro Gly Lys Gly Ser His His His His His
465                 470                 475
```

```
<210> SEQ ID NO 83
<211> LENGTH: 272
<212> TYPE: PRT
<213> ORGANISM: Homo sapiens

<400> SEQUENCE: 83

Phe Thr Val Thr Val Pro Lys Asp Leu Tyr Val Val Glu Tyr Gly Ser
1                   5                   10                  15

Asn Met Thr Ile Glu Cys Lys Phe Pro Val Glu Lys Gln Leu Asp Leu
                    20                  25                  30

Ala Ala Leu Ile Val Tyr Trp Glu Met Glu Asp Lys Asn Ile Ile Gln
                    35                  40                  45

Phe Val His Gly Glu Glu Asp Leu Lys Val Gln His Ser Ser Tyr Arg
                    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                    85                  90                  95

Met Ile Ser Tyr Gly Gly Ala Asp Tyr Lys Arg Ile Thr Val Lys Val
                    100                 105                 110

Asn Ala Pro Tyr Asn Lys Ile Asn Gln Arg Ile Leu Val Val Asp Pro
                    115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                    165                 170                 175

Ser Thr Leu Arg Ile Asn Thr Thr Asn Glu Ile Phe Tyr Cys Thr
                    180                 185                 190

Phe Arg Arg Leu Asp Pro Glu Glu Asn His Thr Ala Glu Leu Val Ile
                    195                 200                 205
```

```
Pro Glu Leu Pro Leu Ala His Pro Pro Asn Glu Arg Thr His Leu Val
    210                 215                 220

Ile Leu Gly Ala Ile Leu Leu Cys Leu Gly Val Ala Leu Thr Phe Ile
225                 230                 235                 240

Phe Arg Leu Arg Lys Gly Arg Met Met Asp Val Lys Lys Cys Gly Ile
                245                 250                 255

Gln Asp Thr Asn Ser Lys Lys Gln Ser Asp Thr His Leu Glu Glu Thr
                260                 265                 270
```

<210> SEQ ID NO 84
<211> LENGTH: 272
<212> TYPE: PRT
<213> ORGANISM: Mus musculus

<400> SEQUENCE: 84

```
Phe Thr Ile Thr Ala Pro Lys Asp Leu Tyr Val Glu Tyr Gly Ser
1               5                   10                  15

Asn Val Thr Met Glu Cys Arg Phe Pro Val Glu Arg Glu Leu Asp Leu
                20                  25                  30

Leu Ala Leu Val Val Tyr Trp Glu Lys Glu Asp Glu Gln Val Ile Gln
                35                  40                  45

Phe Val Ala Gly Glu Glu Asp Leu Lys Pro Gln His Ser Asn Phe Arg
            50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
                100                 105                 110

Asn Ala Pro Tyr Arg Lys Ile Asn Gln Arg Ile Ser Val Asp Pro Ala
                115                 120                 125

Thr Ser Glu His Glu Leu Ile Cys Gln Ala Glu Gly Tyr Pro Glu Ala
    130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
                180                 185                 190

Trp Arg Ser Gln Pro Gly Gln Asn His Thr Ala Glu Leu Ile Ile Pro
                195                 200                 205

Glu Leu Pro Ala Thr His Pro Pro Gln Asn Arg Thr His Trp Val Leu
    210                 215                 220

Leu Gly Ser Ile Leu Leu Phe Leu Ile Val Val Ser Thr Val Leu Leu
225                 230                 235                 240

Phe Leu Arg Lys Gln Val Arg Met Leu Asp Val Glu Lys Cys Gly Val
                245                 250                 255

Glu Asp Thr Ser Ser Lys Asn Arg Asn Asp Thr Gln Phe Glu Glu Thr
                260                 265                 270
```

<210> SEQ ID NO 85
<211> LENGTH: 457
<212> TYPE: PRT
<213> ORGANISM: Artificial Sequence
<220> FEATURE:
<223> OTHER INFORMATION: Synthetic

```
<400> SEQUENCE: 85

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Pro Tyr Ile Ile
        355                 360                 365

Pro Pro Tyr Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415
```

```
Leu Tyr Ser Lys Leu Thr Val Gly Ala Asp Arg Trp Leu Glu Gly Asn
                420                 425                 430

Val Phe Ser Cys Ser Val Met His Glu Ala Leu His Asn His Tyr Thr
            435                 440                 445

Gln Lys Ser Leu Ser Leu Ser Pro Gly
    450                 455

<210> SEQ ID NO 86
<211> LENGTH: 214
<212> TYPE: PRT
<213> ORGANISM: Artificial Sequence
<220> FEATURE:
<223> OTHER INFORMATION: Synthetic

<400> SEQUENCE: 86

Asp Ile Gln Met Thr Gln Ser Pro Ser Thr Leu Ser Ala Ser Val Arg
1               5                  10                  15

Asp Arg Val Ile Ile Thr Cys Arg Ala Ser Gln Ser Ile Gly Asn Arg
            20                  25                  30

Leu Ala Trp Tyr Gln His Lys Pro Gly Lys Ala Pro Lys Leu Leu Ile
        35                  40                  45

Tyr Glu Ala Ser Thr Ser Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 87
<211> LENGTH: 457
<212> TYPE: PRT
<213> ORGANISM: Artificial Sequence
<220> FEATURE:
<223> OTHER INFORMATION: Synthetic

<400> SEQUENCE: 87

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
```

```
            35                  40                  45
Gly Trp Ile Ser Ala Tyr Ser Gly Gly Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Leu Phe Pro Thr Ile Phe Gly Val Ser Tyr Tyr Tyr Tyr
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Pro Tyr Ile Ile
                355                 360                 365

Pro Pro Tyr Asn Gln Val Ser Leu Thr Cys Leu Val Lys Gly Phe Tyr
                370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Gly Ala Asp Arg Trp Leu Glu Gly Asn
                420                 425                 430

Val Phe Ser Cys Ser Val Met His Glu Ala Leu His Asn His Tyr Thr
                435                 440                 445

Gln Lys Ser Leu Ser Leu Ser Pro Gly
450                 455
```

<210> SEQ ID NO 88
<211> LENGTH: 214
<212> TYPE: PRT
<213> ORGANISM: Artificial Sequence
<220> FEATURE:
<223> OTHER INFORMATION: Synthetic

<400> SEQUENCE: 88

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 89
<211> LENGTH: 457
<212> TYPE: PRT
<213> ORGANISM: Artificial Sequence
<220> FEATURE:
<223> OTHER INFORMATION: Synthetic

<400> SEQUENCE: 89

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys 85                  90                  95
Ala Arg Asp Leu Phe Pro Thr Ile Phe Gly Val Ser Tyr Tyr Tyr Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Pro Tyr Ile Ile
        355                 360                 365

Pro Pro Tyr Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Gly Ala Asp Arg Trp Leu Glu Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
    450                 455

<210> SEQ ID NO 90
<211> LENGTH: 215
<212> TYPE: PRT
<213> ORGANISM: Artificial Sequence
<220> FEATURE:
<223> OTHER INFORMATION: Synthetic

<400> SEQUENCE: 90

```
Asp Ile Gln Met Thr Gln Ser Pro Ser Thr Leu Ser Ala Ser Val Gly
1               5                   10                  15
Asp Arg Val Thr Ile Thr Cys Arg Ala Ser Gln Ser Ile Ser Gly Arg
            20                  25                  30
Leu Ala Trp Tyr Gln Gln Lys Pro Gly Lys Ala Pro Asn Leu Leu Ile
        35                  40                  45
Tyr Glu Ala Ser Asn Leu Glu Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Arg
                85                  90                  95
Val Thr Phe Gly Gln Gly Thr Lys Val Glu Ile Lys Arg Thr Val Ala
            100                 105                 110
Ala Pro Ser Val Phe Ile Phe Pro Pro Ser Asp Glu Gln Leu Lys Ser
        115                 120                 125
Gly Thr Ala Ser Val Val Cys Leu Leu Asn Asn Phe Tyr Pro Arg Glu
    130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
            180                 185                 190
Tyr Ala Cys Glu Val Thr His Gln Gly Leu Ser Ser Pro Val Thr Lys
        195                 200                 205
Ser Phe Asn Arg Gly Glu Cys
    210                 215
```

<210> SEQ ID NO 91
<211> LENGTH: 457
<212> TYPE: PRT
<213> ORGANISM: Artificial Sequence
<220> FEATURE:
<223> OTHER INFORMATION: Synthetic

<400> SEQUENCE: 91

```
Glu Val Gln Leu Val Gln Ser Gly Ala Glu Val Lys Arg Pro Gly Ala
1               5                   10                  15
Ser Val Lys Val Ser Cys Lys Ala Ser Gly Tyr Thr Phe Thr Ser Tyr
            20                  25                  30
Gly Ile Ser Trp Val Arg Gln Ala Pro Gly Gln Gly Leu Glu Trp Met
        35                  40                  45
Gly Trp Ile Ser Ala Tyr Ser Gly Gly Thr Asn Tyr Ala Gln Lys Leu
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Leu Phe Pro Thr Ile Phe Gly Val Ser Tyr Tyr Tyr Tyr
            100                 105                 110
Trp Gly Gln Gly Thr Leu Val Thr Val Ser Ser Ala Ser Thr Lys Gly
        115                 120                 125
Pro Ser Val Phe Pro Leu Ala Pro Ser Ser Lys Ser Thr Ser Gly Gly
```

```
                130              135              140
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Pro Tyr Ile Ile
            355                 360                 365

Pro Pro Tyr Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Gly Ala Asp Arg Trp Leu Glu Gly Asn
                420                 425                 430

Val Phe Ser Cys Ser Val Met His Glu Ala Leu His Asn His Tyr Thr
            435                 440                 445

Gln Lys Ser Leu Ser Leu Ser Pro Gly
    450                 455
```

<210> SEQ ID NO 92  
<211> LENGTH: 217  
<212> TYPE: PRT  
<213> ORGANISM: Artificial Sequence  
<220> FEATURE:  
<223> OTHER INFORMATION: Synthetic

<400> SEQUENCE: 92

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln Phe Pro Gly Lys Ala Pro Lys Leu
```

```
            35                  40                  45
Met Ile Phe Glu Val Thr Asn Arg Pro Ser Gly Val Ser Asp Arg Phe
 50                  55                  60

Ser Gly Ser Lys Ser Asp Asn Thr Ala Ser Leu Thr Ile Ser Gly Leu
 65                  70                  75                  80

Gln Ala Glu Asp Glu Ala Glu Tyr Tyr Cys Ser Ser Phe Lys Arg Gly
                 85                  90                  95

Ser Thr Leu Val Val Phe Gly Gly Thr Lys Leu Thr Val Leu Gly
            100                 105                 110

Gln Pro Ala Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
            195                 200                 205

Lys Thr Val Ala Pro Thr Glu Cys Ser
210                 215

<210> SEQ ID NO 93
<211> LENGTH: 452
<212> TYPE: PRT
<213> ORGANISM: Artificial Sequence
<220> FEATURE:
<223> OTHER INFORMATION: Synthetic

<400> SEQUENCE: 93

Glu Val Gln Leu Val Gln Ser Gly Ala Glu Val Lys Arg Pro Gly Ala
  1               5                  10                  15

Ser Val Lys Val Ser Cys Lys Ala Ser Gly Tyr Thr Phe Thr Ser Tyr
             20                  25                  30

Gly Ile Ser Trp Val Arg Gln Ala Pro Gly Gln Gly Leu Glu Trp Met
         35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
```

```
                 180                 185                 190
Thr Val Pro Ser Ser Leu Gly Thr Gln Thr Tyr Ile Cys Asn Val
            195                 200                 205
Asn His Lys Pro Ser Asn Thr Lys Val Asp Lys Val Glu Pro Lys
        210                 215                 220
Ser Cys Asp Lys Thr His Thr Cys Pro Pro Cys Pro Ala Pro Glu Ala
225                 230                 235                 240
Ala Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly
    450

<210> SEQ ID NO 94
<211> LENGTH: 8
<212> TYPE: PRT
<213> ORGANISM: Artificial Sequence
<220> FEATURE:
<223> OTHER INFORMATION: Synthetic

<400> SEQUENCE: 94

Gly Tyr Thr Phe Thr Ser Tyr Gly
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic

<400> SEQUENCE: 95

Ile Ser Ala Tyr Asn Gly Asn Thr
1               5
```

```
<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Ser Ser Asp Val Gly Gly Tyr Asn Ser
1               5

<210> SEQ ID NO 97
<211> LENGTH: 452
<212> TYPE: PRT
<213> ORGANISM: Artificial Sequence
<220> FEATURE:
<223> OTHER INFORMATION: Synthetic

<400> SEQUENCE: 97

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Ser Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Leu Phe Pro Thr Ile Phe Gly Val Ser Tyr Tyr Tyr Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
        340                 345                 350

Gln Val Tyr Thr Leu Pro Pro Ser Arg Asp Glu Leu Thr Lys Asn Gln
    355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly
    450

<210> SEQ ID NO 98
<211> LENGTH: 8
<212> TYPE: PRT
<213> ORGANISM: Artificial Sequence
<220> FEATURE:
<223> OTHER INFORMATION: Synthetic G1/887_04_G12 and G1/894_08_A05

<400> SEQUENCE: 98

Ile Ser Ala Tyr Asn Ser Asn Thr
1               5

<210> SEQ ID NO 99
<211> LENGTH: 452
<212> TYPE: PRT
<213> ORGANISM: Artificial Sequence
<220> FEATURE:
<223> OTHER INFORMATION: Synthetic

<400> SEQUENCE: 99

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Ser Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly

```
            130                 135                 140
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 100
<211> LENGTH: 6
<212> TYPE: PRT
<213> ORGANISM: Artificial Sequence
<220> FEATURE:
<223> OTHER INFORMATION: Synthetic

<400> SEQUENCE: 100

Gln Ser Ile Ser Gly Arg
1               5

<210> SEQ ID NO 101
<211> LENGTH: 452
<212> TYPE: PRT
```

<213> ORGANISM: Artificial Sequence
<220> FEATURE:
<223> OTHER INFORMATION: Synthetic

<400> SEQUENCE: 101

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Ser Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
```

```
385                 390                 395                 400
Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
        450

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Gly Tyr Pro Phe Thr Ser Tyr Gly
1               5

<210> SEQ ID NO 103
<211> LENGTH: 6
<212> TYPE: PRT
<213> ORGANISM: Artificial Sequence
<220> FEATURE:
<223> OTHER INFORMATION: Synthetic

<400> SEQUENCE: 103

Gln Ser Ile Gly Asn Arg
1               5

<210> SEQ ID NO 104
<211> LENGTH: 452
<212> TYPE: PRT
<213> ORGANISM: Artificial Sequence
<220> FEATURE:
<223> OTHER INFORMATION: Synthetic

<400> SEQUENCE: 104

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Ser Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160
```

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
    450

<210> SEQ ID NO 105
<211> LENGTH: 452
<212> TYPE: PRT
<213> ORGANISM: Artificial Sequence
<220> FEATURE:
<223> OTHER INFORMATION: Synthetic

<400> SEQUENCE: 105

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Ser Asn Thr Asn Tyr Ala Gln Lys Leu
            50                  55                  60

Gln Gly Arg Val Thr Met Thr Thr Asp Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Asp Leu Phe Pro Thr Ile Phe Gly Val Ser Tyr Tyr Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
            450

<210> SEQ ID NO 106
<211> LENGTH: 4

```
<212> TYPE: PRT
<213> ORGANISM: Artificial Sequence
<220> FEATURE:
<223> OTHER INFORMATION: Synthetic

<400> SEQUENCE: 106

Glu Ala Ser Asn
1

<210> SEQ ID NO 107
<211> LENGTH: 452
<212> TYPE: PRT
<213> ORGANISM: Artificial Sequence
<220> FEATURE:
<223> OTHER INFORMATION: Synthetic

<400> SEQUENCE: 107

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Ser Gly Gly Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320
```

```
Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 108
<211> LENGTH: 1356
<212> TYPE: DNA
<213> ORGANISM: Artificial Sequence
<220> FEATURE:
<223> OTHER INFORMATION: Synthetic

<400> SEQUENCE: 108
gaagtgcagc tggtgcagtc cggagccgaa gtcaagaggc tggagcgtc cgtgaaggtg      60 tcctgcaaag cctcaggata caccttcact tcgtacggga tttcctgggt ccgccaagca    120
ccgggtcaag gcttggagtg gatgggatgg atcagcgcgt attccggggg aaccaactac    180
gctcaaaagc tgcagggtcg cgtgaccatg accaccgata cctccacctc aacgcctac     240 atggaactga gatctctgcg gagcgacgac actgccgtgt actactgtgc ccgggacctg    300
ttccccacta tcttcggagt gtcgtactac tactactggg gccaggggac tctcgtgacc    360
gtgtcgagcg ctagcactaa gggcccgtcg gtgttcccgc tggccccatc gtccaagagc    420
acatcagggg gtaccgccgc cctgggctgc cttgtgaagg attactttcc cgagcccgtc    480
acagtgtcct ggaacagcgg agccctgacc tccggagtgc atactttccc ggctgtgctt    540
cagtcctctg gcctgtactc attgtcctcc gtggtcaccg tcccttcgtc ctccctgggc    600
acccagacct atatctgtaa tgtcaaccat aagccctcga caccaaggt cgacaagaag    660 gtcgagccga gtcgtgcga caagactcac acttgcccgc cttgcccagc cccggaactg    720
ctgggtggtc cttcggtgtt cctcttcccg cccaagccga aggataccct gatgatctca    780 cggaccccg aagtgacctg tgtggtggtg gacgtgtccc acgaggaccc ggaagtgaaa    840
ttcaattggt acgtggatgg agtggaagtg cacaacgcca agaccaagcc acgggaagaa    900
cagtacaact ctacctaccg cgtggtgtcc gtgctcactg tgctgcacca agactggctg    960
aacgggaagg agtacaagtg caaagtgtcc aacaaggcgc tgcctgcccc aattgagaaa   1020
actatctcga aagccaaggg acagcctcga gagcctcaag tgtacaccct gcctccctct   1080
cgggacgagc tgaccaagaa ccaagtctcc ctgacctgtc tggtcaaggg attctaccca   1140
tcggatatcg ccgtggaatg ggaaagcaac ggacagcccg agaacaacta caagacgact   1200
ccgcccgtgc tggattccga cgggagcttc ttcttgtact ccaagctgac cgtcgacaag   1260
```

| | |
|---|---|
| agcagatggc agcagggaaa cgtgttctcc tgctccgtga tgcatgaggc gctgcacaac | 1320 |
| cactacactc agaagagctt gtccctgtcg cccgga | 1356 |

<210> SEQ ID NO 109
<211> LENGTH: 1356
<212> TYPE: DNA
<213> ORGANISM: Artificial Sequence
<220> FEATURE:
<223> OTHER INFORMATION: Synthetic

<400> SEQUENCE: 109

| | |
|---|---|
| gaagtgcagc tggtgcagtc cggagccgaa gtcaagaggc tggagcgtc cgtgaaggtg | 60 |
| tcctgcaaag cctcaggata caccttcact tcgtacggga tttcctgggt ccgccaagca | 120 |
| ccgggtcaag gcttggagtg gatgggatgg atcagcgcgt attccggggg aaccaactac | 180 |
| gctcaaaagc tgcagggtcg cgtgaccatg accaccgata cctccacctc aacggcctac | 240 |
| atggaactga gatctctgcg gagcgacgac actgccgtgt actactgtgc ccgggacctg | 300 |
| ttccccacta tcttcggagt gtcgtactac tactactggg gccaggggac tctcgtgacc | 360 |
| gtgtcgagcg ctagcactaa gggcccgtcg gtgttcccgc tggccccatc gtccaagagc | 420 |
| acatcagggg gtaccgccgc cctgggctgc cttgtgaagg attactttcc cgagcccgtc | 480 |
| acagtgtcct ggaacagcgg agccctgacc tccggagtgc atactttccc ggctgtgctt | 540 |
| cagtcctctg gcctgtactc attgtcctcc gtggtcaccg tcccttcgtc ctccctgggc | 600 |
| acccagacct atatctgtaa tgtcaaccat aagccctcga acaccaaggt cgacaagaag | 660 |
| gtcgagccga agtcgtgcga caagactcac acttgcccgc cttgcccagc cccggaagct | 720 |
| gccggtggtc cttcggtgtt cctcttcccg cccaagccga aggatacccct gatgatctca | 780 |
| cggacccccg aagtgacctg tgtggtggtg gacgtgtccc acgaggaccc ggaagtgaaa | 840 |
| ttcaattggt acgtggatgg agtggaagtg cacaacgcca agaccaagcc acgggaagaa | 900 |
| cagtacaact ctacctaccg cgtggtgtcc gtgctcactg tgctgcacca agactggctg | 960 |
| aacgggaagg agtacaagtg caaagtgtcc aacaaggcgc tgcctgcccc aattgagaaa | 1020 |
| actatctcga aagccaaggg acagcctcga gagcctcaag tgtacaccct gcctccctct | 1080 |
| cgggacgagc tgaccaagaa ccaagtctcc ctgacctgtc tggtcaaggg attctaccca | 1140 |
| tcggatatcg ccgtggaatg ggaaagcaac ggacagcccg agaacaacta caagacgact | 1200 |
| ccgcccgtgc tggattccga cgggagcttc ttcttgtact ccaagctgac cgtcgacaag | 1260 |
| agcagatggc agcagggaaa cgtgttctcc tgctccgtga tgcatgaggc gctgcacaac | 1320 |
| cactacactc agaagagctt gtccctgtcg cccgga | 1356 |

<210> SEQ ID NO 110
<211> LENGTH: 369
<212> TYPE: DNA
<213> ORGANISM: Artificial Sequence
<220> FEATURE:
<223> OTHER INFORMATION: Synthetic

<400> SEQUENCE: 110

| | |
|---|---|
| gaagtgcagc tggtgcagtc cggagccgaa gtcaagaggc tggagcgtc cgtgaaggtg | 60 |
| tcctgcaaag cctcaggata caccttcact tcgtacggga tttcctgggt ccgccaagca | 120 |
| ccgggtcaag gcttggagtg gatgggatgg atcagcgcgt attccggggg aaccaactac | 180 |
| gctcaaaagc tgcagggtcg cgtgaccatg accaccgata cctccacctc aacggcctac | 240 |

```
atggaactga gatctctgcg gagcgacgac actgccgtgt actactgtgc ccgggacctg      300
ttccccacta tcttcggagt gtcgtactac tactactggg gccaggggac tctcgtgacc      360
gtgtcgagc                                                              369
```

<210> SEQ ID NO 111
<211> LENGTH: 8
<212> TYPE: PRT
<213> ORGANISM: Artificial Sequence
<220> FEATURE:
<223> OTHER INFORMATION: Synthetic

<400> SEQUENCE: 111

Ile Ser Ala Tyr Ser Gly Gly Thr
1               5

<210> SEQ ID NO 112
<211> LENGTH: 645
<212> TYPE: DNA
<213> ORGANISM: Artificial Sequence
<220> FEATURE:
<223> OTHER INFORMATION: Synthetic

<400> SEQUENCE: 112

```
gacattcaga tgacccaatc cccgtccacg ctgagcgcct ccgtcggtga tcgcgtgaca      60
atcacttgtc gggcgtcgca gtccatctct ggaaggctcg cctggtacca gcagaagcct     120
ggaaaggctc ccaacctcct tatctacgaa gccagcaacc tggagtccgg agtgcctagc     180
cggttcagcg gatcagggtc cggtaccgag ttcaccctga ccatttcctc gctccaacct     240
gaggacttcg ccacctacta ctgccaacag tcctattcaa ctccgcgcgt gaccttcggc     300
cagggcacta aggtcgaaat caaaagaacc gtggcagccc catcggtgtt tatcttcccg     360
ccctcggacg aacagctgaa gtcaggcact gctagcgtgg tctgtctcct gaacaatttc     420
tacccgcgcg aagctaaggt ccagtggaag gtcgacaacg cgctgcagtc cggaaacagc     480
caggagtcag tgaccgagca ggactccaag gattccactt attccctgtc ctccaccctg     540
actttgagca aggccgacta cgagaagcac aaagtgtacg cctgcgaagt gacccatcaa     600
gggctttcgt cgcccgtgac caagagcttc aaccggggcg aatgc                    645
```

<210> SEQ ID NO 113
<211> LENGTH: 324
<212> TYPE: DNA
<213> ORGANISM: Artificial Sequence
<220> FEATURE:
<223> OTHER INFORMATION: Synthetic

<400> SEQUENCE: 113

```
gacattcaga tgacccaatc cccgtccacg ctgagcgcct ccgtcggtga tcgcgtgaca      60
atcacttgtc gggcgtcgca gtccatctct ggaaggctcg cctggtacca gcagaagcct     120
ggaaaggctc ccaacctcct tatctacgaa gccagcaacc tggagtccgg agtgcctagc     180
cggttcagcg gatcagggtc cggtaccgag ttcaccctga ccatttcctc gctccaacct     240
gaggacttcg ccacctacta ctgccaacag tcctattcaa ctccgcgcgt gaccttcggc     300
cagggcacta aggtcgaaat caaa                                            324
```

<210> SEQ ID NO 114
<211> LENGTH: 452
<212> TYPE: PRT
<213> ORGANISM: Artificial Sequence
<220> FEATURE:

<223> OTHER INFORMATION: Synthetic

<400> SEQUENCE: 114

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Ser Gly Gly Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
        420                 425                 430

Val Met His Glu Ala Leu His Asn His Tyr Thr Gln Lys Ser Leu Ser
    435                 440                 445

Leu Ser Pro Gly
    450

<210> SEQ ID NO 115
<211> LENGTH: 1356
<212> TYPE: DNA
<213> ORGANISM: Artificial Sequence
<220> FEATURE:
<223> OTHER INFORMATION: Synthetic

<400> SEQUENCE: 115
gaagtgcagc tggtgcagtc cggagccgaa gtcaagaggc ctggagcgtc cgtgaaggtg      60
tcctgcaaag cctcaggata ccccttcact tcgtacggga tttcctgggt ccgccaagca     120
ccgggtcaag gcttggagtg gatgggatgg atcagcgcgt attccggggg aaccaactac     180
gctcaaaagc tgcagggtcg cgtgaccatg accaccgata cctccacctc aacggcctac     240
atggaactga gatctctgcg gagcgacgac actgccgtgt actactgtgc ccggacctg      300 ttccccacta tcttcggagt gtcgtactac tactactggg gccaggggac tctcgtgacc     360
gtgtcgagcg ctagcactaa gggcccgtcg gtgttcccgc tggccccatc gtccaagagc     420
acatcagggg gtaccgccgc cctgggctgc cttgtgaagg attactttcc cgagcccgtc     480
acagtgtcct ggaacagcgg agccctgacc tccggagtgc atactttccc ggctgtgctt     540
cagtcctctg gcctgtactc attgtcctcc gtggtcaccg tcccttcgtc ctccctgggc     600
acccagacct atatctgtaa tgtcaaccat aagccctcga acaccaaggt cgacaagaag     660
gtcgagccga gtcgtgcga caagactcac acttgcccgc cttgcccagc cccggaactg     720
ctgggtggtc cttcggtgtt cctcttcccg cccaagccga aggatacct gatgatctca      780 cggaccccg aagtgacctg tgtggtggtg gacgtgtccc acgaggaccc ggaagtgaaa      840
ttcaattggt acgtggatgg agtggaagtg cacaacgcca agaccaagcc acgggaagaa     900
cagtacaact ctacctaccg cgtggtgtcc gtgctcactg tgctgcacca agactggctg     960
aacgggaagg agtacaagtg caaagtgtcc aacaaggcgc tgcctgcccc aattgagaaa    1020
actatctcga aagccaaggg acagcctcga gagcctcaag tgtacaccct gcctcctct     1080 cgggacgagc tgaccaagaa ccaagtctcc ctgacctgtc tggtcaaggg attctaccca    1140
tcggatatcg ccgtggaatg ggaaagcaac ggacagcccg agaacaacta caagacgact    1200
ccgcccgtgc tggattccga cgggagcttc ttcttgtact ccaagctgac cgtcgacaag    1260
agcagatggc agcagggaaa cgtgttctcc tgctccgtga tgcatgaggc gctgcacaac    1320
cactacactc agaagagctt gtccctgtcg cccgga                              1356

<210> SEQ ID NO 116
<211> LENGTH: 1356
<212> TYPE: DNA
<213> ORGANISM: Artificial Sequence
<220> FEATURE:
<223> OTHER INFORMATION: Synthetic

<400> SEQUENCE: 116
gaagtgcagc tggtgcagtc cggagccgaa gtcaagaggc ctggagcgtc cgtgaaggtg      60

```
tcctgcaaag cctcaggata ccccttcact tcgtacggga tttcctgggt ccgccaagca    120
ccgggtcaag gcttggagtg gatgggatgg atcagcgcgt attccggggg aaccaactac    180
gctcaaaagc tgcagggtcg cgtgaccatg accaccgata cctccacctc aacggcctac    240
atggaactga gatctctgcg gagcgacgac actgccgtgt actactgtgc ccgggacctg    300
ttccccacta tcttcggagt gtcgtactac tactactggg gccaggggac tctcgtgacc    360
gtgtcgagcg ctagcactaa gggcccgtcg gtgttcccgc tggccccatc gtccaagagc    420
acatcagggg gtaccgccgc cctgggctgc cttgtgaagg attactttcc cgagcccgtc    480
acagtgtcct ggaacagcgg agccctgacc tccggagtgc atactttccc ggctgtgctt    540
cagtcctctg gcctgtactc attgtcctcc gtggtcaccg tcccttcgtc ctccctgggc    600
acccagacct atatctgtaa tgtcaaccat aagccctcga acaccaaggt cgacaagaag    660
gtcgagccga gtcgtgcga caagactcac acttgcccgc cttgcccagc ccggaagct    720 gccggtggtc cttcggtgtt cctcttcccg cccaagccga aggatacct gatgatctca    780 cggacccccg aagtgacctg tgtggtggtg gacgtgtccc acgaggaccc ggaagtgaaa    840
ttcaattggt acgtggatgg agtggaagtg cacaacgcca agaccaagcc acgggaagaa    900
cagtacaact ctacctaccg cgtggtgtcc gtgctcactg tgctgcacca agactggctg    960
aacgggaagg agtacaagtg caaagtgtcc aacaaggcgc tgcctgcccc aattgagaaa   1020
actatctcga aagccaaggg acagcctcga gagcctcaag tgtacaccct gcctccctct   1080
cgggacgagc tgaccaagaa ccaagtctcc ctgacctgtc tggtcaaggg attctaccca   1140
tcggatatcg ccgtggaatg ggaaagcaac ggacagcccg agaacaacta caagacgact   1200
ccgcccgtgc tggattccga cgggagcttc ttcttgtact ccaagctgac cgtcgacaag   1260
agcagatggc agcaggaaaa cgtgttctcc tgctccgtga tgcatgaggc gctgcacaac   1320
cactacactc agaagagctt gtccctgtcg cccgga                             1356
```

<210> SEQ ID NO 117
<211> LENGTH: 369
<212> TYPE: DNA
<213> ORGANISM: Artificial Sequence
<220> FEATURE:
<223> OTHER INFORMATION: Synthetic

<400> SEQUENCE: 117

```
gaagtgcagc tggtgcagtc cggagccgaa gtcaagaggc ctggagcgtc cgtgaaggtg     60
tcctgcaaag cctcaggata ccccttcact tcgtacggga tttcctgggt ccgccaagca    120
ccgggtcaag gcttggagtg gatgggatgg atcagcgcgt attccggggg aaccaactac    180
gctcaaaagc tgcagggtcg cgtgaccatg accaccgata cctccacctc aacggcctac    240
atggaactga gatctctgcg gagcgacgac actgccgtgt actactgtgc ccgggacctg    300
ttccccacta tcttcggagt gtcgtactac tactactggg gccaggggac tctcgtgacc    360
gtgtcgagc                                                            369
```

<210> SEQ ID NO 118
<211> LENGTH: 642
<212> TYPE: DNA
<213> ORGANISM: Artificial Sequence
<220> FEATURE:
<223> OTHER INFORMATION: Synthetic

<400> SEQUENCE: 118

```
gacatccaga tgacgcagag cccgtctacc ctgtccgcct ccgtgagaga tcgcgtgatc    60
atcacctgtc gggccagcca gtccatcgga aaccgcttgg cgtggtacca gcacaagcct   120
gggaaggctc cgaagctgct catctacgaa gcctcgactt cggagactgg tgtccctagc   180
cggttcagcg gatcgggatc agggaccgat ttcactctga ccatttcctc cctgcaaccc   240
gaggacttcg ccacctacta ctgccaacag tcatattcca ccccgtacac cttcggacaa   300
ggcaccaagc tcgaaatcaa gcggactgtc gccgcacctt ccgtgttcat tttcccaccc   360
tccgacgaac agctgaaatc gggtacagct agcgtggtct gtctcctgaa caatttctac   420
ccgcgcgaag ctaaggtcca gtggaaggtc gacaacgcgc tgcagtccgg aaacagccag   480
gagtcagtga ccgagcagga ctccaaggat tccacttatt ccctgtcctc caccctgact   540
ttgagcaagg ccgactacga aagcacaaa gtgtacgcct gcgaagtgac ccatcaaggg   600
ctttcgtcgc ccgtgaccaa gagcttcaac cggggcgaat gc                      642
```

<210> SEQ ID NO 119
<211> LENGTH: 321
<212> TYPE: DNA
<213> ORGANISM: Artificial Sequence
<220> FEATURE:
<223> OTHER INFORMATION: Synthetic

<400> SEQUENCE: 119

```
gacatccaga tgacgcagag cccgtctacc ctgtccgcct ccgtgagaga tcgcgtgatc    60
atcacctgtc gggccagcca gtccatcgga aaccgcttgg cgtggtacca gcacaagcct   120
gggaaggctc cgaagctgct catctacgaa gcctcgactt cggagactgg tgtccctagc   180
cggttcagcg gatcgggatc agggaccgat ttcactctga ccatttcctc cctgcaaccc   240
gaggacttcg ccacctacta ctgccaacag tcatattcca ccccgtacac cttcggacaa   300
ggcaccaagc tcgaaatcaa g                                              321
```

<210> SEQ ID NO 120
<211> LENGTH: 452
<212> TYPE: PRT
<213> ORGANISM: Artificial Sequence
<220> FEATURE:
<223> OTHER INFORMATION: Synthetic

<400> SEQUENCE: 120

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
```

```
          130                 135                 140
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 121
<211> LENGTH: 1356
<212> TYPE: DNA
<213> ORGANISM: Artificial Sequence
<220> FEATURE:
<223> OTHER INFORMATION: Synthetic

<400> SEQUENCE: 121
gaagtgcagc tggtgcagtc cggagccgaa gtcaagaggc tggagcgtc cgtgaaggtg      60 tcctgcaaag cctcaggata caccttcact tcgtacggga tttcctgggt ccgccaagca    120
ccgggtcaag gcttggagtg gatgggatgg atcagcgcgt attccggggg aaccaactac    180
gctcaaaagc tgcagggtcg cgtgaccatg accaccgata cctccacctc aacggcctac    240
```

```
atggaactga gatctctgcg gagcgacgac actgccgtgt actactgtgc cgggacctg    300
ttccccacta tcttcggagt gtcgtactac tactactggg gccaggggac tctcgtgacc    360
gtgtcgagcg ctagcactaa gggcccgtcg gtgttcccgc tggccccatc gtccaagagc    420
acatcagggg gtaccgccgc cctgggctgc cttgtgaagg attactttcc cgagcccgtc    480
acagtgtcct ggaacagcgg agccctgacc tccggagtgc atactttccc ggctgtgctt    540
cagtcctctg gcctgtactc attgtcctcc gtggtcaccg tcccttcgtc ctccctgggc    600
acccagacct atatctgtaa tgtcaaccat aagccctcga acaccaaggt cgacaagaag    660
gtcgagccga agtcgtgcga caagactcac acttgcccgc cttgcccagc cccggaactg    720
ctgggtggtc cttcggtgtt cctcttcccg cccaagccga aggatacccct gatgatctca    780
cggaccccccg aagtgacctg tgtggtggtg gacgtgtccc acgaggaccc ggaagtgaaa    840
ttcaattggt acgtggatgg agtggaagtg cacaacgcca agaccaagcc acgggaagaa    900
cagtacaact ctacctaccg cgtggtgtcc gtgctcactg tgctgcacca agactggctg    960
aacgggaagg agtacaagtg caaagtgtcc aacaaggcgc tgcctgcccc aattgagaaa    1020
actatctcga aagccaaggg acagcctcga gagcctcaag tgtacaccct gcctcccctct    1080
cgggacgagc tgaccaagaa ccaagtctcc ctgacctgtc tggtcaaggg attctaccca    1140
tcggatatcg ccgtggaatg ggaaagcaac ggacagcccg agaacaacta caagacgact    1200
ccgcccgtgc tggattccga cgggagcttc ttcttgtact ccaagctgac cgtcgacaag    1260
agcagatggc agcagggaaa cgtgttctcc tgctccgtga tgcatgaggc gctgcacaac    1320
cactacactc agaagagctt gtccctgtcg cccgga                              1356
```

<210> SEQ ID NO 122
<211> LENGTH: 1356
<212> TYPE: DNA
<213> ORGANISM: Artificial Sequence
<220> FEATURE:
<223> OTHER INFORMATION: Synthetic

<400> SEQUENCE: 122

```
gaagtgcagc tggtgcagtc cggagccgaa gtcaagaggc ctggagcgtc cgtgaaggtg    60
tcctgcaaag cctcaggata caccttcact tcgtacggga tttcctgggt ccgccaagca    120
ccgggtcaag gcttggagtg gatgggatgg atcagcgcgt attccggggg aaccaactac    180
gctcaaaagc tgcagggtcg cgtgaccatg accaccgata cctccacctc aacggcctac    240
atggaactga gatctctgcg gagcgacgac actgccgtgt actactgtgc cgggacctg    300
ttccccacta tcttcggagt gtcgtactac tactactggg gccaggggac tctcgtgacc    360
gtgtcgagcg ctagcactaa gggcccgtcg gtgttcccgc tggccccatc gtccaagagc    420
acatcagggg gtaccgccgc cctgggctgc cttgtgaagg attactttcc cgagcccgtc    480
acagtgtcct ggaacagcgg agccctgacc tccggagtgc atactttccc ggctgtgctt    540
cagtcctctg gcctgtactc attgtcctcc gtggtcaccg tcccttcgtc ctccctgggc    600
acccagacct atatctgtaa tgtcaaccat aagccctcga acaccaaggt cgacaagaag    660
gtcgagccga agtcgtgcga caagactcac acttgcccgc cttgcccagc cccggaagct    720
gccggtggtc cttcggtgtt cctcttcccg cccaagccga aggatacccct gatgatctca    780
cggaccccccg aagtgacctg tgtggtggtg gacgtgtccc acgaggaccc ggaagtgaaa    840
ttcaattggt acgtggatgg agtggaagtg cacaacgcca agaccaagcc acgggaagaa    900
```

| | |
|---|---|
| cagtacaact ctacctaccg cgtggtgtcc gtgctcactg tgctgcacca agactggctg | 960 |
| aacgggaagg agtacaagtg caaagtgtcc aacaaggcgc tgcctgcccc aattgagaaa | 1020 |
| actatctcga aagccaaggg acagcctcga gagcctcaag tgtacaccct gcctccctct | 1080 |
| cgggacgagc tgaccaagaa ccaagtctcc ctgacctgtc tggtcaaggg attctaccca | 1140 |
| tcggatatcg ccgtggaatg ggaaagcaac ggacagcccg agaacaacta caagacgact | 1200 |
| ccgcccgtgc tggattccga cgggagcttc ttcttgtact ccaagctgac cgtcgacaag | 1260 |
| agcagatggc agcagggaaa cgtgttctcc tgctccgtga tgcatgaggc gctgcacaac | 1320 |
| cactacactc agaagagctt gtccctgtcg cccgga | 1356 |

<210> SEQ ID NO 123
<211> LENGTH: 369
<212> TYPE: DNA
<213> ORGANISM: Artificial Sequence
<220> FEATURE:
<223> OTHER INFORMATION: Synthetic

<400> SEQUENCE: 123

| | |
|---|---|
| gaagtgcagc tggtgcagtc cggagccgaa gtcaagaggc ctggagcgtc cgtgaaggtg | 60 |
| tcctgcaaag cctcaggata caccttcact tcgtacggga tttcctgggt ccgccaagca | 120 |
| ccgggtcaag gcttggagtg gatgggatgg atcagcgcgt attccggggg aaccaactac | 180 |
| gctcaaaagc tgcagggtcg cgtgaccatg accaccgata cctccacctc aacggcctac | 240 |
| atggaactga gatctctgcg gagcgacgac actgccgtgt actactgtgc ccgggacctg | 300 |
| ttccccacta tcttcggagt gtcgtactac tactactggg gccaggggac tctcgtgacc | 360 |
| gtgtcgagc | 369 |

<210> SEQ ID NO 124
<211> LENGTH: 642
<212> TYPE: DNA
<213> ORGANISM: Artificial Sequence
<220> FEATURE:
<223> OTHER INFORMATION: Synthetic

<400> SEQUENCE: 124

| | |
|---|---|
| gacattcaga tgacccagtc cccgagcacg ctgtccgcaa gcgtggggga cagagtgacc | 60 |
| atcacttgcc gcgcctcaca atccatcagc ggacgcttgg cctggtacca gcagaagccc | 120 |
| ggaaaggccc caaaccttct gatctacgaa gcctcgaacc tggagtcagg cgtcccttcg | 180 |
| cggttctctg gctccggttc cggaactgag ttcaccctca ccatctcgtc cctgcaaccg | 240 |
| gaagatttcg ccacctacta ctgccaacag tcgtactcct ggccccggac attcggacag | 300 |
| ggaaccaaag tcgagattaa gcggactgtg gcggctccta gcgtgttcat ctttccccg | 360 |
| tccgacgaac agctgaagtc cggtaccgct agcgtggtct gtctcctgaa caatttctac | 420 |
| ccgcgcgaag ctaaggtcca gtggaaggtc gacaacgcgc tgcagtccgg aaacagccag | 480 |
| gagtcagtga ccgagcagga ctccaaggat tccacttatt ccctgtcctc cacccctgact | 540 |
| ttgagcaagg ccgactacga gaagcacaaa gtgtacgcct gcgaagtgac ccatcaaggg | 600 |
| ctttcgtcgc ccgtgaccaa gagcttcaac cggggcgaat gc | 642 |

<210> SEQ ID NO 125
<211> LENGTH: 321
<212> TYPE: DNA
<213> ORGANISM: Artificial Sequence
<220> FEATURE:
<223> OTHER INFORMATION: Synthetic

<400> SEQUENCE: 125

```
gacattcaga tgacccagtc cccgagcacg ctgtccgcaa gcgtggggga cagagtgacc    60
atcacttgcc gcgcctcaca atccatcagc ggacgcttgg cctggtacca gcagaagccc   120
ggaaaggccc caaaccttct gatctacgaa gcctcgaacc tggagtcagg cgtcccttcg   180
cggttctctg gctccggttc cggaactgag ttcaccctca ccatctcgtc cctgcaaccg   240
gaagatttcg ccacctacta ctgccaacag tcgtactcct ggccccggac attcggacag   300
ggaaccaaag tcgagattaa g                                             321
```

<210> SEQ ID NO 126
<211> LENGTH: 452
<212> TYPE: PRT
<213> ORGANISM: Artificial Sequence
<220> FEATURE:
<223> OTHER INFORMATION: Synthetic

<400> SEQUENCE: 126

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Ser Gly Gly Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285
```

```
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly
    450

<210> SEQ ID NO 127
<211> LENGTH: 1356
<212> TYPE: DNA
<213> ORGANISM: Artificial Sequence
<220> FEATURE:
<223> OTHER INFORMATION: Synthetic

<400> SEQUENCE: 127
gaagtgcagc tggtgcagtc cggagccgaa gtcaagaggc ctggagcgtc cgtgaaggtg      60
tcctgcaaag cctcaggata caccttcact tcgtacggga tttcctgggt ccgccaagca     120
ccgggtcaag gcttggagtg gatgggatgg atcagcgcgt attccggggg aaccaactac     180
gctcaaaagc tgcagggtcg cgtgaccatg accaccgata cctccacctc aacggcctac     240
atggaactga gatctctgcg gagcgacgac actgccgtgt actactgtgc ccggacctg      300
ttccccacta tcttcggagt gtcgtactac tactactggg gccaggggac tctcgtgacc     360
gtgtcgagcg ctagcactaa gggcccgtcg gtgttcccgc tggccccatc gtccaagagc     420
acatcagggg gtaccgccgc cctgggctgc cttgtgaagg attactttcc cgagcccgtc     480
acagtgtcct ggaacagcgg agccctgacc tccggagtgc atacttttcc ggctgtgctt     540
cagtcctctg gcctgtactc attgtcctcc gtggtcaccg tcccttcgtc ctccctgggc     600
acccagacct atatctgtaa tgtcaaccat aagccctcga caccaaggt cgacaagaag     660
gtcgagccga gtcgtgcga caagactcac acttgcccgc cttgcccagc cccggaactg     720
ctgggtggtc cttcggtgtt cctcttcccg cccaagccga aggatacct gatgatctca     780
cggaccccg aagtgacctg tgtggtggtg gacgtgtccc acgaggaccc ggaagtgaaa     840
ttcaattggt acgtggatgg agtggaagtg cacaacgcca agaccaagcc acgggaagaa     900
cagtacaact ctacctaccg cgtggtgtcc gtgctcactg tgctgcacca agactggctg     960
aacgggaagg agtacaagtg caaagtgtcc aacaaggcgc tgcctgcccc aattgagaaa    1020
actatctcga aagccaaggg acagcctcga gagcctcaag tgtacaccct gcctcccctct   1080
```

| | |
|---|---|
| cgggacgagc tgaccaagaa ccaagtctcc ctgacctgtc tggtcaaggg attctaccca | 1140 |
| tcggatatcg ccgtggaatg ggaaagcaac ggacagcccg agaacaacta caagacgact | 1200 |
| ccgcccgtgc tggattccga cgggagcttc ttcttgtact ccaagctgac cgtcgacaag | 1260 |
| agcagatggc agcagggaaa cgtgttctcc tgctccgtga tgcatgaggc gctgcacaac | 1320 |
| cactacactc agaagagctt gtccctgtcg cccgga | 1356 |

<210> SEQ ID NO 128
<211> LENGTH: 1356
<212> TYPE: DNA
<213> ORGANISM: Artificial Sequence
<220> FEATURE:
<223> OTHER INFORMATION: Synthetic

<400> SEQUENCE: 128

| | |
|---|---|
| gaagtgcagc tggtgcagtc cggagccgaa gtcaagaggc tggagcgtc cgtgaaggtg | 60 |
| tcctgcaaag cctcaggata caccttcact tcgtacggga tttcctgggt ccgccaagca | 120 |
| ccgggtcaag gcttggagtg gatgggatgg atcagcgcgt attccggggg aaccaactac | 180 |
| gctcaaaagc tgcagggtcg cgtgaccatg accaccgata cctccacctc aacggcctac | 240 |
| atggaactga gatctctgcg gagcgacgac actgccgtgt actactgtgc ccgggacctg | 300 |
| ttccccacta tcttcggagt gtcgtactac tactactggg gccaggggac tctcgtgacc | 360 |
| gtgtcgagcg ctagcactaa gggcccgtcg gtgttcccgc tggccccatc gtccaagagc | 420 |
| acatcagggg gtaccgccgc cctgggctgc cttgtgaagg attactttcc cgagcccgtc | 480 |
| acagtgtcct ggaacagcgg agccctgacc tccggagtgc atactttccc ggctgtgctt | 540 |
| cagtcctctg gcctgtactc attgtcctcc gtggtcaccg tcccttcgtc ctccctgggc | 600 |
| acccagacct atatctgtaa tgtcaaccat aagccctcga acaccaaggt cgacaagaag | 660 |
| gtcgagccga gtcgtgcga caagactcac acttgcccgc cttgcccagc cccggaagct | 720 |
| gccggtggtc cttcggtgtt cctcttcccg cccaagccga aggatacccct gatgatctca | 780 |
| cggacccccg aagtgacctg tgtggtggtg gacgtgtccc acgaggaccc ggaagtgaaa | 840 |
| ttcaattggt acgtggatgg agtggaagtg cacaacgcca agaccaagcc acgggaagaa | 900 |
| cagtacaact ctacctaccg cgtggtgtcc gtgctcactg tgctgcacca agactggctg | 960 |
| aacgggaagg agtacaagtg caaagtgtcc aacaaggcgc tgcctgcccc aattgagaaa | 1020 |
| actatctcga aagccaaggg acagcctcga gagcctcaag tgtacaccct gcctccctct | 1080 |
| cgggacgagc tgaccaagaa ccaagtctcc ctgacctgtc tggtcaaggg attctaccca | 1140 |
| tcggatatcg ccgtggaatg ggaaagcaac ggacagcccg agaacaacta caagacgact | 1200 |
| ccgcccgtgc tggattccga cgggagcttc ttcttgtact ccaagctgac cgtcgacaag | 1260 |
| agcagatggc agcagggaaa cgtgttctcc tgctccgtga tgcatgaggc gctgcacaac | 1320 |
| cactacactc agaagagctt gtccctgtcg cccgga | 1356 |

<210> SEQ ID NO 129
<211> LENGTH: 369
<212> TYPE: DNA
<213> ORGANISM: Artificial Sequence
<220> FEATURE:
<223> OTHER INFORMATION: Synthetic

<400> SEQUENCE: 129

| | |
|---|---|
| gaagtgcagc tggtgcagtc cggagccgaa gtcaagaggc tggagcgtc cgtgaaggtg | 60 |
| tcctgcaaag cctcaggata caccttcact tcgtacggga tttcctgggt ccgccaagca | 120 |

```
ccgggtcaag gcttggagtg gatgggatgg atcagcgcgt attccggggg aaccaactac    180
gctcaaaagc tgcagggtcg cgtgaccatg accaccgata cctccacctc aacggcctac    240
atggaactga gatctctgcg gagcgacgac actgccgtgt actactgtgc ccgggacctg    300
ttccccacta tcttcggagt gtcgtactac tactactggg gccaggggac tctcgtgacc    360
gtgtcgagc                                                             369
```

<210> SEQ ID NO 130
<211> LENGTH: 651
<212> TYPE: DNA
<213> ORGANISM: Artificial Sequence
<220> FEATURE:
<223> OTHER INFORMATION: Synthetic

<400> SEQUENCE: 130

```
cagtcggccc ttactcaacc cgcgtcagtc tccggtagcc ccggacagtc catcacgatt     60
tcgtgcaccg gaaccagcag cgatgtcggg ggatacaact acgtgtcctg gtaccagcag    120
ttcccgggaa aggcccctaa gctgatgatc ttcgaagtca ctaacagacc ttccggagtg    180
tcggaccggt tctccggctc caagtccgac aacactgcga gcctgaccat ctcgggcctg    240
caagccgagg acgaagccga gtactactgt agctcattca gcgcggttc cacccctgtg    300 gtgttcggcg gtggcactaa gctcaccgtg ctggacagc cagccgcagc tcctagcgtg    360
accttgttcc cccgtcgag cgaagaactg caggccaaca aggccaccct cgtctgcctg    420
atctccgact ctaccctgg ggccgtgact gtggcttgga aggccgattc aagcccagtg    480
aaagccggag tggaaaccac cactccgtcc aagcagtcga caataagta tgccgcgtcc    540 tcctacctgt cgctgacccc ggagcagtgg aagtcccatc ggtcctactc ctgccaagtc    600
acccacgaag ggtccactgt ggagaaaaca gtggctccca ccgagtgctc t             651
```

<210> SEQ ID NO 131
<211> LENGTH: 336
<212> TYPE: DNA
<213> ORGANISM: Artificial Sequence
<220> FEATURE:
<223> OTHER INFORMATION: Synthetic

<400> SEQUENCE: 131

```
cagtcggccc ttactcaacc cgcgtcagtc tccggtagcc ccggacagtc catcacgatt     60
tcgtgcaccg gaaccagcag cgatgtcggg ggatacaact acgtgtcctg gtaccagcag    120
ttcccgggaa aggcccctaa gctgatgatc ttcgaagtca ctaacagacc ttccggagtg    180
tcggaccggt tctccggctc caagtccgac aacactgcga gcctgaccat ctcgggcctg    240
caagccgagg acgaagccga gtactactgt agctcattca gcgcggttc cacccctgtg    300 gtgttcggcg gtggcactaa gctcaccgtg ctggga                               336
```

<210> SEQ ID NO 132
<211> LENGTH: 9
<212> TYPE: PRT
<213> ORGANISM: Artificial Sequence
<220> FEATURE:
<223> OTHER INFORMATION: Synthetic

<400> SEQUENCE: 132

```
Ser Ser Asp Val Gly Gly Tyr Asn Tyr
1               5
```

```
<210> SEQ ID NO 133
<211> LENGTH: 452
<212> TYPE: PRT
<213> ORGANISM: Artificial Sequence
<220> FEATURE:
<223> OTHER INFORMATION: Synthetic

<400> SEQUENCE: 133
```

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Val | Lys | Arg | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Tyr |
| | | | 20 | | | | | 25 | | | | | 30 | | |
| Gly | Ile | Ser | Trp | Val | Arg | Gln | Ala | Pro | Gly | Gln | Gly | Leu | Glu | Trp | Met |
| | | 35 | | | | | 40 | | | | | 45 | | | |
| Gly | Trp | Ile | Ser | Ala | Tyr | Gly | Gly | Ser | Thr | Asn | Tyr | Ala | Gln | Lys | Leu |
| | 50 | | | | | 55 | | | | | 60 | | | | |
| Gln | Gly | Arg | Val | Thr | Met | Thr | Thr | Asp | Thr | Ser | Thr | Ser | Thr | Ala | Tyr |
| 65 | | | | | 70 | | | | | 75 | | | | | 80 |
| Met | Glu | Leu | Arg | Ser | Leu | Arg | Ser | Asp | Asp | Thr | Ala | Val | Tyr | Tyr | Cys |
| | | | | 85 | | | | | 90 | | | | | 95 | |
| Ala | Arg | Asp | Leu | Phe | Pro | Thr | Ile | Phe | Gly | Val | Ser | Tyr | Tyr | Tyr | Tyr |
| | | | 100 | | | | | 105 | | | | | 110 | | |
| Trp | Gly | Gln | Gly | Thr | Leu | Val | Thr | Val | Ser | Ser | Ala | Ser | Thr | Lys | Gly |
| | | 115 | | | | | 120 | | | | | 125 | | | |
| Pro | Ser | Val | Phe | Pro | Leu | Ala | Pro | Ser | Ser | Lys | Ser | Thr | Ser | Gly | Gly |
| | 130 | | | | | 135 | | | | | 140 | | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Gln | Thr | Tyr | Ile | Cys | Asn | Val |
| | | 195 | | | | | 200 | | | | | 205 | | | |
| Asn | His | Lys | Pro | Ser | Asn | Thr | Lys | Val | Asp | Lys | Lys | Val | Glu | Pro | Lys |
| | 210 | | | | | 215 | | | | | 220 | | | | |
| Ser | Cys | Asp | Lys | Thr | His | Thr | Cys | Pro | Pro | Cys | Pro | Ala | Pro | Glu | Leu |
| 225 | | | | | 230 | | | | | 235 | | | | | 240 |
| Leu | Gly | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ile | Ser | Arg | Thr | Pro | Glu | Val | Thr | Cys | Val | Val | Val | Asp | Val |
| | | | 260 | | | | | 265 | | | | | 270 | | |
| Ser | His | Glu | Asp | Pro | Glu | Val | Lys | Phe | Asn | Trp | Tyr | Val | Asp | Gly | Val |
| | | 275 | | | | | 280 | | | | | 285 | | | |
| Glu | Val | His | Asn | Ala | Lys | Thr | Lys | Pro | Arg | Glu | Glu | Gln | Tyr | Asn | Ser |
| | 290 | | | | | 295 | | | | | 300 | | | | |
| Thr | Tyr | Arg | Val | Val | Ser | Val | Leu | Thr | Val | Leu | His | Gln | Asp | Trp | Leu |
| 305 | | | | | 310 | | | | | 315 | | | | | 320 |
| Asn | Gly | Lys | Glu | Tyr | Lys | Cys | Lys | Val | Ser | Asn | Lys | Ala | Leu | Pro | Ala |
| | | | | 325 | | | | | 330 | | | | | 335 | |
| Pro | Ile | Glu | Lys | Thr | Ile | Ser | Lys | Ala | Lys | Gly | Gln | Pro | Arg | Glu | Pro |
| | | | 340 | | | | | 345 | | | | | 350 | | |
| Gln | Val | Tyr | Thr | Leu | Pro | Pro | Ser | Arg | Asp | Glu | Leu | Thr | Lys | Asn | Gln |
| | | 355 | | | | | 360 | | | | | 365 | | | |
| Val | Ser | Leu | Thr | Cys | Leu | Val | Lys | Gly | Phe | Tyr | Pro | Ser | Asp | Ile | Ala |

```
                370                 375                 380
Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly
            450

<210> SEQ ID NO 134
<211> LENGTH: 123
<212> TYPE: PRT
<213> ORGANISM: Artificial Sequence
<220> FEATURE:
<223> OTHER INFORMATION: Synthetic

<400> SEQUENCE: 134

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Gly Gly Ser Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
                100                 105                 110

Trp Gly Gln Gly Thr Leu Val Thr Val Ser Ser
        115                 120

<210> SEQ ID NO 135
<211> LENGTH: 8
<212> TYPE: PRT
<213> ORGANISM: Artificial Sequence
<220> FEATURE:
<223> OTHER INFORMATION: Synthetic

<400> SEQUENCE: 135

Ile Ser Ala Tyr Gly Gly Ser Thr
1               5

<210> SEQ ID NO 136
<211> LENGTH: 17
<212> TYPE: PRT
<213> ORGANISM: Artificial Sequence
<220> FEATURE:
<223> OTHER INFORMATION: Synthetic

<400> SEQUENCE: 136

Trp Ile Ser Ala Tyr Gly Gly Ser Thr Asn Tyr Ala Gln Lys Leu Gln
1               5                   10                  15

Gly
```

<210> SEQ ID NO 137
<211> LENGTH: 216
<212> TYPE: PRT
<213> ORGANISM: Artificial Sequence
<220> FEATURE:
<223> OTHER INFORMATION: Synthetic

<400> SEQUENCE: 137

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Val Thr Phe Gly Gln Gly Thr Lys Val Glu Ile Lys Arg Thr Ala Ala
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 138
<211> LENGTH: 108
<212> TYPE: PRT
<213> ORGANISM: Artificial Sequence
<220> FEATURE:
<223> OTHER INFORMATION: Synthetic

<400> SEQUENCE: 138

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95
```

Val Thr Phe Gly Gln Gly Thr Lys Val Glu Ile Lys
            100                 105

<210> SEQ ID NO 139
<211> LENGTH: 452
<212> TYPE: PRT
<213> ORGANISM: Artificial Sequence
<220> FEATURE:
<223> OTHER INFORMATION: Synthetic

<400> SEQUENCE: 139

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

```
Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450
```

<210> SEQ ID NO 140
<211> LENGTH: 123
<212> TYPE: PRT
<213> ORGANISM: Artificial Sequence
<220> FEATURE:
<223> OTHER INFORMATION: Synthetic

<400> SEQUENCE: 140

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120
```

<210> SEQ ID NO 141
<211> LENGTH: 216
<212> TYPE: PRT
<213> ORGANISM: Artificial Sequence
<220> FEATURE:
<223> OTHER INFORMATION: Synthetic

<400> SEQUENCE: 141

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
```

```
                65                  70                  75                  80
Glu Asp Phe Ala Thr Tyr Tyr Cys Gln Gln Ser Tyr Ser Thr Pro Arg
                    85                  90                  95

Val Thr Phe Gly Gln Gly Thr Lys Val Glu Ile Lys Arg Thr Ala Ala
                100                 105                 110

Ala Ala Pro Ser Val Phe Ile Phe Pro Pro Ser Asp Glu Gln Leu Lys
                115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys
        210                 215

<210> SEQ ID NO 142
<211> LENGTH: 108
<212> TYPE: PRT
<213> ORGANISM: Artificial Sequence
<220> FEATURE:
<223> OTHER INFORMATION: Synthetic

<400> SEQUENCE: 142

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
                20                  25                  30

Leu Ala Trp Tyr Gln Gln Lys Pro Gly Lys Ala Pro Asn Leu Leu Ile
            35                  40                  45

Tyr Glu Ala Ser Asn Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                    85                  90                  95

Val Thr Phe Gly Gln Gly Thr Lys Val Glu Ile Lys
                100                 105

<210> SEQ ID NO 143
<211> LENGTH: 452
<212> TYPE: PRT
<213> ORGANISM: Artificial Sequence
<220> FEATURE:
<223> OTHER INFORMATION: Synthetic

<400> SEQUENCE: 143

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45
```

```
Gly Trp Ile Ser Ala Tyr Ser Gly Asn Ala Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
    450
```

<210> SEQ ID NO 144
<211> LENGTH: 123
<212> TYPE: PRT
<213> ORGANISM: Artificial Sequence
<220> FEATURE:
<223> OTHER INFORMATION: Synthetic

<400> SEQUENCE: 144

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Ala Asn Tyr Ala Gln Lys Leu
    50                  55                  60

Gln Gly Arg Val Thr Met Thr Thr Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120
```

<210> SEQ ID NO 145
<211> LENGTH: 8
<212> TYPE: PRT
<213> ORGANISM: Artificial Sequence
<220> FEATURE:
<223> OTHER INFORMATION: Synthetic

<400> SEQUENCE: 145

```
Ile Ser Ala Tyr Ser Gly Asn Ala
1               5
```

<210> SEQ ID NO 146
<211> LENGTH: 17
<212> TYPE: PRT
<213> ORGANISM: Artificial Sequence
<220> FEATURE:
<223> OTHER INFORMATION: Synthetic

<400> SEQUENCE: 146

```
Trp Ile Ser Ala Tyr Ser Gly Asn Ala Asn Tyr Ala Gln Lys Leu Gln
1               5                   10                  15

Gly
```

<210> SEQ ID NO 147
<211> LENGTH: 216
<212> TYPE: PRT
<213> ORGANISM: Artificial Sequence
<220> FEATURE:
<223> OTHER INFORMATION: Synthetic

<400> SEQUENCE: 147

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45
```

Tyr Glu Ala Ser Asn Leu Glu Ser Gly Val Pro Ser Arg Phe Ser Gly
            50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Arg
                85                  90                  95

Val Thr Phe Gly Gln Gly Thr Lys Val Glu Ile Lys Arg Thr Ala Ala
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Leu Tyr Ala Cys Glu Val Thr His Gln Gly Leu Ser Ser Pro Val Thr
                195                 200                 205

Lys Ser Phe Asn Arg Gly Glu Cys
        210                 215

<210> SEQ ID NO 148
<211> LENGTH: 108
<212> TYPE: PRT
<213> ORGANISM: Artificial Sequence
<220> FEATURE:
<223> OTHER INFORMATION: Synthetic

<400> SEQUENCE: 148

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
 65                 70                  75                  80

Glu Asp Phe Ala Thr Tyr Tyr Cys Gln Gln Ser Tyr Ser Thr Pro Arg
                85                  90                  95

Val Thr Phe Gly Gln Gly Thr Lys Val Glu Ile Lys
            100                 105

<210> SEQ ID NO 149
<211> LENGTH: 452
<212> TYPE: PRT
<213> ORGANISM: Artificial Sequence
<220> FEATURE:
<223> OTHER INFORMATION: Synthetic

<400> SEQUENCE: 149

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr

```
                20                  25                  30
Gly Ile Ser Trp Val Arg Gln Ala Pro Gly Gln Gly Leu Glu Trp Met
             35                  40                  45
Gly Trp Ile Ser Ala Tyr Gly Ser Thr Asn Tyr Ala Gln Lys Leu
 50                  55                  60
Gln Gly Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                 85                  90                  95
Ala Arg Asp Leu Phe Pro Thr Ile Phe Gly Val Ser Tyr Tyr Tyr
             100                 105                 110
Trp Gly Gln Gly Thr Leu Val Thr Val Ser Ser Ala Ser Thr Lys Gly
             115                 120                 125
Pro Ser Val Phe Pro Leu Ala Pro Ser Ser Lys Ser Thr Ser Gly Gly
             130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
             165                 170                 175
Pro Ala Val Leu Gln Ser Ser Gly Leu Tyr Ser Leu Ser Ser Val Val
             180                 185                 190
Thr Val Pro Ser Ser Ser Leu Gly Thr Gln Thr Tyr Ile Cys Asn Val
             195                 200                 205
Asn His Lys Pro Ser Asn Thr Lys Val Asp Lys Lys Val Glu Pro Lys
             210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
             245                 250                 255
Leu Met Ile Ser Arg Thr Pro Glu Val Thr Cys Val Val Val Asp Val
             260                 265                 270
Ser His Glu Asp Pro Glu Val Lys Phe Asn Trp Tyr Val Asp Gly Val
             275                 280                 285
Glu Val His Asn Ala Lys Thr Lys Pro Arg Glu Glu Gln Tyr Asn Ser
             290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                 325                 330                 335
Pro Ile Glu Lys Thr Ile Ser Lys Ala Lys Gly Gln Pro Arg Glu Pro
             340                 345                 350
Gln Val Tyr Thr Leu Pro Pro Ser Arg Asp Glu Leu Thr Lys Asn Gln
             355                 360                 365
Val Ser Leu Thr Cys Leu Val Lys Gly Phe Tyr Pro Ser Asp Ile Ala
             370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                 405                 410                 415
Thr Val Asp Lys Ser Arg Trp Gln Gln Gly Asn Val Phe Ser Cys Ser
             420                 425                 430
Val Met His Glu Ala Leu His Asn His Tyr Thr Gln Lys Ser Leu Ser
             435                 440                 445
```

Leu Ser Pro Gly
    450

<210> SEQ ID NO 150
<211> LENGTH: 123
<212> TYPE: PRT
<213> ORGANISM: Artificial Sequence
<220> FEATURE:
<223> OTHER INFORMATION: Synthetic

<400> SEQUENCE: 150

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Gly Gly Ser Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120

<210> SEQ ID NO 151
<211> LENGTH: 215
<212> TYPE: PRT
<213> ORGANISM: Artificial Sequence
<220> FEATURE:
<223> OTHER INFORMATION: Synthetic

<400> SEQUENCE: 151

Asp Ile Gln Met Thr Gln Ser Pro Ser Thr Leu Ser Ala Ser Val Arg
1               5                   10                  15

Asp Arg Val Ile Ile Thr Cys Arg Ala Ser Gln Ser Ile Gly Asn Arg
            20                  25                  30

Leu Ala Trp Tyr Gln His Lys Pro Gly Lys Ala Pro Lys Leu Leu Ile
        35                  40                  45

Tyr Glu Ala Ser Ser Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg Thr Ala Ala Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu

```
                    165                 170                 175
Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 152
<211> LENGTH: 107
<212> TYPE: PRT
<213> ORGANISM: Artificial Sequence
<220> FEATURE:
<223> OTHER INFORMATION: Synthetic

<400> SEQUENCE: 152

Asp Ile Gln Met Thr Gln Ser Pro Ser Thr Leu Ser Ala Ser Val Arg
1               5                   10                  15

Asp Arg Val Ile Ile Thr Cys Arg Ala Ser Gln Ser Ile Gly Asn Arg
            20                  25                  30

Leu Ala Trp Tyr Gln His Lys Pro Gly Lys Ala Pro Lys Leu Leu Ile
        35                  40                  45

Tyr Glu Ala Ser Thr Ser Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 153
<211> LENGTH: 452
<212> TYPE: PRT
<213> ORGANISM: Artificial Sequence
<220> FEATURE:
<223> OTHER INFORMATION: Synthetic

<400> SEQUENCE: 153

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 154
<211> LENGTH: 123
<212> TYPE: PRT
<213> ORGANISM: Artificial Sequence
<220> FEATURE:
<223> OTHER INFORMATION: Synthetic

<400> SEQUENCE: 154

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Ser Gly Gly Thr Asn Tyr Ala Gln Lys Leu
            50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Leu Phe Pro Thr Ile Phe Gly Val Ser Tyr Tyr Tyr Tyr
                100                 105                 110

Trp Gly Gln Gly Thr Leu Val Thr Val Ser Ser
            115                 120

<210> SEQ ID NO 155
<211> LENGTH: 215
<212> TYPE: PRT
<213> ORGANISM: Artificial Sequence
<220> FEATURE:
<223> OTHER INFORMATION: Synthetic

<400> SEQUENCE: 155

Asp Ile Gln Met Thr Gln Ser Pro Ser Thr Leu Ser Ala Ser Val Arg
 1               5                  10                  15

Asp Arg Val Ile Ile Thr Cys Arg Ala Ser Gln Ser Ile Gly Asn Arg
                 20                  25                  30

Leu Ala Trp Tyr Gln His Lys Pro Gly Lys Ala Pro Lys Leu Leu Ile
             35                  40                  45

Tyr Glu Ala Ser Thr Ser Glu Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Tyr
                 85                  90                  95

Thr Phe Gly Gln Gly Thr Lys Leu Glu Ile Lys Arg Thr Ala Ala Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 156
<211> LENGTH: 107
<212> TYPE: PRT
<213> ORGANISM: Artificial Sequence
<220> FEATURE:
<223> OTHER INFORMATION: Synthetic

<400> SEQUENCE: 156

Asp Ile Gln Met Thr Gln Ser Pro Ser Thr Leu Ser Ala Ser Val Arg
 1               5                  10                  15

```
Asp Arg Val Ile Ile Thr Cys Arg Ala Ser Gln Ser Ile Gly Asn Arg
            20                  25                  30

Leu Ala Trp Tyr Gln His Lys Pro Gly Lys Ala Pro Lys Leu Leu Ile
        35                  40                  45

Tyr Glu Ala Ser Ser Glu Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
                100                 105

<210> SEQ ID NO 157
<211> LENGTH: 452
<212> TYPE: PRT
<213> ORGANISM: Artificial Sequence
<220> FEATURE:
<223> OTHER INFORMATION: Synthetic

<400> SEQUENCE: 157

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Ala Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270
```

```
Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 158
<211> LENGTH: 123
<212> TYPE: PRT
<213> ORGANISM: Artificial Sequence
<220> FEATURE:
<223> OTHER INFORMATION: Synthetic

<400> SEQUENCE: 158

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Ala Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120

<210> SEQ ID NO 159
<211> LENGTH: 215
<212> TYPE: PRT
<213> ORGANISM: Artificial Sequence
<220> FEATURE:
<223> OTHER INFORMATION: Synthetic
```

<400> SEQUENCE: 159

Asp Ile Gln Met Thr Gln Ser Pro Ser Thr Leu Ser Ala Ser Val Arg
1               5                   10                  15

Asp Arg Val Ile Ile Thr Cys Arg Ala Ser Gln Ser Ile Gly Asn Arg
            20                  25                  30

Leu Ala Trp Tyr Gln His Lys Pro Gly Lys Ala Pro Lys Leu Leu Ile
        35                  40                  45

Tyr Glu Ala Ser Thr Ser Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg Thr Ala Ala Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 160
<211> LENGTH: 107
<212> TYPE: PRT
<213> ORGANISM: Artificial Sequence
<220> FEATURE:
<223> OTHER INFORMATION: Synthetic

<400> SEQUENCE: 160

Asp Ile Gln Met Thr Gln Ser Pro Ser Thr Leu Ser Ala Ser Val Arg
1               5                   10                  15

Asp Arg Val Ile Ile Thr Cys Arg Ala Ser Gln Ser Ile Gly Asn Arg
            20                  25                  30

Leu Ala Trp Tyr Gln His Lys Pro Gly Lys Ala Pro Lys Leu Leu Ile
        35                  40                  45

Tyr Glu Ala Ser Thr Ser Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 161
<211> LENGTH: 452
<212> TYPE: PRT

<213> ORGANISM: Artificial Sequence
<220> FEATURE:
<223> OTHER INFORMATION: Synthetic

<400> SEQUENCE: 161

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Arg | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Tyr |
| | | | 20 | | | | | 25 | | | | | 30 | | |
| Gly | Ile | Ser | Trp | Val | Arg | Gln | Ala | Pro | Gly | Gln | Gly | Leu | Glu | Trp | Met |
| | | 35 | | | | | 40 | | | | | 45 | | | |
| Gly | Trp | Ile | Ser | Ala | Tyr | Gly | Gly | Ser | Thr | Asn | Tyr | Ala | Gln | Lys | Leu |
| | 50 | | | | | 55 | | | | | 60 | | | | |
| Gln | Gly | Arg | Val | Thr | Met | Thr | Thr | Asp | Thr | Ser | Thr | Ser | Thr | Ala | Tyr |
| 65 | | | | | 70 | | | | | 75 | | | | | 80 |
| Met | Glu | Leu | Arg | Ser | Leu | Arg | Ser | Asp | Asp | Thr | Ala | Val | Tyr | Tyr | Cys |
| | | | | 85 | | | | | 90 | | | | | 95 | |
| Ala | Arg | Asp | Leu | Phe | Pro | Thr | Ile | Phe | Gly | Val | Ser | Tyr | Tyr | Tyr | Tyr |
| | | | 100 | | | | | 105 | | | | | 110 | | |
| Trp | Gly | Gln | Gly | Thr | Leu | Val | Thr | Val | Ser | Ser | Ala | Ser | Thr | Lys | Gly |
| | | 115 | | | | | 120 | | | | | 125 | | | |
| Pro | Ser | Val | Phe | Pro | Leu | Ala | Pro | Ser | Ser | Lys | Ser | Thr | Ser | Gly | Gly |
| | 130 | | | | | 135 | | | | | 140 | | | | |
| Thr | Ala | Ala | Leu | Gly | Cys | Leu | Val | Lys | Asp | Tyr | Phe | Pro | Glu | Pro | Val |
| 145 | | | | | 150 | | | | | 155 | | | | | 160 |
| Thr | Val | Ser | Trp | Asn | Ser | Gly | Ala | Leu | Thr | Ser | Gly | Val | His | Thr | Phe |
| | | | | 165 | | | | | 170 | | | | | 175 | |
| Pro | Ala | Val | Leu | Gln | Ser | Ser | Gly | Leu | Tyr | Ser | Leu | Ser | Ser | Val | Val |
| | | | 180 | | | | | 185 | | | | | 190 | | |
| Thr | Val | Pro | Ser | Ser | Ser | Leu | Gly | Thr | Gln | Thr | Tyr | Ile | Cys | Asn | Val |
| | | 195 | | | | | 200 | | | | | 205 | | | |
| Asn | His | Lys | Pro | Ser | Asn | Thr | Lys | Val | Asp | Lys | Val | Glu | Pro | Lys |
| | 210 | | | | | 215 | | | | | 220 | | | | |
| Ser | Cys | Asp | Lys | Thr | His | Thr | Cys | Pro | Pro | Cys | Pro | Ala | Pro | Glu | Leu |
| 225 | | | | | 230 | | | | | 235 | | | | | 240 |
| Leu | Gly | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ile | Ser | Arg | Thr | Pro | Glu | Val | Thr | Cys | Val | Val | Val | Asp | Val |
| | | | 260 | | | | | 265 | | | | | 270 | | |
| Ser | His | Glu | Asp | Pro | Glu | Val | Lys | Phe | Asn | Trp | Tyr | Val | Asp | Gly | Val |
| | | 275 | | | | | 280 | | | | | 285 | | | |
| Glu | Val | His | Asn | Ala | Lys | Thr | Lys | Pro | Arg | Glu | Glu | Gln | Tyr | Asn | Ser |
| | 290 | | | | | 295 | | | | | 300 | | | | |
| Thr | Tyr | Arg | Val | Val | Ser | Val | Leu | Thr | Val | Leu | His | Gln | Asp | Trp | Leu |
| 305 | | | | | 310 | | | | | 315 | | | | | 320 |
| Asn | Gly | Lys | Glu | Tyr | Lys | Cys | Lys | Val | Ser | Asn | Lys | Ala | Leu | Pro | Ala |
| | | | | 325 | | | | | 330 | | | | | 335 | |
| Pro | Ile | Glu | Lys | Thr | Ile | Ser | Lys | Ala | Lys | Gly | Gln | Pro | Arg | Glu | Pro |
| | | | 340 | | | | | 345 | | | | | 350 | | |
| Gln | Val | Tyr | Thr | Leu | Pro | Pro | Ser | Arg | Asp | Glu | Leu | Thr | Lys | Asn | Gln |
| | | 355 | | | | | 360 | | | | | 365 | | | |
| Val | Ser | Leu | Thr | Cys | Leu | Val | Lys | Gly | Phe | Tyr | Pro | Ser | Asp | Ile | Ala |
| | 370 | | | | | 375 | | | | | 380 | | | | |
| Val | Glu | Trp | Glu | Ser | Asn | Gly | Gln | Pro | Glu | Asn | Asn | Tyr | Lys | Thr | Thr |

```
385                 390                 395                 400
Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly
        450

<210> SEQ ID NO 162
<211> LENGTH: 123
<212> TYPE: PRT
<213> ORGANISM: Artificial Sequence
<220> FEATURE:
<223> OTHER INFORMATION: Synthetic

<400> SEQUENCE: 162

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Gly Gly Ser Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
                100                 105                 110

Trp Gly Gln Gly Thr Leu Val Thr Val Ser Ser
            115                 120

<210> SEQ ID NO 163
<211> LENGTH: 215
<212> TYPE: PRT
<213> ORGANISM: Artificial Sequence
<220> FEATURE:
<223> OTHER INFORMATION: Synthetic

<400> SEQUENCE: 163

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
                20                  25                  30

Leu Ala Trp Tyr Gln Gln Lys Pro Gly Lys Ala Pro Asn Leu Leu Ile
            35                  40                  45

Tyr Glu Ala Ser Asn Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Trp Pro Arg
                85                  90                  95

Thr Phe Gly Gln Gly Thr Lys Val Glu Ile Lys Arg Thr Ala Ala Ala
                100                 105                 110
```

```
Ala Pro Ser Val Phe Ile Phe Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 164
<211> LENGTH: 107
<212> TYPE: PRT
<213> ORGANISM: Artificial Sequence
<220> FEATURE:
<223> OTHER INFORMATION: Synthetic

<400> SEQUENCE: 164

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Trp Pro Arg
                85                  90                  95

Thr Phe Gly Gln Gly Thr Lys Val Glu Ile Lys
            100                 105

<210> SEQ ID NO 165
<211> LENGTH: 452
<212> TYPE: PRT
<213> ORGANISM: Artificial Sequence
<220> FEATURE:
<223> OTHER INFORMATION: Synthetic

<400> SEQUENCE: 165

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 166
<211> LENGTH: 215
<212> TYPE: PRT
<213> ORGANISM: Artificial Sequence
<220> FEATURE:
<223> OTHER INFORMATION: Synthetic

<400> SEQUENCE: 166

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
            35                  40                  45

Tyr Glu Ala Ser Asn Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Trp Pro Arg
                85                  90                  95

Thr Phe Gly Gln Gly Thr Lys Val Glu Ile Lys Arg Thr Ala Ala Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 167
<211> LENGTH: 107
<212> TYPE: PRT
<213> ORGANISM: Artificial Sequence
<220> FEATURE:
<223> OTHER INFORMATION: Synthetic

<400> SEQUENCE: 167

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
            35                  40                  45

Tyr Glu Ala Ser Asn Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Trp Pro Arg
                85                  90                  95

Thr Phe Gly Gln Gly Thr Lys Val Glu Ile Lys
            100                 105

<210> SEQ ID NO 168
<211> LENGTH: 452
<212> TYPE: PRT
<213> ORGANISM: Artificial Sequence
```

```
<220> FEATURE:
<223> OTHER INFORMATION: Synthetic

<400> SEQUENCE: 168

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Ala Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400
```

```
Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
            450

<210> SEQ ID NO 169
<211> LENGTH: 123
<212> TYPE: PRT
<213> ORGANISM: Artificial Sequence
<220> FEATURE:
<223> OTHER INFORMATION: Synthetic

<400> SEQUENCE: 169

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Ala Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120

<210> SEQ ID NO 170
<211> LENGTH: 215
<212> TYPE: PRT
<213> ORGANISM: Artificial Sequence
<220> FEATURE:
<223> OTHER INFORMATION: Synthetic

<400> SEQUENCE: 170

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Trp Pro Arg
                85                  90                  95

Thr Phe Gly Gln Gly Thr Lys Val Glu Ile Lys Arg Thr Ala Ala Ala
            100                 105                 110

Ala Pro Ser Val Phe Ile Phe Pro Pro Ser Asp Glu Gln Leu Lys Ser
```

```
                115                 120                 125
Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
                195                 200                 205

Ser Phe Asn Arg Gly Glu Cys
    210                 215

<210> SEQ ID NO 171
<211> LENGTH: 107
<212> TYPE: PRT
<213> ORGANISM: Artificial Sequence
<220> FEATURE:
<223> OTHER INFORMATION: Synthetic

<400> SEQUENCE: 171

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Ser Trp Pro Arg
                85                  90                  95

Thr Phe Gly Gln Gly Thr Lys Val Glu Ile Lys
            100                 105

<210> SEQ ID NO 172
<211> LENGTH: 452
<212> TYPE: PRT
<213> ORGANISM: Artificial Sequence
<220> FEATURE:
<223> OTHER INFORMATION: Synthetic

<400> SEQUENCE: 172

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Gly Gly Ser Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

```
Ala Arg Asp Leu Phe Pro Thr Ile Phe Gly Val Ser Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450

<210> SEQ ID NO 173
<211> LENGTH: 123
<212> TYPE: PRT
<213> ORGANISM: Artificial Sequence
<220> FEATURE:
<223> OTHER INFORMATION: Synthetic

<400> SEQUENCE: 173
```

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Gly Gly Ser Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
            115                 120

<210> SEQ ID NO 174
<211> LENGTH: 216
<212> TYPE: PRT
<213> ORGANISM: Artificial Sequence
<220> FEATURE:
<223> OTHER INFORMATION: Synthetic

<400> SEQUENCE: 174

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
            35                  40                  45

Tyr Glu Ala Ser Asn Leu Glu Ser Gly Val Pro Ser Arg Phe Ser Gly
50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Gln Ala Asn Thr Phe Pro Arg
            85                  90                  95

Val Ser Phe Gly Gly Gly Thr Lys Val Glu Ile Lys Arg Thr Ala Ala
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
            195                 200                 205

Lys Ser Phe Asn Arg Gly Glu Cys
            210                 215

<210> SEQ ID NO 175
<211> LENGTH: 108

```
<212> TYPE: PRT
<213> ORGANISM: Artificial Sequence
<220> FEATURE:
<223> OTHER INFORMATION: Synthetic

<400> SEQUENCE: 175

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Gln Ala Asn Thr Phe Pro Arg
                85                  90                  95

Val Ser Phe Gly Gly Gly Thr Lys Val Glu Ile Lys
            100                 105

<210> SEQ ID NO 176
<211> LENGTH: 452
<212> TYPE: PRT
<213> ORGANISM: Artificial Sequence
<220> FEATURE:
<223> OTHER INFORMATION: Synthetic

<400> SEQUENCE: 176

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220
```

-continued

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly
    450

<210> SEQ ID NO 177
<211> LENGTH: 123
<212> TYPE: PRT
<213> ORGANISM: Artificial Sequence
<220> FEATURE:
<223> OTHER INFORMATION: Synthetic

<400> SEQUENCE: 177

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120

```
<210> SEQ ID NO 178
<211> LENGTH: 216
<212> TYPE: PRT
<213> ORGANISM: Artificial Sequence
<220> FEATURE:
<223> OTHER INFORMATION: Synthetic

<400> SEQUENCE: 178

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Gln Ala Asn Thr Phe Pro Arg
                85                  90                  95

Val Ser Phe Gly Gly Gly Thr Lys Val Glu Ile Lys Arg Thr Ala Ala
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 179
<211> LENGTH: 108
<212> TYPE: PRT
<213> ORGANISM: Artificial Sequence
<220> FEATURE:
<223> OTHER INFORMATION: Synthetic

<400> SEQUENCE: 179

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Gln Ala Asn Thr Phe Pro Arg
```

```
                85                  90                  95

Val Ser Phe Gly Gly Gly Thr Lys Val Glu Ile Lys
            100                 105

<210> SEQ ID NO 180
<211> LENGTH: 452
<212> TYPE: PRT
<213> ORGANISM: Artificial Sequence
<220> FEATURE:
<223> OTHER INFORMATION: Synthetic

<400> SEQUENCE: 180

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Ala Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Leu Phe Pro Thr Ile Phe Gly Val Ser Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Cys Pro Ala Pro Glu Leu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
```

```
                    340                 345                 350
Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly
            450

<210> SEQ ID NO 181
<211> LENGTH: 123
<212> TYPE: PRT
<213> ORGANISM: Artificial Sequence
<220> FEATURE:
<223> OTHER INFORMATION: Synthetic

<400> SEQUENCE: 181

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Ala Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser
        115                 120

<210> SEQ ID NO 182
<211> LENGTH: 216
<212> TYPE: PRT
<213> ORGANISM: Artificial Sequence
<220> FEATURE:
<223> OTHER INFORMATION: Synthetic

<400> SEQUENCE: 182

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60
```

-continued

```
Ser Gly Ser Gly Thr Glu Phe Thr Leu Thr Ile Asn Ser Leu Gln Pro
 65                  70                  75                  80

Asp Asp Phe Ala Thr Tyr Tyr Cys Gln Gln Ala Asn Thr Phe Pro Arg
                 85                  90                  95

Val Ser Phe Gly Gly Gly Thr Lys Val Glu Ile Lys Arg Thr Ala Ala
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Leu Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 183
<211> LENGTH: 108
<212> TYPE: PRT
<213> ORGANISM: Artificial Sequence
<220> FEATURE:
<223> OTHER INFORMATION: Synthetic

<400> SEQUENCE: 183

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Gly Arg
            20                  25                  30

Leu Ala Trp Tyr Gln Gln Lys Pro Gly Lys Ala Pro Asn Leu Leu Ile
        35                  40                  45

Tyr Glu Ala Ser Asn Leu Glu Ser Gly Val Pro Ser Arg Phe Ser Gly
    50                  55                  60

Ser Gly Ser Gly Thr Glu Phe Thr Leu Thr Ile Asn Ser Leu Gln Pro
 65                  70                  75                  80

Asp Asp Phe Ala Thr Tyr Tyr Cys Gln Gln Ala Asn Thr Phe Pro Arg
                 85                  90                  95

Val Ser Phe Gly Gly Gly Thr Lys Val Glu Ile Lys
            100                 105
```

<210> SEQ ID NO 184
<211> LENGTH: 433
<212> TYPE: PRT
<213> ORGANISM: Artificial Sequence
<220> FEATURE:
<223> OTHER INFORMATION: Synthetic

<400> SEQUENCE: 184

```
Met Arg Ile Phe Ala Val Phe Ile Phe Thr Ile Tyr Trp His Leu Leu
 1               5                  10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45
```

```
Asp Leu Thr Ser Leu Ile Val Tyr Trp Glu Met Glu Asp Lys Asn Ile
    50                  55                  60

Ile Gln Phe Val His Gly Glu Glu Asp Leu Lys Val Gln His Ser Asn
 65              70                  75                  80

Tyr Arg Gln Arg Ala Gln Leu Leu Lys Asp Gln Leu Ser Leu Gly Asn
                85                  90                  95

Ala Ala Leu Arg Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Leu Asn
            180                 185                 190

Val Thr Ser Thr Leu Arg Ile Asn Thr Thr Ala Asn Glu Ile Phe Tyr
        195                 200                 205

Cys Ile Phe Arg Arg Leu Asp Pro Glu Glu Asn His Thr Ala Glu Leu
    210                 215                 220

Val Ile Pro Glu Leu Pro Leu Ala Leu Pro Pro Asn Glu Arg Thr Ala
225                 230                 235                 240

Ala Ala Thr Ser Ile Thr Ala Tyr Lys Ser Glu Gly Glu Ser Ala Glu
                245                 250                 255

Phe Ser Phe Pro Leu Asn Leu Gly Glu Glu Ser Leu Gln Gly Glu Leu
            260                 265                 270

Arg Trp Lys Ala Glu Lys Ala Pro Ser Ser Gln Ser Trp Ile Thr Phe
        275                 280                 285

Ser Leu Lys Asn Gln Lys Val Ser Val Gln Lys Ser Thr Ser Asn Pro
    290                 295                 300

Lys Phe Gln Leu Ser Glu Thr Leu Pro Leu Thr Leu Gln Ile Pro Gln
305                 310                 315                 320

Val Ser Leu Gln Phe Ala Gly Ser Gly Asn Leu Thr Leu Thr Leu Asp
                325                 330                 335

Arg Gly Ile Leu Tyr Gln Glu Val Asn Leu Val Val Met Lys Val Thr
            340                 345                 350

Gln Pro Asp Ser Asn Thr Leu Thr Cys Glu Val Met Gly Pro Thr Ser
        355                 360                 365

Pro Lys Met Arg Leu Ile Leu Lys Gln Glu Asn Gln Glu Ala Arg Val
    370                 375                 380

Ser Arg Gln Glu Lys Val Ile Gln Val Gln Ala Pro Glu Ala Gly Val
385                 390                 395                 400

Trp Gln Cys Leu Leu Ser Glu Gly Glu Glu Val Lys Met Asp Ser Lys
                405                 410                 415

Ile Gln Val Leu Ser Lys Gly Leu Asn Gly Ser His His His His
            420                 425                 430

His
```

ANTIBODY MOLECULES

RELATED APPLICATION

This Application is a national stage filing under 35 U.S.C. § 371 of International Patent Application No. PCT/EP2019/068804, filed Jul. 12, 2019, the entire contents of which is incorporated herein by reference in its entirety.

FIELD OF THE INVENTION

The invention relates to antibodies and antigen-binding fragments thereof that bind to programmed-death ligand 1 (PD-L1). The antibodies or antigen-binding fragments thereof comprise a CDR-based antigen-binding site for PD-L1. Antibodies or antigen-binding fragments thereof of the invention may find application, for example, in cancer therapy.

BACKGROUND TO THE INVENTION

Programmed cell death 1 (PD-1) is a cell-surface receptor, its ligands PD-L1 (CD274, B7-H1) and PD-L2 (B7-DC) deliver inhibitory signals that regulate the balance between T cell activation, tolerance, and immunopathology. PD-L1 is transiently expressed on all immune cells and some tumour cells.

PD-L1 is a type I transmembrane protein with two Ig-like domains within the extracellular region, a transmembrane domain and a short cytoplasmic domain. The complete human PD-L1 (hPD-L1) sequence can be found under GENBANK® Accession No. Q9NZQ7. The cytoplasmic domain has no known signal transduction motif suggesting that there is no signalling by PD-L1 on interaction of the ligand with its receptor. The molecular weight of PD-L1 is 40 kDa (290 amino acids), it is encoded by the CD274 gene on human chromosome 9 and on mouse chromosome 19. PD-L1 is a member of the B7 protein family and shares approximately 20% amino acid sequence identity with B7.1 and B7.2. Human PD-L1 shares 70% and 93% amino acid identity with the murine and cynomolgus orthologs of PD-L1, respectively.

Human PD-L1 binds to its receptor, PD-1, with an affinity (KD) of 770 nM. PD-1 is expressed on activated T cells, B cells, and myeloid cells; it modulates activation or inhibition of cellular immune responses. Binding of PD-L1 to PD-1 delivers an inhibitory signal, reducing cytokine production and suppressing proliferation of T cells. Consequently, PD-L1 expression by cells can mediate protection against cytotoxic T lymphocyte (CTL) killing and is a regulatory mechanism that dampens chronic immune responses during viral infections. Cancer, as a chronic and pro-inflammatory disease, subverts this immune-protective pathway through up-regulation of PD-L1 expression to evade the host immune response. In the context of an active immune response, IFNγ also upregulates the expression of PD-L1. PD-L1 also mediates immune suppression through interaction with another protein, B7.1 (also known as CD80), blocking its ability to deliver one of the secondary signals of activation on T cells through CD28. In terms of PD-L1 expression on tumour cells and its engagement with B7.1, the relevance of this specific interaction in tumour immune resistance is still unclear.

PD-L1 expression has been shown in a wide variety of solid tumours. Of 654 samples examined in one study, spanning 19 tumours from different sites, 89 (14%) were PD-L1 positive (5% frequency). The highest PD-L1 positive frequencies were seen in head and neck (17/54; 31%), cervical (10/34; 29%), cancer of unknown primary origin (CUP; 8/29; 28%), glioblastoma multiforme (GBM; 5/20; 25%), bladder (8/37; 21%), oesophageal (16/80; 20%), triple negative (TN) breast (6/33; 18%), and hepatocarcinoma (6/41; 15%) (Grosso et al., 2013). Tumour-associated expression of PD-L1 has been shown to confer immune resistance and potentially protect tumour cells from T cell mediated apoptosis.

Therapies targeting PD-L1 have shown excellent results in murine in vivo studies. In the B16 murine model of melanoma, treatment with anti-PD-L1 therapy combined with either GVAX or FVAX vaccination strategies resulted in a significant effect both on survival (30 days for control vs 52 days for PD-L1-treated) and percentage of tumour-free (5%) animals upon conclusion of the study (Curran et al., 2010). Anti-PD-L1 therapy has also been used to study the mechanism of immune suppression in the P815 murine mastoma model. P815 cells injected into mice normally trigger a strong immune response, which results in their rejection. When PD-L1 is expressed on P815 cells, these cells escape immune attack, which in turn can be negated through administration of anti-PD-L1 antibodies (Iwai et al., 2002). It is evident that targeting the PD-1/PD-L1 axis in immunogenic human cancers (Herbst et al, 2014) results in a survival advantage through stimulation of an anti-cancer immune response (Wolchok et al., 2013; Larkin et al., 2015).

Atezolizumab (MPDL3280A, RG7466, TECENTRIQ™) is a humanized IgG1 antibody which binds to PD-L1. It is in clinical trials as a monotherapy and also in combination with other biologic and/or small molecule therapies for treatment of solid cancers, including colorectal cancer, breast cancer, non-small-cell lung carcinoma, bladder cancer, and renal cell carcinoma. Treatment with atezolizumab resulted in objective response rates (ORR) of 23% in NSCLC, 36% melanoma, 33% bladder, 14% in RCC, and 13% in head and neck cancers (Herbst et al., 2014; Powles et al., 2014).

In May 2016 the FDA granted accelerated approval to atezolizumab for locally advanced or metastatic urothelial carcinoma treatment after failure of cisplatin-based chemotherapy; however, the confirmatory trial failed to achieve its primary endpoint of overall survival. In October 2016, the FDA approved atezolizumab for the treatment of patients with metastatic non-small cell lung cancer (NSCLC) who had disease progression during or following platinum-containing chemotherapy. Patients with EGFR or ALK genomic tumor aberrations are required to have disease progression on FDA-approved therapy for these aberrations prior to receiving atezolizumab. Atezolizumab in combination with avastin and standard chemotherapy for some patients with lung cancer is under FDA priority review, a decision being expected by 5 Sep. 2018. The most common adverse effects reported in clinical studies of atezolizumab were fatigue, decreased appetite, nausea, and infections; urinary tract infection was the most common severe adverse effect.

Avelumab (MSB0010718C, BAVENCIO™) is a fully human IgG1 antibody which binds to PD-L1 and is undergoing clinical testing in a number of cancers including bladder cancer, gastric cancer, head and neck cancer, mesothelioma, non-small-cell lung carcinoma, ovarian cancer, renal cancer and Merkel-cell carcinoma. Avelumab received orphan drug designation by the European Medicines Agency (EMA) for the treatment of gastric cancer in January 2017. In 2017 the FDA and the EMA approved avelumab for Merkel-cell carcinoma (an aggressive skin cancer) in adults and pediatric patients 12 years and older. Approval was based on data from an open-label, single-arm, multi-center clinical trial (JAVELIN Merkel 200 trial). All patients had histologically-confirmed metastatic MCC with disease progression on or after chemotherapy administered for metastatic disease. The overall response rate (ORR) was assessed by an independent review committee according to Response Evaluation Criteria in Solid Tumors (RECIST) 1.1. The ORR was 33% (95% confidence interval [CI]: 23.3, 43.8), with 11% complete and 22% partial response rates. Among the 29 responding patients, the response duration ranged from 2.8 to 23.3+ months with 86% of responses durable for 6 months or longer. Responses were observed in patients regardless of PD-L1 tumor expression or presence of Merkel cell polyomavirus. Safety data were evaluated in 1738 patients. The most common serious adverse reactions to avelumab were immune-mediated adverse reactions (pneumonitis, hepatitis, colitis, adrenal insufficiency, hypo- and hyperthyroidism, diabetes mellitus, and nephritis) and life-threatening infusion reactions. Among the 88 patients enrolled in the JAVELIN Merkel 200 trial, the most common adverse reactions were fatigue, musculoskeletal pain, diarrhea, nausea, infusion-related reaction, rash, decreased appetite, and peripheral edema. Serious adverse reactions that occurred in more than one patient in the trial were acute kidney injury, anemia, abdominal pain, ileus, asthenia, and cellulitis.

Durvalumab (MEDI4736, IMFINZI™) is a human IgG1 antibody which binds to PD-L1 and is being tested in clinical trials alone or in combination with tremelimumab in non-small-cell lung cancer, squamous cell carcinoma of the head and neck, bladder cancer, pancreatic cancer and with other biologic and small molecules in trials for additional solid cancers such as gastric cancers, melanoma and unresectable hepatocellular carcinoma.

Durvalumab was approved by the FDA for the treatment of patients with locally advanced or metastatic urothelial carcinoma who either have disease progression during or following platinum-containing chemotherapy or have disease progression within 12 months of neoadjuvant or adjuvant treatment with platinum-containing chemotherapy.

A phase 1B clinical trial of durvalumab and tremelimumab showed some activity in non-small cell lung cancer (NSCLC). However, in July 2017, AstraZeneca announced that a phase III trial of durvalumab with tremelimumab as a first-line treatment of non-small cell lung cancer had failed to meet its primary endpoint of progression-free survival.

Early results of a phase I trial combining durvalumab and gefitinib in lung cancer patients were reported to have "showed promise". A phase 1 clinical trial is in progress using durvalumab with a TLR 7/8 agonist (MEDI 9197) for solid tumors. A Phase 1b/2a trial is in progress combining durvalumab with an HPV DNA vaccine (MEDI 0457) in patients with HPV-associated recurrent/metastatic head and neck cancer.

In November 2017, the double-blinded phase 3 AstraZeneca PACIFIC clinical trial reported the efficacy of durvalumab in the treatment of stage III non-small cell lung cancer. A cohort of 709 patients with stage III NSCLC, who did not have disease progression after two or more cycles of a platinum-based chemotherapy, were randomly assigned to receive durvalumab or a placebo as consolidation therapy for their lung cancer. Durvalumab increased the median progression-free survival from 5.6 months (placebo) to 16.8 months (durvalumab); the 12 month progression-free survival rate was increased from 35.3% (placebo) to 55.9% (durvalumab), and the 18 month progression-free survival rate was increased from 27.0% (placebo) to 44.2% (durvalumab). The median time to death or distant metastases increased from 14.6 months (placebo) to 23.2 months (durvalumab). However, extreme side effects were also increased from 26.1% of patients (placebo) to 29.9% of patients (durvalumab).

Adverse effects were reported following exposure to durvalumab in 182 patients with locally advanced or metastatic urothelial carcinoma whose disease has progressed during or after one standard platinum-based regimen. Patients received 10 mg/kg durvalumab via intravenous infusion every 2 weeks. The median duration of exposure was 10.2 weeks (range: 0.14, 52.4). Thirty-one percent (31%) of patients had a drug delay or interruption for an adverse reaction. The most common (>2%) were liver injury (4.9%), urinary tract infection (3.3%), acute kidney injury (3.3%), and musculoskeletal pain (2.7%). The most common adverse reactions 15%) were fatigue (39%), musculoskeletal pain (24%), constipation (21%), decreased appetite (19%), nausea (16%), peripheral edema (15%) and urinary tract infection (15%). The most common Grade 3 or 4 adverse reactions 3%) were fatigue, urinary tract infection, musculoskeletal pain, abdominal pain, dehydration, and general physical health deterioration. Eight patients (4.4%) who were treated with durvalumab experienced Grade 5 adverse events of cardiorespiratory arrest, general physical health deterioration, sepsis, ileus, pneumonitis, or immune-mediated hepatitis. Three additional patients were experiencing infection and disease progression at the time of death. Durvalumab was discontinued for adverse reactions in 3.3% of patients. Serious adverse reactions occurred in 46% of patients. The most frequent serious adverse reactions (>2%) were acute kidney injury (4.9%), urinary tract infection (4.4%), musculoskeletal pain (4.4%), liver injury (3.3%), general physical health deterioration (3.3%), sepsis, abdominal pain, pyrexia/tumor associated fever (2.7% each). Immune-mediated adverse reactions requiring systemic corticosteroids or hormone replacement therapy occurred in 8.2% (15/182) patients, including 5.5% (10/182) patients who required systemic corticosteroid therapy and 2.7% (5/182) patients who required only hormone replacement therapy. Seven patients (3.8%) received an oral prednisone dose equivalent to >40 mg daily for an immune-mediated adverse reaction.

Further anti-PD-L1 antibodies including BMS-936559 have been tested in clinical trials, and others are in preclinical testing.

WO2013181634 (Sorrento Therapeutics) describes PD-L1 antibodies. Only one antibody disclosed, "SH1E2" (SEQ ID NO: 147/148 in that application), is said to exhibit improved T-cell activation, measured by the percentage of CD25 positive cells, when compared to PD-L1 antibodies 10A5 and YW234.55570 disclosed in the art.

Infectious diseases show many parallels with oncology. It is thought that the role of PD-L1 in immune regulation could be harnessed to maximize the immune response against pathogens. Immunomodulation in infectious disease is an emerging area of medicine and early reviews suggest that PD-L1 blockade may improve biological responses to infection, in particular, by helping to counteract T cell exhaustion, manage immune-mediated clearance and generate long-term immunity (Wykes and Lewin, 2017). Thus, there also remains a need in the art for additional molecules which can target PD-L1 and which find application in the treatment of infectious diseases.

Antibodies that target PD-L1 may also be useful to treat conditions associated with inflammation, such as vascular inflammation and stroke.

Whilst there are various anti-PD-L1 therapeutics in development, current data shows that overall treatment with existing anti-PD-L1 monotherapies results in a response in less than 50% of cancer patients. The spectrum and severity of reported adverse reactions differs between antibodies in clinical testing. To increase the objective response rate (ORR), and/or seek to reduce adverse effects, anti-PD-L1 antibodies may be combined with other biologics, such as antibodies against other checkpoint regulators, as well as with small molecule therapies and other immune system activating approaches, such as tumour vaccines.

Thus, there remains a need in the art for additional molecules which can target PD-L1 and which find application in cancer therapy.

STATEMENTS OF INVENTION

The present inventors have prepared anti-PD-L1 antibodies by screening a phage library, followed by mutagenesis, screening, selection, and light chain shuffling to isolate anti-PD-L1 antibodies with affinity for PD-L1 and activity in a T cell activation assay.

Further rounds of mutagenesis, screening and selection were performed to remove potential sites for post-translational modifications and to improve the biophysical properties of the selected antibodies.

The above approach enabled identification of anti-PD-L1 antibodies which showed excellent binding to PD-L1 and activity in T cell activation assays. Based on these characteristics, it is expected that the antibodies of the invention will find application in the treatment of human cancers, as well as infectious and inflammatory diseases, through inhibition of PD-L1.

Antibodies of the invention were also shown to have a high affinity for cynomolgus PD-L1, comparable to their affinity for human PD-L1. Antibodies of the invention also showed measurable affinity for mouse PD-L1.

In addition, antibodies to PD-L1 were identified that had a relatively high melting temperature, which can be expected to have enhanced stability, beneficial in the manufacture and storage of the antibodies.

The invention provides:
1. An antibody or antigen-binding fragment thereof, capable of binding specifically to PD-L1, comprising a variable heavy (VH) domain comprising heavy chain complementarity determining regions (CDRs): HCDR1, HCRD2 and HCDR3, characterised in that the amino acid sequence of HCDR1 (amino acids 31 to 35) is SYGIS (SEQ ID NO: 1); the amino acid sequence of HCDR2 is WISAYX$_1$X$_2$X$_3$X$_4$NYAQKLQG (SEQ ID NO: 2); and the amino acid sequence of HCDR3 is DLFPTIFGVSYYYY (SEQ ID NO: 3); wherein X$_1$ is S or N or G; X$_2$ is G or S; X$_3$ is or G, N or S; and X$_4$ is T or A, and wherein the sequences are defined by Kabat nomenclature.
2. An antibody or antigen-binding fragment thereof according to clause 1, characterised in that the amino acid sequence of HCDR1 (amino acids 31 to 35) is SYGIS (SEQ ID NO: 1); the amino acid sequence of HCDR2 is WISAYX$_1$X$_2$X$_3$X$_4$NYAQKLQG (SEQ ID NO: 2); and the amino acid sequence of HCDR3 is DLFPTIFGVSYYYY (SEQ ID NO: 3); wherein X$_1$ is S or N; X$_2$ is G or S; X$_3$ is G or N; and X$_4$ is T, and wherein the sequences are defined by Kabat nomenclature.
3. An antibody or antigen-binding fragment thereof according to clause 1 or clause 2, wherein the amino acid at position 28 preceding HCDR1 is P or T.
4. An antibody or antigen-binding fragment thereof according to any preceding clause, wherein the sequence X$_1$X$_2$X$_3$X$_4$ (SEQ ID NO: 4) (residues 54-57) of HCDR2 is selected from SGGT (SEQ ID NO: 5), NSNT (SEQ ID NO: 6), GGST (SEQ ID NO: 7) and SGNA (SEQ ID NO: 8).
5. An antibody or antigen-binding fragment thereof according to any preceding clause, wherein the residue at HCDR1 position 28 (Kabat nomenclature) is P and the sequence X$_1$X$_2$X$_3$X$_4$ (SEQ ID NO: 4 (residues 54-57) of HCDR2 is SGGT (SEQ ID NO: 5).
6. An antibody or antigen-binding fragment thereof according to any preceding clause, comprising a variable light (VL) domain comprising light chain complementarity determining regions: LCDR1, LCDR2 and LCDR3, characterised in that:
(a) the VL is a kappa VL and the amino acid sequence of LCDR1 is RASQSIX$_5$X$_6$RLA (SEQ ID NO: 9); the amino acid sequence of LCDR2 is EASX$_7$X$_8$EX$_9$ (SEQ ID NO: 10); and the amino acid sequence of LCDR3 is QQX$_{10}$X$_{11}$X$_{12}$X$_{13}$PX$_{14}$X$_{15}$X$_{16}$ (SEQ ID NO: 11); wherein X$_5$ is G or S; X$_6$ is N or G; X$_7$ is T or N; X$_8$ is S or L; X$_9$ is T or S; X$_{10}$ is S or A; X$_{11}$ is Y or N; X$_{12}$ is S or T; X$_{13}$ is T, W or F; X$_{14}$ is absent or R; X$_{15}$ is Y, R or V; and X$_{16}$ is T or S; or,
(b) the VL is a lambda VL and the amino acid sequence of LCDR1 is TGTSSDVGGYNX$_{17}$VS (SEQ ID NO: 12); the amino acid sequence of LCDR2 is EVTNRPS (SEQ ID NO: 13); and the amino acid sequence of LCDR3 is SSFKRGSTLVV (SEQ ID NO: 14); wherein X$_{17}$ is Y or S; and wherein the sequences are defined by Kabat nomenclature.
7. An antibody or antigen-binding fragment thereof according to clause 6, wherein the VL domain is a kappa VL and the amino acid sequence of LCDR1 is RASQSIGNRLA (SEQ ID NO: 15), the amino acid sequence of LCDR2 is EASTSET (SEQ ID NO: 16), and the amino acid sequence of LCDR3 is QQSYSTPYT (SEQ ID NO: 17).
8. An antibody or antigen-binding fragment thereof according to any preceding clause comprising an antigen-binding site comprising the CDRs (HCDR1, HCRD2, HCDR3, LCDR1, LCDR2 and LCDR3, respectively) of antibody:
(a) G1AA/E12v2 of SEQ ID NO: 1, 18, 3, 15, 16 and 17;
(b) G1AA/G12v2 of SEQ ID NO: 1, 18, 3, 19, 20 and 21;
(c) G1AA/E05v2 of SEQ ID NO: 1, 18, 3, 19, 20 and 22;
(d) G1/887_04_E12 of SEQ ID NO: 1, 23, 3, 15, 16 and 17;
(e) G1/887_04_G12 of SEQ ID NO: 1, 23, 3, 19, 20 and 21;
(f) G1/894_08_E05 of SEQ ID NO: 1, 23, 3, 19, 20 and 22;
(g) G1/894_08_A05 of SEQ ID NO: 1, 23, 3, 19, 20 and 24;
(h) G1AA/lambdav3 of SEQ ID NO: 1, 18, 3, 25, 13 and 14;
(i) G1/280_02_G02_NS of SEQ ID NO: 1, 23, 3, 26, 13 and 14 or
(j) G1/280_02_G02 of SEQ ID NO: 1, 78, 3, 26, 13 and 14;
wherein the sequences are defined according to Kabat nomenclature.

9. An antibody or antigen-binding fragment according to any preceding clause, wherein the antigen-binding site comprises the VH and/or VL domain of antibody:
(a) G1AA/E12v2 of SEQ ID NO: 27 and 28, respectively;
(b) G1AA/G12v2 of SEQ ID NO: 29 and 30, respectively;
(c) G1AA/E05v2 of SEQ ID NO: 31 and 32, respectively;
(d) G1/887_04_E12 of SEQ ID NO: 33 and 34, respectively;
(e) G1/887_04_G12 of SEQ ID NO: 35 and 36, respectively;
(f) G1/894_08_E05 of SEQ ID NO: 37 and 38, respectively;
(g) G1/894_08_A05 of SEQ ID NO: 39 and 40, respectively;
(h) G1AA/lambdav3 of SEQ ID NO: 41 and 42, respectively;
(i) G1/280_02_G02_NS of SEQ ID NO: 43 and 44, respectively; or
(j) G1/280_02_G02 of SEQ ID NO: 45 and 46, respectively;
wherein the sequences are defined according to the Kabat nomenclature.
10. The antibody molecule according to any preceding clause, wherein the antibody molecule comprises the heavy chain and/or light chain of antibody:
(a) G1AA/E12v2 of SEQ ID NO: 47 and 48, respectively;
(b) G1AA/G12v2 of SEQ ID NO: 49 and 50, respectively;
(c) G1AA/E05v2 of SEQ ID NO: 51 and 52, respectively;
(d) G1/887_04_E12 of SEQ ID NO: 53 and 54, respectively;
(e) G1/887_04_G12 of SEQ ID NO: 55 and 56, respectively;
(f) G1/894_08_E05 of SEQ ID NO: 57 and 58, respectively;
(g) G1/894_08_A05 of SEQ ID NO: 59 and 60, respectively;
(h) G1AA/lambdav3 of SEQ ID NO: 61 and 62, respectively;
(i) G1/280_02_G02_NS of SEQ ID NO: 63 and 64, respectively; or
(j) G1/280_02_G02 of SEQ ID NO: 65 and 66, respectively;
wherein the sequences are defined according to Kabat nomenclature.
11. An antibody or antigen-binding fragment thereof according to any preceding clause, comprising the HCDRs (HCDR1, HCDR2 and HCDR3) and/or LCDRs (LCDR1, LCDR2 and LCDR3); VH and/or VL; Fab; light chain and/or heavy chain of antibody G1AA/E12v2, G1AA/G12v2 or G1AA/E05v2.
12. The antibody or antigen-binding fragment thereof, according to any preceding clause, comprising the HCDRs (HCDR1, HCDR2 and HCDR3) and/or LCDRs (LCDR1, LCDR2 and LCDR3); VH and/or VL; Fab; light chain and/or heavy chain of antibody G1AA/E12v2 or G1/E12v2.
13. An antibody or antigen-binding fragment thereof according to any preceding clause, wherein the VH has at least 95, 96, 97, 98 or 99% identity to the VH of an antibody selected from G1AA/E12v2 of SEQ ID NO: 27, G1AA/G12v2 of SEQ ID NO: 29, G1AA/E05v2 of SEQ ID NO: 31, G1/887_04_E12 of SEQ ID NO: 33, G1/887_04_G12 of SEQ ID NO: 35, G1/894_08_E05 of SEQ ID NO: 37, G1/894_08_A05 of SEQ ID NO: 39 G1AA/lambdav3 of SEQ ID NO: 41, G1/280_02_G02_NS of SEQ ID NO: 43 and G1/280_02_G02 of SEQ ID NO: 45.

14. An antibody or antigen-binding fragment thereof, according to any preceding clause, wherein the antibody molecule, or antigen-binding fragment, binds to human PD-L1.
15. An antibody or antigen-binding fragment thereof, according to any preceding clause, wherein the antibody molecule, or antigen-binding fragment, binds to cynomolgus PD-L1.
16. An antibody or antigen-binding fragment thereof, according to any preceding clause, wherein the antibody or antigen-binding fragment, binds to mouse PD-L1.
17. An antibody or antigen-binding fragment thereof, according to any preceding clause, wherein the antibody or antigen-binding fragment has an affinity (KD) for recombinant human PD-L1 and for recombinant cynomolgus PD-L1 of less than 2 nM, preferably less than 1 nM, more preferably less than 0.75 nM, yet more preferably less than 0.5 nM when measured by SPR (e.g., Biacore).
18. An antibody or antigen-binding fragment thereof, according to any preceding clause, wherein the antibody or antigen-binding fragment thereof enhances T-cell activation when assessed in a Mixed Lymphocyte Reaction (MLR) assay.
19. An antibody or antigen-binding fragment thereof, according to any preceding clause, wherein the antibody or antigen-binding fragment, is a multispecific, preferably a bispecific, molecule comprising at least a second antigen-binding site.
20. An antibody or antigen-binding fragment, according to any preceding clause, wherein the antibody or antigen-binding fragment thereof, comprises a second antigen-binding site located in a constant domain of the antibody or antigen-binding fragment.
21. An antibody or antigen-binding fragment thereof, according to clause 20, wherein the second antigen-binding site comprises:
(a) a first sequence in the AB structural loop and/or a second sequence in the EF structural loop of a constant heavy domain,
(b) a first sequence in the AB structural loop and a second sequence in the EF structural loop of a constant heavy domain,
(c) a first sequence in the AB structural loop and/or a second sequence in the EF structural loop and/or a third sequence in the CD structural loop of a constant heavy domain
(d) a first sequence in the AB structural loop, a second sequence in the EF structural loop and a third sequence in the CD structural loop of a constant heavy domain
22. An antibody or antigen-binding fragment thereof, according to clause 20 or 21, wherein the constant heavy domain is a CH3 domain.
23. An antibody or antigen-binding fragment thereof, according to any preceding clause, wherein the antibody is an immunoglobulin G (IgG), or antigen-binding fragment thereof.
24. An antibody or antigen-binding fragment thereof, according to clause 23, wherein the antibody is an IgG1 or fragment thereof, or an IgG4 or fragment thereof.
25. An antibody or antigen-binding fragment thereof, according to clause 23 or clause 24, wherein the antibody is an IgG1 or fragment thereof with a modified Fc region.
26. An antibody or antigen-binding fragment thereof, according to clause 24 or 25, wherein the 27. An antibody or antigen-binding fragment thereof, according to clause 25 or 26, wherein the modified Fc has reduced ADCC and/or CDC relative to IgG1.
28. An antibody or antigen-binding fragment thereof, according to any of clauses 25 to 27, wherein the modified Fc region comprises a LALA, LALA-PA or LALA-PG modification.
29. An antibody or antigen-binding fragment thereof, according to any of clauses 25 to 28, wherein the antibody is an IgG1 or antigen-binding fragment thereof comprising a LALA modification in the Fc region.
30. An antibody or antigen-binding fragment thereof, according to any of clauses 19 to 29, wherein the second antigen-binding site binds to an inhibitory checkpoint molecule, costimulatory molecule or tumour-associated antigen.

In an antibody or antigen-binding fragment thereof, according to the invention, the second antigen-binding site may bind to an inhibitory checkpoint molecule, such as CTLA-4, LAG-3, TIGIT, TIM-3, VISTA, CD73, CSF-1R, KIR. B7-H3, B7-H4, 2B4, NKG2A, CD47, SIRPa, BTLA, CCR4, CD200R, or TGFbeta.

In an antibody or antigen-binding fragment thereof, according to the invention, the second antigen-binding site may bind to and be an agonist for a costimulatory molecule expressed by T cells such as OX40, ICOS, CD40, HVEM, NKG2D, or TNFR2.

In an antibody or antigen-binding fragment thereof, according to the invention, the second antigen-binding site may bind to a tumour-associated antigen (TAA), such as c-Met, B7-H3, B7-H4, EGFR, HER-2, EPCAM, CEACAM, FAP, VEGF, MSLN, GPC3, CD38, CD19, or CD20.

31. An antibody or antigen-binding fragment thereof, according to any of clauses 19 to 30, wherein the second antigen-binding site does not bind to OX40, Inducible T-cell COStimulator (ICOS) or CD137.
32. An antibody or antigen-binding fragment thereof, according to any of clauses 19 to 30, wherein the second antigen-binding site does not bind to CD27 or glucocorticoid-induced TNFR-related protein (GITR).
33. An antibody or antigen-binding fragment thereof, according to any of clauses 19 to 30, wherein the second antigen-binding site does not bind to lymphocyte-activation gene 3 (LAG-3).
34. A conjugate or fusion comprising an antibody or antigen-binding fragment thereof according to any preceding clause and an immune system modulator (agonist or antagonist), a cytotoxic molecule, or a radioisotope.
35. An antibody, antigen-binding fragment thereof, conjugate or fusion according to any preceding clause having a detectable label.
36. A nucleic acid molecule or set of nucleic acid molecules encoding an antibody, antigen-binding fragment thereof, conjugate or fusion according to any preceding clause.
37. A nucleic acid molecule or set of nucleic acid molecules according to clause 36, wherein the nucleic acid molecule or set of nucleic acid molecules comprises cDNA sequence encoding one or more of the VH and/or VL, Fab, heavy and/or light chain of:
   (a) G1AA/E12v2 or G1/E12v2;
   (b) G1AA/E05v2 or G1/E05v2;
   (c) G1AA/G12v2 or G1/G12v2;
   (d) G1/887_04_E12;
   (e) G1/894_08_E05;
   (f) G1/887_04_G12;
   (g) G1/894_08_A05;
   (h) G1AA/lambdav3;
   (i) G1/280_02_G02_NS; or
   (j) G1/280_02_G02.
38. A nucleic acid molecule or set of nucleic acid molecules according to clause 37, comprising a first nucleic acid sequence and a second nucleic acid sequence, wherein:
   (a) the first nucleic acid sequence comprises a VH cDNA sequence encoding the VH of antibody G1AA/E12v2 of SEQ ID NO: 27 and the second nucleic acid sequence comprises a VL cDNA sequence encoding the VL of antibody G1AA/E12v2 of SEQ ID NO: 28;
   (b) the first nucleic acid sequence comprises a VH cDNA sequence encoding the VH of antibody G1AA/G12v2 of SEQ ID NO: 29 and the second nucleic acid sequence comprises a VL cDNA sequence encoding the VL of antibody G1AA/G12v2 of SEQ ID NO: 30;
   (c) the first nucleic acid sequence comprises a VH cDNA sequence encoding the VH of antibody G1AA/E05v2 of SEQ ID NO: 31 and the second nucleic acid sequence comprises a VL cDNA sequence encoding the VL of antibody G1AA/E05v2 of SEQ ID NO: 32;
   (d) the first nucleic acid sequence comprises a VH cDNA sequence encoding the VH of antibody G1/887_04_E12 of SEQ ID NO: 33 and the second nucleic acid sequence comprises the VL cDNA sequence of antibody G1/887_04_E12 of SEQ ID NO: 34;
   (e) the first nucleic acid sequence comprises a VH cDNA sequence encoding the VH of antibody G1/887_04_G12 of SEQ ID NO: 35 and the second nucleic acid sequence comprises a VL cDNA sequence encoding the VL of antibody G1/887_04_G12 of SEQ ID NO: 36;
   (f) the first nucleic acid sequence comprises a VH cDNA sequence encoding the VH of antibody G1/894_08_E05 of SEQ ID NO: 37 and the second nucleic acid sequence comprises a VL cDNA sequence encoding the VL of antibody G1/894_08_E05 of SEQ ID NO: 38;
   (g) the first nucleic acid sequence comprises a VH cDNA sequence encoding the VH of antibody G1/894_08_A05 of SEQ ID NO: 39 and the second nucleic acid sequence comprises a VL cDNA sequence encoding the VL of antibody G1/894_08_A05 of SEQ ID NO: 40;
   (h) the first nucleic acid sequence comprises a VH cDNA sequence encoding the VH of antibody G1AA/lambdav3 of SEQ ID NO: 41 and the second nucleic acid sequence comprises a VL cDNA sequence encoding the VL of antibody G1AA/lambdav3 of SEQ ID NO: 42;
   (i) the first nucleic acid sequence comprises a VH cDNA sequence encoding the VH of antibody G1/280_02_G02_NS of SEQ ID NO: 43 and the second nucleic acid sequence comprises a VL cDNA sequence encoding the VL of antibody G1/280_02_G02_NS of SEQ ID NO: 44; or
   (i) the first nucleic acid sequence comprises a VH cDNA sequence encoding the VH of antibody G1/280_02_G02 of SEQ ID NO: 45 and the second nucleic acid sequence comprises a VL cDNA sequence encoding the VL of antibody G1/280_02_G02 of SEQ ID NO: 46.

39. A vector or set of vectors comprising the nucleic acid molecule or set of nucleic acid molecules of any of clauses 36 to 38.
40. A recombinant host cell comprising a nucleic acid molecule or set of nucleic acid molecules of any of clauses 36 to 38, or the vector or set of vectors of clause 39.
41. A method of producing an antibody antigen-binding fragment thereof, conjugate or fusion according to any preceding clause, comprising culturing the recombinant host cell of clause 40 under conditions suitable for production of the antibody, antigen-binding fragment, conjugate or fusion.
42. The method of clause 41 further comprising isolating and/or purifying the antibody, antigen-binding fragment, conjugate or fusion.
43. A composition (e.g., pharmaceutical composition) comprising the antibody, antigen-binding fragment, conjugate or fusion according to any of clauses 1 to 42 and an excipient (e.g., pharmaceutically-acceptable excipient).
44. An antibody, antigen-binding fragment, conjugate or fusion according to any of clauses 1 to 35 or composition according to clause 43 for use in a method for treatment of the human or animal body by therapy.
45. A method for treatment of a disease or disorder in a patient comprising administering to the patient a therapeutically-effective amount of an antibody, antigen-binding fragment thereof, conjugate or fusion according to any of clauses 1 to 35 or composition according to clause 43.
46. The use of an antibody, antigen-binding fragment thereof, conjugate or fusion according to any of clauses 1 to 35 or composition according to clause 43 in the manufacture of a medicament for the treatment of the human or animal body.
47. An antibody, antigen-binding fragment thereof, conjugate or fusion according to any of clauses 1 to 35 or composition according to clause 43 for use according to clause 44 in a method of treatment that comprises administering the antibody, antigen-binding fragment thereof, conjugate, fusion or composition to the human or animal body in combination with a second therapeutic.
48. A method of clause 45, or use of clause 46, wherein the method further comprises administering a therapeutically-effective amount of a second therapeutic to the patient.
49. An antibody, antigen-binding fragment thereof, conjugate, fusion or composition for use according to clause 47, or in a method of clause 48, wherein the second therapeutic is a radiotherapy, preferably targeted radiotherapy.
50. An antibody, antigen-binding fragment, conjugate or fusion according to any of clauses 1 to 35 or composition according to clause 43 for use in a diagnostic method practised on the human or animal body or practised in vitro on a sample from on the human or animal body.
51. A method of detecting a disease or disorder in a patient, the method comprising the use of an antibody, antigen-binding fragment thereof, conjugate or fusion according to any of clauses 1 to 35 or of a composition according to clause 43.
52. The use of an antibody, antigen-binding fragment thereof, conjugate or fusion according to any of clauses 1 to 35 or of a composition according to clause 43 in the manufacture of a diagnostic product.

Treatment against various types of cancer using anti-PD-L1 or anti-PD-1 antibodies has been investigated in clinical trials and shown promising results. These include solid tumours such as ovarian cancer, prostate cancer, colorectal cancer, fibrosarcoma, renal cell carcinoma, melanoma (advanced and metastatic melanoma), pancreatic cancer, breast cancer, glioblastoma multiforme, lung cancer (such as non-small cell lung cancer and small cell lung cancer), head and neck cancer (such as head and neck squamous cell carcinoma), stomach cancer (gastric cancer), bladder cancer, cervical cancer, uterine cancer (uterine endometrial cancer, uterine cervical cancer), vulvar cancer, testicular cancer, penile cancer, esophageal cancer, hepatocellular carcinoma, nasopharyngeal cancer, Merkel cell carcinoma, mesothelioma, DNA mismatch repair deficient colorectal cancer, DNA mismatch repair deficient endometrial cancer, thyroid cancer, Hodgkin's lymphoma, non-Hodgkin's lymphoma (such as diffuse large B-cell lymphoma, follicular lymphoma, indolent non-Hodgkin's lymphoma, mantle cell lymphoma), leukaemia (such as chronic lymphocytic leukaemia, myeloid leukaemia, acute lymphoblastoid leukaemia, or chronic lymphoblastoid leukaemia), multiple myeloma, and peripheral T-cell lymphoma. The antibody or antigen-binding fragment thereof of the invention thus may find application in the treatment of these cancers. Tumours of these cancers are known, or expected, to contain immune cells, such as TILs, expressing PD-L1.

In particular, treatment of melanoma, colorectal cancer, breast cancer, bladder cancer, renal cell carcinoma, gastric cancer, head and neck cancer (such as squamous cell carcinoma of the head and neck), mesothelioma, lung cancer (such as non-small-cell lung cancer), ovarian cancer, Merkel-cell carcinoma, pancreatic cancer, melanoma and hepatocellular carcinoma using anti-PD-L1 antibodies has been investigated in clinical trials and shown promising results. Thus, the cancer to be treated using an antibody or antigen-binding fragment thereof of the invention may be a melanoma, colorectal cancer, breast cancer, bladder cancer, renal cell carcinoma, bladder cancer, gastric cancer, head and neck cancer (such as squamous cell carcinoma of the head and neck), mesothelioma, lung cancer (such as non-small-cell lung cancer), ovarian cancer, Merkel-cell carcinoma, pancreatic cancer, melanoma, or hepatocellular carcinoma.

Cancer may be characterised by the abnormal proliferation of malignant cancer cells. Where the application refers to a particular type of cancer, such as breast cancer, this refers to a malignant transformation of the relevant tissue, in this case a breast tissue. A cancer which originates from malignant transformation of a different tissue, e.g., ovarian tissue, may result in metastatic lesions in another location in the body, such as the breast, but is not thereby a breast cancer as referred to herein but an ovarian cancer.

The cancer may be a primary or secondary cancer. Thus, an antibody or antigen-binding fragment thereof of the invention may be for use in a method of treating cancer in a patient, wherein the cancer is a primary tumour and/or a tumour metastasis.

An antibody or antigen-binding fragment thereof of the invention may also be expected to find application in the treatment of infectious diseases, such as viral, bacterial, fungal and/or parasitic infections. Preferably, the infectious disease is a viral, bacterial or fungal disease, more preferably a viral or bacterial disease, most preferably a viral disease. The infectious disease may be chronic or acute, but is preferably chronic.

Examples of viral diseases which may be treated with an antibody or antigen-binding fragment thereof according to the invention include: human immunodeficiency virus (HIV), influenza virus, enterovirus, hepatitis B virus (HBV), hepatitis C virus (HCV), hepatitis A virus (HAV), hepatitis D virus (HDV), and hepatitis E virus (HEV), respiratory syncytial virus (RSV), herpesvirus (such as Epstein-Barr virus, herpes simplex virus 1 (HSV-1), herpes simplex virus 2 (HSV-2), cytomegalovirus (CMV)), and papillomavirus infection.

Examples of bacterial diseases which may be treated with an antibody or antigen-binding fragment thereof of the invention include: *Mycobacterium tuberculosis*, gram-negative bacteria (such as *Acinetobacter, Klebisella, Enterobacter*), gram-positive bacteria (such as *Clostridium difficile, Staphylococcus aureus*), and *Listeria* (e.g., *Listeria monocytogenes*) infection.

Examples of fungal diseases which may be treated with an antibody or antigen-binding fragment thereof of the invention include: *Aspergillus* and *Candida* infection.

Examples of parasitic diseases which may be treated with an antibody or antigen-binding fragment thereof of the invention include: Malaria, *Toxoplasma*, and *Leishmania* infection.

An antibody or antigen-binding fragment thereof according to the invention is designed to be used in methods of treatment of patients, preferably human patients. An antibody or antigen-binding fragment thereof of the invention will usually be administered in the form of a pharmaceutical composition, which may comprise at least one additional component, such as a pharmaceutically acceptable excipient. For example, a pharmaceutical composition of the invention, may comprise, in addition to the antibody or antigen-binding fragment thereof, a pharmaceutically-acceptable excipient, carrier, buffer, stabiliser or other materials well known to those skilled in the art. Such materials should be non-toxic and should not interfere with the efficacy of the antibody or antigen-binding fragment thereof. The precise nature of the carrier or other material will depend on the route of administration, which may be by injection, e.g., intravenous or subcutaneous. The antibody or antigen-binding fragment thereof may be administered intravenously, or subcutaneously.

Liquid pharmaceutical compositions generally comprise a liquid carrier such as water or physiological saline solution. For subcutaneous or intravenous injection, or injection at the site of affliction, the antibody or antigen-binding fragment thereof, or pharmaceutical composition comprising the antibody or antigen-binding fragment thereof, is preferably in the form of a parenterally acceptable aqueous solution which is pyrogen-free and has suitable pH, isotonicity and stability.

A composition comprising an antibody or antigen-binding fragment thereof according to the invention may be administered alone or in combination with other treatments, concurrently or sequentially or as a combined preparation with another therapeutic agent or agents, dependent upon the condition to be treated. For example, an antibody or fragment thereof of the invention may be administered in combination with an existing therapeutic agent for the disease to be treated, e.g., a cancer as mentioned above. For example, an antibody or fragment thereof of the invention may be administered to the patient in combination with a second anti-cancer therapy, such as chemotherapy, anti-tumour vaccination (also referred to as a cancer vaccination), radiotherapy, immunotherapy, an oncolytic virus, chimeric antigen receptor (CAR) T-cell therapy, or hormone therapy.

It is expected that the antibody or fragment thereof of the invention may act as an adjuvant in anti-cancer therapy, such as chemotherapy, anti-tumour vaccination, or radiotherapy. Without wishing to be bound by theory, it is thought that administration of the antibody or fragment thereof to the patient as part of chemotherapy, anti-tumour vaccination, or radiotherapy will trigger a greater immune response against the cancer associated antigen PD-L1, than is achieved with chemotherapy, anti-tumour vaccination, or radiotherapy alone.

A method of treating cancer in a patient may thus comprise administering to the patient a therapeutically effective amount of an antibody or fragment thereof according to the invention in combination with a chemotherapeutic agent, anti-tumour vaccine, radionuclide, immunotherapeutic agent, oncolytic virus, CAR-T cell, or agent for hormone therapy. The chemotherapeutic agent, anti-tumour vaccine, radionuclide, immunotherapeutic agent, oncolytic virus, CAR-T cell, or agent for hormone therapy is preferably a chemotherapeutic agent, anti-tumour vaccine, radionuclide, immunotherapeutic agent, oncolytic virus, CAR-T cell, or agent for hormone therapy for the cancer in question, i.e., a chemotherapeutic agent, anti-tumour vaccine, radionuclide, immunotherapeutic agent, oncolytic virus, CAR-T cell, or agent for hormone therapy which has been shown to be effective in the treatment of the cancer in question. The selection of a suitable chemotherapeutic agent, anti-tumour vaccine, radionuclide, immunotherapeutic agent, oncolytic virus, CAR-T cell, or agent for hormone therapy, which have been shown to be effective for the cancer in question, is well within the capabilities of the skilled practitioner.

For example, where the method comprises administering to the patient a therapeutically effective amount of an antibody or fragment thereof according to the invention in combination with a chemotherapeutic agent, the chemotherapeutic agent may be selected from the group consisting of: taxanes, cytotoxic antibiotics, tyrosine kinase inhibitors, PARP inhibitors, B_RAF enzyme inhibitors, alkylating agents, platinum analogues, nucleoside analogues, thalidomide derivatives, antineoplastic chemotherapeutic agents and others. Taxanes include docetaxel, paclitaxel and nab-paclitaxel; cytotoxic antibiotics include actinomycin, bleomycin, anthracyclines, doxorubicin and valrubicin; tyrosine kinase inhibitors include sunitinib, erlotinib, gefitinib, axitinib, PLX3397, imatinib, cobemitinib and trametinib; PARP inhibitors include piraparib; B-Raf enzyme inhibitors include vemurafenib and dabrafenib; alkylating agents include dacarbazine, cyclophosphamide, temozolomide; platinum analogues include carboplatin, cisplatin and oxaliplatin; nucleoside analogues include gemcitabine and azacitidine; antineoplastics include fludarabine. Other chemotherapeutic agents suitable for use in the invention include methotrexate, defactinib, entinostat, pemetrexed, capecitabine, eribulin, irinotecan, fluorouracil, and vinblastine.

Vaccination strategies for the treatment of cancers have been implemented in the clinic and discussed in detail within scientific literature (such as Rosenberg S. Development of Cancer Vaccines. ASCO Educational Book Spring: 60-62 (2000)). This mainly involves strategies to prompt the immune system to respond to various cellular markers expressed by autologous or allogenic cancer cells by using those cells as a vaccination method, both with or without granulocyte-macrophage colony-stimulating factor (GM- CSF). GM-CSF provokes a strong response in antigen presentation and works particularly well when employed with said strategies.

Where a method of the invention comprises administering to the patient a therapeutically-effective amount of an antibody or fragment thereof according to the invention in combination with an immunotherapeutic agent, the immunotherapeutic agent may be selected from the group consisting of: antibodies binding to a checkpoint inhibitor, costimulatory molecule or soluble factor, such as antibodies binding to CTLA-4, LAG-3, TIGIT, TIM-3, VISTA, CD73, CSF-1R, KIR, OX40, CD40, HEVM, TGFB, IL-10, CSF-1. Alternatively, the immunotherapeutic agent may one or more cytokines or cytokine-based therapies selected from the group consisting of IL-2, prodrug of conjugated IL2, GM-CSF, IL-7, IL-12, IL-9, IL-15, IL-18, IL-21, and type I interferon.

Administration may be in a "therapeutically effective amount", this being an amount which is sufficient to show benefit to a patient. Such benefit may be at least amelioration of at least one symptom. Thus, "treatment" of a specified disease refers to amelioration of at least one symptom. The actual amount administered, and rate and time-course of administration, will depend on the nature and severity of what is being treated, the particular patient being treated, the clinical condition of the individual patient, the cause of the disorder, the site of delivery of the composition, the type of antibody or fragment thereof, the method of administration, the scheduling of administration and other factors known to medical practitioners. Prescription of treatment, e.g., decisions on dosage etc., is within the responsibility of general practitioners and other medical doctors, and may depend on the severity of the symptoms and/or progression of a disease being treated. Appropriate doses of antibody or fragment thereof are well known in the art (Ledermann et al. (1991) Int. J. Cancer 47: 659-664; and Bagshawe et al. (1991) Antibody, Immunoconjugates and Radiopharmaceuticals 4: 915-922). Specific dosages indicated herein, or in the Physician's Desk Reference (2003) as appropriate for an antibody or fragment thereof being administered, may be used. A therapeutically-effective amount or suitable dose of an antibody or fragment thereof can be determined by comparing its in vitro activity and in vivo activity in an animal model. Methods for extrapolation of effective dosages in mice and other test animals to humans are known. The precise dose will depend upon a number of factors, including the size and location of the area to be treated, and the precise nature of the specific binding member. Treatments may be repeated at daily, twice-weekly, weekly or monthly intervals, at the discretion of the physician. Treatment may be given before and/or after surgery, and may be administered or applied directly at the anatomical site of surgical treatment.

DETAILED DESCRIPTION

The invention relates to antibodies and antigen-binding fragments thereof that comprise a CDR-based antigen-binding site for PD-L1. An antibody or antigen-binding fragment thereof of the invention may be produced by recombinant means. A "recombinant antibody" is an antibody which has been produced by a recombinantly engineered host cell. An antibody or antigen-binding fragment thereof in accordance with the invention is optionally isolated or purified.

The term "PD-L1" may refer to human PD-L1, murine, in particular mouse PD-L1, and/or cynomolgus monkey PD-L1, unless the context requires otherwise. Preferably the term "PD-L1" refers to human PD-L1, unless the context requires otherwise.

The term "antibody molecule" describes an immunoglobulin whether natural or partly or wholly synthetically produced. The antibody molecule may be human or humanised. The antibody molecule is preferably a monoclonal antibody molecule. Examples of antibodies are the immunoglobulin isotypes, such as immunoglobulin G, and their isotypic subclasses, such as IgG1, IgG2, IgG3 and IgG4, as well as fragments thereof. The four human subclasses (IgG1, IgG2, IgG3 and IgG4) each contain a different heavy chain; but they are highly homologous and differ mainly in the hinge region and the extent to which they activate the host immune system. IgG1 and IgG4 contain two inter-chain disulphide bonds in the hinge region, IgG2 has 4 and IgG3 has 11 inter-chain disulphide bonds.

The terms "antibody" and "antibody molecule", as used herein, includes antibody fragments, such as Fab and scFv fragments, provided that said fragments comprise a CDR-based antigen binding site for PD-L1. Unless the context requires otherwise, the terms "antibody" or "antibody molecule", as used herein, is thus equivalent to "antibody or antigen-binding fragment thereof".

Antibodies are immunoglobulins, which have the same basic structure consisting of two heavy and two light chains forming two Fab arms containing identical domains that are attached by a flexible hinge region to the stem of the antibody, the Fc domain, giving the classical 'Y' shape. The Fab domains consist of two variable and two constant domains, with a variable heavy (VH) and constant heavy 1 (CH1) domain on the heavy chain and a variable light (VL) and constant light (CL) domain on the light chain. The two variable domains (VH and VL) form the variable fragment (Fv), which provides the CDR-based antigen specificity of the antibody, with the constant domains (CH1 and VL) acting as a structural framework. Each variable domain contains three hypervariable loops, known as complementarity determining regions (CDRs). On each of the VH and VL the three CDRs (CDR1, CDR2, and CDR3) are flanked by four less-variable framework (FR) regions (FR1, FW2, FW3 and FW4) to give a structure FW1-CDR1-FW2-CDR2-FW3-CDR3-FW4. The CDRs provide a specific antigen recognition site on the surface of the antibody.

Both Kabat and ImMunoGeneTics (IMGT) numbering nomenclature is used herein. Generally, unless otherwise indicated (explicitly or by context) amino acid residues are numbered herein according to the Kabat numbering scheme (Kabat et al., 1991). For those instances when IMGT numbering is used, amino acid residues are numbered herein according to the ImMunoGeneTics (IMGT) numbering scheme. The IMGT numbering scheme is described in Lefranc et al., 2005.

When the sequences are defined by IMGT nomenclature, the invention provides:

1A. An antibody or antigen-binding fragment thereof, capable of binding specifically to PD-L1 comprising a variable heavy (VH) domain comprising heavy chain CDRs: HCDR1, HCRD2 and HCDR3, each flanked by framework (FW) regions, characterised in that the amino acid sequence of HCDR1 is GYX$_1$FTSYG (SEQ ID NO: 67); the amino acid sequence of HCDR2 is ISAYX$_2$X$_3$X$_4$X$_5$ (SEQ ID NO: 68); and the amino acid sequence of HCDR3 is ARDLFPTIFGVSYYYY (SEQ ID NO: 69); wherein X$_1$ is P or T; X$_2$ is S, N or G, preferably S or N; X$_3$ is G or S; X$_4$ is G, N or S, preferably G or N; and X$_5$ is T or A, preferably T, and wherein the sequences are defined by the ImMunoGeneTics (IMGT) nomenclature.

2A. An antibody or antigen-binding fragment thereof according to clause 1A, wherein the sequence $X_2X_3X_4X_5$ (SEQ ID NO: 4) (residues 62-65) of HCDR2 is selected from SGGT (SEQ ID NO: 5), NSNT (SEQ ID NO: 6), GGST (SEQ ID NO: 7) and SGNA (SEQ ID NO: 8). (IMGT nomenclature).

3A. An antibody or antigen-binding fragment thereof according to clause 1A or 2A, wherein $X_1$ is P and $X_2X_3X_4X_5$ of HCDR2 is SGGT (SEQ ID NO: 5) (IMGT nomenclature).

4A. An antibody or antigen-binding fragment thereof according to any of clauses 1A to 3A comprising a variable light (VL) domain comprising a LCDR1, LCDR2 and LCDR3, characterised in that:

(a) the VL is a kappa VL and the amino acid sequence of LCDR1 is QSIX$_6$X$_7$R (SEQ ID NO: 70); the amino acid sequence of LCDR2 is EAS (SEQ ID NO: 71); and the amino acid sequence of LCDR3 is QQX$_8$X$_9$X$_{10}$TPYT (SEQ ID NO: 72), QQX$_8$X$_9$X$_{10}$TPRVT (SEQ ID NO: 73), QQX$_8$X$_9$X$_{10}$FPRVS (SEQ ID NO: 74), or QQX$_8$X$_9$X$_{10}$WPRT (SEQ ID NO: 75); wherein $X_6$ is G or S; $X_7$ is N or G; $X_8$ is S or A; $X_9$ is Y or N; and $X_{10}$ is S or T; or, (b) the VL is a lambda VL and the amino acid sequence of LCDR1 is SSDVGGYNX$_{11}$ (SEQ ID NO: 76), the amino acid sequence of LCDR2 is EVT (SEQ ID NO: 77) and the amino acid sequence of LCDR3 is SSFKRGSTLVV (SEQ ID NO: 14); wherein $X_{11}$ is Y or S; and wherein the sequences are defined by IMGT nomenclature.

5A. An antibody antigen-binding fragment thereof according to any of clauses 1A to 4A, comprising an antigen-binding site comprising:

(a) the CDRs of antibody G1AA/E12v2;
(b) the CDRs of antibody G1AA/G12v2;
(c) the CDRs of antibody G1AA/E05v2;
(d) the CDRs of antibody G1/887_04_E12;
(e) the CDRs of antibody G1/887_04_G12;
(f) the CDRs of antibody G1/894_08_E05;
(g) the CDRs of antibody G1/894_08_A05;
(h) the CDRs of antibody G1AA/lambdav3; or
(i) the CDRs of antibody G1/280_02_G02_NS;
(j) the CDRs of antibody G1/280_02_G02;
wherein the sequences are defined according to the ImMunoGeneTics (IMGT) numbering scheme It is possible to take monoclonal and other antibodies and use techniques of recombinant DNA technology to produce other antibodies or chimeric molecules which generally retain the specificity of the original antibody. Such techniques may involve introducing the CDRs into a different immunoglobulin framework, or grafting variable regions onto a different immunoglobulin constant region. Introduction of the CDRs of one immunoglobulin into another immunoglobulin is described for example in EP-A-184187, GB2188638A or EP-A-239400. Alternatively, a hybridoma or other cell producing an antibody molecule may be subject to genetic mutation or other changes, which may or may not alter the binding specificity of antibodies produced.

As antibodies can be modified in a number of ways, the term "antibody" should be construed as covering antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

An example of an antibody fragment comprising both CDR sequences and CH3 domain is a minibody, which comprises a scFv joined to a CH3 domain (Hu et al., 1996).

An antibody or antigen-binding fragment of the invention binds to PD-L1, in particular human PD-L1. Binding in this context may refer to specific binding. The term "specific" may refer to the situation in which the antibody molecule will not show any significant binding to molecules other than its specific binding partner(s), here PD-L1. The term "specific" is also applicable where the antibody molecule is specific for particular epitopes, such as epitopes on PD-L1, that are carried by a number of antigens in which case the antibody molecule will be able to bind to the various antigens carrying the epitope.

Amino acids may be referred to by their one letter or three letter codes, or by their full name. The one and three letter codes, as well as the full names, of each of the twenty standard amino acids are set out below.

| Amino acid | One letter code | Three letter code |
| --- | --- | --- |
| alanine | A | Ala |
| arginine | R | Arg |
| asparagine | N | Asn |
| aspartic acid | D | Asp |
| cysteine | C | Cys |
| glutamic acid | E | Glu |
| glutamine | Q | Gln |
| glycine | G | Gly |
| histidine | H | His |
| isoleucine | I | Ile |
| leucine | L | Leu |
| lysine | K | Lys |
| methionine | M | Met |
| phenylalanine | F | Phe |
| proline | P | Pro |
| serine | S | Ser |
| threonine | T | Thr |
| tryptophan | W | Trp |
| tyrosine | Y | Tyr |
| valine | V | Val |

Amino Acids, One and Three-Letter Codes

In preferred embodiments, the PD-L1 antibody of the invention comprises the HCDR3 sequence of E12v2 (SEQ ID NO: 3); it is preferred that the antibody further comprises the HCDR2 sequence of E12v2 (SEQ ID NO: 18); it is preferred that the PD-L1 antibody of the invention yet further comprises the HCDR1 sequence of E12v2 (SEQ ID NO: 1). In preferred embodiments the HCDR2 sequence is HCDR2 sequence of E12v2 (SEQ ID NO: 18) and the amino acid at position 28 in the VH (Kabat) is proline. In particularly preferred embodiments the PD-L1 antibody of the invention comprises the HCDR3 sequence of SEQ ID NO: 3, the HCDR2 sequence of SEQ ID NO: 18 and the amino acid at position 28 in the VH (Kabat) is proline. In more particularly preferred embodiments the PD-L1 antibody of the invention comprises the HCDR3 sequence of SEQ ID NO: 3, the HCDR2 sequence of SEQ ID NO: 18, and the HCDR1 sequence of SEQ ID NO: 1 and the amino acid at position 28 in the VH (Kabat) is proline.

Antibodies of the invention may comprise one or more, e.g., 1, 2, 3, 4, 5, 6, 7, 8, 9 or 10 further amino acid modifications in the VH and/or VL sequences, provided that functional properties of the antibody are retained.

A modification may be an amino acid substitution, deletion or insertion. Preferably, the modification is a substitution.

In preferred embodiments in which one or more amino acids are substituted with another amino acid, the substitutions may conservative substitutions, for example according to the following chart. In some embodiments, amino acids in the same category in the middle column are substituted for one another, i.e. a non-polar amino acid is substituted with another non-polar amino acid, for example. In some embodiments, amino acids in the same line in the rightmost column are substituted for one another.

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

In some embodiments, substitution(s) may be functionally conservative. That is, in some embodiments the substitution may not affect (or may not substantially affect) one or more functional properties (e.g., binding affinity) of the antibody molecule comprising the substitution as compared to the equivalent unsubstituted antibody molecule.

In a preferred embodiment, a PD-L1 antibody of the invention may comprise a VH and/or VL domain sequence with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the VH and/or VL sequences of the invention set forth herein.

In a preferred embodiment, an antibody of the invention comprises the HCDR3 domain of E12v2 set forth in SEQ ID NO: 3.

In another preferred embodiment, an antibody of the invention comprises the VH domain of E12v2 set forth in SEQ ID NO: 27 or a VH domain with an amino acid sequence which has at least 95%, at least 96%, at least 97%, at least 98%, or at least 99% sequence identity to the sequence set forth in SEQ ID NO: 27.

In a preferred embodiment, an antibody of the invention comprises a VH domain comprising the HCDR3 set forth in SEQ ID NO: 3 and the VH domain has an amino acid sequence with at least 70%, at least 75%, at least 80%, at least 85%, at least 90%, at least 95%, at least 96%, at least 97%, at least 98%, or at least 99% sequence identity to the sequence set forth in SEQ ID NO: 27.

In a preferred embodiment, an antibody of the invention comprises a VH domain comprising the HCDR3 of E12v2 set forth in SEQ ID NO: 3 and a HCDR2 selected from those set forth in SEQ ID NO: 18, 23 or 24 and the VH domain has an amino acid sequence with at least 70%, at least 75%, at least 80%, at least 85%, at least 90%, at least 95%, at least 96%, at least 97%, at least 98%, or at least 99% sequence identity to the sequence set forth in SEQ ID NO: 27.

In a preferred embodiment, an antibody of the invention comprises a VH domain comprising the HCDR3 of E12v2 set forth in SEQ ID NO: 3, a HCDR2 domain selected from those set forth in SEQ ID NO: 18, 23 or 24, a proline at position 28, and the VH domain has an amino acid sequence with at least 70%, at least 75%, at least 80%, at least 85%, at least 90%, at least 95%, at least 96%, at least 97%, at least 98%, or at least 99% sequence identity to the sequence set forth in SEQ ID NO: 27.

In a preferred embodiment, an antibody of the invention comprises a VL domain comprising a VL domain of E12v2 set forth in SEQ ID NO: 28 or an amino acid sequence with at least 70%, at least 75%, at least 80%, at least 85%, at least 90%, at least 95%, at least 96%, at least 97%, at least 98%, or at least 99% sequence identity to the sequence set forth in SEQ ID NO: 28.

Sequence identity is commonly defined with reference to the algorithm GAP (Wisconsin GCG package, Accelerys Inc, San Diego USA). GAP uses the Needleman and Wunsch algorithm to align two complete sequences, maximising the number of matches and minimising the number of gaps. Generally, default parameters are used, with a gap creation penalty equaling 12 and a gap extension penalty equaling 4. Use of GAP may be preferred but other algorithms may be used, e.g., BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), or the TBLASTN program, of Altschul et al. (1990) supra, generally employing default parameters. In particular, the psi-Blast algorithm (Nucl. Acids Res. (1997) 25 3389-3402) may be used. Sequence identity may be defined using the Bioedit, ClustalW algorithm.

The antibody may comprise a CH2 domain. The CH2 domain is preferably located at the N-terminus of the CH3 domain, as in the case in a human IgG molecule. The CH2 domain of the antibody is preferably the CH2 domain of human IgG1, IgG2, IgG3, or IgG4, more preferably the CH2 domain of human IgG1. The sequences of human IgG domains are known in the art.

The antibody may comprise an immunoglobulin hinge region, or part thereof, at the N-terminus of the CH2 domain. The immunoglobulin hinge region allows the two CH2-CH3 domain sequences to associate and form a dimer. Preferably, the hinge region, or part thereof, is a human IgG1, IgG2, IgG3 or IgG4 hinge region, or part thereof. More preferably, the hinge region, or part thereof, is an IgG1 hinge region, or part thereof.

The sequence of the CH3 domain, is not particularly limited. Preferably, the CH3 domain is a human immunoglobulin G domain, such as a human IgG1, IgG2, IgG3, or IgG4 CH3 domain, most preferably a human IgG1 CH3 domain.

An antibody of the invention may comprise a human IgG1, IgG2, IgG3, or IgG4 constant region. The sequences of human IgG1, IgG2, IgG3, or IgG4 CH3 domains are known in the art.

The heavy chain of the antibody molecule may optionally comprise an additional lysine residue (K) at the C-terminus of the heavy chain CH3 domain sequence.

Immunoglobulins are known to have a modular architecture comprising discrete domains, which can be combined in a multitude of different ways to create multispecific, e.g., bispecific, trispecific, or tetraspecific antibody formats. Exemplary multispecific antibody formats are described in Spiess et al., 2015 and Kontermann, 2012, for example. The antibodies of the invention may be employed in such multispecific formats.

For example, an antibody of the invention may be a heterodimeric antibody molecule, such as a heterodimeric complete immunoglobulin molecule, or a fragment thereof. In this case, one part of the antibody will have a sequence or sequences as described herein. For example, where the antibody of the invention is a bispecific heterodimeric antibody molecule, the antibody may comprise a heavy chain and light chain as described herein paired with a heavy chain and light chain comprising a VH domain and a VL domain, respectively, which bind an antigen other than PD-L1. Techniques for preparing heterodimeric antibodies are known in the art and include knobs-into-holes (KIHs) technology, which involves engineering the CH3 domains of an antibody molecule to create either a "knob" or a "hole" to promote chain heterodimerization. Alternatively, heterodimeric antibodies can be prepared through the introduction of charge pairs into the antibody molecule to avoid homodimerization of CH3 domains by electrostatic repulsion and to direct heterodimerization by electrostatic attraction. Examples of heterodimeric antibody formats include CrossMab, mAb-Fv, SEED-body, and KIH IgG.

Alternatively, a multispecific antibody molecule may comprise a complete immunoglobulin molecule or a fragment thereof and an additional antigen-binding moiety or moieties. The antigen-binding moiety may for example be an Fv, scFv or single domain antibody, and may be fused to the complete immunoglobulin molecule or a fragment thereof. Examples of multispecific antibody molecules comprising additional antigen-binding moieties fused to a complete immunoglobulin molecule include DVD-IgG, DVI-IgG, scFv4-IgG, IgG-scFv, and scFv-IgG molecules (Spiess et al., 2015; FIG. 1). Examples of multispecific antibody molecules comprising additional antigen-binding moieties fused to an immunoglobulin fragment include BiTE molecules, diabodies, and DART molecules, for example (Spiess et al., 2015; FIG. 1). Other suitable formats would be readily apparent to the skilled person.

In addition to the CDR-based PD-L1-binding site, e.g., in the VH of an antibody, the antibody may further comprise one or more additional antigen-binding sites to create a bi- or multi-specific molecule. The antibody may comprise a CH3-based or CH2-based antigen-binding site. CDR-based antigen binding sites are found in naturally-occurring immunoglobulin molecules and their structure is well-known in the art. Where the antibody or antigen-binding fragment thereof comprises a CDR-based antigen binding site, the antibody or antigen-binding fragment thereof is preferably an antibody molecule. The bi- or multispecific antibody molecule may comprise a CDR-based antigen binding site for PD-L1 and a CH3-based or CH2-based binding site for a second target. In a preferred embodiment, the antibody molecule is a human immunoglobulin G molecule, such as a human IgG1, IgG2, IgG3 or IgG4 molecule, more preferably a human IgG1 molecule.

Optionally, antibody or antigen-binding fragments thereof of the invention may have a second antigen-binding site located in a constant domain, preferably CH3 or CH2, of the antibody.

Alternatively or additionally, an antibody or antigen-binding fragment thereof of the invention may comprise a further CDR-based antigen-binding site (e.g., as formed by a VH and a VL) for a second or third target antigen. Thus, an antibody molecule, or antigen-binding fragment thereof, according to the invention may be a multispecific, preferably a bispecific, molecule comprising a second antigen-binding site.

The second antigen binding site, when present, may be a CH3-based or CH2-based antigen-binding site or a CDR-based antigen-binding site, and may bind an antigen such that the binding of said antigen is expected to be beneficial in the context of cancer treatment.

The antibody molecule may be a mAb² (TM) bispecific antibody. A mAb² bispecific antibody, as referred to herein, is an IgG immunoglobulin which includes a CDR-based antigen binding site in each of its variable regions and at least one antigen binding site in a constant domain of the antibody molecule.

In one embodiment, when the antibody or antigen-binding fragment thereof comprises a second antigen-binding site, e.g., a CH3-based, CH2-based or CDR-based antigen-binding site, the second antigen binding site may bind to a non-redundant and complementary inhibitory checkpoint molecule, such as CTLA-4, LAG-3, TIGIT, TIM-3, VISTA, CD73, CSF-1R, KIR, B7-H3, B7-H4, 2B4, NKG2A, CD47, SIRPa, BTLA, CCR4, CD200R, or TGFbeta.

The inhibition of the PD-1/PD-L1 axis and the stimulation of costimulatory molecules represent complementary strategies to enhance immune responses in human patients. The reversal of T cell exhaustion through checkpoint blockade may allow these cells to be activated more potently and to develop full anti-tumour activity. Thus, in another embodiment, an antibody or antigen-binding fragment thereof of the invention may comprise a second antigen-binding site, e.g., a CH3-based, CH2-based or CDR-based antigen-binding site, and the second antigen binding site may bind to, and be an agonist for, a costimulatory molecule expressed by T cells such as OX40, ICOS, CD40, HVEM, NKG2D, or TNFR2.

In a further embodiment, the antibody or antigen-binding fragment thereof of the invention may comprise a second antigen-binding site, e.g., a CH3-based, CH2-based or CDR-based antigen-binding site, and the second antigen-binding site may bind to a tumour associated antigen (TAA). Such antibody or antigen-binding fragment thereof is expected to result in tumour-specific T cell responses through localised immune activation. Examples of TAAs are c-Met, B7-H3, B7-H4, EGFR, HER-2, EPCAM, CEACAM, FAP, VEGF, MSLN, GPC3, CD38, CD19, and CD20.

As detailed above, infectious diseases show many parallels with oncology. The role of PD-L1 in immune regulation could be harnessed to maximise the immune response against pathogens. Immunomodulation in the context of treatment of infectious diseases is an emerging area of medicine and early reviews suggest that PD-L1 blockade may improve biological responses to infection, in particular, helping to counteract T-cell exhaustion, manage immune-mediated clearance, and generate long-term immunity (Wykes and Lewin, 2017).

In some infectious diseases, exaggerated pro-inflammatory responses and suboptimal antigen-specific T-cell activity are the causes of severe tissue damage (Rao et al., 2017). Without wishing to be bound by theory, it is thought that the use of an antibody or antigen-binding fragment thereof of the invention comprising a second antigen-binding site may find application in the treatment of these diseases by localising beneficial immunomodulatory activity to the pathogen environment.

Alternatively, use of an antibody or antigen-binding fragment thereof of the invention comprising a second antigen-binding site which binds to an immune cell target, either for agonism or antagonism, may result in increased T-cell specificity and activity.

Thus, in one embodiment, where the antibody or antigen-binding fragment thereof comprises a second antigen-binding site, the second antigen binding site may bind to an immune cell target, such as PD-1, PD-L2, CTLA-4, LAG-3, TIGIT, TIM3, OX40, CD40, ICOS, CD28, or CD80.

Alternatively, where the antibody or antigen-binding fragment thereof comprises a second antigen-binding site, the second antigen-binding site may bind to a pathogenic target, namely an antigen expressed by a human pathogen. The pathogen may be a virus, bacterium, fungus, or parasite. Preferably the pathogen is a virus, bacterium or fungus. More preferably, the pathogen is a virus or bacterium. Most preferably, the pathogen is a virus. Examples of viral antigens include proteins p24, gp120, and gp41 expressed by human immunodeficiency virus (HIV), hepatitis B surface antigen (HBsAg) expressed by hepatitis B virus (HBV), and hemagglutinin and neuraminidase expressed by influenza virus. Examples of bacterial antigens include Rv1733, Rv2389 and Rv2435n expressed by *Mycobacterium tuberculosis*.

In some embodiments, the second antigen-binding site of the antibody of the invention may not bind to OX40. In addition, or alternatively, the second antigen-binding site of an antibody of the invention may not bind to CD137. In addition, or alternatively, the second antigen-binding site of an antibody of the invention may not bind to CD27. In addition, or alternatively, the second antigen-binding site of an antibody of the invention may not bind to glucocorticoid-induced TNFR-related protein (GITR). In addition, or alternatively, the second antigen-binding site of an antibody of the invention may not bind to lymphocyte-activation gene 3 (LAG-3). In addition, or alternatively, the second antigen-binding site of an antibody of the invention may not bind to Inducible T-cell COStimulator (ICOS).

An antibody of the invention may be conjugated to an immune system modulator, cytotoxic molecule, radioisotope or detectable label. The immune system modulator may be a cytotoxic molecule, such as a cytokine.

The antibody molecule may be conjugated to a bioactive molecule or a detectable label. In this case, the antibody molecule may be referred to as a conjugate. Such conjugates find application in the treatment and/or diagnosis of diseases as described herein.

For example, the bioactive molecule may be an immune system modulator, such as a cytokine, preferably a human cytokine. For example, the cytokine may be a cytokine which stimulates T cell activation and/or proliferation. Examples of cytokines for conjugation to the antibody molecule include IL-2, IL-10, IL-12, IL-15, IL-21, GM-CSF and IFN-gamma.

Alternatively, the bioactive molecule may be a ligand trap, such as a ligand trap of a cytokine, e.g., of TGF-beta or IL-6.

Suitable detectable labels which may be conjugated to antibody molecules are known in the art and include radioisotopes such as iodine-125, iodine-131, yttrium-90, indium-111 and technetium-99; fluorochromes, such as fluorescein, rhodamine, phycoerythrin, Texas Red and cyanine dye derivatives for example, Cy7 and Alexa750; chromogenic dyes, such as diaminobenzidine; latex beads; enzyme labels such as horseradish peroxidase; phosphor or laser dyes with spectrally isolated absorption or emission characteristics; and chemical moieties, such as biotin, which may be detected via binding to a specific cognate detectable moiety, e.g., labelled avidin.

The antibody of the invention may be conjugated to the bioactive molecule or detectable label by means of any suitable covalent or non-covalent linkage, such as a disulphide or peptide bond. Where the bioactive molecule is a cytokine, the cytokine may be joined to the antibody molecule by means of a peptide linker. Suitable peptide linkers are known in the art and may be 5 to 25, 5 to 20, 5 to 15, 10 to 25, 10 to 20, or 10 to 15 amino acids in length.

In some embodiments, the bioactive molecule may be conjugated to the antibody by a cleavable linker. The linker may allow release of the bioactive molecule from the antibody at a site of therapy. Linkers may include amide bonds (e.g., peptidic linkers), disulphide bonds or hydrazones. Peptide linkers for example may be cleaved by site-specific proteases, disulphide bonds may be cleaved by the reducing environment of the cytosol and hydrazones may be cleaved by acid-mediated hydrolysis.

The conjugate may be a fusion protein comprising the antibody of the invention and the bioactive molecule. In this case the bioactive molecule may be conjugated to the antibody by means of a peptide linker or peptide bond. Where the antibody is a multichain molecule, such as where the antibody molecule is or comprises an Fcab or is a mAb$^2$, the bioactive molecule may be conjugated to one or more chains of the antibody molecule. For example, the bioactive molecule may be conjugated to one or both of the heavy chains of the mAb$^2$ molecule. Fusion proteins have the advantage of being easier to produce and purify, facilitating the production of clinical-grade material.

The invention also provides a nucleic acid or set of nucleic acids encoding an antibody or antigen-binding fragment of the invention, as well as a vector comprising such a nucleic acid or set of nucleic acids.

Where the nucleic acid encodes the VH and VL domain, or heavy and light chain, of an antibody molecule of the invention, the two domains or chains may be encoded on two separate nucleic acid molecules.

An isolated nucleic acid molecule may be used to express an antibody molecule of the invention. The nucleic acid will generally be provided in the form of a recombinant vector for expression. Another aspect of the invention thus provides a vector comprising a nucleic acid as described above. Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in a host cell. Vectors may be plasmids, viral e.g., phage, or phagemid, as appropriate.

A nucleic acid molecule or vector as described herein may be introduced into a host cell. Techniques for the introduction of nucleic acid or vectors into host cells are well established in the art and any suitable technique may be employed. A range of host cells suitable for the production of recombinant antibody molecules are known in the art, and include bacterial, yeast, insect or mammalian host cells. A preferred host cell is a mammalian cell, such as a CHO, NS0, or HEK cell, for example a HEK293 cell.

A recombinant host cell comprising a nucleic acid or the vector of the invention is also provided. Such a recombinant host cell may be used to produce an antibody of the invention. Thus, also provided is a method of producing an antibody of the invention, the method comprising culturing the recombinant host cell under conditions suitable for production of the antibody. The method may further comprise a step of isolating and/or purifying the antibody molecule.

Thus the invention provides a method of producing an antibody molecule of the invention comprising expressing a nucleic acid encoding the antibody molecule in a host cell and optionally isolating and/or purifying the antibody molecule thus produced. Methods for culturing host cells are well-known in the art. Techniques for the purification of recombinant antibody molecules are well-known in the art and include, for example HPLC, FPLC or affinity chromatography, e.g., using Protein A or Protein L. In some embodiments, purification may be performed using an affinity tag on antibody molecule. The method may also comprise formulating the antibody molecule into a pharmaceutical composition, optionally with a pharmaceutically-acceptable excipient or other substance as described below.

The antibodies of the invention are expected to find application in therapeutic applications, in particular therapeutic applications in humans, such as cancer treatment and the treatment of infectious diseases. Thus, also provided is a composition such as a pharmaceutical composition comprising an antibody molecule according to the invention and an excipient, such as a pharmaceutically-acceptable excipient.

The invention further provides an antibody molecule of the invention, for use in a method of treatment. Also provided is a method of treating a patient, wherein the method comprises administering to the patient a therapeutically-effective amount of an antibody molecule according to the invention. Further provided is the use of an antibody molecule according to the invention for use in the manufacture of a medicament. A patient, as referred to herein, is preferably a human patient.

The invention also provides an antibody molecule of the invention, for use in a method of treating cancer in a patient. Also provided is a method of treating cancer in a patient, wherein the method comprises administering to the patient a therapeutically-effective amount of an antibody molecule according to the invention. Further provided is the use of an antibody molecule according to the invention for use in the manufacture of a medicament for the treatment of cancer in a patient. The treatment may further comprise administering to the patient a second anti-cancer agent and/or therapy, such as an anti-tumour vaccine and/or a chemotherapeutic agent. The second anti-cancer agent and/or therapy may be administered to the patient simultaneously, separately, or sequentially to the antibody molecule of the invention.

In another aspect, the invention relates to an antibody that binds to PD-L1 for use in a) treating cancer, b) delaying progression of cancer, c) prolonging the survival of a patient suffering from cancer, or d) stimulating a cell-mediated immune response.

The invention also provides an antibody of the invention, for use in a method of treating an infectious disease in a patient. Also provided is a method of treating an infectious disease in a patient, wherein the method comprises administering to the patient a therapeutically-effective amount of an antibody according to the invention. Further provided is the use of an antibody according to the invention for use in the manufacture of a medicament for the treatment of an infectious disease in a patient. The treatment may further comprise administering to the patient a second agent and/or therapy for the treatment of the infectious disease. The second agent and/or therapy may be administered to the patient simultaneously, separately, or sequentially to the antibody or antigen-binding fragment thereof or antibody molecule of the invention.

The antibody molecules as described herein may thus be useful for therapeutic applications, in particular in the treatment of cancer. In addition, the antibody molecules are expected to be useful in the treatment of infectious diseases, such as persistent infectious diseases.

An antibody molecule as described herein may be used in a method of treatment of the human or animal body. Related aspects of the invention provide;

(i) an antibody molecule described herein for use as a medicament,
(ii) an antibody molecule described herein for use in a method of treatment of a disease or disorder,
(iii) the use of an antibody molecule described herein in the manufacture of a medicament for use in the treatment of a disease or disorder; and,
(iv) a method of treating a disease or disorder in an individual, wherein the method comprises administering to the individual a therapeutically effective amount of an antibody molecule as described herein.

The individual may be a patient, preferably a human patient.

Treatment may be any treatment or therapy in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, ameliorating, delaying, abating or arresting one or more symptoms and/or signs of the condition or prolonging survival of an individual or patient beyond that expected in the absence of treatment.

Treatment as a prophylactic measure (i.e., prophylaxis) is also included. For example, an individual susceptible to or at risk of the occurrence or re-occurrence of a disease such as cancer may be treated as described herein. Such treatment may prevent or delay the occurrence or re-occurrence of the disease in the individual.

A method of treatment as described may be comprise administering at least one further treatment to the individual in addition to the antibody molecule. The antibody molecule described herein may thus be administered to an individual alone or in combination with one or more other treatments. Where the antibody molecule is administered to the individual in combination with another treatment, the additional treatment may be administered to the individual concurrently with, sequentially to, or separately from the administration of the antibody molecule. Where the additional treatment is administered concurrently with the antibody molecule, the antibody molecule and additional treatment may be administered to the individual as a combined preparation. For example, the additional therapy may be a known therapy or therapeutic agent for the disease to be treated.

Whilst an antibody molecule may be administered alone, antibody molecules will usually be administered in the form of a pharmaceutical composition, which may comprise at least one component in addition to the antibody molecule. Another aspect of the invention therefore provides a pharmaceutical composition comprising an antibody molecule as described herein. A method comprising formulating an antibody molecule into a pharmaceutical composition is also provided.

Pharmaceutical compositions may comprise, in addition to the antibody molecule, a pharmaceutically acceptable excipient, carrier, buffer, stabilizer or other materials well known to those skilled in the art. The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. The precise nature of the carrier or other material will depend on the route of administration, which may be by infusion, injection or any other suitable route, as discussed below.

For parenteral, for example subcutaneous or intravenous administration, e.g., by injection, the pharmaceutical composition comprising the antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g., Zn-protein complexes); and/or non-ionic surfactants, such as TWEEN™, PLURONICS™ or polyethylene glycol (PEG).

In some embodiments, antibody molecules may be provided in a lyophilised form for reconstitution prior to administration. For example, lyophilised antibody molecules may be re-constituted in sterile water or saline prior to administration to an individual.

Administration may be in a "therapeutically effective amount", this being sufficient to show benefit to an individual. The actual amount administered, and rate and time-course of administration, will depend on the nature and severity of what is being treated, the particular individual being treated, the clinical condition of the individual, the cause of the disorder, the site of delivery of the composition, the type of antibody molecule, the method of administration, the scheduling of administration and other factors known to medical practitioners. Prescription of treatment, e.g., decisions on dosage etc., is within the responsibility of general practitioners and other medical doctors, and may depend on the severity of the symptoms and/or progression of a disease being treated. Appropriate doses of antibody molecules are well known in the art (Ledermann et al., 1991; Bagshawe et al., 1991). Specific dosages indicated herein, or in the Physician's Desk Reference (2003) as appropriate for an antibody molecule being administered, may be used. A therapeutically effective amount or suitable dose of an antibody molecule can be determined by comparing in vitro activity and in vivo activity in an animal model. Methods for extrapolation of effective dosages in mice and other test animals to humans are known. The precise dose will depend upon a number of factors, including whether the size and location of the area to be treated, and the precise nature of the antibody molecule.

A typical antibody dose is in the range 100 µg to 1 g for systemic applications, and 1 µg to 1 mg for topical applications. An initial higher loading dose, followed by one or more lower doses, may be administered. This is a dose for a single treatment of an adult individual, which may be proportionally adjusted for children and infants, and also adjusted for other antibody formats in proportion to molecular weight.

Treatments may be repeated at daily, twice-weekly, weekly or monthly intervals, at the discretion of the physician. The treatment schedule for an individual may be dependent on the pharmocokinetic and pharmacodynamic properties of the antibody composition, the route of administration and the nature of the condition being treated.

Treatment may be periodic, and the period between administrations may be about two weeks or more, e.g., about three weeks or more, about four weeks or more, about once a month or more, about five weeks or more, or about six weeks or more. For example, treatment may be every two to four weeks or every four to eight weeks. Suitable formulations and routes of administration are described above.

In a preferred embodiment, an antibody molecule as described herein may be for use in a method of treating cancer.

Cancer may be characterised by the abnormal proliferation of malignant cancer cells. Where a particular type of cancer, such as breast cancer, is referred to, this refers to an abnormal proliferation of malignant cells of the relevant tissue, such as breast tissue. A secondary cancer which is located in the breast but is the result of abnormal proliferation of malignant cells of another tissue, such as ovarian tissue, is not a breast cancer as referred to herein but an ovarian cancer.

The cancer may be a primary or a secondary cancer. Thus, an antibody molecule as described herein may be for use in a method of treating cancer in an individual, wherein the cancer is a primary tumour and/or a tumour metastasis.

A tumour of a cancer to be treated using an antibody molecule as described herein may comprise cells that express PD-L1, e.g., on their cell surface. In one embodiment, the tumour may have been determined to comprise cells that express PD-L1. Methods for determining the expression of an antigen on a cell surface are known in the art and include, for example, flow cytometry.

For example, the cancer to be treated using an antibody molecule as described herein may be selected from the group consisting of leukaemias, such as acute myeloid leukaemia (AML), chronic myeloid leukaemia (CML), acute lymphoblastic leukaemia (ALL) and chronic lymphocytic leukaemia (CLL); lymphomas, such as Hodgkin lymphoma, non-Hodgkin lymphoma and multiple myeloma; and solid cancers, such as sarcomas (e.g., soft tissue sarcomas), skin cancer (e.g., Merkel cell carcinoma), melanoma, bladder cancer (e.g., urothelial carcinoma), brain cancer (glioblastoma multiforme), breast cancer, uterine/endometrial cancer, ovarian cancer (e.g., ovarian serous cystadenoma), prostate cancer, lung cancer (e.g., non-small cell lung carcinoma (NSCLC) and small cell lung cancer (SCLC)), colorectal cancer (e.g., colorectal adenocarcinoma), cervical cancer (e.g., cervical squamous cell cancer and cervical adenocarcinoma), liver cancer (e.g., hepatocellular carcinoma), head and neck cancer (e.g., head and neck squamous-cell carcinoma), oesophageal cancer, pancreatic cancer, renal cancer (e.g., renal cell cancer), adrenal cancer, stomach cancer (e.g., stomach adenocarcinoma), testicular cancer, cancer of the gall bladder and biliary tracts (e.g., cholangiocarcinoma), thyroid cancer, thymus cancer, bone cancer, and cerebral cancer.

In a preferred embodiment, the cancer to be treated using an antibody molecule as described herein is a solid cancer. More preferably, the cancer to be treated using an antibody molecule as described herein is a solid cancer selected from the group consisting of: sarcoma, melanoma, bladder cancer, brain cancer, breast cancer, ovarian cancer, uterine/endometrial cancer, prostate cancer, lung cancer, colorectal cancer, cervical cancer, liver cancer, head and neck cancer, pancreatic cancer, renal cancer and stomach cancer.

In the context of cancer, treatment may include inhibiting cancer growth, including complete cancer remission, and/or inhibiting cancer metastasis, as well as inhibiting cancer recurrence. Cancer growth generally refers to any one of a number of indices that indicate change within the cancer to a more developed form. Thus, indices for measuring an inhibition of cancer growth include a decrease in cancer cell survival, a decrease in tumour volume or morphology (for example, as determined using computed tomographic (CT), sonography, or other imaging method), a delayed tumour growth, a destruction of tumour vasculature, improved performance in delayed hypersensitivity skin test, an increase in the activity of anti-cancer immune cells or other anti-cancer immune responses, and a decrease in levels of tumour-specific antigens. Activating or enhancing immune responses to cancerous tumours in an individual may improve the capacity of the individual to resist cancer growth, in particular growth of a cancer already present in the subject and/or decrease the propensity for cancer growth in the individual.

In the context of cancer treatment, an antibody molecule as described herein may be administered to an individual in combination with another anti-cancer therapy or therapeutic agent, such as an anti-cancer therapy or therapeutic agent which has been shown to be suitable, or is expected to be suitable, for the treatment of the cancer in question. For example, the antibody molecule may be administered to the individual in combination with a chemotherapeutic agent, radiotherapy, an immunotherapeutic agent, an anti-tumour vaccine, an oncolytic virus, an adoptive cell transfer (ACT) therapy (such as adoptive NK cell therapy or therapy with chimeric antigen receptor (CAR) T-cells, autologous tumour infiltrating lymphocytes (TILs), or gamma/delta T cells, or an agent for hormone therapy.

Without wishing to be bound by theory, it is thought that the antibody molecule described herein may act as an adjuvant in anti-cancer therapy. Specifically, it is thought that administration of the antibody molecule to an in individual in combination with chemotherapy and/or radiotherapy, or in combination with an anti-tumour vaccine, for example, will trigger a greater immune response against the cancer than is achieved with chemotherapy and/or radiotherapy, or with an anti-tumour vaccine, alone.

One or more chemotherapeutic agents for administration in combination with an antibody of the invention as described herein may be selected from the group consisting of: taxanes, cytotoxic antibiotics, tyrosine kinase inhibitors, PARP inhibitors, B-Raf enzyme inhibitors, MEK inhibitors, c-MET inhibitors, VEGFR inhibitors, PDGFR inhibitors, alkylating agents, platinum analogues, nucleoside analogues, antifolates, thalidomide derivatives, antineoplastic chemotherapeutic agents and others. Taxanes include docetaxel, paclitaxel and nab-paclitaxel; cytotoxic antibiotics include actinomycin, bleomycin, and anthracyclines such as doxorubicin, mitoxantrone and valrubicin; tyrosine kinase inhibitors include erlotinib, gefitinib, axitinib, PLX3397, imatinib, cobemitinib and trametinib; PARP inhibitors include piraparib; B-Raf enzyme inhibitors include vemurafenib and dabrafenib; alkylating agents include dacarbazine, cyclophosphamide and temozolomide; platinum analogues include carboplatin, cisplatin and oxaliplatin; nucleoside analogues include azacitidine, capecitabine, fludarabine, fluorouracil and gemcitabine; antifolates include methotrexate and pemetrexed. Other chemotherapeutic agents suitable for use in the present invention include defactinib, entinostat, eribulin, irinotecan and vinblastine.

Preferred therapeutic agents for administration with an antibody molecule as described herein are doxorubicin, mitoxantrone, cyclophosphamide, cisplatin, and oxaliplatin.

A radiotherapy for administration in combination with an antibody molecule as described herein may be external beam radiotherapy or brachytherapy.

An immunotherapeutic agent for administration in combination with an antibody molecule as described herein may be a therapeutic antibody molecule, nucleic acid, cytokine, or cytokine-based therapy. For example, the therapeutic antibody molecule may bind to an immune regulatory molecule, e.g., an inhibitory checkpoint molecule or an immune costimulatory molecule, a receptor of the innate immune system, or a tumour antigen, e.g., a cell surface tumour antigen or a soluble tumour antigen. Examples of immune regulatory molecules to which the therapeutic antibody molecule may bind include CTLA-4, LAG-3, TIGIT, TIM-3, VISTA, PD-1, CD47, CD73, CSF-1R, KIR, OX40, CD40, HVEM, IL-10 and CSF-1. Examples of receptors of the innate immune system to which the therapeutic antibody molecule may bind include TLR1, TLR2, TLR4, TLR5, TLR7, TLR9, RIG-I-like receptors (e.g., RIG-I and MDA-5), and STING. Examples of tumour antigens to which the therapeutic antibody molecule may bind include HER2, EGFR, CD20 and TGF-beta.

The nucleic acid for administration in combination with an antibody molecule as described herein may be a siRNA.

The cytokines or cytokine-based therapy may be selected from the group consisting of: IL-2, prodrug of conjugated IL-2, GM-CSF, IL-7, IL-12, IL-9, IL-15, IL-18, IL-21, and type I interferon.

Anti-tumour vaccines for the treatment of cancer have both been implemented in the clinic and discussed in detail within scientific literature (such as Rosenberg S. Development of Cancer Vaccines. ASCO Educational Book Spring: 60-62 (2000)). This mainly involves strategies to prompt the immune system to respond to various cellular markers expressed by autologous or allogenic cancer cells by using those cells as a vaccination method, both with or without granulocyte-macrophage colony-stimulating factor (GM-CSF). GM-CSF provokes a strong response in antigen presentation and works particularly well when employed with said strategies.

The chemotherapeutic agent, radiotherapy, immunotherapeutic agent, anti-tumour vaccine, oncolytic virus, ACT therapy, or agent for hormone therapy is preferably a chemotherapeutic agent, radiotherapy, immunotherapeutic agent, anti-tumour vaccine, oncolytic virus, ACT therapy, or agent for hormone therapy for the cancer in question, i.e. a chemotherapeutic agent, radiotherapy, immunotherapeutic agent, anti-tumour vaccine, oncolytic virus, ACT therapy, or agent for hormone therapy which has been shown to be effective in the treatment of the cancer in question. The selection of a suitable chemotherapeutic agent, radiotherapy, immunotherapeutic agent, anti-tumour vaccine, oncolytic virus, ACT therapy, or agent for hormone therapy which has been shown to be effective for the cancer in question is well within the capabilities of the skilled practitioner.

In some embodiments for potential therapeutic use, an antibody that does not activate effector functions is preferred.

IgG4 has been used but this sub-class to undergo Fab-arm exchange, where heavy chains can be swapped between IgG4 in vivo. Due to their lack of effector functions, IgG4 antibodies represent the preferred IgG subclass for receptor blocking without cell depletion. IgG4 molecules can exchange half-molecules in a dynamic process termed Fab-arm exchange. This phenomenon can occur between therapeutic antibodies and endogenous IgG4. The S228P mutation has been shown to prevent this recombination process allowing the design of less unpredictable therapeutic IgG4 antibodies.

The CH2 domain is known bind to Fcγ receptors and complement. Binding of the CH2 domain to Fcγ receptors is required antibody-dependent cell-mediated cytotoxicity (ADCC), while binding to complement is required complement-dependent cytotoxicity (CDC). The CH2 domain of the antibody molecule preferably comprise one or more mutations that reduce or abrogate binding of the CH2 domain to one or more Fcγ receptors, such as FcγRI, FcγRIIa, FcγRIIb, FcγRIII, and/or to complement. The inventors postulate that reducing or abrogating binding to Fcγ receptors will decrease or eliminate ADCC mediated by the antibody molecule. Similarly, reducing or abrogating binding to complement is expected to reduce or eliminate CDC mediated by the antibody molecule. Without wishing to be bound by theory, this is expected to reduce or avoid liver inflammation when the antibody molecule is administered to a patient. In addition, reducing or abrogating binding to Fcγ receptors is expected to be useful where the antibody molecule comprises a second antigen-binding site for an immune cell antigen as described herein, where ADCC and/or CDC-mediated killing of immune cells bound by the antibody molecule should be avoided. Mutations to decrease or abrogate binding of the CH2 domain to one or more Fcγ receptors and/or complement are known in the art (Wang et al., 2018). These mutations include the "LALA mutation" described in Bruhns et al., 2009 and Hezareh et al., 2001, which involves substitution of the leucine residues at IMGT positions 1.3 and 1.2 of the CH2 domain with alanine (L1.3A and L1.2A). Alternatively, the generation of a-glycosyl antibodies through mutation of the conserved N-linked glycosylation site by mutating the asparagine (N) at IMGT position 84.4 of the CH2 domain to alanine, glycine or glutamine (N84.4A, N84.4G or N84.4Q) is also known to decrease IgG1 effector function (Wang et al., 2018). As a further alternative, complement activation (C1q binding) and ADCC are known to be reduced through mutation of the proline at IMGT position 114 of the CH2 domain to alanine or glycine (P114A or P114G) (Idusogie et al., 2000; Klein et al., 2016). These mutations may also be combined in order to generate antibody molecules with further reduced or no ADCC or CDC activity.

Thus, the antibody molecule may comprise a CH2 domain, wherein the CH2 domain preferably comprises:

(i) alanine residues at positions 1.3 and 1.2; and/or (ii) an alanine or glycine at position 114; and/or (iii) an alanine, glutamine or glycine at position 84.4;

wherein the amino acid residue numbering is according to the IMGT numbering scheme.

In a preferred embodiment, the antibody molecule comprises a CH2 domain, wherein the CH2 domain comprises:

(i) an alanine residue at position 1.3; and (ii) an alanine residue at position 1.2;

wherein the amino acid residue numbering is according to the IMGT numbering scheme.

In an alternative preferred embodiment, the antibody molecule comprises a CH2 domain, wherein the CH2 domain comprises:

(i) an alanine residue at position 1.3;

(ii) an alanine residue at position 1.2; and (iii) an alanine at position 114;

wherein the amino acid residue numbering is according to the IMGT numbering scheme.

IgG naturally persists for a prolonged period in serum due to FcRn-mediated recycling, giving it a typical half life of approximately 21 days. To prolong half life the pH dependent interaction of the Fc domain with FcRn has been engineered to increase affinity at pH 6.0 while retaining minimal binding at pH 7.4. The mutations T250Q/M428L, conferred an approximately 2-fold increase in IgG half-life in rhesus monkeys. The M252Y/S254T/T256E variant (dubbed YTE), conferred an approximately 4-fold increase in IgG half-life in cynomolgus monkeys. A longer half-life is desirable in some circumstances to decrease the frequency of administration whilst maintaining or improving efficacy of the administered antibody. Antibodies of the invention may be provided as half-life extended variants, engineered to extend half-life in vivo serum following administration, thus antibodies of the invention may be provided as T250Q/M428L or M252Y/S254T/T256E variants.

The antibody molecules of the invention may be useful in the detection of PD-L1, in particular in the detection of cells comprising PD-L1 at their cell surface, i.e. cells expressing cell-surface bound PD-L1. The cells may be immune cells, such as $CD8^+$ T cells, $CD4^+$ T cells, Treg cells, B cells, NK cells, NKT cells, dendritic cells, or TILs, but preferably are $CD8^+$ T cells or TILs.

Thus, the present invention relates to the use of an antibody molecule for detecting the presence of PD-L1, preferably the presence of cells comprising PD-L1 at their cell surface, in a sample. The antibody molecule may be conjugated to a detectable label as described elsewhere herein.

Also provided is an in vitro method of detecting PD-L1, wherein the method comprises incubating the antibody molecule with a sample of interest, and detecting binding of the antibody molecule to the sample, wherein binding of the antibody to the sample indicates the presence of PD-L1. Binding of the antibody molecule to a sample may be detected using an ELISA, for example.

In a preferred embodiment, the present invention relates to an in vitro method of detecting cells comprising PD-L1 at their cell surface, wherein the method comprises incubating the antibody molecule with a cell sample of interest, and determining binding of the antibody molecule to cells present in the sample, wherein binding of the antibody to cells present in sample indicates the presence of cells comprising PD-L1 at their cell surface. Methods for detecting binding of an antibody molecule to cells are known in the art and include ELISAs, and flow-cytometry.

The cell sample of interest may be a tumour sample obtained from an individual.

The antibody molecules of the invention may thus be useful in the detection or diagnosis of disease or disorder, in particular the detection or diagnosis of cancer. The cancer may be a cancer which can be treated with an antibody molecule of the invention as described herein.

Related aspects of the invention thus provide;
(i) an antibody molecule described herein for use as a diagnostic,
(ii) an antibody molecule described herein for use in a method of detecting or diagnosing a disease or disorder, such as cancer,
(iii) the use of an antibody molecule described herein in the manufacture of a diagnostic product for use in the detection or diagnosis of a disease or disorder;
(iv) a method of detecting or diagnosing a disease or disorder in an individual; and
(v) a kit for use in a method of detecting or diagnosing a disease or disorder in an individual, the kit comprising an antibody molecule as described herein.

Further aspects and embodiments of the invention will be apparent to those skilled in the art given the present disclosure, including the following experimental exemplification.

All documents mentioned in this specification are incorporated herein by reference in their entirety.

"and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures provided herein.

LIST OF FIGURES

FIG. 1: Mixed Leukocyte Reaction Assay. The functional activity of the anti-PD-L1 kappa clones, G1/894_8_E05, G1/887_4_E12 and G1/887_4_G12, was tested in a mixed leukocyte reaction assay. All anti-PD-L1 mAbs showed potent activity with $EC_{50}$ values lower than 0.030 nM. No activity was observed for the negative control G1AA/4420.

Figure 2:
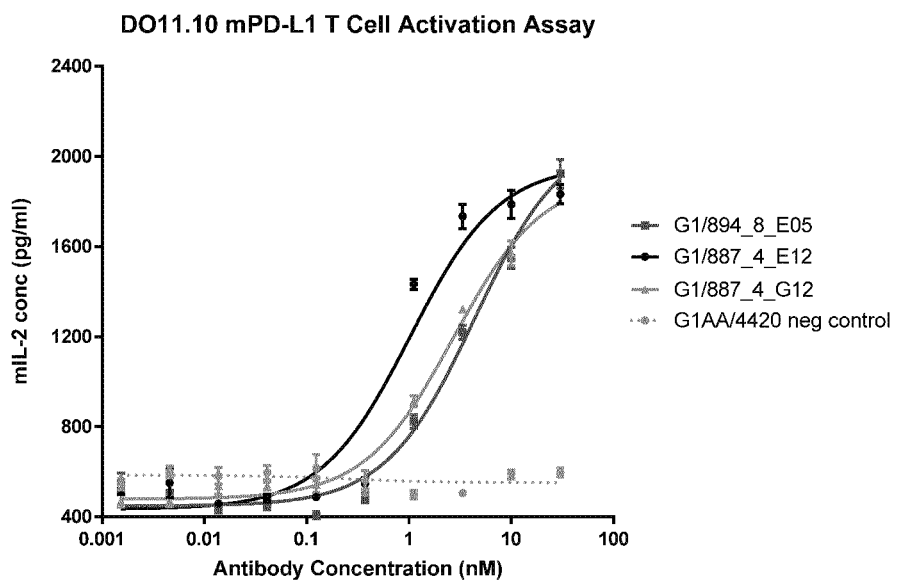

FIG. 2: DO11.10 mouse T cell activation assay. The functional activity of the anti-PD-L1 kappa clones, G1/894_8_E05, G1/887_4_E12 and G1/887_4_G12, towards mouse PD-L1 was tested in a T cell assay with LK35.2 overexpressing mouse PD-L1 and DO11.10 T cells. All anti-PD-L1 mAbs showed potent activity with low nanomolar $EC_{50}$ values. No activity was observed for the negative control G1AA/4420.

Figure 3:
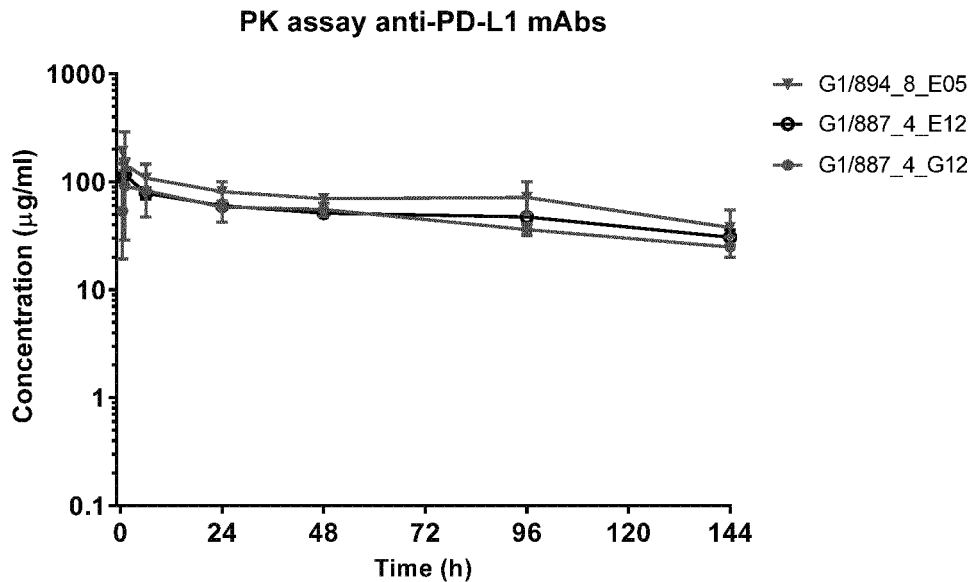

FIG. 3: Pharmacokinetics of anti-PD-L1 mAbs in non-tumour bearing mice.

Figure 4:
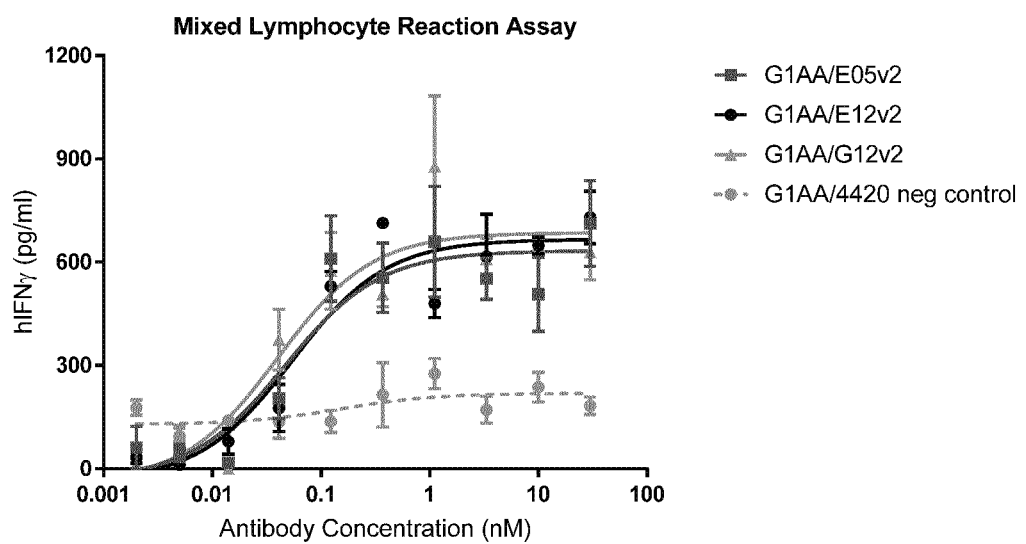

FIG. 4: Mixed Leukocyte Reaction Assay. The functional activity of the anti-PD-L1 kappa clones, G1AA/E05v2, G1AA/E12v2 and G1AA/G12v2 was tested in a mixed leukocyte reaction assay. All anti-PD-L1 mAbs showed potent activity with $EC_{50}$ values below 0.055 nM. No activity was observed for the negative control G1AA/4420.

EXAMPLES

The aim of these experiments was to generate an anti-human-PD-L1 mAb that was cross-reactive with mouse and/or cynomolgus PD-L1 and which was a potent inhibitor (blocker) of PD-1/PD-L1 activity.

Example 1: Isolation of Naïve Anti-PD-L1 Binding mAb: 280_02_G02

1.1 Antigens: CD4 and Fc Tagged Human and Mouse PD-L1

Human and mouse PD-L1 antigens with fusion proteins were generated for use in antibody selections and screening. Antigens were expressed with either a monomeric C-terminal rat CD4, domains 3 and 4 (rCd4) tag (Brown and Barclay, 1994) or a dimeric human IgG1 Fc domain (resulting in hPD-L1-rCD4-His (SEQ ID NO: 79), hPD-L1-Fc-His (SEQ ID NO: 80), mPD-L1-rCD4-His (SEQ ID NO: 81) and mPD-L1-Fc-His (SEQ ID NO: 82). The production of antigens in two different formats enabled the elimination of tag binders during sequential antibody phage display pannings. Expression plasmids encoding the antigens were transfected into HEK293 cells as described by Chapple et al., 2006. Supernatants were harvested 5 days after transfection and the secreted antigens were purified by Ni-NTA sepharose affinity chromatography (Schofield et al., 2007). Biotinylated antigen was prepared using EZ-link Sulfo-NHS-Biotin reagent (Thermo Fisher Scientific, product code 21326) following the manufacturer's recommendations. The biotinylation reaction product was gel filtered and the monomeric fraction was collected. The monomeric fraction was used for all solution-phase phage-display selections. The average number of biotins per molecule was 1 to 3 biotins per PD-L1 monomer as determined using Fluorescence Biotin Quantitation kit (Thermo Fisher Scientific, product code 46610).

1.2 Selections 1.2.1 Library Design

The "IONTAS 1" human antibody phage display library (IONTAS Ltd.) was employed to select for anti-PD-L1 clones. The antibody genes used to construct the IONTAS 1 library were derived from human lymphocytes (42 buffy coat donations) and one tonsil tissue sample. Both the buffy coats and tonsil tissue were obtained under Local Research Ethical Committee approval.

1.2.2 Naïve Solid Phase Selection

Three rounds of solid phase selections were performed with the IONTAS 1 antibody phage display library using antigen that was directly coated onto polystyrene Nunc tubes as described by Schofield et al., 2007. The first, second and third selection rounds employed human PD-L1-Fc-His (SEQ ID NO: 80), mouse PD-L1-rCD4-His (SEQ ID NO: 81) and human PD-L1-Fc-His (SEQ ID NO: 80), respectively. In the first round, Nunc Maxisorp Immunotubes (Thermo Scientific, 444202) were coated overnight with 10 µg/ml of human PD-L1-Fc-His for direct selection. The next day the tubes were rinsed 2× in PBS and then blocked by filling to the top with PBS 2% Marvel/PBS (MPBS) and incubated for 1 hour, then the tubes were washed three times with PBS. Also, the IONTAS 1 antibody phage display library (500 µl) was blocked with 4% MPBS (500 µl) for 1 hour. To each antigen coated immunotube 2% MPBS (179.25 µl), Fc-His (10.75 µl, 2.8 mg/ml) and blocked IONTAS 1 antibody phage display library (110 µl, $2 \times 10^{12}$ colony forming units, 2% MPBS) was added. Fc-His was added to the selection to remove anti-Fc binders binding to the solid phase immobilized Fc tagged antigen. The antibody phage display library was allowed to bind to the directly-immobilized antigen for 1.5 hours at room temperature. After this time, the immuno-tubes were washed 6 times with PBS-T (PBS, pH7.4, 0.1% Tween™-20), then washed 6 times with PBS. Bound phages were eluted and propagated using standard phage recovery procedures. The second round of antibody phage display selection was performed as above, except that mouse PD-L1-rCd4-His (SEQ ID NO: 81) was used to coat the Nunc immunosorb tube, rCd4-His was used instead of Fc-His for the de-selection and the round 1 output phage, selected against human PD-L1-Fc-His, was used as the input phage population. The third round with human PD-L1-Fc-His was performed exactly as round 1.

1.2.3 Chain Shuffling and Solution Phase Selections

The selected variable heavy (VH) anti-PD-L1 antibody population was shuffled with a naïve variable light (VL) antibody population as described by Dyson et al., 2011, and this shuffled, rescued, antibody-phage-display population was employed in solution phase selections. Briefly, panning was performed with human PD-L1-rCd4-His (SEQ ID NO: 79) (10 nM), human PD-L1-rCd4-His (SEQ ID NO: 79) (200 pM) and mouse PD-L1-rCd4-His (SEQ ID NO: 81) (10 nM) at rounds 1, 2 and 3, respectively, and this resulted in an output anti-PD-L1 scFv population termed "Selection 280". This scFv population contained human and mouse anti-PD-L1 binding scFvs, as determined by a phage polyclonal ELISA performed as described by Dyson et al., 2011, and displayed minimal cross-reactivity with human PD1 or with rCd4 or Fc tags.

1.3 Screening: ELISA, Recombinant Blocking Assay, Cell-Based Blocking Assay 1.3.1 Monoclonal scFv ELISA The Selection 280 scFv population from Example 1.2.3 was screened by ELISA to identify the clones which bound best to human PD-L1. The scFv population was subcloned into the soluble scFv vector pSANG10 and E. coli cultures containing soluble scFvs were prepared as described (Martin et al., 2006; Studier, 2005). Soluble scFv were then used in a monoclonal ELISA with immobilised human PD-L1-rCd4-His (SEQ ID NO: 79). Briefly, Nunc Maxisorp plates (Thermo Fisher Scientific, 437111) were coated with human PD-L1-rCd4-His (SEQ ID NO: 79) (5 µg/ml, PBS) overnight, blocked with 2% MPBS for 1 hour and the E. coli culture supernatant (1:2 dilution with 2×2% MPBS) was added and scFv were allowed to bind for 1 hour at room temperature. Bound scFv were detected with anti-FLAG M2 antibody (Sigma, F1804) labelled with europium. A total of 470 clones were screened and this resulted in the identification of 346 anti-PD-L1 clones with a binding signal for PD-L1 at least 10-fold above background compared with "empty" blocked wells containing no antigens. The 192 best anti-human PD-L1 clones assessed by primary ELISA signal were selected for further analysis.

1.3.2 Screening scFv in ELISA-Based PD-L1/PD-1 Blocking Assay

To identify clones that blocked the interaction between PD-L1 and PD1, an ELISA was performed to screen for blocking scFvs. Briefly, nunc maxisorp plates (437111, Thermo Fisher Scientific) were coated with anti-rCd4 (domains 3 and 4) antibody (MCA1022, OX-68, Bio-Rad) overnight, blocked with 3% MPBS and incubated with human PD1-rCd4-His (SEQ ID NO: 79) (5 µg/ml in 3% MPBS) for 1 hour at room temperature. Biotinylated human PD-L1-Fc-His (SEQ ID NO: 79) (50 µl, 0.2 nM), was pre-mixed with E. coli culture supernatant containing scFv. The Nunc 96-well plates were washed 3 times with PBS, 0.1% Tween™-20 (PBS-T) and 3 times with PBS, then the human PD-L1-Fc-His/scFv mix was added and incubated for 1 hour at room temperature. The plates were washed and bound human PD-L1-Fc-His was detected using goat-anti-Fc-biotin (Jackson ImmunoResearch, 109-065-098, Laboratories, 0.1 µg/ml, 3% MPBS) and Streptavidin-Europium (Perkin Elmer, 1244-360) followed by DELFIA enhancement solution (Perkin Elmer, 4001-0010). Of 192 clones screened, 183 displayed at least 90% blocking activity compared with the medium control. The 183 anti-PD-L1 scFv clones identified were screened further for mouse PD-L1 cross-reactivity in a primary ELISA, as described in Example 1.3.1, but using immobilised mouse PD-L1-rCD4-His instead of human PD-L1. This identified 50 mouse cross-reactive anti-PD-L1 clones, which were candidates for conversion to IgG1 format.

1.3.3 Conversion of Blocking Anti-PD-L1 scFv Clones to IgG1 Format

The anti-PD-L1 scFv clones which blocked the interaction between PD-L1 and PD1 were converted to IgG1 format by sub-cloning the VL and VH genes into the IgG1 expression plasmid pINT3-IgG1 and were expressed in HEK293 at 4 ml scale as described by Chapple et al., 2006. The antibodies were batch affinity purified with Protein A sepharose beads (PC-A100) and Proteus "1-step batch" midi-spin columns (Generon, GEN-1SB08) according to the manufacturer's instructions. Dialysis of the purified antibodies was performed with GeBAflex maxi tubes, with an 8 kDa cut-off (Generon, D045). If necessary, the antibodies were concentrated to 2 µM by ultrafiltration.

1.3.4 Screening for PD-L1/PD-1 Blocking Activity in Jurkat-NFAT Reporter Co-Culture Assay The functional activity of the purified anti-PD-L1 mAbs was then assessed in a co-culture reporter assay screen. This screen was performed using the GloResponse NFAT-luc2/PD-1 stable Jurkat cell line (Promega, CS187102) and Thaw-and-Use PD-L1 cells (Promega, CS178103) in accordance with the manufacturer's instructions. The PD-L1 cells were plated in HAM'S-F12 medium containing 10% FBS. The next day PD-1 Jurkat reporter cells (Promega, CS187102) were resuspended in assay medium (90% RPM11640, 1% FBS). Media was removed from the plate containing adhered PD-L1 cells and 40 µl of assay media containing different antibodies at a 2× concentration (200 nM) followed by 40 µl of the PD-1 cell mix was added to the adhered cells. The plate was incubated for 6 hours at 37° C., 5% $CO_2$. BioGlo reagent (Promega, G7940, 80 µl) was added to each well and the luciferase output was read using a BMG pherastar plate reader. This identified antibody G1/280_02_G02 as capable of blocking the interaction of PD-L1 with PD1 in a co-culture assay, as determined by increased luciferase activity compared to controls with no antibody. This activity was confirmed in a dose-response co-culture assay (doubling concentration range: 200 to 1.56 nM) resulting in a calculated half maximal effective concentration ($EC_{50}$) of 4.2 nM.

1.4 Sequence Optimisation

Preliminary analysis of the sequence of the G1/280_02_G02 antibody resulted in the identification of a potential deamidation site in the VH-CDR2, specifically an NG motif at Kabat positions 54 to 55. As deamidation at this site could potentially affect binding, variant clones were produced in which the NG motif was changed to either NA, NS, SG or GG. These modifications did not result in any significant reduction in affinity for recombinant PD-L1 or potency in PD-L1 blocking activity, and the variant clone containing the NS modification, designated G1/280_02_G02_NS, was chosen for use in a light-chain shuffle.

1.5 Summary of Naïve Selections

The phage selections strategies employed identified more than 50 anti-human PD-L1 binding clones with potent in vitro PD-1/PD-L1 blocking activity as well as mouse PD-L1 cross-reactivity. In particular, G1/280_02_G02 showed potent activation in a cell-based PD-L1 reporter assay and was therefore selected for further optimisation.

Example 2: Chain Shuffling to Generate Kappa Light Chain-Containing Anti-PD-L1 Clones The G1/280_02_G02_NS antibody possesses a lambda light chain. As most monoclonal antibodies used in a clinical context to date have kappa light chains (Jain et al., 2017), it was sought, by the use of a chain-shuffling campaign, to generate clones comprising the heavy chain of the G1/280_02_G02_NS antibody but paired with kappa light chains, which retained affinity for human PD-L1 and mouse cross-reactivity. The IONTAS™ kappa-light-chain library in the phage display plasmid pIONTAS-1 (kappa-library) was used to prepare a light-chain-shuffled library of scFv clones comprising the heavy chain of the G1/280_02_G02_NS antibody coupled with light chain variants.

2.1 Phage Selections and Screening Strategy

A number of phage-display solution selections were performed in three rounds using biotinylated human PD-L1-rCD4-His (SEQ ID NO: 79) and mouse PD-L1-rCD4-His antigens (SEQ ID NO: 81). The selections were performed by decreasing the antigen concentrations in every round (varying from 100 to 0.02 nM) and for each round of selection a "no-antigen" control was used. Details of the selections are shown in Table 2.

TABLE 2

| Selection no. | Antigen | Input library | Round |
|---|---|---|---|
| 866 | hPD-L1; 100 nM | Chain shuffled library | 1 |
| 867 | hPD-L1; 10 nM | Chain shuffled library | 1 |
| 868 | hPD-L1; 1 nM | Chain shuffled library | 1 |
| 869 | hPD-L1; 1 nM | Output of 867 | 2 |
| 870 | hPD-L; 0.2 nM | Output of 867 | 2 |
| 871 | hPD-L1; 0.1 nM | Output of 868 | 2 |
| 872 | hPD-L1; 0.02 nM | Output of 868 | 2 |
| 887 | hPD-L1; 0.1 nM | Output of 869 | 3 |
| 888 | mPD-L1; 1.0 nM | Output of 869 | 3 |
| 889 | mPD-L1; 0.1 nM | Output of 869 | 3 |
| 890 | hPD-L1; 0.02 nM | Output of 870 | 3 |
| 891 | mPD-L1; 1.0 nM | Output of 870 | 3 |
| 892 | mPD-L1; 0.1 nM | Output of 870 | 3 |
| 893 | mPD-L1; 1.0 nM | Output of 872 | 3 |
| 894 | mPD-L1; 0.1 nM | Output of 872 | 3 |

Six selection outputs were selected for screening, two from round 2 (nos. 871 and 872) and four from round 3 (nos. 887, 890, 891 and 894) using the soluble scFv expression system as described in section 1.3.1. A total of 1692 soluble scFv clones were screened for binding to immobilised antigen in ELISA (hu-PD-L1-rCD4-His (SEQ ID NO: 79) antigen coated at 3 μg/mL in Dulbecco PBS, 50 μl, onto Maxisorb plates) using the assay described in Example 1.3.1 above using DELFIA enhancement solution.

Of the 1692 clones screened, 1029 clones yielded a signal of more than 2000 RFU in the DELFIA assay, giving a success rate of around 61%. The top 736 clones were then selected and analysed using a secondary assay (affinity ranking) employing three concentrations of hPD-L1-rCD4-His antigen (1.0 nM, 0.2 nM, and 0.04 nM). From the 736 clones screened, the 48 clones which showed the greatest signal were selected for cloning and expression in IgG1 format. Clones were expressed in Expi293F™ (Fisher Scientific cat. no. 13479756) cells at 800 μl scale, and the culture supernatants were harvested on the 5th day post transfection for further screening in IgG1 format.

2.2 SPR Screening

All 48 antibodies were ranked by affinity using SPR (Biacore T200 instrument). For ranking, diluted supernatants (1:10 in running buffer made of 1×PBS and 0.002% Tween™-20) were immobilised onto a Protein-A chip (GE healthcare, product code: 29127556) and human PD-L1-rCD4-His (SEQ ID NO: 79) was flowed over the prepared surface at 50 nM concentration. The association ($k_a$) and dissociation ($k_d$) rate constants generated using this single injection were used to determine an estimated dissociation constant ($K_D$). The $K_D$ values of the clones were compared with that of clone 280_02_G02_NS in Ig1 format (G1/280_02_G02_NS). Ten clones of unique sequence were identified that showed higher affinity for human PD-L1 than clone G1/280_02_G02_NS and were therefore subjected to full kinetic analysis together with clone G1/280_02_G02_NS.

Briefly, SPR experiments were performed using a BIAcore T200 instrument. Antibodies from diluted culture supernatant were captured on a Protein A chip (GE Healthcare, 29127556) over FC2 at a flow rate of 10 μl/min, with 60 seconds contact time. Typically, this resulted in 500-800 RU of antibody captured. Doubling dilutions of PD-L1-rCd4-His, ranging from 50 to 0.05 nM, were injected from 50 nM at a flow rate of 30 μl/min, (Concentration range: 50 nM-0.05 nM) over FC1 and FC2. Association was measured over 180 seconds, and dissociation was measured over 300 seconds. All measurements were performed at 25° C. in PBS, pH 7.4, 0.05% Tween™-20. Kinetic parameters were determined by reference cell subtraction and fitting the sensogram experimental data assuming a 1:1 interaction using the BIAevaluation software (GE, BR-1005-97). The resulting data was fitted using BIAevaluation software and corresponding $k_a$, $k_d$, and $K_D$ values were calculated. Out of the ten clones tested, four antibodies, designated "G1/887_04_E12", "894_08_A05", "G1/894_08_E05" and "G1/887_04_G12", exhibited subnanomolar $K_D$ values, which were lower than the $K_D$ for G1/280_02_G02_NS. The affinity data obtained under the described screening conditions showed that the kappa light chain shuffle described in Example 2 allowed the heavy chain of the G1/280_02_G02_NS antibody to be paired not only with a lambda light chain but also with kappa light chains to produce antibodies with good, and in fact improved, affinity for recombinant human PD-L1. Accurate affinities generated with low levels of captured mAb are reported in Table 3 Section 3.2.

Example 3: Characterisation of Kappa Clones in IgG1 Format 3.1 Cell Based PD-1/PD-L1 Blocking Assay The ability of the anti-PD-L1 clones containing a kappa light chain, G1/887_04_E12, G1/894_08_E05 and G1/887_04_G12, to block the interaction between PD1 and PD-L1 was assessed in a bioluminescent cell-based assay using a PD1/PD-L1 Blockade Bioassay product (Promega, J1250/J1255) in accordance with the manufacturer's recommendations. The blocking activity was compared to the G1/280_02_G02_NS clone.

Briefly, all antibodies were expressed and purified as described in section 1.3.3 and tested at 3-fold dilutions from 100 nM to 35 μM (eight concentrations) in duplicates. The calculated $IC_{50}$ values are shown in Table 3. All clones tested were shown to be potent inhibitors of the PD1/PD-L1 interaction, with the three kappa light chain-containing clones G1/887_04_E12, G1/894_08_E05 and G1/884_04_G12 exhibiting even better $IC_{50}$ values than the lambda light chain-containing clone G1/280_02_G02_NS.

TABLE 3

| Clone ID | IC$_{50}$ (nM) |
| --- | --- |
| G1/280_02_G02_NS | 0.51 |
| G1/887_04_E12 | 0.35 |
| G1/894_08_E05 | 0.36 |
| G1/887_04_G12 | 0.33 |

3.2 Affinities

The binding of the anti-PD-L1 mAbs G1/887_04_E12, G1/887_04_G12 and G1/894_08_E05 to recombinant human biotinylated human PD-L1-Avi-His (Acro Biosystems, PD1-H82E5), cynomolgus PD-L1-His (Acro Biosystems, PD1-C52H4) and mouse PD-L1-His (Acro Biosystems, PD1-M5220) was then measured by SPR using a Biacore T200 instrument (GE Healthcare). Affinities were compared to the 280_02_G02_NS clone in IgG1 format (G1AA/280_02_G02_NS; the "AA" in this clone name denotes that this clone also contained the "LALA" mutation in the CH2 domain).

Briefly, the anti-PD-L1 mAbs, diluted in HBS-EP buffer (GE Healthcare, BR100188) at 2 µg/ml, were injected individually on flows cell 2, 3 and 4 of a Protein A chip (GE Healthcare, 29127556) at 30 µl/min to achieve a final response of approximately 110 RU. The recombinant human, cynomolgus and mouse PD-L1-His antigens, diluted in HBS-EP buffer, were injected on flow cell 1, 2, 3 or 4 as appropriate at a concentration range of 81 nM to 0.037 nM with 3-fold dilutions for 4 min at 75 µl/min and then allowed to dissociate in buffer for 10 min. Regeneration was achieved by injecting 10 mM glycine-HCL pH1.5 (GE Healthcare, Human Antibody Capture Kit, BR00356) for 30 sec at a rate of 30 µl/min. Subtracted data (flow cell 2–flow cell 1, flow cell 3–flow cell 1, or flow cell 4–flow cell 1) were analysed using BIAevaluation 3.2 Software (GE Healthcare) to identify binding using the model 1:1 binding with mass transfer, with refractive index (RI) constant 0. To determine the affinities of the mouse PD-L1 binding curves, the Rmax of the corresponding human binding profiles was used.

The binding data demonstrated that the G1AA/280_02_G02_NS clone and the G1/894_08_E05, G1/887_04_E12 and G1/887_04_G12 clones bound to human and cynomolgus PD-L1 with low single-digit nanomolar or subnanomolar affinities and were fully human/cynomolgus cross-reactive (Table 4). In comparison to the G1AA/280_02_G02_NS clone, the binding affinities of the G1/894_08E05, G1/887_04_E12 and G1/887_04_G12 clones were about 1.8 to 4.8 fold higher for human PD-L1 and 2.7 to 4.7 fold higher for cynomolgus PD-L1. The affinities of the clones for recombinant mouse PD-L1 were lower, with K$_D$ values ranging from 38 to 225 nM, with the highest affinity being observed for the G1/887_04_E12 clone. These data show that the heavy chain of the G1AA/280_02_G02_NS antibody can be paired with both lambda and kappa light chains to produce antibodies with good (and in the case of kappa light chain pairing, subnanomolar) affinities for recombinant human and cynomolgus PD-L1, as well as some, albeit lower, affinity for recombinant mouse PD-L1.

TABLE 4

| Clone | Human PD-L1-His K$_D$ (nM) | Cynomolgus PD-L1-His K$_D$ (nM) | Mouse PD-L1-His K$_D$ (nM) |
| --- | --- | --- | --- |
| G1AA/280_2_G02_NS | 1.10 | 1.32 | 137 |
| G1/894_08_E05 | 0.60 | 0.49 | 223 |
| G1/887_04_E12 | 0.23 | 0.28 | 38 |
| G1/887_04_G12 | 0.39 | 0.45 | 225 |

3.3 Binding of Anti-PD-L1 mAbs to Cell Expressed PD-L1

3.3.1 Generation of Cells Overexpressing Human PD-L1

To assess binding of the anti-PD-L1 mAbs G1/894_08_E05, G1/887_04_E12 and G1/887_04_G12 to cell surface PD-L1, HEK293 cells overexpressing human PD-L1 were generated.

Human PD-L1 sequence (SEQ ID NO: 83) was subcloned into pcDNA™5/FRT vector (ThermoFisher Scientific Cat. No. V601020) using KpnI and NotI restriction sites and the vector was then transformed into Flp-In T-REx 293 cell line (Life Technologies, R780-07) using Lipofectamine 2000 (Life Technologies, 11668-019). Cells were grown in DMEM containing 10% FBS, 100 µg/ml Hygromycin B (Melford Laboratories Ltd, Z2475) and 15 µg/ml Blasticidin (Melford Laboratories Ltd, B1105) for 3-4 weeks until colonies of stably transformed cells had formed. These colonies were amplified in the presence of 1 µg/ml doxycycline (Sigma Aldrich, D9891) and tested for expression of PD-L1 using PE-conjugated anti-human PD-L1 (MIH1) antibody (BD Biosciences, 557924). Cells were detached using cell dissociation buffer, washed once with PBS, plated at 2×10$^5$ cells in wells of a 96-well plate and then incubated with antibody diluted 1:20 in PBS for 1 hour at 4° C., before being washed again in PBS and measured using an Accuri C6 cytometer (BD Biosciences). The data was analysed using FlowJoX software. Expression of human PD-L1 was detected in the cell line.

3.3.2 Cell Binding Assay: Cell Binding to HEK293-hPD-L1 and Control HEK-FRT Shows Specific Binding.

The anti-human PD-L1 mAbs, G1/894_08_E05, G1/887_04_E12 and G1/887_04_G12 were then tested for binding to HEK293 cells expressing human PD-L1 using flow cytometry. Non-specific binding was also assessed by testing binding to HEK293 parental cells lacking human PD-L1 (Flp-In T-Rex 293 cell line, Life Technologies, R780-07).

HEK293 and HEK293.hPD-L1 suspensions were prepared in PBS containing 0.5% BSA (Sigma, A7906) and seeded at 1×10$^5$ cell/well in 100 µl in round bottomed 96-well plates (VWR, 734-1797). Cells were washed once in 100 µl 1×DPBS and mAbs G1/894_08_E05, G1/887_04_E12 and G1/887_04_G12 were diluted (1.10$^{-6}$-0.013 nM, 5-fold dilutions) in 100 µl 1×DPBS (Gibco, 14190-094). The washed cells were resuspended in the diluted antibody mixture, incubated at 4° C. for 30 minutes, and then washed once in PBS. 100 µl/well of secondary antibody (Alexa Fluor 647-AffiniPure Goat Anti-Human IgG, F(ab')2 Fragment Specific, Stratech Scientific, 109-605-006-JIR) diluted 1:1000 in PBS was then added, the cells/antibody mixture was incubated for 20 mins at 4° C., and the cells were then washed again with PBS and resuspended in 100 µl of PBS containing 7AAD (1:1000, Biotium, 40043) before being analysed using a Canto II flow cytometer (BD Bioscience). Dead cells were excluded and the fluorescence in the FITC channel (488 nm/530/30) was measured. The geometric mean fluorescence intensity (GMFI) values were plotted against the log concentration of antibody and the resulting curves were fitted using the log (agonist) versus response equation in GraphPad Prism.

The G1/894_08_E05, G1/887_04_E12 and G1/887_04_G12 clones were found to bind to cell surface human PD-L1 with $EC_{50}$ values in the range of 0.26-0.29 nM (see Table 5). No binding to parental HEK293 cells was observed showing the specificity of the binding. Therefore, all mAb clones tested bound specifically to PD-L1, with no non-specific binding observed.

TABLE 5

| Clone | HEK293:hPD-L1 $EC_{50}$ (nM) | HEK293-FRT negative control cells |
|---|---|---|
| G1/894_08_E05 | 0.29 | No binding |
| G1/887_04_E12 | 0.26 | No binding |
| G1/887_04_G12 | 0.27 | No binding |

3.4 Activity of Anti-PD-L1 mAbs in Mixed Lymphocyte Reaction Assay

The activity of the anti-PD-L1 mAbs was tested in a Mixed Lymphocyte Reaction (MLR) assay. An MLR assay measures the cellular immune response that occurs between two allogeneic lymphocyte populations (same species but genetically distinct). The assay uses CD4+ T cells from one donor and monocyte derived dendritic cells (iDCs) from another donor. As the immune cells contain physiological levels of immune checkpoint regulators, the MLR assay can be used to confirm that T cell activation is enhanced by the mAb in a human system.

3.4.1 Generation of Expanded CD4+ T Cells

PBMCs were isolated from leukocyte cones by Ficoll gradient separation. CD4+ T cells were isolated using a Human CD4+ T Cell Isolation Kit (Miltenyi Biotec Ltd, 130-096-533) according to the manufacturer's instructions. Human T-Activator CD3/CD28 Dynabeads (Life Technologies, 11131D) were resuspended by vortexing. Beads were transferred to a sterile 15 ml tube and 10 ml RPMI (Life Technologies, 61870044) with 10% FBS (Life Technologies, 10270106) and 1× Penicillin Streptomycin (Life Technologies, 15140122) was added to wash the Dynabeads. The supernatant was discarded. The required amount of CD4+ T cells at $1.0 \times 10^6$ cells/ml in RPMI with 10% FBS and 1× Penicillin Streptomycin Solution and 50 IU/ml recombinant human IL2 (Peprotech, 200-02-50 µg) with 3:1 bead to cell ratio was transferred to a T75 flask (Greiner Bio-one, 690195) and incubated at 37° C.+5% $CO_2$. After 3 days the cells were gently resuspended and counted. The cell density was maintained between $0.8-1 \times 10^6$ cells/ml by adding fresh media (RPMI-10% FBS+Penicillin Streptomycin Solution 1×+50 IU/ml rhuIL2) as needed. On day 7 or 8, the CD3/28 beads were removed and CD4+ T cells were rested overnight at $1 \times 10^6$ cells/ml fresh media RPMI-10% FBS+Penicillin Streptomycin Solution 1× with reduced 10 IU/ml rhuIL2. The cells were stored frozen until required.

3.4.2 Generation of iDC

Untouched monocytes were isolated from human PBMCs using a Human Pan Monocyte Isolation Kit, (Miltenyi Biotec Ltd, 130-096-537) following the manufacturer's instructions. Monocytes were differentiated to iDCs using Human Mo-DC Differentiation Medium (Miltenyi Biotec Ltd, 130-094-812) following the manufacturer's instructions.

3.4.3 MLR Assay

Expanded T cells were thawed one day before the experiment, washed with AIM V Medium (Gibco, 12055-091) and incubated at 3TC, 5% $CO_2$ in AIM V Medium overnight. The anti-human PD-L1 mAbs, G1/894_08_E05, G1/887_04_E12 and G1/887_04_G12 were diluted at 4× the final concentration in triplicate in 50 µl AIM V Medium in 96 well round bottom plates (VWR, 734-1797). An anti-FITC antibody, designated 4420 (Bedzyk et al., 1989; Bedzyk et al., 1990), containing the LALA mutation was included as negative control. A 3-fold dilution series starting from 30 nM to 0.002 nM was tested. Both $1 \times 10^4$ iDC cells suspended in 50 µl AIM V Medium and $1 \times 10^5$ expanded CD4+ T cells suspended in 100 µl AIM V Medium were added to the antibody dilutions and incubated for 5 days at 37° C.+5% $CO_2$. The following controls were included: CD4+ T cells alone, iDC alone, CD4+ T cells+iDCs, and AIM V Medium only. Supernatants were harvested, samples were diluted (1:25) and interferon gamma (IFN-γ) concentrations measured using Human IFN gamma ELISA Ready-SET-Go! Kit (Life Technologies, 88-7316-77). Plates were read at 450 nm using the plate reader with the Gen5 Software, BioTek. Absorbance values of 630 nm were subtracted from those of 450 nm (Correction). The standard curve for calculation of cytokine concentration was based on a four parameter logistic curve fit (Gen5 Software, BioTek). The concentration of human IFN-γ was plotted vs the log concentration of antibody and the resulting curves were fitted using the log (agonist) vs response equation in GraphPad Prism.

The anti-human PD-L1 mAbs, G1/894_08_E05, G1/887_04_E12 and G1/887_04_G12, showed potent activity in the MLR assay with $EC_{50}$ values of less than 0.030 nM and a maximum level of IFN-γ ($E_{max}$) of greater than 10000 µg/ml (Table 6, representative FIG. 1). The $EC_{50}$ indicates the concentration of mAb at which half of the response is achieved, whereas the $E_{max}$ is an absolute value that indicates the maximum concentration of IFN-γ achieved in the assay. No activity was observed with the negative control G1AA/4420 mAb, as expected.

TABLE 6

| | Functional activity in MLR assay | |
|---|---|---|
| Clone | $EC_{50}$ (nM) | $E_{max}$ (pg/ml) |
| G1/894_08_E05 | 0.024 | 14620 |
| G1/887_04_E12 | 0.029 | 11440 |
| G1/887_04_G12 | 0.021 | 12670 |
| G1AA/4420 negative control | No activity | |

3.5 Activity of Anti-PD-L1 mAbs in a Mouse DO11.10 T Cell Activation Assay

As the anti-human PD-L1 mAbs G1/887_04_E12, G1/887_4_G12 and G1/894_08_E05 were shown to be weakly crossreactive to mouse PD-L1 (see Example 3.2, Table 4) their functional activity towards mouse PD-L1 was examined in an interleukin-2 (IL-2) release assay based on the DO11.10 OVA T-lymphocyte and LK35.2 B-lymphocyte hybridoma cell lines. IL-2 release is a marker of T cell activation. T cells expressing endogenous murine PD-1 were transfected with empty vector (pLVX). B-cells were transfected with a mouse PD-L1 construct.

3.5.1 Production of T Cell Lines with an Empty Vector

Lentiviral transduction methodology was used to generate DO11.10 cells (National Jewish Health) containing the empty lentiviral vector pLVX using the Lenti-X HTX Packaging System (Clontech, 631249). Lenti-X expression vector (pLVX) (Clontech, 631253) was co-transfected with a Lenti-X HTX Packaging Mix into the Lenti-X 293T Cell Line (Clontech, 632180) to generate virus. The DO11.10 cell line was transduced using the lentiviral particles produced with the Lenti-X HTX Packaging System.

3.5.2 Production of Antigen Presenting Cells Over-Expressing PD-L1

Lentiviral transduction methodology was used to generate LK35.2 B cell lymphoma cells (ATCC, HB-98) over-expressing mouse PD-L1 using the Lenti-X HTX Packaging System (Clontech, 631249). Lenti-X expression vector (pLVX) (Clontech, 631253) containing, mouse PD-L1 cDNA (encoding the mouse PD-L1 of SEQ ID NO: 84), was co-transfected with a Lenti-X HTX Packaging Mix into the Lenti-X 293T Cell Line (Clontech, 632180) to generate virus. The LK35.2 cell line was transduced using the lentiviral vectors produced with the Lenti-X HTX Packaging System.

3.5.3 Mouse DO11.10 T Cell Activation Assay

Dilutions of the anti-PD-L1 mAbs G1/887_04_E12, G1/887_04_G12 and G1/894_08_E05 or the anti-FITC negative control mAb (G1AA/4420) were prepared in experimental media (DMEM (Gibco, 61965-026), 10% FBS (Gibco, 10270-106), 1 mM Sodium Pyruvate (Gibco, 11360-070)). The mAbs were mixed 1:1 with $4\times10^5$/ml LK35.2 mPD-L1 cells in experimental media in presence of 2.46 µM OVA peptide (H-ISQAVHAAHAEINEAGR-OH, Pepscan) (100 µL LK35.2 mPD-L1 cells (B cell hybridoma transduced with a lentiviral vector containing mPD-L1 to over-express mouse PD-L1)/mAb mix per well in 96-round bottom plate) and incubated at 37° C., 5% $CO_2$ for 1 hour. $2\times10^5$ DO11.10 pLVX cells (DO11.10 T cell hybridoma transduced with an empty lentiviral vector) per ml in 100 µl volume experimental media were added to 100 µl of the LK35.2 mPD-L1/(mAbs) mix. The cells were then mixed before being incubated at 37° C., 5% $CO_2$ for 24 hours. Supernatants were collected and assayed with mouse IL-2 ELISA kit (eBioscience, 88-7024-88 or R&D systems, SM2000) following the manufacturer's instructions. Plates were read at 450 nm using the plate reader with the Gen5 Software, BioTek. Absorbance values of 570 nm were subtracted from those of 450 nm (Correction). The standard curve for calculation of cytokine concentration was based on a four parameter logistic curve fit (Gen5 Software, BioTek). The concentration of mouse IL-2 was plotted vs the log concentration of mAb and the resulting curves were fitted using the log (agonist) vs response equation in GraphPad Prism.

The results are shown in FIG. 2 and Table 7. The anti-human PD-L1 mAbs showed significant activity in the mouse T cell activation assay with potencies (E050) in the range of 1-4.4 nM. No activity was observed with the negative control mAb as expected. Of the three clones tested, G1/887_04_E12, which showed the highest affinity for recombinant mouse PD-L1 (see Table 4), was also the most potent clone in the T cell activation assay. The differences in potency were smaller than the measured affinities which is likely due to the high overexpression of mouse PD-L1 on the LK35.2 cells in this assay.

TABLE 7

| Clone | Functional activity in mPD-L1 DO11.10 T Cell Activation Assay | |
|---|---|---|
| | $EC_{50}$ (nM) | $E_{max}$ (pg/ml) |
| G1/894_08_E05 | 4.37 | 2112 |
| G1/887_04_E12 | 1.02 | 1966 |
| G1/887_04_G12 | 2.71 | 1912 |
| G1AA/4420 negative control | No activity | |

3.6 Pharmacokinetics in Naïve Mice

To investigate the in vivo pharmacokinetics (PK), the anti-PD-L1 mAbs G1/894_08_E05, G1/887_04_E12, and G1/887_04_G12 were tested in a research-grade PK study in which the mAbs were administered to non-tumour bearing mice and the concentrations in the blood serum were measured over time.

C57/BL6 mice (female 9-10 weeks old) were divided into 4 groups of 3 animals to receive a single dose of the test antibody administered intravenously. The animals were dosed once with the anti-PD-L1 mAbs at 8 mg/kg. Antibodies were administered intravenously (100 µl, tail vein) and then blood samples (20 µl, tail vein) were collected at 7 different time points, from 3 mice per time point. The time points were 0.5, 1, 6, 24, 48, 96 and 144 hours post-dosing. Blood was allowed to clot at room temperature for 2 hours, spun in a centrifuge at 2000 g for 20 min, then the serum was recovered and stored at −80° C. For the analysis, all the serum samples were thawed and analysed at the same time on a Gyrolab xPlore machine (Gyrolab Technologies) using the 200-3W-002-A program. Biotinylated goat anti-human IgG-heavy and light chain monkey-adsorbed (Cambridge Bioscience, A80-319B) was used as the capture reagent and goat anti-human IgG-AF647 (Cambridge Bioscience, 2040-31) as the detection reagent. The concentration of human IgG was measured in each serum sample and real drug concentration was calculated based on titration curves for each compound to eliminate potential differences in detection. Additional standard curves were performed to validate that binding to the capture or detection anti-human IgG mAb was not altered by the mAbs.

The anti-PD-L1 mAbs showed no initial rapid clearance and exposure levels were maintained at more than 24 µg/ml during the 6-day period (FIG. 3). This data is as expected for mAbs and in line with published anti-PD-L1 mAb data (Deng et al., 2016).

3.7 Summary of Characterisation of Kappa Clones in IgG1 Format

The anti-PD-L1 mAbs G1/894_08_E05, G1/887_04_E12, and G1/887_04_G12, containing the selected kappa light chains demonstrated cynomolgus and mouse PD-L1 cross-reactivity, showed specific binding to cell surface-expressed PD-L1, and showed even higher affinity for recombinant human and cynomolgus PD-L1 than the lambda light chain-containing clone G1/280_02_G02. The anti-PD-L1 mAbs G1/894_08_E05, G1/887_04_E12, and G1/887_04_G12 were shown to be potent activators of human T cells in vitro, to have functional mouse crossreactivity, and to have satisfactory PK profiles in non-tumour bearing mice.

Example 4: Sequence Optimisation

4.1 Identification and Removal of Potential Protein Deamidation Sites

Analysis of the sequence of the G1/280_02_G02_NS clone resulted in the identification of the sequence NSNT (SEQ ID NO: 6) in the H-CDR2 loop (at Kabat positions 54-57) as a potential deamidation site, which, if deamidated, could affect binding. The heavy chain of this clone was retained in all kappa light chain-containing clones obtained by the chain shuffling campaign described in Example 2, so this potential deamidation site was also present in clones G1/887_04_E12, G1/894_08_A05, G1/894_08_E05 and G1/887_4_G12. Using specific primers closest to germline sequence, the NSNT (SEQ ID NO: 6) sequence was changed in the four kappa light chain-containing clones by site-directed mutagenesis to either GGST (SEQ ID NO: 7), SGGT (SEQ ID NO: 5) or SGNA (SEQ ID NO: 8) to produce the variant clones identified in Table 8. At the same time as removing this potential deamidation site, the role of the proline residue at Kabat position 28 in the VH region of the G1/887_04_E12 clone, which was unintentionally introduced into the sequence of this antibody during the kappa light chain shuffle, was also investigated by reverting it back to a threonine residue as contained in the G1/280_02_G02_NS clone. The parent and resulting variant clones (all in IgG1 format) were transfected at 0.8 ml scale, and culture supernatants harvested five days after transfections were used to determine the affinities of the clones for human and cynomolgus PD-L1-rCD4-His by SPR. Cyno PD-L1-rCD4-His was generated as described in Example 1.1. With the exception of the variant clones derived from the G1/887_04_E12 clone, all variant clones retained their subnanomolar affinities for human and cynomolgus PD-L1 as compared to their respective parent clone (see Table 8).

TABLE 8

| Clone ID | H-CDR2 (position 54-57) "NSNT" motif or germline (GGST, SGGT, or SGNA) | H-CDR1 Proline (position 28) | hPDL1 $K_D$ (nM) | cPDL1 $K_D$ (nM) |
|---|---|---|---|---|
| G1/280_02_G02_NS | — | − | 1.20 | 1.80 |
| G1/887_04_E12 (Parent) | NSNT (SEQ ID NO: 6) | + | 0.21 | 0.25 |
| G1/929_01_A01 | GGST (SEQ ID NO: 7) | − | 2.66 | 3.18 |
| G1/929_01_A02 | SGGT (SEQ ID NO: 5) | − | 3.07 | 3.64 |
| G1/929_01_A03 | SGNA (SEQ ID NO: 8) | − | 2.66 | 3.31 |
| G1/894_08_A05 (Parent) | NSNT (SEQ ID NO: 6) | − | 0.42 | 0.57 |
| G1/929_01_A04 | GGST (SEQ ID NO: 7) | − | 0.47 | 0.60 |
| G1/929_01_A05 | SGGT (SEQ ID NO: 5) | − | 0.55 | 0.62 |
| G1/929_01_A06 | SGNA (SEQ ID NO: 8) | − | 0.45 | 0.58 |
| G1/894_08_E05 (Parent) | NSNT (SEQ ID NO: 6) | − | 0.48 | 0.59 |
| G1/929_01_A07 | GGST (SEQ ID NO: 7) | − | 0.47 | 0.59 |
| G1/929_01_A08 | SGGT (SEQ ID NO: 5) | − | 0.50 | 0.65 |
| G1/929_01_A09 | SGNA (SEQ ID NO: 8) | − | 0.49 | 0.57 |
| G1/887_04_G12 (Parent) | NSNT (SEQ ID NO: 6) | − | 0.36 | 0.50 |
| G1/929_01_A10 | GGST (SEQ ID NO: 7) | − | 0.42 | 0.60 |
| G1/929_01_A11 | SGGT (SEQ ID NO: 5) | − | 0.51 | 0.57 |
| G1/929_01_A12 | SGNA (SEQ ID NO: 8) | − | 0.51 | 0.66 |

The much-reduced affinities of the G1/929_01_A01, G1/929_01_A02 and G1/929_01_A03 clones compared to their parent (G1/887_04_E12) were considered likely to be due to the removal of the proline in the VH region at Kabat position 28 rather than to the presence of the GGST (SEQ ID NO: 7), SGGT (SEQ ID NO: 5) and SGNA (SEQ ID NO: 8) substitutions in H-CDR2. It was surprising that this proline residue in the G1/887_04_E12 clone appeared to be important for its affinity for PD-L1. The variants derived from the three parent clones G1/887_04_E12, G1/894_08_E05 and G1/887_04_G12 which contained the SGGT (SEQ ID NO: 5) substitution in their H-CDR2 (positions 54-57), namely clones G1/929_01_A02, G1/929_01_A08 and G1/929_01_A11, were selected for further characterisation on the basis that this SGGT (SEQ ID NO: 5) substitution was closest to germline sequence.

Using site-directed mutagenesis, the potential deamidation site (NSNT (SEQ ID NO: 6) at Kabat position 54 to 57) in the H-CDR2 loop of the G1/280_02_G02_NS clone was also modified to SGGT (SEQ ID NO: 5). Additionally, a further potential deamidation site (NS motif) identified at Kabat positions 31 to 32 in the CDR1 of the lambda light chain of this clone was modified to NY by mutating serine 32 (Kabat numbering) to a tyrosine, as tyrosine is found at this position in several germline sequences, such as IGLV2-8-01, IGLV2-8-02, IGLV2-8-03, IGLV2-11-01, IGLV2-11-02, IGLV2-11-03 and IGLV2-14-01, IGLV2-14-02, IGLV2-14-03, IGLV2-14-04. The combination of these modifications yielded the lambda light chain-containing clone G1/lambdav3, which was also selected for further characterisation.

Example 5: Characterisation of mAbs/mAb²

5.1 Cloning and Production of Clones in mAb and mAb² Format

The threonine residue at Kabat position 28 in the VH region of the G1/929_01_A02 "SGGT" variant clone identified in Example 4 was mutated to a proline, as is present at the same position in its parent clone G1/887_04_E12, with a view to improving its affinity for human and cynomolgus PD-L1. Transient expression in HEK293-6E cells and purification using mAb Select SuRe protein A columns was used to produce this modified variant clone and the other three "SGGT" variant clones (G1/929_01_A08, G1/929_01_A11 and G1/lambdav3) identified in Example 4 in IgG1 format and with the LALA mutation to enable testing of their functional activity in the absence of effector function. The resulting mAbs were designated G1AA/E12v2, G1AA/E05v2, G1AA/G12v2 and G1AA/lambdav3. The heavy and light chain sequences respectively are shown in SEQ ID NO: 47 and SEQ ID NO: 48 for G1AA/E12v2; SEQ ID NO: 49 and SEQ ID NO: 50 for G1AA/G12v2; SEQ ID NO: 51 and SEQ ID NO: 52 for G1AA/E05v2, and SEQ ID NO: 61 and SEQ ID NO: 62 for G1AA/lambdav3.

The CDR-based antigen-binding sites of a mAb can be combined with Fcab (fragment crystallisable antigen-binding) moieties generated in a constant domain to provide bispecific antibodies referred to as mAb².

The anti-PD-L1 antibodies of the invention were produced in anti-CD137/anti-PD-L1 mAb² format to test their specificity for human PD-L1. The mAb² were produced in IgG1 LALA format, with the heavy chain having an anti-human CD137 binding site in the CH3 domain of the Fcab moiety and a VH domain from anti-PD-L1 mAb clone G1AA/E12v2, G1AA/E05v2, G1AA/G12v2 or G1AA/lambdav3. To generate the mAb², the heavy chains were co-transfected with the corresponding light chain of the anti-PD-L1 mAbs. The mAb² were produced by transient expression in HEK293-6E cells and purified using mAb Select SuRe protein A columns to yield clones FS22-172-003AA/E12v2, FS22-172-003AA/G12v2, FS22-172-003AA/E05v2 and FS22-172-003AA/lambdav3. The heavy and light chain sequences respectively are shown in SEQ ID NO: 85 and SEQ ID NO: 86 for FS22-172-003AA/E12v2, SEQ ID NO: 87 and SEQ ID NO: 88 for FS22-172-003AA/G12v2, SEQ ID NO: 89 and SEQ ID NO: 90 for FS22-172-003AA/E05v2, and SEQ ID NO: 91 and SEQ ID NO: 92 for FS22-172-003AA/lambdav3.

5.2 Affinities of mAb for Human and Cynomolgus PD-L1

To determine whether the further sequence modifications present in G1AA/lambdav3 (namely, NSNT (SEQ ID NO: 6) to SGGT (SEQ ID NO: 5) in the VH-CDR2, NS to NY in the VL-CDR1, and the LALA mutation) and the kappa light chain-containing mAbs G1AA/E12v2, G1AA/E05v2, and G1AA/G12v2 (namely, the LALA mutation and, in G1AA/E12v2 only, threonine to proline at Kabat position 28 in the VH region) had affected binding kinetics, the affinities of these anti-PD-L1 mAbs for human and cynomolgus PD-L1 were determined as described in Example 3.2. The mAbs G1AA/lamdav3, G1AA/E05v2, G1AA/E12v2 and G1AA/G12v2 exhibited affinities for human and cynomolgus PD-L1 similar to those observed in Example 3.2 (Table 4) for mAbs G1AA/280_02_G02_NS, G1/894_08_E05, G1/887_04_E12 and G1/887_04_G12, demonstrating that the binding affinities of the mAbs and mAb$^2$ tested were not affected by the modification of the potential deamidation sites or the introduction of the LALA mutation. The G1AA/E12v2 mAb showed the lowest $K_D$ value of all four mAbs tested (0.21 nM for human PD-L1, and 0.37 nM for cynomolgus PD-L1).

The VH of G1AA/E12v2 differs from that of G1/929_01_A02 (Example 4, Table 8) by one residue; G1AA/E12v2 has a proline at Kabat position 28 whereas G1/929_01_A02 has a threonine at this position. G1/929_01_A02 had a greater than 10-fold lower affinity for both human and cynomolgus PD-L1 when compared to G1AA/E12v2; this data demonstrates the importance of the proline residue at position 28 (Kabat nomenclature) in the VH of clone G1AA/E12v2 for its affinity for human and cynomolgus PD-L1.

TABLE 9

| mAb | Human PD-L1-His $K_D$ (nM) | Cyno PD-L1-His $K_D$ (nM) |
|---|---|---|
| G1AA/lambdav3 | 1.34 | 2.45 |
| G1AA/E05v2 | 0.50 | 0.89 |
| G1AA/E12v2 | 0.21 | 0.37 |
| G1AA/G12v2 | 0.44 | 0.75 |

5.3 Specificity for PD-L1 Family Members

PD-L1 belongs to the B7 homology family of immune checkpoint regulators (Ni and Dong, 2017). To analyse specificity of the anti-PD-L1 Fab arms of the mAb$^2$ clones FS22-172-003AA/lambdav3, FS22-172-003AA/E05v2, FS22-172-003AA/E12v2 and FS22-172-003AA/G12v2, their ability to bind to closely-related family members was tested using SPR. The aim was to demonstrate specificity by showing no binding of the mAb$^2$ to closely-related antigens at a concentration of 1 µM, but showing binding to PD-L1 receptors at a concentration of 1 nM.

Flow cells on CM5 chips were immobilised with approximately 1000 RU of either human PD-L2-Fc (R&D Biosystems, 1224-PL), CD80-Fc (R&D Biosystems, 140-B1), PD-1-His (R&D Biosystems, 8986-PD), B7-H3-His (F-star in-house production), PD-L1-Fc (R&D Biosystems, 156-B7) or PD-L1-His (Acrobiosystems, PD1-H83F3). Flow cell 1 was run as a blank immobilisation. The mAb$^2$ were diluted to 1 µM and 1 nM in 1×HBS-EP buffer (GE Healthcare, product code BR100188), allowed to flow over the chip for 3 min and then allowed to dissociate for 4 min. A 30-seconds injection of 10 mM glycine pH 1.5 was used for regeneration. Positive control mAbs were injected at 50-100 nM to demonstrate the coating of each antigen. Binding levels were determined at the end of the association phase and compared.

All the mAb$^2$ clones tested showed a high level of specificity, with less than 10 RU of mAb$^2$ binding to the four antigens detected at 1 µM compared to a range of 105 to 570 RU of binding response detected at 1 nM for binding to either human PD-L1-Fc or PD-L1-His. These results showed that specificity of the Fab arms for PD-L1 was retained regardless of the modifications made to the CDRs to remove potential deamidation sites, and that the introduction of the LALA mutation and producing the Fabs in mAb$^2$ format did not affect their binding to PD-L1.

5.4 Activity of Anti-Human PD-L1 mAbs in MLR

The anti-PD-L1 mAbs, G1AA/E05v2, G1AA/E12v2 and G1AA/G05v2 were tested in a Mixed Lymphocyte Reaction (MLR) assay as described in Example 3.4. G1AA/4420 was used as a negative control. The data are shown in Table 10 and FIG. 4. The mAbs G1AA/E05v2, G1AA/E12v2 and G1AA/G12v2 showed potent activity in the MLR assay with $EC_{50}$ values of less than 0.054 nM and a maximum level of IFN-γ (Emax) of greater than 600 µg/ml (Table 10, FIG. 4. The $EC_{50}$ and especially the Emax values were significantly different from those described in Example 3.4. This difference is believed to be due to donor variability, as the response depends on the allogenic reaction between T cells from one donor and the monocyte derived dendritic cells from another donor. The potency of the anti-human PD-L1 mAbs was consistent with the data described in Example 3.4, as was the ranking of the clones by order of potency. No activity was observed for the negative control G1AA/4420 mAb, as expected.

TABLE 10

| | Functional activity in MLR Assay | |
|---|---|---|
| Clone | $EC_{50}$ (nM) | $E_{max}$ (pg/ml) |
| G1AA/E05v2 | 0.047 | 632 |
| G1AA/E12v2 | 0.054 | 666 |
| G1AA/G12v2 | 0.040 | 686 |
| G1AA/4420 negative control | No activity | |

5.5 Expression, Purification and Analytical Characterisation of Anti-PD-L1 mAbs

The mAbs G1AA/E05v2, G1AA/E12v2 and G1AA/G12v2 were produced at lab-scale and characterised by the standard analytical methods of SEC and Differential Scanning calorimetry (DSC).

5.5.1 Lab Scale Expression and Purification of Anti-PD-L1 mAbs

DNA sequences encoding the mAbs G1AA/E05v2, G1AA/E12v2 and G1AA/G12v2 were transfected into HEK293 6E (National Research Council Canada) cells using PEIpro (Polyplus, France). After 5 days, cell culture fluids were harvested, and purified on MabSelect Protein-A pre-packed columns using AKTAxpress instrument (both GE Healthcare, Uppsala, Sweden). Equilibration of the columns was carried out in 50 mM Tris, 250 mM NaCl at pH 7.0 followed by loading with harvested cell culture fluid. The resin was washed using 50 mM Tris, 250 mM NaCl at pH 7.0 and this was followed by eluting the mAb using buffer at pH of less than 3.5.

5.5.2 Analysis by SE-UPLC

Post-purification SE-UPLC was performed within 24 hours of purification (material was stored at 4° C.) using an Acquity H-Class Bio UPLC (Waters Corp. UK) to measure the percentage of monomer. An Acquity UPLC BEH200 SEC 1.7 mm column (4.6×150 mm) was used, the mobile phase consisted of 250 mM sodium phosphate, 100 mM L-Arginine at pH 6.8. Quantification of monomer, low molecular and high molecular weight species was performed using Empower software (Waters Corp, UK).

5.5.3 Thermostability

The melting temperature ($T_m$) of G1AA/E05v2, G1AA/E12v2 and G1AA/G12v2 was measured using a Microcal VP-capillary differential scanning calorimeter (DSC). G1AA/lambdav3 was included to assess the difference between the kappa and lambda light chain-containing mAbs. Samples were measured in sample buffer at a concentration of 0.2 mg/ml. The scan rate was set at 60° C./hr and data were collected between 35° C. and 100° C. Data analysis was performed with Origin 7.0 software. As the DSC peaks of the Fab and CH3 were overlapping, one value was reported.

TABLE 11

| mAb | Monomer purity post-Protein A % | Tm of Fab/CH3 |
| --- | --- | --- |
| G1AA/E05v2 | 99.48 ± 0.01% | 80.4-82.8° C. |
| G1AA/E12v2 | 98.85 ± 0.07% | 81.4-84.1° C. |
| G1AA/G12v2 | 99.83 ± 0.11% | 78.1-81.3° C. |
| G1AA/lambdav3 | 99.75 ± 0.25% | 68.1° C. |

A summary of the results is shown in Table 11. The three mAbs: G1AA/E05v2, G1AA/E12v2 and G1AA/G12v2 showed favourable analytical characterisation parameters; monomer purity post-protein A was greater than 98% and the thermal stability of the Fab transition (Tm) was found to be at the higher end of transitions typically reported for IgG1, with G1AA/E12v2 appearing to be the most thermally stable (Fab/CH3 $T_M$=81.4-84.1° C.). The lambda light chain mAb, G1AA/lambdav3, had a lower Tm than the three kappa light chain-containing mAbs.

REFERENCES

Bedzyk W D, Johnson L S, Riordan G S, Voss E W Jr. Comparison of variable region primary structures within an anti-fluorescein idiotype family. *J. Biol. Chem.* 264(3), 1565-69 (1989).

Bedzyk W D, Weidner K M, Denzin L K, Johnson L S, Hardman K D, Pantoliano M W, Asel E D, Voss E W Jr. Immunological and structural characterization of a high affinity anti-fluorescein single-chain antibody. *J Biol Chem.* 265(30), 18615-20 (1990).

Brown M H, Barclay A N. Expression of immunoglobulin and scavenger receptor superfamily domains as chimeric proteins with domains 3 and 4 of CD4 for ligand analysis. Protein Eng. 7(4), 515-21 (1994).

Bruhns P, Iannascoli B, England P, Mancardi D A, Fernandez N, Jorieux S, Daëron M. Specificity and affinity of human Fcγ receptors and their polymorphic variants for human IgG subclasses. Blood 113(16), 3716-25 (2009).

Chapple S D, Crofts A M, Shadbolt S P, McCafferty J, Dyson M R. Multiplexed expression and screening for recombinant protein production in mammalian cells. BMC Biotechnol. 6:49 (2006).

Curran M A, Montalvo W, Yagita H, Allison J P. PD-1 and CTLA-4 combination blockade expands infiltrating T cells and reduces regulatory T and myeloid cells within B16 melanoma tumors. Proc. Natl. Acad. Sci. U.S.A. 107(9), 4275-80 (2010).

Deng R, Bumbaca D, Pastuskovas C V, Boswell C A, West D, Cowan K J, Chiu H, McBride J, Johnson C, Xin Y, Koeppen H, Leabman M and Iyer S. Preclinical pharmacokinetics, pharmacodynamics, tissue distribution, and tumor penetration of anti-PD-L1 monoclonal antibody, an immune checkpoint inhibitor. MAbs 8(3), 593-603 (2016).

Dyson M R, Zheng Y, Zhang C, Colwill K, Pershad K, Kay B K, Pawson T, McCafferty J: Mapping protein interactions by combining antibody affinity maturation and mass spectrometry. Anal. Biochem. 417(1), 25-35 (2011).

Grosso J, Inzunza D, Wu Q, Simon J, Singh P, Zhang X, Phillips T, Simmons P, Cogswell J. Programmed death-ligand 1 (PD-L1) expression in various tumor types. J. Immunother Cancer. 1(Suppl 1), 53 (2013).

Herbst R S, Soria J C, Kowanetz M, Fine G D, Hamid O, Gordon M S, Sosman J A, McDermott D F, Powderly J D, Gettinger S N, Kohrt H E, Horn L, Lawrence D P, Rost S, Leabman M, Xiao Y, Mokatrin A, Koeppen H, Hegde P S, Mailman I, Chen D S, Hodi F S. Predictive correlates of response to the anti-PD-L1 antibody MPDL3280A in cancer patients. Nature 515(7528), 563-7 (2014).

Hezareh M, Hessell A J, Jensen R C, van de Winkel J G, Parren P W. Effector function activities of a panel of mutants of a broadly neutralizing antibody against human immunodeficiency virus type 1. J. Virol. 75(24), 12161-8 (2001).

Hu S, Shively L, Raubitschek A, Sherman M, Williams L E, Wong J Y, Shively J E, Wu A M. Minibody: A novel engineered anti-carcinoembryonic antigen antibody fragment (single-chain Fv-CH3) which exhibits rapid, high-level targeting of xenografts. Cancer Res. 56(13), 3055-61 (1996).

Idusogie E E, Presta L G, Gazzano-Santoro H, Totpal K, Wong P Y, Ultsch M, Meng Y G, Mulkerrin M G. Mapping of the C1q binding site on rituxan, a chimeric antibody with a human IgG1 Fc. J. Immunol. 164(8), 4178-84 (2000).

Iwai Y, Ishida M, Tanaka Y, Okazaki T, Honjo T, Minato N. Involvement of PD-L1 on tumor cells in the escape from host immune system and tumor immunotherapy by PD-L1 blockade. Proc. Natl. Acad. Sci. U.S.A. 99(19), 12293-7 (2002).

Jain T, Sun T, Durand S, Hall A, Houston N R, Nett J H, Sharkey B, Bobrowicz B, Caffry I, Yu Y, Cao Y, Lynaugh H, Brown M, Baruah H, Gray L T, Krauland E M, Xu Y, Vasquez M and Wittrup K D. Biophysical properties of the clinical-stage antibody landscape. PNAS 114 (5), 944-949 (2017).

Kabat E A, Wu T T, Perry H M, Gottesman K S, Foeller C. Sequences of Proteins of Immunological Interest, 5th ed. NIH Publication No. 91-3242. Washington, D.C.: U.S. Department of Health and Human Services (1991).

Kontermann R E. Dual targeting strategies with bispecific antibodies. MAbs 4(2), 182-97 (2012).

Klein C, Schaefer W, Regula J T. The use of CrossMAb technology for the generation of bi- and multispecific antibodies. MAbs. 8(6), 1010-20 (2016).

Larkin J, Hodi F S, Wolchok J D. Combined nivolumab and ipilimumab or monotherapy in untreated melanoma. N Engl J Med. 373(13), 1270-1 (2015).

Lefranc M P, Pommié C, Kaas Q, Duprat E, Bosc N, Guiraudou D, Jean C, Ruiz M, Da Piédade I, Rouard M, Foulquier E, Thouvenin V, Lefranc G. IMGT unique numbering for immunoglobulin and T cell receptor constant domains and Ig superfamily C-like domains. Dev. Comp. Immunol. 29(3), 185-203 (2005).

Martin C D, Rojas G, Mitchell J N, Vincent K J, Wu J, McCafferty J, Schofield D J. A simple vector system to improve performance and utilisation of recombinant antibodies. BMC Biotechnol. 6, 46 (2006).

Ni L, Dong C. New B7 family checkpoints in human cancers. Mol. Cancer Ther. 16(7), 1203-11 (2017).

Powles T, Eder J P, Fine G D, Braiteh F S, Loriot Y, Cruz C, Bellmunt J, Burris H A, Petrylak D P, Teng S L, Shen X, Boyd Z, Hegde P S, Chen D S, Vogelzang N J. MPDL3280A (anti-PD-L1) treatment leads to clinical activity in metastatic bladder cancer. Nature 515(7528), 558-62 (2014).

Rao M, Valentini D, Dodoo E, Zumla A, Maeurer M. Anti-PD-1/PD-L1 therapy for infectious diseases: learning from the cancer paradigm. Int. J. Infect. Dis. 56, 221-228 (2017).

Schofield D J, Pope A R, Clementel V, Buckell J, Chapple SDj, Clarke K F, Conquer J S, Crofts A M, Crowther S R, Dyson M R, Flack G, Griffin G J, Hooks Y, Howat W J, Kolb-Kokocinski A, Kunze S, Martin C D, Maslen G L, Mitchell J N, O'Sullivan M, Perera R L, Roake W, Shadbolt S P, Vincent K J, Watford A, Wilson W E, Xie J, Young J L, McCafferty J. Application of phage display to high throughput antibody generation and characterization. Genome Biol. 8(11), R254 (2007).

Spiess C, Zhai Q, Carter P J. Alternative molecular formats and therapeutic applications for bispecific antibodies. Mol. Immunol. 67(2 Pt A), 95-106 (2015).

Studier F W. Protein production by auto-induction in high density shaking cultures. Protein Expr. Purif. 41(1), 207-34 (2005).

Wang X, Mathieu M, Brerski R J. IgG Fc engineering to modulate antibody effector functions. Protein Cell. 9(1), 63-73 (2018).

Wolchok J D, Kluger H, Callahan M K, Postow M A, Rizvi N A, Lesokhin A M, Segal N H, Ariyan C E, Gordon R A, Reed K, Burke M M, Caldwell A, et al. Nivolumab plus ipilimumab in advanced melanoma. N. Engl. J. Med. 369(2), 122-33 (2013).

Wykes M N, Lewin S R. Immune checkpoint blockade in infectious diseases. Nat. Rev. Immunol. 18(2), 91-104 (2017).

SEQUENCE LISTING INFORMATION

Antibody Sequences
Notes:
  i. The complete heavy chain, variable domain is shown in italics, CDRs according to the Kabat scheme are shown in italics and underlined, CDRs according to the IMGT scheme are shown in bold italics, therefore any overlapping IMGT and Kabat CDR sequences are shown in bold, italics and underlined, and, where applicable, location of LALA mutation is shown in bold and underlined.
  ii. Amino acid and cDNA sequences for complete heavy chain are provided without optional C-terminal lysine.
  iii. Complete light chain, variable domain are shown in italics, CDRs according to the Kabat scheme are shown in italics and underlined, CDRs according to the IMGT scheme are shown in bold italics, therefore any overlapping IMGT and Kabat CDR sequences are shown in bold, italics and underlined.
  iv. In the amino acid sequence of variable domains, CDRs according to the Kabat scheme are shown in italics and underlined, CDRs according to the IMGT scheme are shown in bold italics, therefore any overlapping IMGT and Kabat CDR sequences are shown in bold, italics and underlined.
  v. CDR amino acid sequences according to both Kabat and IMGT schemes are provided.

| Amino acid sequence of heavy and light chains, variable domains and CDRs of G1/280_02_G02 | |
|---|---|
| Heavy chain AA (without LALA) (SEQ ID NO: 65) | EVQLVQSGAEVKRPGASVKVSCKASGYTFTSYGI*SWVRQAPGQG LEWMGWISAYNGNTNYAQKLQGR*VTMTTDTSTSTAYMELRSLRS DDTAVYYCARDLFPTIFGVSYYYYWGQGTLVTVSSASTKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVEPKS CDKTHTCPPCPAPELLGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG |
| Heavy chain AA (with LALA) (SEQ ID NO: 93) | EVQLVQSGAEVKRPGASVKVSCKASGYTFTSYGI*SWVRQAPGQG LEWMGWISAYNGNTNYAQKLQGR*VTMTTDTSTSTAYMELRSLRS DDTAVYYCARDLFPTIFGVSYYYYWGQGTLVTVSSASTKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVEPKS CDKTHTCPPCPAPEAAGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG |
| VH domain AA (SEQ ID NO: 45) | EVQLVQSGAEVKRPGASVKVSCKASGYTFTSYGI*SWVRQAPGQG LEWMGWISAYNGNTNYAQKLQGR*VTMTTDTSTSTAYMELRSLRS DDTAVYYCARDLFPTIFGVSYYYYWGQGTLVTVSS |
| HCDR1 (AA) (IMGT) (SEQ ID NO: 94) | GYTFTSYG |

-continued

| Amino acid sequence of heavy and light chains, variable domains and CDRs of G1/280_02_G02 | |
|---|---|
| HCDR1 (AA) (Kabat)<br>(SEQ ID NO: 1) | SYGIS |
| HCDR2 (AA) (IMGT)<br>(SEQ ID NO: 95) | ISAYNGNT |
| HCDR2 (AA) (Kabat)<br>(SEQ ID NO: 78) | WISAYNGNTNYAQKLQG |
| HCDR3 (AA) (IMGT)<br>(SEQ ID NO: 69) | ARDLFPTIFGVSYYYY |
| HCDR3 (AA) (Kabat)<br>(SEQ ID NO: 3) | DLFPTIFGVSYYYY |
| Light chain AA<br>(SEQ ID NO: 66) | *QSALTQPASVSGSPGQSITISCTGTSSDVGGYNSVSWYQQFPGKA PKLMIFEVTNRPSGVSDRFSGSKSDNTASLTISGLQAEDEAEYYCS SFKRGSTLVVFGGGTKLTVL*GQPAAAPSVTLFPPSSEELQANKATL VCLISDFYPGAVTVAWKADSSPVKAGVETTTPSKQSNNKYAASSYL SLTPEQWKSHRSYSCQVTHEGSTVEKTVAPTECS |
| VL domain AA<br>(SEQ ID NO: 46) | *QSALTQPASVSGSPGQSITISCTGTSSDVGGYNSVSWYQQFPGKA PKLMIFEVTNRPSGVSDRFSGSKSDNTASLTISGLQAEDEAEYYCS SFKRGSTLVVFGGGTKLTVL* |
| LCDR1 (AA) (IMGT)<br>(SEQ ID NO: 96) | SSDVGGYNS |
| LCDR1 (AA) (Kabat)<br>(SEQ ID NO: 26) | TGTSSDVGGYNSVS |
| LCDR2 (AA) (IMGT)<br>(SEQ ID NO: 77) | EVT |
| LCDR2 (AA) (Kabat)<br>(SEQ ID NO: 13) | EVTNRPS |
| LCDR3 (AA) (IMGT)<br>(SEQ ID NO: 14) | SSFKRGSTLVV |
| LCDR3 (AA) (Kabat)<br>(SEQ ID NO: 14) | SSFKRGSTLVV |

| Amino acid sequence of heavy and light chains, variable domains and CDRs of G1/280_02_G02_NS | |
|---|---|
| Heavy chain AA<br>(without LALA)<br>(SEQ ID NO: 63) | *EVQLVQSGAEVKRPGASVKVSCKASGYTFTSYGISWVRQAPGQG LEWMGWISAYNSNTNYAQKLQGRVTMTTDTSTSTAYMELRSLRS DDTAVYYCARDLFPTIFGVSYYYYWGQGTLVTVSS*ASTKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVEPKS CDKTHTCPPCPAPELLGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG |
| Heavy chain AA<br>(with LALA)<br>(SEQ ID NO: 97) | *EVQLVQSGAEVKRPGASVKVSCKASGYTFTSYGISWVRQAPGQG LEWMGWISAYNSNTNYAQKLQGRVTMTTDTSTSTAYMELRSLRS DDTAVYYCARDLFPTIFGVSYYYYWGQGTLVTVSS*ASTKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVEPKS CDKTHTCPPCPAPEAAGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG |
| VH domain AA<br>(SEQ ID NO: 43) | *EVQLVQSGAEVKRPGASVKVSCKASGYTFTSYGISWVRQAPGQG LEWMGWISAYNSNTNYAQKLQGRVTMTTDTSTSTAYMELRSLRS DDTAVYYCARDLFPTIFGVSYYYYWGQGTLVTVSS* |

| Amino acid sequence of heavy and light chains, variable domains and CDRs of G1/280_02_G02_NS |  |
|---|---|
| HCDR1 (AA) (IMGT)<br>(SEQ ID NO: 94) | GYTFTSYG |
| HCDR1 (AA) (Kabat)<br>(SEQ ID NO: 1) | SYGIS |
| HCDR2 (AA) (IMGT)<br>(SEQ ID NO: 98) | ISAYNSNT |
| HCDR2 (AA) Kabat)<br>(SEQ ID NO: 23) | WISAYNSNTNYAQKLQG |
| HCDR3 (AA) (IMGT)<br>(SEQ ID NO: 69) | ARDLFPTIFGVSYYYY |
| HCDR3 (AA) (Kabat)<br>(SEQ ID NO: 3) | DLFPTIFGVSYYYY |
| Light chain AA<br>(SEQ ID NO: 64) | QSALTQPASVSGSPGQSITISCTGTSSDVGGYNSVSWYQQFPGKA<br>PKLMIFEVTNRPSGVSDRFSGSKSDNTASLTISGLQAEDEAEYYCS<br>SFKRGSTLVVFGGGTKLTVLGQPAAAPSVTLFPPSSEELQANKATL<br>VCLISDFYPGAVTVAWKADSSPVKAGVETTTPSKQSNNKYAASSYL<br>SLTPEQWKSHRSYSCQVTHEGSTVEKTVAPTECS |
| VL domain AA<br>(SEQ ID NO: 44) | QSALTQPASVSGSPGQSITISCTGTSSDVGGYNSVSWYQQFPGKA<br>PKLMIFEVTNRPSGVSDRFSGSKSDNTASLTISGLQAEDEAEYYCS<br>SFKRGSTLVVFGGGTKLTVL |
| LCDR1 (AA) (IMGT)<br>(SEQ ID NO: 96) | SSDVGGYNS |
| LCDR1 (AA) (Kabat)<br>(SEQ ID NO: 26) | TGTSSDVGGYNSVS |
| LCDR2 (AA) (IMGT)<br>(SEQ ID NO: 77) | EVT |
| LCDR2 (AA) (Kabat)<br>(SEQ ID NO: 13) | EVTNRPS |
| LCDR3 (AA) (IMGT)<br>(SEQ ID NO: 14) | SSFKRGSTLVV |
| LCDR3 (AA) (Kabat)<br>(SEQ ID NO: 14) | SSFKRGSTLVV |

| Amino acid sequence of heavy and light chains, variable domains and CDRs of G1/894_08_E05 |  |
|---|---|
| Heavy chain AA<br>(without LALA)<br>(SEQ ID NO: 57) | EVQLVQSGAEVKRPGASVKVSCKASGYTFTSYGISWVRQAPGQG<br>LEWMGWISAYNSNTNYAQKLQGRVTMTTDTSTSTAYMELRSLRS<br>DDTAVYYCARDLFPTIFGVSYYYYWGQGTLVTVSSASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| Heavy chain AA<br>(with LALA)<br>(SEQ ID NO: 99) | EVQLVQSGAEVKRPGASVKVSCKASGYTFTSYGISWVRQAPGQG<br>LEWMGWISAYNSNTNYAQKLQGRVTMTTDTSTSTAYMELRSLRS<br>DDTAVYYCARDLFPTIFGVSYYYYWGQGTLVTVSSASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPKS<br>CDKTHTCPPCPAPEAAGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |

-continued

| Amino acid sequence of heavy and light chains, variable domains and CDRs of G1/894_08_E05 | |
|---|---|
| VH domain AA (SEQ ID NO: 37) | EVQLVQSGAEVKRPGASVKVSCKASGYTFTSYGISWVRQAPGQG LEWMGWISAYNSNTNYAQKLQGRVTMTTDTSTSTAYMELRSLRS DDTAVYYC<u>ARDLFPTIFGVSYYYY</u>WGQGTLVTVSS |
| HCDR1 (AA) (IMGT) (SEQ ID NO: 94) | GYTFTSYG |
| HCDR1 (AA) (Kabat) (SEQ ID NO: 1) | SYGIS |
| HCDR2 (AA) (IMGT) (SEQ ID NO: 98) | ISAYNSNT |
| HCDR2 (AA) Kabat) (SEQ ID NO: 23) | WISAYNSNTNYAQKLQG |
| HCDR3 (AA) (IMGT) (SEQ ID NO: 69) | ARDLFPTIFGVSYYYY |
| HCDR3 (AA) (Kabat) (SEQ ID NO: 3) | DLFPTIFGVSYYYY |
| Light chain AA (SEQ ID NO: 58) | DIQMTQSPSTLSASVGDRVTITCRASQSISGRLAWYQQKPGKAPNL LIYEASNLESGVPSRFGSGSGSTEFTLTISSLQPEDFATYYC<u>QQSY STPRVT</u>FGQGTKVEIKRTAAAAPSVFIFPPSDEQLKSG-TASVVCLLN NFYPREAKVQWKVDNALQSGNSQESVTEQDSKDSTYSLSSTLTLS KADYEKHKLYACEVTHQGLSSPVTKSFNRGEC |
| VL domain AA (SEQ ID NO: 38) | DIQMTQSPSTLSASVGDRVTITCRASQSISGRLAWYQQKPGKAPNL LIYEASNLESGVPSRFGSGSGSTEFTLTISSLQPEDFATYYC<u>QQSY STPRVT</u>FGQGTKVEIK |
| LCDR1 (AA) (IMGT) (SEQ ID NO: 100) | QSISGR |
| LCDR1 (AA) (Kabat) (SEQ ID NO: 19) | RASQSISGRLA |
| LCDR2 (AA) (IMGT) (SEQ ID NO: 71) | EAS |
| LCDR2 (AA) (Kabat) (SEQ ID NO: 20) | EASNLES |
| LCDR3 (AA) (IMGT) (SEQ ID NO: 22) | QQSYSTPRVT |
| LCDR3 (AA) (Kabat) (SEQ ID NO: 22) | QQSYSTPRVT |

| Amino acid sequence of heavy and light chains, variable domains and CDRs of G1/887_04_E12 | |
|---|---|
| Heavy chain AA (without LALA) (SEQ ID NO: 53) | EVQLVQSGAEVKRPGASVKVSCKASGYPFTSYGISWVRQAPGQG LEWMGWISAYNSNTNYAQKLQGRVTMTTDTSTSTAYMELRSLRS DDTAVYYCARDLFPTIFGVSYYYYWGQGTLVTVSSASTKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVEPKS CDKTHTCPPCPAPELLGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG |
| Heavy chain AA (with LALA) (SEQ ID NO: 101) | EVQLVQSGAEVKRPGASVKVSCKASGYPFTSYGISWVRQAPGQG LEWMGWISAYNSNTNYAQKLQGRVTMTTDTSTSTAYMELRSLRS DDTAVYYCARDLFPTIFGVSYYYYWGQGTLVTVSSASTKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVEPKS CDKTHTCPPCPAPEAAGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRD |

| | |
|---|---|
| | ELTKNQVSLTCLVKGFYPSDIAVEWESNGQPENNYKTTPPVLDSD GSFFLYSKLTVDKSRWQQGNVFSCSVMHEALHNHYTQKSLSLSPG |
| VH domain AA (SEQ ID NO: 33) | EVQLVQSGAEVKRPGASVKVSCKASGYPFTSYGISWVRQAPGQG LEWMGWISAYNSNTNYAQKLQGRVTMTTDTSTSTAYMELRSLRS DDTAVYYCARDLFPTIFGVSYYYYWGQGTLVTVSS |
| HCDR1 (AA) (IMGT) (SEQ ID NO: 102) | GYPFTSYG |
| HCDR1 (AA) (Kabat) (SEQ ID NO: 1) | SYGIS |
| HCDR2 (AA) (IMGT) (SEQ ID NO: 98) | ISAYNSNT |
| HCDR2 (AA) (Kabat) (SEQ ID NO: 23) | WISAYNSNTNYAQKLQG |
| HCDR3 (AA) (IMGT) (SEQ ID NO: 69) | ARDLFPTIFGVSYYYY |
| HCDR3 (AA) (Kabat) (SEQ ID NO: 3) | DLFPTIFGVSYYYY |
| Light chain AA (SEQ ID NO: 54) | DIQMTQSPSTLSASVRDRVIITCRASQSIGNRLAWYQHKPGKAPKL LIYEASTSETGVPSRFSGSGSGTDFTLTISSLQPEDFATYYCQQSY STPYTFGQGTKLEIKRTAAAAPSVFIFPPSDEQLKSG- TASVVCLLNN FYPREAKVQWKVDNALQSGNSQESVTEQDSKDSTYSLSSTLTLSK ADYEKHKLYACEVTHQGLSSPVTKSFNRGEC |
| VL domain AA (SEQ ID NO: 34) | DIQMTQSPSTLSASVRDRVIITCRASQSIGNRLAWYQHKPGKAPKL LIYEASTSETGVPSRFSGSGSGTDFTLTISSLQPEDFATYYCQQSY STPYTFGQGTKLEIK |
| LCDR1 (AA) (IMGT) (SEQ ID NO: 103) | QSIGNR |
| LCDR1 (AA) (Kabat) (SEQ ID NO: 15) | RASQSIGNRLA |
| LCDR2 (AA) (IMGT) (SEQ ID NO: 71) | EAS |
| LCDR2 (AA) (Kabat) (SEQ ID NO: 16) | EASTSET |
| LCDR3 (AA) (IMGT) (SEQ ID NO: 17) | QQSYSTPYT |
| LCDR3 (AA) (Kabat) (SEQ ID NO: 17) | QQSYSTPYT |

| Amino acid sequence of heavy and light chains, variable domains and CDRs of G1/887_04_G12 | |
|---|---|
| Heavy chain AA (without LALA) (SEQ ID NO: 55) | EVQLVQSGAEVKRPGASVKVSCKASGYTFTSYGISWVRQAPGQG LEWMGWISAYNSNTNYAQKLQGRVTMTTDTSTSTAYMELRSLRS DDTAVYYCARDLFPTIFGVSYYYYWGQGTLVTVSSASTKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVEPKS CDKTHTCPPCPAPELLGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG |
| Heavy chain AA (with LALA) (SEQ ID NO: 104) | EVQLVQSGAEVKRPGASVKVSCKASGYTFTSYGISWVRQAPGQG LEWMGWISAYNSNTNYAQKLQGRVTMTTDTSTSTAYMELRSLRS DDTAVYYCARDLFPTIFGVSYYYYWGQGTLVTVSSASTKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVEPKS |

| | |
|---|---|
| | CDKTHTCPPCPAPEAAGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| VH domain AA<br>(SEQ ID NO: 35) | *EVQLVQSGAEVKRPGASVKVSCKASGYTFTSYGISWVRQAPGQG<br>LEWMGWISAYNSNTNYAQKLQGRVTMTTDTSTSTAYMELRSLRS<br>DDTAVYYCARDLFPTIFGVSYYYYWGQGTLVTVSS* |
| HCDR1 (AA) (IMGT)<br>(SEQ ID NO: 94) | GYTFTSYG |
| HCDR1 (AA) (Kabat)<br>(SEQ ID NO: 1) | SYGIS |
| HCDR2 (AA) (IMGT)<br>(SEQ ID NO: 98) | ISAYNSNT |
| HCDR2 (AA) Kabat<br>(SEQ ID NO: 23) | WISAYNSNTNYAQKLQG |
| HCDR3 (AA) (IMGT)<br>(SEQ ID NO: 69) | ARDLFPTIFGVSYYYY |
| HCDR3 (AA) (Kabat)<br>(SEQ ID NO: 3) | DLFPTIFGVSYYYY |
| Light chain AA<br>(SEQ ID NO: 56) | *DIQMTQSPSTLSASVGDRVTITCRASQSISGRLAWYQQKPGKAPNL<br>LIYEASNLESGVPSRFSGSGSGTEFTLTISSLQPEDFATYYCQQSY<br>SWPRTFGQGTKVEIKRTAAAAPSVFIFPPSDEQLKSGTASVVCLLN<br>NFYPREAKVQWKVDNALQSGNSQESVTEQDSKDSTYSLSSTLTLS<br>KADYEKHKLYACEVTHQGLSSPVTKSFNRGEC* |
| VL domain AA<br>(SEQ ID NO: 36) | *DIQMTQSPSTLSASVGDRVTITCRASQSISGRLAWYQQKPGKAPNL<br>LIYEASNLESGVPSRFSGSGSGTEFTLTISSLQPEDFATYYCQQSY<br>SWPRTFGQGTKVEIK* |
| LCDR1 (AA) (IMGT)<br>(SEQ ID NO: 100) | QSISGR |
| LCDR1 (AA) (Kabat)<br>(SEQ ID NO: 19) | RASQSISGRLA |
| LCDR2 (AA) (IMGT)<br>(SEQ ID NO: 77) | EASN |
| LCDR2 (AA) (Kabat)<br>(SEQ ID NO: 20) | EASNLES |
| LCDR3 (AA) (IMGT)<br>(SEQ ID NO: 21) | QQSYSWPRT |
| LCDR3 (AA) (Kabat)<br>(SEQ ID NO: 21) | QQSYSWPRT |

| | |
|---|---|
| Amino acid sequence of heavy and light chains, variable domains and CDRs of G1/894_08_A05 | |
| Heavy chain AA<br>(without LALA)<br>(SEQ ID NO: 59) | *EVQLVQSGAEVKRPGASVKVSCKASGYTFTSYGISWVRQAPGQG<br>LEWMGWISAYNSNTNYAQKLQGRVTMTTDTSTSTAYMELRSLRS<br>DDTAVYYCARDLFPTIFGVSYYYYWGQGTLVTVSS*ASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| Heavy chain AA<br>(with LALA)<br>(SEQ ID NO: 105) | *EVQLVQSGAEVKRPGASVKVSCKASGYTFTSYGISWVRQAPGQG<br>LEWMGWISAYNSNTNYAQKLQGRVTMTTDTSTSTAYMELRSLRS<br>DDTAVYYCARDLFPTIFGVSYYYYWGQGTLVTVSS*ASTKGPSVFPL |

| | |
|---|---|
| | APSSKSTSGGTAALGCLVKDYFPEPVTVSWNSGALTSGVHTFPAV<br>LQSSGLYSLSSVVTVPSSSLGTQTYICNVNHKPSNTKVDKKVEPKS<br>CDKTHTCPPCPAPEAAGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| VH domain AA<br>(SEQ ID NO: 39) | *EVQLVQSGAEVKRPGASVKVSCKASGYTFTSYGISWVRQAPGQG<br>LEWMGWISAYNSNTNYAQKLQGRVTMTTDTSTSTAYMELRSLRS<br>DDTAVYYCARDLFPTIFGVSYYYYWGQGTLVTVSS* |
| HCDR1 (AA) (IMGT)<br>(SEQ ID NO: 94) | GYTFTSYG |
| HCDR1 (AA) (Kabat)<br>(SEQ ID NO: 1) | SYGIS |
| HCDR2 (AA) (IMGT)<br>(SEQ ID NO: 98) | ISAYNSNT |
| HCDR2 (AA) Kabat)<br>(SEQ ID NO: 23) | WISAYNSNTNYAQKLQG |
| HCDR3 (AA) (IMGT)<br>(SEQ ID NO: 69) | ARDLFPTIFGVSYYYY |
| HCDR3 (AA) (Kabat)<br>(SEQ ID NO: 3) | DLFPTIFGVSYYYY |
| Light chain AA<br>(SEQ ID NO: 60) | *DIQMTQSPSTLSASVGDRVTITCRASQSISGRLAWYQQKPGKAPNL<br>LIYEASNLESGVPSRFSGSGSGTEFTLTINSLQPDDFATYYCQQAN<br>TFPRVSFGGGTKVEIKRTAAAAPSVFIFPPSDEQLKSG-<br>TASVVCLLN<br>NFYPREAKVQWKVDNALQSGNSQESVTEQDSKDSTYSLSSTLTLS<br>KADYEKHKLYACEVTHQGLSSPVTKSFNRGEC* |
| VL domain AA<br>(SEQ ID NO: 40) | *DIQMTQSPSTLSASVGDRVTITCRASQSISGRLAWYQQKPGKAPNL<br>LIYEASNLESGVPSRFSGSGSGTEFTLTINSLQPDDFATYYCQQAN<br>TFPRVSFGGGTKVEIK* |
| LCDR1 (AA) (IMGT)<br>(SEQ ID NO: 100) | QSISGR |
| LCDR1 (AA) (Kabat)<br>(SEQ ID NO: 19) | RASQSISGRLA |
| LCDR2 (AA) (IMGT)<br>(SEQ ID NO: 106) | EASN |
| LCDR2 (AA) Kabat)<br>(SEQ ID NO: 20) | EASNLES |
| LCDR3 (AA) (IMGT)<br>(SEQ ID NO: 24) | QQANTFPRVS |
| LCDR3 (AA) (Kabat)<br>(SEQ ID NO: 24) | QQANTFPRVS |

Amino acid and cDNA sequences of heavy and light chains and
variable domains of G1AA/E05v2 and amino acid sequence of CDRs

| | |
|---|---|
| Heavy chain AA<br>(without LALA)<br>(SEQ ID NO: 107) | *EVQLVQSGAEVKRPGASVKVSCKASGYTFTSYGISWVRQAPGQG<br>LEWMGWISAYSGGTNYAQKLQGRVTMTTDTSTSTAYMELRSLRS<br>DDTAVYYCARDLFPTIFGVSYYYYWGQGTLVTVSS*ASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |

| Amino acid and cDNA sequences of heavy and light chains and variable domains of G1AA/E05v2 and amino acid sequence of CDRs |  |
| --- | --- |
| Heavy chain DNA (without LALA) (SEQ ID NO: 108) | GAAGTGCAGCTGGTGCAGTCCGGAGCCGAAGTCAAGAGGCCT<br>GGGAGCGTCCGTGAAGGTGTCCTGCAAAGCCTCAGGATACACCT<br>TCACTTCGTACGGGATTTCCTGGGTCCGCCAAGCACCGGGTCA<br>AGGCTTGGAGTGGATGGGATGGATCAGCGCGTATTCCGGGGGA<br>ACCAACTACGCTCAAAAGCTGCAGGGTCGCGTGACCATGACCA<br>CCGATACCTCCACCTCAACGGCCTACATGGAACTGAGATCTCTG<br>CGGAGCGACGACACTGCCGTGTACTACTGTGCCCGGGACCTGT<br>TCCCCACTATCTTCGGAGTGTCGTACTACTACTACTGGGGCAG<br>GGGACTCTCGTGACCGTGTCGAGCGCTAGCACTAAGGGCCCGT<br>CGGTGTTCCCGCTGGCCCCATCGTCAAGAGCACATCAGGGGG<br>TACCGCCGCCCTGGGCTGCCTTGTGAAGGATTACTTTCCCGAG<br>CCCGTCACAGTGTCCTGGAACAGCGGAGCCCTGACCTCCGGAG<br>TGCATACTTTCCCGGCTGTGCTTCAGTCCTCTGGCCTGTACTCA<br>TTGTCCTCCGTGGTCACCGTCCCTTCGTCCTCCCTGGGCACCC<br>AGACCTATATCTGTAATGTCAACCATAAGCCCTCGAACACCAAG<br>GTCGACAAGAAGGTCGAGCCGAAGTCGTGCGACAAGACTCACA<br>CTTGCCCGCCTTGCCCAGCCCCGGAACTGCTGGGTGGTCCTTC<br>GGTGTTCCTCTTCCCGCCCAAGCCGAAGGATACCCTGATGATCT<br>CACCGGACCCCCGAAGTGACCTGTGTGGTGGTGGACGTGTCCCA<br>CGAGGACCCGGAAGTGAAATTCAATTGGTACGTGGATGGAGTG<br>GAAGTGCACAACGCCAAGACCAAGCCACGGGAAGAACAGTACA<br>ACTCTACCTACCGCGTGGTGTCCGTGCTCACTGTGCTGCACCAA<br>GACTGGCTGAACGGGAAGGAGTACAAGTGCAAAGTGTCCAACA<br>AGGCGCTGCCTGCCCCAATTGAGAAAACTATCTCGAAAGCCAA<br>GGGACAGCCTCGAGAGCCTCAAGTGTACACCCTGCCTCCCTCT<br>CGGGACGAGCTGACCAAGAACCAAGTCTCCCTGACCTGTCTGG<br>TCAAGGGATTCTACCCATCGGATATCGCCGTGGAATGGGAAAG<br>CAACGGACAGCCCGAGAACAACTACAAGACGACTCCGCCCGTG<br>CTGGATTCCGACGGGAGCTTCTTCTTGTACTCCAAGCTGACCGT<br>CGACAAGAGCAGATGGCAGCAGGGAAACGTGTTCTCCTGCTCC<br>GTGATGCATGAGGCGCTGCACAACCACTACACTCAGAAGAGCT<br>TGTCCCTGTCGCCCGGA |
| Heavy chain AA (with LALA) (SEQ ID NO: 51) | *EVQLVQSGAEVKRPGASVKVSCKASGYTFTSYGISWVRQAPGQG*<br>*LEWMGWISAYSGGTNYAQKLQGRVTMTTDTSTSTAYMELRSLRS*<br>*DDTAVYYCARDLFPTIFGVSYYYYWGQGTLVTVSS*ASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPKS<br>CDKTHTCPPCPAPEAAGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| Heavy chain DNA (with LALA) (SEQ ID NO: 109) | GAAGTGCAGCTGGTGCAGTCCGGAGCCGAAGTCAAGAGGCCT<br>GGGAGCGTCCGTGAAGGTGTCCTGCAAAGCCTCAGGATACACCT<br>TCACTTCGTACGGGATTTCCTGGGTCCGCCAAGCACCGGGTCA<br>AGGCTTGGAGTGGATGGGATGGATCAGCGCGTATTCCGGGGGA<br>ACCAACTACGCTCAAAAGCTGCAGGGTCGCGTGACCATGACCA<br>CCGATACCTCCACCTCAACGGCCTACATGGAACTGAGATCTCTG<br>CGGAGCGACGACACTGCCGTGTACTACTGTGCCCGGGACCTGT<br>TCCCCACTATCTTCGGAGTGTCGTACTACTACTACTGGGGCAG<br>GGGACTCTCGTGACCGTGTCGAGCGCTAGCACTAAGGGCCCGT<br>CGGTGTTCCCGCTGGCCCCATCGTCAAGAGCACATCAGGGGG<br>TACCGCCGCCCTGGGCTGCCTTGTGAAGGATTACTTTCCCGAG<br>CCCGTCACAGTGTCCTGGAACAGCGGAGCCCTGACCTCCGGAG<br>TGCATACTTTCCCGGCTGTGCTTCAGTCCTCTGGCCTGTACTCA<br>TTGTCCTCCGTGGTCACCGTCCCTTCGTCCTCCCTGGGCACCC<br>AGACCTATATCTGTAATGTCAACCATAAGCCCTCGAACACCAAG<br>GTCGACAAGAAGGTCGAGCCGAAGTCGTGCGACAAGACTCACA<br>CTTGCCCGCCTTGCCCAGCCCCGGAAGCTGCGGTGGTCCTTC<br>GGTGTTCCTCTTCCCGCCCAAGCCGAAGGATACCCTGATGATCT<br>CACCGGACCCCCGAAGTGACCTGTGTGGTGGTGGACGTGTCCCA<br>CGAGGACCCGGAAGTGAAATTCAATTGGTACGTGGATGGAGTG<br>GAAGTGCACAACGCCAAGACCAAGCCACGGGAAGAACAGTACA<br>ACTCTACCTACCGCGTGGTGTCCGTGCTCACTGTGCTGCACCAA<br>GACTGGCTGAACGGGAAGGAGTACAAGTGCAAAGTGTCCAACA<br>AGGCGCTGCCTGCCCCAATTGAGAAAACTATCTCGAAAGCCAA<br>GGGACAGCCTCGAGAGCCTCAAGTGTACACCCTGCCTCCCTCT<br>CGGGACGAGCTGACCAAGAACCAAGTCTCCCTGACCTGTCTGG<br>TCAAGGGATTCTACCCATCGGATATCGCCGTGGAATGGGAAAG<br>CAACGGACAGCCCGAGAACAACTACAAGACGACTCCGCCCGTG<br>CTGGATTCCGACGGGAGCTTCTTCTTGTACTCCAAGCTGACCGT<br>CGACAAGAGCAGATGGCAGCAGGGAAACGTGTTCTCCTGCTCC<br>GTGATGCATGAGGCGCTGCACAACCACTACACTCAGAAGAGCT<br>TGTCCCTGTCGCCCGGA |

| | |
|---|---|
| Amino acid and cDNA sequences of heavy and light chains and variable domains of G1AA/E05v2 and amino acid sequence of CDRs | |
| VH domain AA (SEQ ID NO: 31) | EVQLVQSGAEVKRPGASVKVSCKASGYTFTSYGISWVRQAPGQG LEWMGWISAYSGGTNYAQKLQGRVTMTTDTSTSTAYMELRSLRS DDTAVYYCARDLFPTIFGVSYYYYWGQGTLVTVSS |
| VH domain DNA (SEQ ID NO: 110) | GAAGTGCAGCTGGTGCAGTCCGGAGCCGAAGTCAAGAGGCCT GGAGCGTCCGTGAAGGTGTCCTGCAAAGCCTCAGGATACACCT TCACTTCGTACGGGATTTCCTGGGTCCGCCAAGCACCGGGTCA AGGCTTGGAGTGGATGGGATGGATCAGCGCGTATTCCGGGGA ACCAACTACGCTCAAAAGCTGCAGGGTCGCGTGACCATGACCA CCGATACCTCCACCTCAACGGCCTACATGGAACTGAGATCTCTG CGGAGCGACGACACTGCCGTGTACTACTGTGCCCGGGACCTGT TCCCCACTATCTTCGGAGTGTCGTACTACTACTACTGGGGCCAG GGGACTCTCGTGACCGTGTCGAGC |
| HCDR1 (AA) (IMGT) (SEQ ID NO: 94) | GYTFTSYG |
| HCDR1 (AA) (Kabat) (SEQ ID NO: 1) | SYGIS |
| HCDR2 (AA) (IMGT) (SEQ ID NO: 111) | ISAYSGGT |
| HCDR2 (AA) (Kabat) (SEQ ID NO: 18) | WISAYSGGTNYAQKLQG |
| HCDR3 (AA) (IMGT) (SEQ ID NO: 69) | ARDLFPTIFGVSYYYY |
| HCDR3 (AA) (Kabat) (SEQ ID NO: 3) | DLFPTIFGVSYYYY |
| Light chain AA (SEQ ID NO: 52) | DIQMTQSPSTLSASVGDRVTITCRASQSISGRLAWYQQKPGKAPNL LIYEASNLESGVPSRFSGSGSGTEFTLTISSLQPEDFATYYCQQSY STPRVTFGQGTKVEIKRTVAAPSVFIFPPSDEQLKSG-TASVVCLLNN FYPREAKVQWKVDNALQSGNSQESVTEQDSKDSTYSLSSTLTLSK ADYEKHKVYACEVTHQGLSSPVTKSFNRGEC |
| Light chain DNA (SEQ ID NO: 112) | GACATTCAGATGACCCAATCCCCGTCCACGCTGAGCGCCTCCG TCGGTGATCGCGTGACAATCACTTGTCGGGCGTCGCAGTCCAT CTCTGGAAGGCTCGCCTGGTACCAGCAGAAGCCTGGAAAGGCT CCCAACCTCCTTATCTACGAAGCCAGCAACCTGGAGTCCGGAG TGCCTAGCCGGTTCAGCGGATCAGGGTCCGGTACCGAGTTCAC CCTGACCATTTCCTCGCTCCAACCTGAGGACTTCGCCACCTACT ACTGCCAACAGTCCTATTCAACTCCGCGCGTGACCTTCGGCCA GGGCACTAAGGTCGAAATCAAAAGAACCGTGGCAGCCCCATCG GTGTTTATCTTCCCGCCCTCGGACGAACAGCTGAAGTCAGGCA CTGCTAGCGTGGTCTGTCTCCTGAACAATTTCTACCCGCGCGAA GCTAAGGTCCAGTGGAAGGTCGACAACGCGCTGCAGTCCGGAA ACAGCCAGGAGTCAGTGACCGAGCAGGACTCCAAGGATTCCAC TTATTCCCTGTCCTCCACCCTGACTTTGAGCAAGGCCGACTACG AGAAGCACAAAGTGTACGCCTGCGAAGTGACCCATCAAGGGCT TTCGTCGCCCGTGACCAAGAGCTTCAACCGGGGCGAATGC |
| VL domain AA (SEQ ID NO: 32) | DIQMTQSPSTLSASVGDRVTITCRASQSISGRLAWYQQKPGKAPNL LIYEASNLESGVPSRFSGSGSGTEFTLTISSLQPEDFATYYCQQSY STPRVTFGQGTKVEIK |
| VL domain DNA (SEQ ID NO: 113) | GACATTCAGATGACCCAATCCCCGTCCACGCTGAGCGCCTCCG TCGGTGATCGCGTGACAATCACTTGTCGGGCGTCGCAGTCCAT CTCTGGAAGGCTCGCCTGGTACCAGCAGAAGCCTGGAAAGGCT CCCAACCTCCTTATCTACGAAGCCAGCAACCTGGAGTCCGGAG TGCCTAGCCGGTTCAGCGGATCAGGGTCCGGTACCGAGTTCAC CCTGACCATTTCCTCGCTCCAACCTGAGGACTTCGCCACCTACT ACTGCCAACAGTCCTATTCAACTCCGCGCGTGACCTTCGGCCA GGGCACTAAGGTCGAAATCAAA |
| LCDR1 (AA) (IMGT) (SEQ ID NO: 100) | QSISGR |
| LCDR1 (AA) (Kabat) (SEQ ID NO: 19) | RASQSISGRLA |
| LCDR2 (AA) (IMGT) (SEQ ID NO: 71) | EAS |

| Amino acid and cDNA sequences of heavy and light chains and variable domains of G1AA/E05v2 and amino acid sequence of CDRs |  |
| --- | --- |
| LCDR2 (AA) (Kabat)<br>(SEQ ID NO: 20) | EASNLES |
| LCDR3 (AA) (IMGT)<br>(SEQ ID NO: 22) | QQSYSTPRVT |
| LCDR3 (AA) (Kabat)<br>(SEQ ID NO: 22) | QQSYSTPRVT |

| Amino acid and cDNA sequences of heavy and light chains and variable domains of G1AA/E12v2 and amino acid sequence of CDRs |  |
| --- | --- |
| Heavy chain AA<br>(without LALA)<br>(SEQ ID NO: 114) | EVQLVQSGAEVKRPGASVKVSCKASGYPFTSYGISWVRQAPGQG<br>LEWMGWISAYSGGTNYAQKLQGRVTMTTDTSTSTAYMELRSLRS<br>DDTAVYYCARDLFPTIFGVSYYYYWGQGTLVTVSSASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| Heavy chain DNA<br>(without LALA)<br>(SEQ ID NO: 115) | GAAGTGCAGCTGGTGCAGTCCGGAGCCGAAGTCAAGAGGCCT<br>GGAGCGTCCGTGAAGGTGTCCTGCAAAGCCTCAGGATACCCCT<br>TCACTTCGTACGGGATTTCCTGGGTCCGCCAAGCACCGGGTCA<br>AGGCTTGGAGTGGATGGGATGGATCAGCGCGTATTCCGGGGGA<br>ACCAACTACGCTCAAAAGCTGCAGGGTCGCGTGACCATGACCA<br>CCGATACCTCCACCTCAACGGCCTACATGGAACTGAGATCTCTG<br>CGGAGCGACGACACTGCCGTGTACTACTGTGCCCGGGACCTGT<br>TCCCCACTATCTTCGGAGTGTCGTACTACTACTACTGGGGCCAG<br>GGGACTCTCGTGACCGTGTCGAGCGCTAGCACTAAGGGCCCGT<br>CGGTGTTCCCGCTGGCCCCATCGTCCAAGAGCACATCAGGGGG<br>TACCGCCGCCCTGGGCTGCCTTGTGAAGGATTACTTTCCCGAG<br>CCCGTCACAGTGTCCTGGAACAGCGGAGCCCTGACCTCCGGAG<br>TGCATACTTTCCCGGCTGTGCTTCAGTCCTCTGGCCTGTACTCA<br>TTGTCCTCCGTGGTCACCGTCCCTTCGTCCTCCCTGGGCACCC<br>AGACCTATATCTGTAATGTCAACCATAAGCCCTCGAACACCAAG<br>GTCGACAAGAAGGTCGAGCCGAAGTCGTGCGACAAGACTCACA<br>CTTGCCCGCCTTGCCCAGCCCCGGAACTGCTGGGTGGTCCTTC<br>GGTGTTCCTCTTCCCGCCCAAGCCGAAGGATACCCTGATGATCT<br>CACGGACCCCCGAAGTGACCTGTGTGGTGGTGGACGTGTCCCA<br>CGAGGACCCGGAAGTGAAATTCAATTGGTACGTGGATGGAGTG<br>GAAGTGCACAACGCCAAGACCAAGCCACGGGAAGAACAGTACA<br>ACTCTACCTACCGCGTGGTGTCCGTGCTCACTGTGCTGCACCAA<br>GACTGGCTGAACGGGAAGGAGTACAAGTGCAAAGTGTCCAACA<br>AGGCGCTGCCTGCCCCAATTGAGAAAACTATCTCGAAAGCCAA<br>GGGACAGCCTCGAGAGCCTCAAGTGTACACCCTGCCTCCCTCT<br>CGGGACGAGCTGACCAAGAACCAAGTCTCCCTGACCTGTCTGG<br>TCAAGGGATTCTACCCATCGGATATCGCCGTGGAATGGGAAAG<br>CAACGGACAGCCCGAGAACAACTACAAGACGACTCCGCCCGTG<br>CTGGATTCCGACGGGAGCTTCTTCTTGTACTCCAAGCTGACCGT<br>CGACAAGAGCAGATGGCAGCAGGGAAACGTGTTCTCCTGCTCC<br>GTGATGCATGAGGCGCTGCACAACCACTACACTCAGAAGAGCT<br>TGTCCCTGTCGCCCGGA |
| Heavy chain AA<br>(with LALA)<br>(SEQ ID NO: 47) | EVQLVQSGAEVKRPGASVKVSCKASGYPFTSYGISWVRQAPGQG<br>LEWMGWISAYSGGTNYAQKLQGRVTMTTDTSTSTAYMELRSLRS<br>DDTAVYYCARDLFPTIFGVSYYYYWGQGTLVTVSSASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPKS<br>CDKTHTCPPCPAPEAAGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| Heavy chain DNA<br>(with LALA)<br>(SEQ ID NO: 116) | GAAGTGCAGCTGGTGCAGTCCGGAGCCGAAGTCAAGAGGCCT<br>GGAGCGTCCGTGAAGGTGTCCTGCAAAGCCTCAGGATACCCCT<br>TCACTTCGTACGGGATTTCCTGGGTCCGCCAAGCACCGGGTCA<br>AGGCTTGGAGTGGATGGGATGGATCAGCGCGTATTCCGGGGGA<br>ACCAACTACGCTCAAAAGCTGCAGGGTCGCGTGACCATGACCA |

| | |
|---|---|
| | CCGATACCTCCACCTCAACGGCCTACATGGAACTGAGATCTCTG<br>CGGAGCGACGACACTGCCGTGTACTACTGTGCCCGGGACCTGT<br>TCCCCACTATCTTCGGAGTGTCGTACTACTACTACTGGGGCCAG<br>GGGACTCTCGTGACCGTGTCGAGCGCTAGCACTAAGGGCCCGT<br>CGGTGTTCCCGCTGGCCCCATCGTCCAAGAGCACATCAGGGGG<br>TACCGCCGCCCTGGGCTGCCTTGTGAAGGATTACTTTCCCGAA<br>CCCGTCACAGTGTCCTGGAACAGCGGAGCCCTGACCTCCGGAG<br>TGCATACTTTCCCGGCTGTGCTTCAGTCCTCTGGCCTGTACTCA<br>TTGTCCTCCGTGGTCACCGTCCCTTCGTCCTCCCTGGGCACCC<br>AGACCTATATCTGTAATGTCAACCATAAGCCCTCGAACACCAAG<br>GTCGACAAGAAGGTCGAGCCGAAGTCGTGCGACAAGACTCACA<br>CTTGCCCGCCTTGCCCAGCCCCGGAAGCTGCCGGTGGTCCTTC<br>GGTGTTCCTCTTCCCGCCCAAGCCGAAGGATACCCTGATGATCT<br>CACCGGACCCCCGAAGTGACCTGTGTGGTGGTGGACGTGTCCCA<br>CGAGGACCCGGAAGTGAAATTCAATTGGTACGTGGATGGAGTG<br>GAAGTGCACAACGCCAAGACCAAGCCACGGGAAGAACAGTACA<br>ACTCTACCTACCGCGTGGTGTCCGTGCTCACTGTGCTGCACCAA<br>GACTGGCTGAACGGGAAGGAGTACAAGTGCAAAGTGTCCAACA<br>AGGCGCTGCCTGCCCCAATTGAGAAAACTATCTCGAAAGCCAA<br>GGGACAGCCTCGAGAGCCTCAAGTGTACACCCTGCCTCCCTCT<br>CGGGACGAGCTGACCAAGAACCAAGTCTCCCTGACCTGTCTGG<br>TCAAGGGATTCTACCCATCGGATATCGCCGTGGAATGGGAAAG<br>CAACGGACAGCCCGAGAACAACTACAAGACGACTCCGCCCGTG<br>CTGGATTCCGACGGGAGCTTCTTCTTGTACTCCAAGCTGACCGT<br>CGACAAGAGCAGATGGCAGCAGGGAAACGTGTTCTCCTGCTCC<br>GTGATGCATGAGGCGCTGCACAACCACTACACTCAGAAGAGCT<br>TGTCCCTGTCGCCCGGA |
| VH domain AA<br>(SEQ ID NO: 27) | *EVQLVQSGAEVKRPGASVKVSCKASGYPFTSYGISWVRQAPGQG<br>LEWMGWISAYSGGTNYAQKLQGRVTMTTDT*STS*TAYMELRSLRS<br>DDTAVYYCARDLFPTIFGVSYYYYWGQGTLVTVSS* |
| VH domain DNA<br>(SEQ ID NO: 117) | GAAGTGCAGCTGGTGCAGTCCGGAGCCGAAGTCAAGAGGCCT<br>GGAGCGTCCGTGAAGGTGTCCTGCAAAGCCTCAGGATACCCCT<br>TCACTTCGTACGGGATTTCCTGGGTCCGCCAAGCACCGGGTCA<br>AGGCTTGGAGTGGATGGGATGGATCAGCGCGTATTCCGGGGGA<br>ACCAACTACGCTCAAAAGCTGCAGGGTCGCGTGACCATGACCA<br>CCGATACCTCCACCTCAACGGCCTACATGGAACTGAGATCTCTG<br>CGGAGCGACGACACTGCCGTGTACTACTGTGCCCGGGACCTGT<br>TCCCCACTATCTTCGGAGTGTCGTACTACTACTACTGGGGCCAG<br>GGGACTCTCGTGACCGTGTCGAGC |
| HCDR1 (AA) (IMGT)<br>(SEQ ID NO: 102) | GYPFTSYG |
| HCDR1 (AA) (Kabat)<br>(SEQ ID NO: 1) | SYGIS |
| HCDR2 (AA) (IMGT)<br>(SEQ ID NO: 111) | ISAYSGGT |
| HCDR2 (AA) (Kabat)<br>(SEQ ID NO: 18) | WISAYSGGTNYAQKLQG |
| HCDR3 (AA) (IMGT)<br>(SEQ ID NO: 69) | ARDLFPTIFGVSYYYY |
| HCDR3 (AA) (Kabat)<br>(SEQ ID NO: 3) | DLFPTIFGVSYYYY |
| Light chain AA<br>(SEQ ID NO: 48) | *DIQMTQSPSTLSASVRDRVIITCRASQSIGNRLAWYQHKPGKAPKL<br>LIYEASTSETGVPSRFSGSGSGTDFTLTISSLQPEDFATYYCQQSY<br>STPYTFGQGTKLEIK*RTVAAPSVFIFPPSDEQLKSG-<br>TASVVCLLNNF<br>YPREAKVQWKVDNALQSGNSQESVTEQDSKDSTYSLSSTLTLSKA<br>DYEKHKVYACEVTHQGLSSPVTKSFNRGEC |
| Light chain DNA<br>(SEQ ID NO: 118) | GACATCCAGATGACGCAGAGCCCGTCTACCCTGTCCGCCTCCG<br>TGAGAGATCGCGTGATCATCACCTGTCGGGCCAGCCAGTCCAT<br>CGGAAACCGCTTGGCGTGGTACCAGCACAAGCCTGGGAAGGCT<br>CCGAAGCTGCTCATCTACGAAGCCTCGACTTCGGAGACTGGTG<br>TCCCTAGCCGGTTCAGCGGATCGGGATCAGGGACCGATTTCAC<br>TCTGACCATTTCCTCCCTGCAACCCGAGGACTTCGCCACCTACT<br>ACTGCCAACAGTCATATTCCACCCCGTACACCTTCGGACAAGGC<br>ACCAAGCTCGAAATCAAGCGGACTGTCGCCGCACCTTCCGTGT<br>TCATTTTCCCACCCTCCGACGAACAGCTGAAATCGGGTACAGCT<br>AGCGTGGTCTGTCTCCTGAACAATTTCTACCCGCGCGAAGCTAA |

| | |
|---|---|
| | Amino acid and cDNA sequences of heavy and light chains and variable domains of G1AA/E12v2 and amino acid sequence of CDRs |
| | GGTCCAGTGGAAGGTCGACAACGCGCTGCAGTCCGGAAACAGC<br>CAGGAGTCAGTGACCGAGCAGGACTCCAAGGATTCCACTTATTC<br>CCTGTCCTCCACCCTGACTTTGAGCAAGGCCGACTACGAGAAG<br>CACAAAGTGTACGCCTGCGAAGTGACCCATCAAGGGCTTTCGT<br>CGCCCGTGACCAAGAGCTTCAACCGGGGCGAATGC |
| VL domain AA<br>(SEQ ID NO: 28) | *DIQMTQSPSTLSASVRDRVIITCRASQSIGNRLAWYQHKPGKAPKL<br>LIYEASTSETGVPSRFSGSGSGTDFTLTISSLQPEDFATYYCQQSY<br>STPYTFGQGTKLEIK* |
| VL domain DNA<br>(SEQ ID NO: 119) | GACATCCAGATGACGCAGAGCCCGTCTACCCTGTCCGCCTCCG<br>TGAGAGATCGCGTGATCATCACCTGTCGGGCCAGCCAGTCCAT<br>CGGAAACCGCTTGGCGTGGTACCAGCACAAGCCTGGGAAGGCT<br>CCGAAGCTGCTCATCTACGAAGCCTCGACTTCGGAGACTGGTG<br>TCCCTAGCCGGTTCAGCGGATCGGGATCAGGGACCGATTTCAC<br>TCTGACCATTTCCTCCCTGCAACCCGAGGACTTCGCCACCTACT<br>ACTGCCAACAGTCATATTCCACCCCGTACACCTTCGGACAAGGC<br>ACCAAGCTCGAAATCAAG |
| LCDR1 (AA) (IMGT)<br>(SEQ ID NO: 103) | QSIGNR |
| LCDR1 (AA) (Kabat)<br>(SEQ ID NO: 15) | RASQSIGNRLA |
| LCDR2 (AA) (IMGT)<br>(SEQ ID NO: 71) | EAS |
| LCDR2 (AA) (Kabat)<br>(SEQ ID NO: 16) | EASTSET |
| LCDR3 (AA) (IMGT)<br>(SEQ ID NO: 17) | QQSYSTPYT |
| LCDR3 (AA) (Kabat)<br>(SEQ ID NO: 17) | QQSYSTPYT |

| | |
|---|---|
| | Amino acid and cDNA sequences of heavy and light chains and variable domains of G1AA/G12v2 and amino acid sequence of CDRs |
| Heavy chain AA<br>(without LALA)<br>(SEQ ID NO: 120) | *EVQLVQSGAEVKRPGASVKVSCKASGYTFTSYGISWVRQAPGQG<br>LEWMGWISAYSGGTNYAQKLQGRVTMTTDTSTSTAYMELRSLRS<br>DDTAVYYCARDLFPTIFGVSYYYYWGQGTLVTVSS*ASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| Heavy chain DNA<br>(without LALA)<br>(SEQ ID NO: 121) | GAAGTGCAGCTGGTGCAGTCCGGAGCCGAAGTCAAGAGGCCT<br>GGAGCGTCCGTGAAGGTGTCCTGCAAAGCCTCAGGATACACCT<br>TCACTTCGTACGGGATTTCCTGGGTCCGCCAAGCACCGGGTCA<br>AGGCTTGGAGTGGATGGGATGGATCAGCGCGTATTCCGGGGGA<br>ACCAACTACGCTCAAAAGCTGCAGGGTCGCGTGACCATGACCA<br>CCGATACCTCCACCTCAACGGCCTACATGGAACTGAGATCTCTG<br>CGGAGCGACGACACTGCCGTGTACTACTGTGCCCGGGACCTGT<br>TCCCCACTATCTTCGGAGTGTCGTACTACTACTACTGGGGCCAG<br>GGGACTCTCGTGACCGTGTCGAGCGCTAGCACTAAGGGCCCGT<br>CGGTGTTCCCGCTGGCCCCATCGTCCAAGAGCACATCAGGGGG<br>TACCGCCGCCCTGGGCTGCCTTGTGAAGGATTACTTTCCCGAG<br>CCCGTCACAGTGTCCTGGAACAGCGGAGCCCTGACCTCCGGAG<br>TGCATACTTTCCCGGCTGTGCTTCAGTCCTCTGGCCTGTACTCA<br>TTGTCCTCCGTGGTCACCGTCCCTTCGTCCTCCCTGGGCACCC<br>AGACCTATATCTGTAATGTCAACCATAAGCCCTCGAACACCAAG<br>GTCGACAAGAAGGTCGAGCCGAAGTCGTGCGACAAGACTCACA<br>CTTGCCCGCCTTGCCCAGCCCCGGAACTGCTGGGTGGTCCTTC<br>GGTGTTCCTCTTCCCGCCCAAGCCGAAGGATACCCTGATGATCT<br>CACGGACCCCCGAAGTGACCTGTGTGGTGGTGGACGTGTCCCA<br>CGAGGACCCGGAAGTGAAATTCAATTGGTACGTGGATGGAGTG<br>GAAGTGCACAACGCCAAGACCAAGCCACGGGAAGAACAGTACA<br>ACTCTACCTACCGCGTGGTGTCCGTGCTCACTGTGCTGCACCAA |

| | |
|---|---|
| | Amino acid and cDNA sequences of heavy and light chains and variable domains of G1AA/G12v2 and amino acid sequence of CDRs |
| | GACTGGCTGAACGGGAAGGAGTACAAGTGCAAAGTGTCCAACA<br>AGGCGCTGCCTGCCCCAATTGAGAAAACTATCTCGAAAGCCAA<br>GGGACAGCCTCGAGAGCCTCAAGTGTACACCCTGCCTCCCTCT<br>CGGGACGAGCTGACCAAGAACCAAGTCTCCCTGACCTGTCTGG<br>TCAAGGGATTCTACCCATCGGATATCGCCGTGGAATGGGAAAG<br>CAACGGACAGCCCGAGAACAACTACAAGACGACTCCGCCCGTG<br>CTGGATTCCGACGGGAGCTTCTTCTTGTACTCCAAGCTGACCGT<br>CGACAAGAGCAGATGGCAGCAGGGAAACGTGTTCTCCTGCTCC<br>GTGATGCATGAGGCGCTGCACAACCACTACACTCAGAAGAGCT<br>TGTCCCTGTCGCCCGGA |
| Heavy chain AA<br>(with LALA)<br>(SEQ ID NO: 49) | *EVQLVQSGAEVKRPGASVKVSCKASGYTFTSYGISWVRQAPGQG<br>LEWMGWISAYSGGTNYAQKLQGRVTMTTDTSTSTAYMELRSLRS<br>DDTAVYYCARDLFPTIFGVSYYYYWGQGTLVTVSS*ASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPKS<br>CDKTHTCPPCPAPEAAGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| Heavy chain DNA<br>(with LALA)<br>(SEQ ID NO: 122) | GAAGTGCAGCTGGTGCAGTCCGGAGCCGAAGTCAAGAGGCCT<br>GGAGCGTCCGTGAAGGTGTCCTGCAAAGCCTCAGGATACACCT<br>TCACTTCGTACGGGATTTCCTGGGTCCGCCAAGCACCGGGTCA<br>AGGCTTGGAGTGGATGGGATGGATCAGCGCGTATTCCGGGGGA<br>ACCAACTACGCTCAAAAGCTGCAGGGTCGCGTGACCATGACCA<br>CCGATACCTCCACCTCAACGGCCTACATGGAACTGAGATCTCTG<br>CGGAGCGACGACACTGCCGTGTACTACTGTGCCCGGGACCTGT<br>TCCCCACTATCTTCGGAGTGTCGTACTACTACTACTGGGGCCAG<br>GGGACTCTCGTGACCGTGTCGAGCGCTAGCACTAAGGGCCCGT<br>CGGTGTTCCCGCTGGCCCCATCGTCCAAGAGCACATCAGGGGG<br>TACCGCCGCCCTGGGCTGCCTTGTGAAGGATTACTTTCCCGAG<br>CCCGTCACAGTGTCCTGGAACAGCGGAGCCCTGACCTCCGGAG<br>TGCATACTTTCCCGGCTGTGCTTCAGTCCTCTGGCCTGTACTCA<br>TTGTCCTCCGTGGTCACCGTCCCTTCGTCCTCCCTGGGCACCC<br>AGACCTATATCTGTAATGTCAACCATAAGCCCTCGAACACCAAG<br>GTCGACAAGAAGGTCGAGCCGAAGTCGTGCGACAAGACTCACA<br>CTTGCCCGCCTTGCCCAGCCCCGGAAGCTGCCGGTGGTCCTTC<br>GGTGTTCCTCTTCCCGCCCAAGCCTGAAGGATACCCTGATGATCT<br>CACGGACCCCCGAAGTGACCTGTGTGGTGGTGGACGTGTCCCA<br>CGAGGACCCGGAAGTGAAATTCAATTGGTACGTGGATGGAGTG<br>GAAGTGCACAACGCCAAGACCAAGCCACGGGAAGAACAGTACA<br>ACTCTACCTACCGCGTGGTGTCCGTGCTCACTGTGCTGCACCAA<br>GACTGGCTGAACGGGAAGGAGTACAAGTGCAAAGTGTCCAACA<br>AGGCGCTGCCTGCCCCAATTGAGAAAACTATCTCGAAAGCCAA<br>GGGACAGCCTCGAGAGCCTCAAGTGTACACCCTGCCTCCCTCT<br>CGGGACGAGCTGACCAAGAACCAAGTCTCCCTGACCTGTCTGG<br>TCAAGGGATTCTACCCATCGGATATCGCCGTGGAATGGGAAAG<br>CAACGGACAGCCCGAGAACAACTACAAGACGACTCCGCCCGTG<br>CTGGATTCCGACGGGAGCTTCTTCTTGTACTCCAAGCTGACCGT<br>CGACAAGAGCAGATGGCAGCAGGGAAACGTGTTCTCCTGCTCC<br>GTGATGCATGAGGCGCTGCACAACCACTACACTCAGAAGAGCT<br>TGTCCCTGTCGCCCGGA |
| VH domain AA<br>(SEQ ID NO: 29) | *EVQLVQSGAEVKRPGASVKVSCKASGYTFTSYGISWVRQAPGQG<br>LEWMGWISAYSGGTNYAQKLQGRVTMTTDTSTSTAYMELRSLRS<br>DDTAVYYCARDLFPTIFGVSYYYYWGQGTLVTVSS* |
| VH domain DNA<br>(SEQ ID NO: 123) | GAAGTGCAGCTGGTGCAGTCCGGAGCCGAAGTCAAGAGGCCT<br>GGAGCGTCCGTGAAGGTGTCCTGCAAAGCCTCAGGATACACCT<br>TCACTTCGTACGGGATTTCCTGGGTCCGCCAAGCACCGGGTCA<br>AGGCTTGGAGTGGATGGGATGGATCAGCGCGTATTCCGGGGGA<br>ACCAACTACGCTCAAAAGCTGCAGGGTCGCGTGACCATGACCA<br>CCGATACCTCCACCTCAACGGCCTACATGGAACTGAGATCTCTG<br>CGGAGCGACGACACTGCCGTGTACTACTGTGCCCGGGACCTGT<br>TCCCCACTATCTTCGGAGTGTCGTACTACTACTACTGGGGCCAG<br>GGGACTCTCGTGACCGTGTCGAGC |
| HCDR1 (AA) (IMGT)<br>(SEQ ID NO: 94) | GYTFTSYG |
| HCDR1 (AA) (Kabat)<br>(SEQ ID NO: 1) | SYGIS |

Amino acid and cDNA sequences of heavy and light chains and variable domains of G1AA/G12v2 and amino acid sequence of CDRs

| | |
|---|---|
| HCDR2 (AA) (IMGT) (SEQ ID NO: 111) | ISAYSGGT |
| HCDR2 (AA) Kabat (SEQ ID NO: 18) | WISAYSGGTNYAQKLQG |
| HCDR3 (AA) (IMGT) (SEQ ID NO: 69) | ARDLFPTIFGVSYYYY |
| HCDR3 (AA) (Kabat) (SEQ ID NO: 3) | DLFPTIFGVSYYYY |
| Light chain AA (SEQ ID NO: 50) | *DIQMTQSPSTLSASVGDRVTITCRASQSISGRLAWYQQKPGKAPNL LIYEASNLESGVPSRFSGSGSGTEFTLTISSLQPEDFATYYCQQSY SWPRTFGQGTKVEIK*RTVAAPSVFIFPPSDEQLKSGTASVVCLLNN FYPREAKVQWKVDNALQSGNSQESVTEQDSKDSTYSLSSTLTLSK ADYEKHKVYACEVTHQGLSSPVTKSFNRGEC |
| Light chain DNA (SEQ ID NO: 124) | GACATTCAGATGACCCAGTCCCCGAGCACGCTGTCCGCAAGCG TGGGGGACAGAGTGACCATCACTTGCCGCGCCTCACAATCCAT CAGCGGACGCTTGGCCTGGTACCAGCAGAAGCCCGGAAAGGC CCCAAACCTTCTGATCTACGAAGCCTCGAACCTGGAGTCAGGC GTCCCTTCGCGGTTCTCTGGCTCCGGTTCCGGAACTGAGTTCA CCCTCACCATCTCGTCCCTGCAACCGGAAGATTTCGCCACCTAC TACTGCCAACAGTCGTACTCCTGGCCCCGGACATTCGGACAGG GAACCAAAGTCGAGATTAAGCGGACTGTGGCGGCTCCAGCGT GTTCATCTTTCCCCCGTCCGACGAACAGCTGAAGTCCGGTACC GCTAGCGTGGTCTGTCTCCTGAACAATTTCTACCCGCGCGAAGC TAAGGTCCAGTGGAAGGTCGACAACGCGCTGCAGTCCGGAAAC AGCCAGGAGTCAGTGACCGAGCAGGACTCCAAGGATTCCACTT ATTCCCTGTCCTCCACCCTGACTTTGAGCAAGGCCGACTACGAG AAGCACAAAGTGTACGCCTGCGAAGTGACCCATCAAGGGCTTT CGTCGCCCGTGACCAAGAGCTTCAACCGGGGCGAATGC |
| VL domain AA (SEQ ID NO: 30) | *DIQMTQSPSTLSASVGDRVTITCRASQSISGRLAWYQQKPGKAPNL LIYEASNLESGVPSRFSGSGSGTEFTLTISSLQPEDFATYYCQQSY SWPRTFGQGTKVEIK* |
| VL domain DNA (SEQ ID NO: 125) | GACATTCAGATGACCCAGTCCCCGAGCACGCTGTCCGCAAGCG TGGGGGACAGAGTGACCATCACTTGCCGCGCCTCACAATCCAT CAGCGGACGCTTGGCCTGGTACCAGCAGAAGCCCGGAAAGGC CCCAAACCTTCTGATCTACGAAGCCTCGAACCTGGAGTCAGGC GTCCCTTCGCGGTTCTCTGGCTCCGGTTCCGGAACTGAGTTCA CCCTCACCATCTCGTCCCTGCAACCGGAAGATTTCGCCACCTAC TACTGCCAACAGTCGTACTCCTGGCCCCGGACATTCGGACAGG GAACCAAAGTCGAGATTAAG |
| LCDR1 (AA) (IMGT) (SEQ ID NO: 100) | QSISGR |
| LCDR1 (AA) (Kabat) (SEQ ID NO: 19) | RASQSISGRLA |
| LCDR2 (AA) (IMGT) (SEQ ID NO: 71) | EAS |
| LCDR2 (AA) Kabat (SEQ ID NO: 20) | EASNLES |
| LCDR3 (AA) (IMGT) (SEQ ID NO: 21) | QQSYSWPRT |
| LCDR3 (AA) (Kabat) (SEQ ID NO: 21) | QQSYSWPRT |

Amino acid and cDNA sequences of heavy and light chains and variable domains of G1AA/lambdav3 and amino acid sequence of CDRs

| | |
|---|---|
| Heavy chain AA (without LALA) (SEQ ID NO: 126) | *EVQLVQSGAEVKRPGASVKVSCKASGYTFTSYGISWVRQAPGQG LEWMGWISAYSGGTNYAQKLQGRVTMTTDTSTSTAYMELRSLRS DDTAVYYCARDLFPTIFGVSYYYYWGQGTLVTVSS*ASTKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVEPKS |

| | |
|---|---|
| | CDKTHTCPPCPAPELLGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| Heavy chain DNA<br>(without LALA)<br>(SEQ ID NO: 127) | GAAGTGCAGCTGGTGCAGTCCGGAGCCGAAGTCAAGAGGCCT<br>GGAGCGTCCGTGAAGGTGTCCTGCAAAGCCTCAGGATACACCT<br>TCACTTCGTACGGGATTTCCTGGGTCCGCCAAGCACCGGGTCA<br>AGGCTTGGAGTGGATGGGATGGATCAGCGCGTATTCCGGGGGA<br>ACCAACTACGCTCAAAAGCTGCAGGGTCGCGTGACCATGACCA<br>CCGATACCTCCACCTCAACGGCCTACATGGAACTGAGATCTCTG<br>CGGAGCGACGACACTGCCGTGTACTACTGTGCCCGGGACCTGT<br>TCCCCACTATCTTCGGAGTGTCGTACTACTACTACTGGGGCCAG<br>GGGACTCTCGTGACCGTGTCGAGCGCTAGCACTAAGGGCCCGT<br>CGGTGTTCCCGCTGGCCCCATCGTCCAAGAGCACATCAGGGGG<br>TACCGCCGCCCTGGGCTGCCTTGTGAAGGATTACTTTCCCGAG<br>CCCGTCACAGTGTCCTGGAACAGCGGAGCCCTGACCTCCGGAG<br>TGCATACTTTCCCGGCTGTGCTTCAGTCCTCTGGCCTGTACTCA<br>TTGTCCTCCGTGGTCACCGTCCCTTCGTCCTCCCTGGGCACCC<br>AGACCTATATCTGTAATGTCAACCATAAGCCCTCGAACACCAAG<br>GTCGACAAGAAGGTCGAGCCGAAGTCGTGCGACAAGACTCACA<br>CTTGCCCGCCTTGCCCAGCCCCGGAACTGCTGGGTGGTCCTTC<br>GGTGTTCCTCTTCCCGCCCAAGCCGAAGGATACCCTGATGATCT<br>CACGGACCCCCGAAGTGACCTGTGTGGTGGTGGACGTGTCCCA<br>CGAGGACCCGGAAGTGAAATTCAATTGGTACGTGGATGGAGTG<br>GAAGTGCACAACGCCAAGACCAAGCCACGGGAAGAACAGTACA<br>ACTCTACCTACCGCGTGGTGTCCGTGCTCACTGTGCTGCACCAA<br>GACTGGCTGAACGGGAAGGAGTACAAGTGCAAAGTGTCCAACA<br>AAGGCGCTGCCTGCCCCAATTGAGAAAACTATCTCGAAAGCCAA<br>GGGACAGCCTCGAGAGCCTCAAGTGTACACCCTGCCTCCCTCT<br>CGGGACGAGCTGACCAAGAACCAAGTCTCCCTGACCTGTCTGG<br>TCAAGGGATTCTACCCATCGGATATCGCCGTGGAATGGGAAAG<br>CAACGGACAGCCCGAGAACAACTACAAGACGACTCCGCCCGTG<br>CTGGATTCCGACGGGAGCTTCTTCTTGTACTCCAAGCTGACCGT<br>CGACAAGAGCAGATGGCAGCAGGGAAACGTGTTCTCCTGCTCC<br>GTGATGCATGAGGCGCTGCACAACCACTACACTCAGAAGAGCT<br>TGTCCCTGTCGCCCGGA |
| Heavy chain AA<br>(with LALA)<br>(SEQ ID NO: 61) | *EVQLVQSGAEVKRPGASVKVSCKASGYTFTSYGISWVRQAPGQG*<br>*LEWMGWISAYSGGTNYAQKLQGRVTMTTDTSTSTAYMELRSLRS*<br>*DDTAVYYCARDLFPTIFGVSYYYYWGQGTLVTVSS*ASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPKS<br>CDKTHTCPPCPAPEAAGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| Heavy chain DNA<br>(with LALA)<br>(SEQ ID NO: 128) | GAAGTGCAGCTGGTGCAGTCCGGAGCCGAAGTCAAGAGGCCT<br>GGAGCGTCCGTGAAGGTGTCCTGCAAAGCCTCAGGATACACCT<br>TCACTTCGTACGGGATTTCCTGGGTCCGCCAAGCACCGGGTCA<br>AGGCTTGGAGTGGATGGGATGGATCAGCGCGTATTCCGGGGGA<br>ACCAACTACGCTCAAAAGCTGCAGGGTCGCGTGACCATGACCA<br>CCGATACCTCCACCTCAACGGCCTACATGGAACTGAGATCTCTG<br>CGGAGCGACGACACTGCCGTGTACTACTGTGCCCGGGACCTGT<br>TCCCCACTATCTTCGGAGTGTCGTACTACTACTACTGGGGCCAG<br>GGGACTCTCGTGACCGTGTCGAGCGCTAGCACTAAGGGCCCGT<br>CGGTGTTCCCGCTGGCCCCATCGTCCAAGAGCACATCAGGGGG<br>TACCGCCGCCCTGGGCTGCCTTGTGAAGGATTACTTTCCCGAG<br>CCCGTCACAGTGTCCTGGAACAGCGGAGCCCTGACCTCCGGAG<br>TGCATACTTTCCCGGCTGTGCTTCAGTCCTCTGGCCTGTACTCA<br>TTGTCCTCCGTGGTCACCGTCCCTTCGTCCTCCCTGGGCACCC<br>AGACCTATATCTGTAATGTCAACCATAAGCCCTCGAACACCAAG<br>GTCGACAAGAAGGTCGAGCCGAAGTCGTGCGACAAGACTCACA<br>CTTGCCCGCCTTGCCCAGCCCCGGAAGCTGCCGGTGGTCCTTC<br>GGTGTTCCTCTTCCCGCCCAAGCCGAAGGATACCCTGATGATCT<br>CACGGACCCCCGAAGTGACCTGTGTGGTGGTGGACGTGTCCCA<br>CGAGGACCCGGAAGTGAAATTCAATTGGTACGTGGATGGAGTG<br>GAAGTGCACAACGCCAAGACCAAGCCACGGGAAGAACAGTACA<br>ACTCTACCTACCGCGTGGTGTCCGTGCTCACTGTGCTGCACCAA<br>GACTGGCTGAACGGGAAGGAGTACAAGTGCAAAGTGTCCAACA<br>AAGGCGCTGCCTGCCCCAATTGAGAAAACTATCTCGAAAGCCAA<br>GGGACAGCCTCGAGAGCCTCAAGTGTACACCCTGCCTCCCTCT<br>CGGGACGAGCTGACCAAGAACCAAGTCTCCCTGACCTGTCTGG |

Amino acid and cDNA sequences of heavy and light chains and variable domains of G1AA/lambdav3 and amino acid sequence of CDRs

|  |  |
|---|---|
|  | TCAAGGGATTCTACCCATCGGATATCGCCGTGGAATGGGAAAG<br>CAACGGACAGCCCGAGAACAACTACAAGACGACTCCGCCCGTG<br>CTGGATTCCGACGGGAGCTTCTTCTTGTACTCCAAGCTGACCGT<br>CGACAAGAGCAGATGGCAGCAGGGAAACGTGTTCTCCTGCTCC<br>GTGATGCATGAGGCGCTGCACAACCACTACACTCAGAAGAGCT<br>TGTCCCTGTCGCCCGGA |
| VH domain AA<br>(SEQ ID NO: 41) | EVQLVQSGAEVKRPGASVKVSCKASGYTFTSYGISWVRQAPGQG<br>LEWMGWISAYSGGTNYAQKLQGRVTMTTDTSTSTAYMELRSLRS<br>DDTAVYYCARDLFPTIFGVSYYYWGQGTLVTVSS |
| VH domain DNA<br>(SEQ ID NO: 129) | GAAGTGCAGCTGGTGCAGTCCGGAGCCGAAGTCAAGAGGCCT<br>GGAGCGTCCGTGAAGGTGTCCTGCAAAGCCTCAGGATACACCT<br>TCACTTCGTACGGGATTTCCTGGGTCCGCCAAGCACCGGGTCA<br>AGGCTTGGAGTGGATGGGATGGATCAGCGCGTATTCCGGGGGA<br>ACCAACTACGCTCAAAAGCTGCAGGGTCGCGTGACCATGACCA<br>CCGATACCTCCACCTCAACGGCCTACATGGAACTGAGATCTCTG<br>CGGAGCGACGACACTGCCGTGTACTACTGTGCCCGGGACCTGT<br>TCCCCACTATCTTCGGAGTGTCGTACTACTACTACTGGGGCCAG<br>GGGACTCTCGTGACCGTGTCGAGC |
| HCDR1 (AA) (IMGT)<br>(SEQ ID NO: 94) | GYTFTSYG |
| HCDR1 (AA) (Kabat)<br>(SEQ ID NO: 1) | SYGIS |
| HCDR2 (AA) (IMGT)<br>(SEQ ID NO: 111) | ISAYSGGT |
| HCDR2 (AA) (Kabat)<br>(SEQ ID NO: 18) | WISAYSGGTNYAQKLQG |
| HCDR3 (AA) (IMGT)<br>(SEQ ID NO: 69) | ARDLFPTIFGVSYYYY |
| HCDR3 (AA) (Kabat)<br>(SEQ ID NO: 3) | DLFPTIFGVSYYYY |
| Light chain AA<br>(SEQ ID NO: 62) | *QSALTQPASVSGSPGQSITISCTGTSSDVGGYNYVSWYQQFPGKA<br>PKLMIFEVTNRPSGVSDRFSGSKSDNTASLTISGLQAEDEAEYYCS<br>SFKRGSTLVVFGGGTKLTVL*GQPAAAPSVTLFPPSSEELQANKATL<br>VCLISDFYPGAVTVAWKADSSPVKAGVETTTPSKQSNNKYAASSYL<br>SLTPEQWKSHRSYSCQVTHEGSTVEKTVAPTECS |
| Light chain DNA<br>(SEQ ID NO: 130) | CAGTCGGCCCTTACTCAACCCGCGTCAGTCTCCGGTAGCCCCG<br>GACAGTCCATCACGATTTCGTGCACCGGAACCAGCAGCGATGT<br>CGGGGGATACAACTACGTGTCCTGGTACCAGCAGTTCCCGGGA<br>AAGGCCCCTAAGCTGATGATCTTCGAAGTCACTAACAGACCTTC<br>CGGAGTGTCGGACCGGTTCTCCGGCTCCAAGTCCGACAACACT<br>GCGAGCCTGACCATCTCGGGCCTGCAAGCCGAGGACGAAGCC<br>GAGTACTACTGTAGCTCATTCAAGCGCGGTTCCACCCTCGTGGT<br>GTTCGGCGGTGGCACTAAGCTCACCGTGCTGGGACAGCCAGCC<br>GCAGCTCCTAGCGTGACCTTGTTCCCCCCGTCGAGCGAAGAAC<br>TGCAGGCCAACAAGGCCACCCTCGTCTGCCTGATCTCCGACTT<br>CTACCCTGGGGCCGTGACTGTGGCTTGGAAGGCCGATTCAAGC<br>CCAGTGAAAGCCGGAGTGGAAACCACCACTCCGTCCAAGCAGT<br>CGAACAATAAGTATGCCGCGTCCTCCTACCTGTCGCTGACCCC<br>GGAGCAGTGGAAGTCCCATCGGTCCTACTCCTGCCAAGTCACC<br>CACGAAGGGTCCACTGTGGAGAAAACAGTGGCTCCCACCGAGT<br>GCTCT |
| VL domain AA<br>(SEQ ID NO: 42) | *QSALTQPASVSGSPGQSITISCTGTSSDVGGYNYVSWYQQFPGKA<br>PKLMIFEVTNRPSGVSDRFSGSKSDNTASLTISGLQAEDEAEYYCS<br>SFKRGSTLVVFGGGTKLTVL* |
| VL domain DNA<br>(SEQ ID NO: 131) | CAGTCGGCCCTTACTCAACCCGCGTCAGTCTCCGGTAGCCCCG<br>GACAGTCCATCACGATTTCGTGCACCGGAACCAGCAGCGATGT<br>CGGGGGATACAACTACGTGTCCTGGTACCAGCAGTTCCCGGGA<br>AAGGCCCCTAAGCTGATGATCTTCGAAGTCACTAACAGACCTTC<br>CGGAGTGTCGGACCGGTTCTCCGGCTCCAAGTCCGACAACACT<br>GCGAGCCTGACCATCTCGGGCCTGCAAGCCGAGGACGAAGCC<br>GAGTACTACTGTAGCTCATTCAAGCGCGGTTCCACCCTCGTGGT<br>GTTCGGCGGTGGCACTAAGCTCACCGTGCTGGGA |

| Amino acid and cDNA sequences of heavy and light chains and variable domains of G1AA/lambdav3 and amino acid sequence of CDRs | |
|---|---|
| LCDR1 (AA) (IMGT)<br>(SEQ ID NO: 132) | SSDVGGYNY |
| LCDR1 (AA) (Kabat)<br>(SEQ ID NO: 25) | TGTSSDVGGYNYVS |
| LCDR2 (AA) (IMGT)<br>(SEQ ID NO: 77) | EVT |
| LCDR2 (AA) (Kabat)<br>(SEQ ID NO: 13) | EVTNRPS |
| LCDR3 (AA) (IMGT)<br>(SEQ ID NO: 14) | SSFKRGSTLVV |
| LCDR3 (AA) (Kabat)<br>(SEQ ID NO: 14) | SSFKRGSTLVV |

| Amino acid sequence of heavy and light chains, variable domains and CDRs of G1/929_01_A07 | |
|---|---|
| Heavy chain AA<br>(without LALA)<br>(SEQ ID NO: 133) | EVQLVQSGAEVKRPGASVKVSCKASGYTFTSYGISWVRQAPGQG LEWMGWISAYGGSTNYAQKLQGRVTMTTDTSTSTAYMELRSLRS DDTAVYYCARDLFPTIFGVSYYYYWGQGTLVTVSSASTKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVEPKS CDKTHTCPPCPAPELLGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG |
| VH domain AA<br>(SEQ ID NO: 134) | EVQLVQSGAEVKRPGASVKVSCKASGYTFTSYGISWVRQAPGQG LEWMGWISAYGGSTNYAQKLQGRVTMTTDTSTSTAYMELRSLRS DDTAVYYCARDLFPTIFGVSYYYYWGQGTLVTVSS |
| HCDR1 (AA) (IMGT)<br>(SEQ ID NO: 94) | GYTFTSYG |
| HCDR1 (AA) (Kabat)<br>(SEQ ID NO: 1) | SYGIS |
| HCDR2 (AA) (IMGT)<br>(SEQ ID NO: 135) | ISAYGGST |
| HCDR2 (AA) (Kabat)<br>(SEQ ID NO: 136) | WISAYGGSTNYAQKLQG |
| HCDR3 (AA) (IMGT)<br>(SEQ ID NO: 69) | ARDLFPTIFGVSYYYY |
| HCDR3 (AA) (Kabat)<br>(SEQ ID NO: 3) | DLFPTIFGVSYYYY |
| Light chain AA<br>(SEQ ID NO: 137) | DIQMTQSPSTLSASVGDRVTITCRASQSISGRLAWYQQKPGKAPNL LIYEASNLESGVPSRFSGSGSGTEFTLTISSLQPEDFATYYCQQSY STPRVTFGQGTKVEIKRTAAAPSVFIFPPSDEQLKSGTASVVCLLN NFYPREAKVQWKVDNALQSGNSQESVTEQDSKDSTYSLSSTLTLS KADYEKHKLYACEVTHQGLSSPVTKSFNRGEC |
| VL domain AA<br>(SEQ ID NO: 138) | DIQMTQSPSTLSASVGDRVTITCRASQSISGRLAWYQQKPGKAPNL LIYEASNLESGVPSRFSGSGSGTEFTLTISSLQPEDFATYYCQQSY STPRVTFGQGTKVEIK |
| LCDR1 (AA) (IMGT)<br>(SEQ ID NO: 100) | QSISGR |
| LCDR1 (AA) (Kabat)<br>(SEQ ID NO: 19) | RASQSISGRLA |
| LCDR2 (AA) (IMGT)<br>(SEQ ID NO: 71) | EAS |

-continued

| Amino acid sequence of heavy and light chains, variable domains and CDRs of G1/929_01_A07 | |
|---|---|
| LCDR2 (AA) (Kabat)<br>(SEQ ID NO: 20) | EASNLES |
| LCDR3 (AA) (IMGT)<br>(SEQ ID NO: 22) | QQSYSTPRVT |
| LCDR3 (AA) (Kabat)<br>(SEQ ID NO: 22) | QQSYSTPRVT |

| Amino acid sequence of heavy and light chains, variable domains and CDRs of G1/929_01_A08<br>(This clone is the same as G1AA/E05v2 but without the LALA mutation.) | |
|---|---|
| Heavy chain AA<br>(without LALA)<br>(SEQ ID NO: 139) | EVQLVQSGAEVKRPGASVKVSCKASGYTFTSYGISWVRQAPGQG<br>LEWMGWISAYSGGTNYAQKLQGRVTMTTDTSTSTAYMELRSLRS<br>DDTAVYYCARDLFPTIFGVSYYYYWGQGTLVTVSSASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| VH domain AA<br>(SEQ ID NO: 140) | EVQLVQSGAEVKRPGASVKVSCKASGYTFTSYGISWVRQAPGQG<br>LEWMGWISAYSGGTNYAQKLQGRVTMTTDTSTSTAYMELRSLRS<br>DDTAVYYCARDLFPTIFGVSYYYYWGQGTLVTVSS |
| HCDR1 (AA) (IMGT)<br>(SEQ ID NO: 94) | GYTFTSYG |
| HCDR1 (AA) (Kabat)<br>(SEQ ID NO: 1) | SYGIS |
| HCDR2 (AA) (IMGT)<br>(SEQ ID NO: 111) | ISAYSGGT |
| HCDR2 (AA) Kabat<br>(SEQ ID NO: 18) | WISAYSGGTNYAQKLQG |
| HCDR3 (AA) (IMGT)<br>(SEQ ID NO: 69) | ARDLFPTIFGVSYYYY |
| HCDR3 (AA) (Kabat)<br>(SEQ ID NO: 3) | DLFPTIFGVSYYYY |
| Light chain AA<br>(SEQ ID NO: 141) | DIQMTQSPSTLSASVGDRVTITCRASQSISGRLAWYQQKPGKAPNL<br>LIYEASNLESGVPSRFSGSGSGTEFTLTISSLQPEDFATYYCQQSY<br>STPRVTFGQGTKVEIKRTAAAPSVFIFPPSDEQLKSGTASVVCLLN<br>NFYPREAKVQWKVDNALQSGNSQESVTEQDSKDSTYSLSSTLTLS<br>KADYEKHKLYACEVTHQGLSSPVTKSFNRGEC |
| VL domain AA<br>(SEQ ID NO: 142) | DIQMTQSPSTLSASVGDRVTITCRASQSISGRLAWYQQKPGKAPNL<br>LIYEASNLESGVPSRFSGSGSGTEFTLTISSLQPEDFATYYCQQSY<br>STPRVTFGQGTKVEIK |
| LCDR1 (AA) (IMGT)<br>(SEQ ID NO: 100) | QSISGR |
| LCDR1 (AA) (Kabat)<br>(SEQ ID NO: 19) | RASQSISGRLA |
| LCDR2 (AA) (IMGT)<br>(SEQ ID NO: 71) | EAS |
| LCDR2 (AA) (Kabat)<br>(SEQ ID NO: 20) | EASNLES |
| LCDR3 (AA) (IMGT)<br>(SEQ ID NO: 22) | QQSYSTPRVT |

| | |
|---|---|
| | Amino acid sequence of heavy and light chains, variable domains and CDRs of G1/929_01_A08 (This clone is the same as G1AA/E05v2 but without the LALA mutation.) |
| LCDR3 (AA) (Kabat) (SEQ ID NO: 22) | QQSYSTPRVT |

| | |
|---|---|
| | Amino acid sequence of heavy and light chains, variable domains and CDRs of G1/929_01_A09 |
| Heavy chain AA (without LALA) (SEQ ID NO: 143) | EVQLVQSGAEVKRPGASVKVSCKASGYTFTSYGISWVRQAPGQG LEWMGWISAYSGNANYAQKLQGRVTMTTDTSTSTAYMELRSLRS DDTAVYYCARDLFPTIFGVSYYYYWGQGTLVTVSSASTKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVEPKS CDKTHTCPPCPAPELLGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG |
| VH domain AA (SEQ ID NO: 144) | EVQLVQSGAEVKRPGASVKVSCKASGYTFTSYGISWVRQAPGQG LEWMGWISAYSGNANYAQKLQGRVTMTTDTSTSTAYMELRSLRS DDTAVYYCARDLFPTIFGVSYYYYWGQGTLVTVSS |
| HCDR1 (AA) (IMGT) (SEQ ID NO: 94) | GYTFTSYG |
| HCDR1 (AA) (Kabat) (SEQ ID NO: 1) | SYGIS |
| HCDR2 (AA) (IMGT) (SEQ ID NO: 145) | ISAYSGNA |
| HCDR2 (AA) (Kabat) (SEQ ID NO: 146) | WISAYSGNANYAQKLQG |
| HCDR3 (AA) (IMGT) (SEQ ID NO: 69) | ARDLFPTIFGVSYYYY |
| HCDR3 (AA) (Kabat) (SEQ ID NO: 3) | DLFPTIFGVSYYYY |
| Light chain AA (SEQ ID NO: 147) | DIQMTQSPSTLSASVGDRVTITCRASQSISGRLAWYQQKPGKAPNL LIYEASNLESGVPSRFSGSGSGTEFTLTISSLQPEDFATYYCQQSY STPRVTFGQGTKVEIKRTAAAAPSVFIFPPSDEQLKSGTASVVCLLN NFYPREAKVQWKVDNALQSGNSQESVTEQDSKDSTYSLSSTLTLS KADYEKHKLYACEVTHQGLSSPVTKSFNRGEC |
| VL domain AA (SEQ ID NO: 148) | DIQMTQSPSTLSASVGDRVTITCRASQSISGRLAWYQQKPGKAPNL LIYEASNLESGVPSRFSGSGSGTEFTLTISSLQPEDFATYYCQQSY STPRVTFGQGTKVEIK |
| LCDR1 (AA) (IMGT) (SEQ ID NO: 100) | QSISGR |
| LCDR1 (AA) (Kabat) (SEQ ID NO: 19) | RASQSISGRLA |
| LCDR2 (AA) (IMGT) (SEQ ID NO: 71) | EAS |
| LCDR2 (AA) (Kabat) (SEQ ID NO: 20) | EASNLES |
| LCDR3 (AA) (IMGT) (SEQ ID NO: 22) | QQSYSTPRVT |
| LCDR3 (AA) (Kabat) (SEQ ID NO: 22) | QQSYSTPRVT |

| Amino acid sequence of heavy and light chains, variable domains and CDRs of G1/929_01_A01 |  |
|---|---|
| Heavy chain AA (without LALA) (SEQ ID NO: 149) | EVQLVQSGAEVKRPGASVKVSCKASGYTFTSYGISWVRQAPGQG LEWMGWISAYGGSTNYAQKLQGRVTMTTDTSTSTAYMELRSLRS DDTAVYYCARDLFPTIFGVSYYYYWGQGTLVTVSSASTKGPSVFPL APSSKSTSGGTAALGCLVKDYFPEPVTVSWNSGALTSGVHTPAV LQSSGLYSLSSVVTVPSSSLGTQTYICNVNHKPSNTKVDKKVEPKS CDKTHTCPPCPAPELLGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG |
| VH domain AA (SEQ ID NO: 150) | EVQLVQSGAEVKRPGASVKVSCKASGYPFTSYGISWVRQAPGQG LEWMGWISAYGGSTNYAQKLQGRVTMTTDTSTSTAYMELRSLRS DDTAVYYCARDLFPTIFGVSYYYYWGQGTLVTVSS |
| HCDR1 (AA) (IMGT) (SEQ ID NO: 102) | GYPFTSYG |
| HCDR1 (AA) (Kabat) (SEQ ID NO: 1) | SYGIS |
| HCDR2 (AA) (IMGT) (SEQ ID NO: 135) | ISAYGGST |
| HCDR2 (AA) (Kabat) (SEQ ID NO: 136) | WISAYGGSTNYAQKLQG |
| HCDR3 (AA) (IMGT) (SEQ ID NO: 69) | ARDLFPTIFGVSYYYY |
| HCDR3 (AA) (Kabat) (SEQ ID NO: 3) | DLFPTIFGVSYYYY |
| Light chain AA (SEQ ID NO: 151) | DIQMTQSPSTLSASVRDRVIITCRASQSIGNRLAWYQHKPGKAPKL LIYEASTSETGVPSRFSGSGSGTDFTLTISSLQPEDFATYYCQQSY STPYTFGQGTKLEIKRTAAAPSVFIFPPSDEQLKSGTASVVCLLNN FYPREAKVQWKVDNALQSGNSQESVTEQDSKDSTYSLSSTLTLSK ADYEKHKLYACEVTHQGLSSPVTKSFNRGEC |
| VL domain AA (SEQ ID NO: 152) | DIQMTQSPSTLSASVRDRVIITCRASQSIGNRLAWYQHKPGKAPKL LIYEASTSETGVPSRFSGSGSGTDFTLTISSLQPEDFATYYCQQSY STPYTFGQGTKLEIK |
| LCDR1 (AA) (IMGT) (SEQ ID NO: 103) | QSIGNR |
| LCDR1 (AA) (Kabat) (SEQ ID NO: 15) | RASQSIGNRLA |
| LCDR2 (AA) (IMGT) (SEQ ID NO: 71) | EAS |
| LCDR2 (AA) (Kabat) (SEQ ID NO: 16) | EASTSET |
| LCDR3 (AA) (IMGT) (SEQ ID NO: 17) | QQSYSTPYT |
| LCDR3 (AA) (Kabat) (SEQ ID NO: 17) | QQSYSTPYT |

| Amino acid sequence of heavy and light chains, variable domains and CDRs of G1/929_01_A02 |  |
|---|---|
| Heavy chain AA (without LALA) (SEQ ID NO: 153) | EVQLVQSGAEVKRPGASVKVSCKASGYTFTSYGISWVRQAPGQG LEWMGWISAYGGTNYAQKLQGRVTMTTDTSTSTAYMELRSLRS DDTAVYYCARDLFPTIFGVSYYYYWGQGTLVTVSSASTKGPSVFPL APSSKSTSGGTAALGCLVKDYFPEPVTVSWNSGALTSGVHTPAV LQSSGLYSLSSVVTVPSSSLGTQTYICNVNHKPSNTKVDKKVEPKS CDKTHTCPPCPAPELLGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG |

-continued

| Amino acid sequence of heavy and light chains, variable domains and CDRs of G1/929_01_A02 | |
|---|---|
| VH domain AA (SEQ ID NO: 154) | EVQLVQSGAEVKRPGASVKVSCKASGYPFTSYGISWVRQAPGQG LEWMGWISAYSGGTNYAQKLQGRVTMTTDTSTSTAYMELRSLRS DDTAVYYC<u>ARDLFPTIFGVSYYYY</u>WGQGTLVTVSS |
| HCDR1 (AA) (IMGT) (SEQ ID NO: 102) | GYPFTSYG |
| HCDR1 (AA) (Kabat) (SEQ ID NO: 1) | SYGIS |
| HCDR2 (AA) (IMGT) (SEQ ID NO: 111) | ISAYSGGT |
| HCDR2 (AA) Kabat (SEQ ID NO: 18) | WISAYSGGTNYAQKLQG |
| HCDR3 (AA) (IMGT) (SEQ ID NO: 69) | ARDLFPTIFGVSYYYY |
| HCDR3 (AA) (Kabat) (SEQ ID NO: 3) | DLFPTIFGVSYYYY |
| Light chain AA (SEQ ID NO: 155) | DIQMTQSPSTLSASVRDRVIITCRASQSIGNRLAWYQHKPGKAPKL LIYEASTSETGVPSRFSGSGSGTDFTLTISSLQPEDFATYYC<u>QQSY STPYT</u>FGQGTKLEIKRTAAAAPSVFIFPPSDEQLKSGTASVVCLLNN FYPREAKVQWKVDNALQSGNSQESVTEQDSKDSTYSLSSTLTLSK ADYEKHKLYACEVTHQGLSSPVTKSFNRGEC |
| VL domain AA (SEQ ID NO: 156) | DIQMTQSPSTLSASVRDRVIITCRASQSIGNRLAWYQHKPGKAPKL LIYEASTSETGVPSRFSGSGSGTDFTLTISSLQPEDFATYYC<u>QQSY STPYT</u>FGQGTKLEIK |
| LCDR1 (AA) (IMGT) (SEQ ID NO: 103) | QSIGNR |
| LCDR1 (AA) (Kabat) (SEQ ID NO: 15) | RASQSIGNRLA |
| LCDR2 (AA) (IMGT) (SEQ ID NO: 71) | EAS |
| LCDR2 (AA) (Kabat) (SEQ ID NO: 16) | EASTSET |
| LCDR3 (AA) (IMGT) (SEQ ID NO: 17) | QQSYSTPYT |
| LCDR3 (AA) (Kabat) (SEQ ID NO: 17) | QQSYSTPYT |

| Amino acid sequence of heavy and light chains, variable domains and CDRs of G1/929_01_A03 | |
|---|---|
| Heavy chain AA (without LALA) (SEQ ID NO: 157) | EVQLVQSGAEVKRPGASVKVSCKASGYTFTSYGISWVRQAPGQG LEWMGWISAYSGNANYAQKLQGRVTMTTDTSTSTAYMELRSLRS DDTAVYYC<u>ARDLFPTIFGVSYYYY</u>WGQGTLVTVSSASTKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVEPKS CDKTHTCPPCPAPELLGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG |
| VH domain AA (SEQ ID NO: 158) | EVQLVQSGAEVKRPGASVKVSCKASGYPFTSYGISWVRQAPGQG LEWMGWISAYSGNANYAQKLQGRVTMTTDTSTSTAYMELRSLRS DDTAVYYC<u>ARDLFPTIFGVSYYYY</u>WGQGTLVTVSS |
| HCDR1 (AA) (IMGT) (SEQ ID NO: 102) | GYPFTSYG |

Amino acid sequence of heavy and light chains, variable domains and CDRs of G1/929_01_A03

HCDR1 (AA) (Kabat)　　SYGIS
(SEQ ID NO: 1)

HCDR2 (AA) (IMGT)　　ISAYSGNA
(SEQ ID NO: 145)

HCDR2 (AA) (Kabat)　　WISAYSGNANYAQKLQG
(SEQ ID NO: 146)

HCDR3 (AA) (IMGT)　　ARDLFPTIFGVSYYYY
(SEQ ID NO: 69)

HCDR3 (AA) (Kabat)　　DLFPTIFGVSYYYY
(SEQ ID NO: 3)

Light chain AA　　*DIQMTQSPSTLSASVRDRVIITCRASQSIGNRLAWYQHKPGKAPKL*
(SEQ ID NO: 159)　　*LIYEASTSETGVPSRFSGSGSGTDFTLTISSLQPEDFATYYCQQSY*
　　　　　　　　　　　*STPYTFGQGTKLEIK*RTAAAAPSVFIFPPSDEQLKSGTASVVCLLNN
　　　　　　　　　　　FYPREAKVQWKVDNALQSGNSQESVTEQDSKDSTYSLSSTLTLSK
　　　　　　　　　　　ADYEKHKLYACEVTHQGLSSPVTKSFNRGEC VL domain AA　　*DIQMTQSPSTLSASVRDRVIITCRASQSIGNRLAWYQHKPGKAPKL*
(SEQ ID NO: 160)　　*LIYEASTSETGVPSRFSGSGSGTDFTLTISSLQPEDFATYYCQQSY*
　　　　　　　　　　　*STPYTFGQGTKLEIK*

LCDR1 (AA) (IMGT)　　QSIGNR
(SEQ ID NO: 103)

LCDR1 (AA) (Kabat)　　RASQSIGNRLA
(SEQ ID NO: 15)

LCDR2 (AA) (IMGT)　　EAS
(SEQ ID NO: 71)

LCDR2 (AA) (Kabat)　　EASTSET
(SEQ ID NO: 16)

LCDR3 (AA) (IMGT)　　QQSYSTPYT
(SEQ ID NO: 17)

LCDR3 (AA) (Kabat)　　QQSYSTPYT
(SEQ ID NO: 17)

Amino acid sequence of heavy and light chains, variable domains and CDRs of G1/929_01_A10

Heavy chain AA　　*EVQLVQSGAEVKRPGASVKVSCKASGYTFTSYGISWVRQAPGQG*
(without LALA)　　*LEWMGWISAYGGSTNYAQKLQGRVTMTTDTSTSTAYMELRSLRS*
(SEQ ID NO: 161)　　*DDTAVYYCARDLFPTIFGVSYYYYWGQGTLVTVSS*ASTKGPSVFPL
　　　　　　　　　　　APSSKSTSGGTAALGCLVKDYFPEPVTVSWNSGALTSGVHTFPAV
　　　　　　　　　　　LQSSGLYSLSSVVTVPSSSLGTQTYICNVNHKPSNTKVDKKVEPKS
　　　　　　　　　　　CDKTHTCPPCPAPELLGGPSVFLFPPKPKDTLMISRTPEVTCVVVD
　　　　　　　　　　　VSHEDPEVKFNWYVDGVEVHNAKTKPREEQYNSTYRVVSVLTVLH
　　　　　　　　　　　QDWLNGKEYKCKVSNKALPAPIEKTISKAKGQPREPQVYTLPPSRD
　　　　　　　　　　　ELTKNQVSLTCLVKGFYPSDIAVEWESNGQPENNYKTTPPVLDSD
　　　　　　　　　　　GSFFLYSKLTVDKSRWQQGNVFSCSVMHEALHNHYTQKSLSLSPG VH domain AA　　*EVQLVQSGAEVKRPGASVKVSCKASGYTFTSYGISWVRQAPGQG*
(SEQ ID NO: 162)　　*LEWMGWISAYGGSTNYAQKLQGRVTMTTDTSTSTAYMELRSLRS*
　　　　　　　　　　　*DDTAVYYCARDLFPTIFGVSYYYYWGQGTLVTVSS*

HCDR1 (AA) (IMGT)　　GYTFTSYG
(SEQ ID NO: 94)

HCDR1 (AA) (Kabat)　　SYGIS
(SEQ ID NO: 1)

HCDR2 (AA) (IMGT)　　ISAYGGST
(SEQ ID NO: 135)

HCDR2 (AA) (Kabat)　　WISAYGGSTNYAQKLQG
(SEQ ID NO: 136)

| Amino acid sequence of heavy and light chains, variable domains and CDRs of G1/929_01_A10 |  |
|---|---|
| HCDR3 (AA) (IMGT) (SEQ ID NO: 69) | ARDLFPTIFGVSYYYY |
| HCDR3 (AA) (Kabat) (SEQ ID NO: 3) | DLFPTIFGVSYYYY |
| Light chain AA (SEQ ID NO: 163) | DIQMTQSPSTLSASVGDRVTITCRASQSISGRLAWYQQKPGKAPNL LIYEASNLESGVPSRFSGSGSGTEFTLTISSLQPEDFATYYCQQSY SWPRTFGQGTKVEIKRTAAAAPSVFIFPPSDEQLKSGTASVVCLLN NFYPREAKVQWKVDNALQSGNSQESVTEQDSKDSTYSLSSTLTLS KADYEKHKLYACEVTHQGLSSPVTKSFNRGEC |
| VL domain AA (SEQ ID NO: 164) | DIQMTQSPSTLSASVGDRVTITCRASQSISGRLAWYQQKPGKAPNL LIYEASNLESGVPSRFSGSGSGTEFTLTISSLQPEDFATYYCQQSY SWPRTFGQGTKVEIK |
| LCDR1 (AA) (IMGT) (SEQ ID NO: 100) | QSISGR |
| LCDR1 (AA) (Kabat) (SEQ ID NO: 19) | RASQSISGRLA |
| LCDR2 (AA) (IMGT) (SEQ ID NO: 106) | EASN |
| LCDR2 (AA) (Kabat) (SEQ ID NO: 20) | EASNLES |
| LCDR3 (AA) (IMGT) (SEQ ID NO: 21) | QQSYSWPRT |
| LCDR3 (AA) (Kabat) (SEQ ID NO: 21) | QQSYSWPRT |

| Amino acid sequence of heavy and light chains, variable domains and CDRs of G1/929_01_A11 (This clone is the same as G1AA/G12v2 but without the LALA mutation.) |  |
|---|---|
| Heavy chain AA (without LALA) (SEQ ID NO: 165) | EVQLVQSGAEVKRPGASVKVSCKASGYTFTSYGISWVRQAPGQG LEWMGWISAYGGSTNYAQKLQGRVTMTTDTSTSTAYMELRSLRS DDTAVYYCARDLFPTIFGVSYYYYWGQGTLVTVSSAS- TKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVE- PKS CDKTHTCPPCPAPELLGGPSVFLFPPKPKDTLMISRTPE- VTCVVVD VSHEDPEVKFNWYVDGVEVHNAKTKPREEQYNSTYRVVSVLTVLH QDWLNGKEYKCKVSNKALPA- PIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG |
| VH domain AA (SEQ ID NO: 29) | EVQLVQSGAEVKRPGASVKVSCKASGYTFTSYGISWVRQAPGQG LEWMGWISAYGGSTNYAQKLQGRVTMTTDTSTSTAYMELRSLRS DDTAVYYCARDLFPTIFGVSYYYYWGQGTLVTVSS |
| HCDR1 (AA) (IMGT) (SEQ ID NO: 94) | GYTFTSYG |
| HCDR1 (AA) (Kabat) (SEQ ID NO: 1) | SYGIS |
| HCDR2 (AA) (IMGT) (SEQ ID NO: 111) | ISAYSGGT |
| HCDR2 (AA) (Kabat) (SEQ ID NO: 18) | WISAYGGTNYAQKLQG |
| HCDR3 (AA) (IMGT) (SEQ ID NO: 69) | ARDLFPTIFGVSYYYY |

-continued

| Amino acid sequence of heavy and light chains, variable domains and CDRs of G1/929_01_A11 (This clone is the same as G1AA/G12v2 but without the LALA mutation.) | |
|---|---|
| HCDR3 (AA) (Kabat) (SEQ ID NO: 3) | DLFPTIFGVSYYYY |
| Light chain AA (SEQ ID NO: 166) | DIQMTQSPSTLSASVGDRVTITCRASQSISGR-LAWYQQKPGKAPNLLIYEASNLESGVPSRFSGSGSGTEFTLTISSLQPEDFATYYCQQSYSWPRTFGQGTKVEIKRTAAAAPSVFIFPPSDEQLKSG-TASVVCLLNNFYPREAKVQWKVDNALQSGNSQESVTEQDSKDSTYSLSSTLTLSKADYEKHKLYACEVTHQGLSSPVTKSFNRGEC |
| VL domain AA (SEQ ID NO: 167) | DIQMTQSPSTLSASVGDRVTITCRASQSISGR-LAWYQQKPGKAPNLLIYEASNLESGVPSRFSGSGSGTEFTLTISSLQPEDFATYYCQQSYSWPRTFGQGTKVEIK |
| LCDR1 (AA) (IMGT) (SEQ ID NO: 100) | QSISGR |
| LCDR1 (AA) (Kabat) (SEQ ID NO: 19) | RASQSISGRLA |
| LCDR2 (AA) (IMGT) (SEQ ID NO: 106) | EASN |
| LCDR2 (AA) (Kabat) (SEQ ID NO: 20) | EASNLES |
| LCDR3 (AA) (IMGT) (SEQ ID NO: 21) | QQSYSWPRT |
| LCDR3 (AA) (Kabat) (SEQ ID NO: 21) | QQSYSWPRT |

| Amino acid sequence of heavy and light chains, variable domains and CDRs of G1/929_01_A12 | |
|---|---|
| Heavy chain AA (without LALA) (SEQ ID NO: 168) | EVQLVQSGAEVKRPGASVKVSCKASGYTFTSYGISWVRQAPGQGLEWMGWISAYGGSTNYAQKLQGRVTMTTDTSTSTAYMELRSLRSDDTAVYYCARDLFPTIFGVSYYYYWGQGTLVTVSSAS-TKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVE-PKSCDKTHTCPPCPAPELLGGPSVFLFPPKPKDTLMISRTPE-VTCVVVDVSHEDPEVKFNWYVDGVEVHNAKTKPREEQYNSTYRVVSVLTVLHQDWLNGKEYKCKVSNKALPA-PIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG |
| VH domain AA (SEQ ID NO: 169) | EVQLVQSGAEVKRPGASVKVSCKASGYTFTSYGISWVRQAPGQGLEWMGWISAYGGSTNYAQKLQGRVTMTTDTSTSTAYMELRSLRSDDTAVYYCARDLFPTIFGVSYYYYWGQGTLVTVSS |
| HCDR1 (AA) (IMGT) (SEQ ID NO: 94) | GYTFTSYG |
| HCDR1 (AA) (Kabat) (SEQ ID NO: 1) | SYGIS |
| HCDR2 (AA) (IMGT) (SEQ ID NO: 145) | ISAYSGNA |
| HCDR2 (AA) (Kabat) (SEQ ID NO: 146) | WISAYSGNANYAQKLQG |
| HCDR3 (AA) (IMGT) (SEQ ID NO: 69) | ARDLFPTIFGVSYYYY |

-continued

| Amino acid sequence of heavy and light chains, variable domains and CDRs of G1/929_01_A12 |  |
|---|---|
| HCDR3 (AA) (Kabat)<br>(SEQ ID NO: 3) | DLFPTIFGVSYYYY |
| Light chain AA<br>(SEQ ID NO: 170) | DIQMTQSPSTLSASVGDRVTITCRASQSISGR-<br>LAWYQQKPGKAPNL<br>LIYEASNLESGVPSRFSGSGSGTEFTLTISSLQPEDFA-<br>TYYCQQSY<br>SWPRTFGQGTKVEIKRTAAAPSVFIFPPSDEQLKSG-<br>TASVVCLLN<br>NFYPREAKVQWKVDNALQSGNSQESVTEQDSKDSTYSLSSTLTLS<br>KADYEKHKLYACEVTHQGLSSPVTKSFNRGEC |
| VL domain AA<br>(SEQ ID NO: 171 ) | DIQMTQSPSTLSASVGDRVTITCRASQSISGR-<br>LAWYQQKPGKAPNL<br>LIYEASNLESGVPSRFSGSGSGTEFTLTISSLQPEDFA-<br>TYYCQQSY<br>SWPRTFGQGTKVEIK |
| LCDR1 (AA) (IMGT)<br>(SEQ ID NO: 100) | QSISGR |
| LCDR1 (AA) (Kabat)<br>(SEQ ID NO: 19) | RASQSISGRLA |
| LCDR2 (AA) (IMGT)<br>(SEQ ID NO: 106) | EASN |
| LCDR2 (AA) (Kabat)<br>(SEQ ID NO: 20) | EASNLES |
| LCDR3 (AA) (IMGT)<br>(SEQ ID NO: 21) | QQSYSWPRT |
| LCDR3 (AA) (Kabat)<br>(SEQ ID NO: 21) | QQSYSWPRT |

| Amino acid sequence of heavy and light chains, variable domains and CDRs of G1/929_01_A04 |  |
|---|---|
| Heavy chain AA<br>(without LALA)<br>(SEQ ID NO: 172) | EVQLVQSGAEVKRPGASVKVSCKASGYTFTSYGISWVRQAPGQG<br>LEWMGWISAYGGSTNYAQKLQGRVTMTTDTSTSTAYMELRSLRS<br>DDTAVYYCARDLFPTIFGVSYYYYWGQGTLVTVSSASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| VH domain AA<br>(SEQ ID NO: 173) | EVQLVQSGAEVKRPGASVKVSCKASGYTFTSYGISWVRQAPGQG<br>LEWMGWISAYGGSTNYAQKLQGRVTMTTDTSTSTAYMELRSLRS<br>DDTAVYYCARDLFPTIFGVSYYYYWGQGTLVTVSS |
| HCDR1 (AA) (IMGT)<br>(SEQ ID NO: 94) | GYTFTSYG |
| HCDR1 (AA) (Kabat)<br>(SEQ ID NO: 1) | SYGIS |
| HCDR2 (AA) (IMGT)<br>(SEQ ID NO: 135) | ISAYGGST |
| HCDR2 (AA) (Kabat)<br>(SEQ ID NO: 136) | WISAYGGSTNYAQKLQG |
| HCDR3 (AA) (IMGT)<br>(SEQ ID NO: 69) | ARDLFPTIFGVSYYYY |
| HCDR3 (AA) (Kabat)<br>(SEQ ID NO: 3) | DLFPTIFGVSYYYY |

| Amino acid sequence of heavy and light chains, variable domains and CDRs of G1/929_01_A04 | |
|---|---|
| Light chain AA<br>(SEQ ID NO: 174) | DIQMTQSPSTLSASVGDRVTITCRASQSISGRLAWYQQKPGKAPNL<br>LIYEASNLESGVPSRFSGSGSGTEFTLTINSLQPDDFATYYCQQAN<br>TFPRVSFGGGTKVEIKRTAAAAPSVFIFPPSDEQLKSG-<br>TASVVCLLN<br>NFYPREAKVQWKVDNALQSGNSQESVTEQDSKDSTYSLSSTLTLS<br>KADYEKHKLYACEVTHQGLSSPVTKSFNRGEC |
| VL domain AA<br>(SEQ ID NO: 175) | DIQMTQSPSTLSASVGDRVTITCRASQSISGRLAWYQQKPGKAPNL<br>LIYEASNLESGVPSRFSGSGSGTEFTLTINSLQPDDFATYYCQQAN<br>TFPRVSFGGGTKVEIK |
| LCDR1 (AA) (IMGT)<br>(SEQ ID NO: 100) | QSISGR |
| LCDR1 (AA) (Kabat)<br>(SEQ ID NO: 19) | RASQSISGRLA |
| LCDR2 (AA) (IMGT)<br>(SEQ ID NO: 106) | EASN |
| LCDR2 (AA) (Kabat)<br>(SEQ ID NO: 20) | EASNLES |
| LCDR3 (AA) (IMGT)<br>(SEQ ID NO: 24) | QQANTFPRVS |
| LCDR3 (AA) (Kabat)<br>(SEQ ID NO: 24) | QQANTFPRVS |

| Amino acid sequence of heavy and light chains, variable domains and CDRs of G1/929_01_A05 | |
|---|---|
| Heavy chain AA<br>(without LALA)<br>(SEQ ID NO: 176) | EVQLVQSGAEVKRPGASVKVSCKASGYTFTSYGISWVRQAPGQG<br>LEWMGWISAYGGSTNYAQKLQGRVTMTTDTSTSTAYMELRSLRS<br>DDTAVYYCARDLFPTIFGVSYYYYWGQGTLVTVSSASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELTKNQVSLTCLVKGFYPSDIAVEWESNGQPENNYKTTPPVLDSD<br>GSFFLYSKLTVDKSRWQQGNVFSCSVMHEALHNHYTQKSLSLSPG |
| VH domain AA<br>(SEQ ID NO: 177) | EVQLVQSGAEVKRPGASVKVSCKASGYTFTSYGISWVRQAPGQG<br>LEWMGWISAYGGSTNYAQKLQGRVTMTTDTSTSTAYMELRSLRS<br>DDTAVYYCARDLFPTIFGVSYYYYWGQGTLVTVSS |
| HCDR1 (AA) (IMGT)<br>(SEQ ID NO: 94) | GYTFTSYG |
| HCDR1 (AA) (Kabat)<br>(SEQ ID NO: 1) | SYGIS |
| HCDR2 (AA) (IMGT)<br>(SEQ ID NO: 111) | ISAYSGGT |
| HCDR2 (AA) (Kabat)<br>(SEQ ID NO: 18) | WISAYSGGTNYAQKLQG |
| HCDR3 (AA) (IMGT)<br>(SEQ ID NO: 69) | ARDLFPTIFGVSYYYY |
| HCDR3 (AA) (Kabat)<br>(SEQ ID NO: 3) | DLFPTIFGVSYYYY |
| Light chain AA<br>(SEQ ID NO: 178) | DIQMTQSPSTLSASVGDRVTITCRASQSISGRLAWYQQKPGKAPNL<br>LIYEASNLESGVPSRFSGSGSGTEFTLTINSLQPDDFATYYCQQAN<br>TFPRVSFGGGTKVEIKRTAAAAPSVFIFPPSDEQLKSG-<br>TASVVCLLN<br>NFYPREAKVQWKVDNALQSGNSQESVTEQDSKDSTYSLSSTLTLS<br>KADYEKHKLYACEVTHQGLSSPVTKSFNRGEC |

| Amino acid sequence of heavy and light chains, variable domains and CDRs of G1/929_01_A05 | |
|---|---|
| VL domain AA (SEQ ID NO: 179) | DIQMTQSPSTLSASVGDRVTITCRASQSISGRLAWYQQKPGKAPNL LIYEASNLESGVPSRFSGSGSGTEFTLTINSLQPDDFATYYCQQAN TFPRVSFGGGTKVEIK |
| LCDR1 (AA) (IMGT) (SEQ ID NO: 100) | QSISGR |
| LCDR1 (AA) (Kabat) (SEQ ID NO: 19) | RASQSISGRLA |
| LCDR2 (AA) (IMGT) (SEQ ID NO: 106) | EASN |
| LCDR2 (AA) (Kabat) (SEQ ID NO: 20) | EASNLES |
| LCDR3 (AA) (IMGT) (SEQ ID NO: 24) | QQANTFPRVS |
| LCDR3 (AA) (Kabat) (SEQ ID NO: 24) | QQANTFPRVS |

| Amino acid sequence of heavy and light chains, variable domains and CDRs of G1/929_01_A06 | |
|---|---|
| Heavy chain AA (without LALA) (SEQ ID NO: 180) | EVQLVQSGAEVKRPGASVKVSCKASGYTFTSYGISWVRQAPGQG LEWMGWISAYGGSTNYAQKLQGRVTMTTDTSTSTAYMELRSLRS DDTAVYYCARDLFPTIFGVSYYYYWGQGTLVTVSSASTKGPSVFPL APSSKSTSGGTAALGCLVKDYFPEPVTVSWNSGALTSGVHTFPAV LQSSGLYSLSSVVTVPSSSLGTQTYICNVNHKPSNTKVDKKVEPKS CDKTHTCPPCPAPELLGGPSVFLFPPKPKDTLMISRTPEVTCVVVD VSHEDPEVKFNWYVDGVEVHNAKTKPREEQYNSTYRVVSVLTVLH QDWLNGKEYKCKVSNKALPAPIEKTISKAKGQPREPQVYTLPPSRD ELTKNQVSLTCLVKGFYPSDIAVEWESNGQPENNYKTTPPVLDSD GSFFLYSKLTVDKSRWQQGNVFSCSVMHEALHNHYTQKSLSLSPG |
| VH domain AA (SEQ ID NO: 181) | EVQLVQSGAEVKRPGASVKVSCKASGYTFTSYGISWVRQAPGQG LEWMGWISAYGGSTNYAQKLQGRVTMTTDTSTSTAYMELRSLRS DDTAVYYCARDLFPTIFGVSYYYYWGQGTLVTVSS |
| HCDR1 (AA) (IMGT) (SEQ ID NO: 94) | GYTFTSYG |
| HCDR1 (AA) (Kabat) (SEQ ID NO: 1) | SYGIS |
| HCDR2 (AA) (IMGT) (SEQ ID NO: 145) | ISAYSGNA |
| HCDR2 (AA) (Kabat) (SEQ ID NO: 146) | WISAYSGNANYAQKLQG |
| HCDR3 (AA) (IMGT) (SEQ ID NO: 69) | ARDLFPTIFGVSYYYY |
| HCDR3 (AA) (Kabat) (SEQ ID NO: 3) | DLFPTIFGVSYYYY |
| Light chain AA (SEQ ID NO: 182) | DIQMTQSPSTLSASVGDRVTITCRASQSISGRLAWYQQKPGKAPNL LIYEASNLESGVPSRFSGSGSGTEFTLTINSLQPDDFATYYCQQAN TFPRVSFGGGTKVEIKRTAAAAPSVFIFPPSDEQLKSG- TASVVCLLN NFYPREAKVQWKVDNALQSGNSQESVTEQDSKDSTYSLSSTLTLS KADYEKHKLYACEVTHQGLSSPVTKSFNRGEC |
| VL domain AA (SEQ ID NO: 183) | DIQMTQSPSTLSASVGDRVTITCRASQSISGRLAWYQQKPGKAPNL LIYEASNLESGVPSRFSGSGSGTEFTLTINSLQPDDFATYYCQQAN TFPRVSFGGGTKVEIK |
| LCDR1 (AA) (IMGT) (SEQ ID NO: 100) | QSISGR |
| LCDR1 (AA) (Kabat) (SEQ ID NO: 19) | RASQSISGRLA |
| LCDR2 (AA) (IMGT (SEQ ID NO: 106) | EASN |

| Amino acid sequence of heavy and light chains, variable domains and CDRs of G1/929_01_A06 |
| --- |

LCDR2 (AA) (Kabat) EASNLES
(SEQ ID NO: 20)

LCDR3 (AA) (IMGT) QQANTFPRVS
(SEQ ID NO: 24)

LCDR3 (AA) (Kabat) QQANTFPRVS
(SEQ ID NO: 24)

mAbs Tested in mAb² Format
Notes:
  i. In the heavy chain sequence, variable domain in italics and, where applicable, location of LALA mutation in bold and underlined.
  ii. In the light chain sequence, variable domain shown in italics.

| Amino acid sequence of heavy and light chain of FS22-172-003AA/E05v2 mAb² |
| --- |

Heavy chain AA *EVQLVQSGAEVKRPGASVKVSCKASGYTFTSYGISWVRQAPGQG*
(with LALA) *LEWMGWISAYSGGTNYAQKLQGRVTMTTDTSTSTAYMELRSLRS*
(SEQ ID NO: 89) *DDTAVYYCARDLFPTIFGVSYYYYWGQGTLVTVSS*ASTKGPSVFPL
APSSKSTSGGTAALGCLVKDYFPEPVTVSWNSGALTSGVHTFPAV
LQSSGLYSLSSVVTVPSSSLGTQTYICNVNHKPSNTKVDKKVEPKS
CDKTHTCPPCPAPEAAGGPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSRD
ELPYIIPPYNQVSLTCLVKGFYPSDIAVEWESNGQPEN-
NYKTTPPVL
DSDGSFFLYSKLTVGADRWLEGNVFSCSVMHEALHNHYTQKSLSL
SPG Light chain AA *DIQMTQSPSTLSASVGDRVTITCRASQSISGRLAWYQQKPGKAPNL*
(SEQ ID NO: 90) *LIYEASNLESGVPSRFSGSGSGTEFTLTISSLQPEDFATYYCQQ-
SYS
TPRVTFGQGTKVEIK*RTVAAPSVFIFPPSDEQLKSG-
TASVVCLLNNF
YPREAKVQWKVDNALQSGNSQESVTEQDSKDSTYSLSSTLTLSKA
DYEKHKVYACEVTHQGLSSPVTKSFNRGEC

| Amino acid sequence of heavy and light chain of FS22-172-003AA/E12v2 mAb² |
| --- |

Heavy chain AA *EVQLVQSGAEVKRPGASVKVSCKASGYTFTSYGISWVRQAPGQG*
(with LALA) *LEWMGWISAYSGGTNYAQKLQGRVTMTTDTSTSTAYMELRSLRS*
(SEQ ID NO: 85) *DDTAVYYCARDLFPTIFGVSYYYYWGQGTLVTVSS*ASTKGPSVFPL
APSSKSTSGGTAALGCLVKDYFPEPVTVSWNSGALTSGVHTFPAV
LQSSGLYSLSSVVTVPSSSLGTQTYICNVNHKPSNTKVDKKVEPKS
CDKTHTCPPCPAPEAAGGPSVFLFPPKPKDTLMISRTPEVTCVVVD
VSHEDPEVKFNWYVDGVEVHNAKTKPREEQYNSTYRVVSVLTVLH
QDWLNGKEYKCKVSNKALPAPIEKTISKAKGQPREPQVYTLPPSRD
ELPYIIPPYNQVSLTCLVKGFYPSDIAVEWESNGQPEN-
NYKTTPPVL
DSDGSFFLYSKLTVGADRWLEGNVFSCSVMHEALHNHYTQKSLSL
SPG Light chain AA *DIQMTQSPSTLSASVGDRVTITCRASQSISGRLAWYQQKPGKAPNL*
(SEQ ID NO: 86) *LIYEASNLESGVPSRFSGSGSGTEFTLTISSLQPEDFATYYCQQ-
SYS
TPRVTFGQGTKVEIK*RTVAAPSVFIFPPSDEQLKSG-
TASVVCLLNNF
YPREAKVQWKVDNALQSGNSQESVTEQDSKDSTYSLSSTLTLSKA
DYEKHKVYACEVTHQGLSSPVTKSFNRGEC

| Amino acid sequence of heavy and light chain of FS22-172-003AA/G12v2 mAb² |
| --- |

| | |
| --- | --- |
| Heavy chain AA (with LALA) (SEQ ID NO: 87) | EVQLVQSGAEVKRPGASVKVSCKASGYTFTSYGISWVRQAPGQG<br>LEWMGWISAYSGGTNYAQKLQGRVTMTTDTSTSTAYMELRSLRS<br>DDTAVYYCARDLFPTIFGVSYYYWGQGTLVTVSSASTKGPSVFPL<br>APSSKSTSGGTAALGCLVKDYFPEPVTVSWNSGALTSGVHTPAV<br>LQSSGLYSLSSVVTVPSSSLGTQTYICNVNHKPSNTKVDKKVEPKS<br>CDKTHTCPPCPAPEAAGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELPYIIPPYNQVSLTCLVKGFYPSDIAVEWESNGQPEN-<br>NYKTTPPVL<br>DSDGSFFLYSKLTVGADRWLEGNVFSCSVMHEALHNHYTQKSLSL<br>SPG |
| Light chain AA (SEQ ID NO: 88) | DIQMTQSPSTLSASVGDRVTITCRASQSISGRLAWYQQKPGKAPNL<br>LIYEASNLESGVPSRFSGSGSGTEFTLTISSLQPEDFATYYCQQ-<br>SYS<br>TPRVTFGQGTKVEIKRTVAAPSVFIFPPSDEQLKSG-<br>TASVVCLLNNF<br>YPREAKVQWKVDNALQSGNSQESVTEQDSKDSTYSLSSTLTLSKA<br>DYEKHKVYACEVTHQGLSSPVTKSFNRGEC |

| Amino acid sequence of heavy and light chain of FS22-172-003AA/lambdav3 mAb² |
| --- |

| | |
| --- | --- |
| Heavy chain AA (with LALA) (SEQ ID NO: 91) | EVQLVQSGAEVKRPGASVKVSCKASGYTFTSYGISWVRQAPGQG<br>LEWMGWISAYSGGTNYAQKLQGRVTMTTDTSTSTAYMELRSLRS<br>DDTAVYYCARDLFPTIFGVSYYYWGQGTLVTVSSASTKGPSVFPL<br>APSSKSTSGGTAALGCLVKDYFPEPVTVSWNSGALTSGVHTPAV<br>LQSSGLYSLSSVVTVPSSSLGTQTYICNVNHKPSNTKVDKKVEPKS<br>CDKTHTCPPCPAPEAAGGPSVFLFPPKPKDTLMISRTPEVTCVVVD<br>VSHEDPEVKFNWYVDGVEVHNAKTKPREEQYNSTYRVVSVLTVLH<br>QDWLNGKEYKCKVSNKALPAPIEKTISKAKGQPREPQVYTLPPSRD<br>ELPYIIPPYNQVSLTCLVKGFYPSDIAVEWESNGQPEN-<br>NYKTTPPVL<br>DSDGSFFLYSKLTVGADRWLEGNVFSCSVMHEALHNHYTQKSLSL<br>SPG |
| Light chain AA (SEQ ID NO: 92) | QSALTQPASVSGSPGQSITISCTGTSSDVGGYNYVSWYQQFPGKA<br>PKLMIFEVTNRPSGVSDRFSGSKSDNTASLTISGLQAEDEAEYYCS<br>SFKRGSTLVVFGGGTKLTVLGQPAAAPSVTLFPPSSEELQANKATL<br>VCLISDFYPGAVTVAWKADSSPVKAGVETTTPSKQSNNKYAASSYL<br>SLTPEQWKSHRSYSCQVTHEGSTVEKTVAPTECS |

Amino Acid Sequences of Recombinant Antigens

| PD-L1-rCd4-His |
| --- |

| | |
| --- | --- |
| Human (SEQ ID NO: 79) | MRIFAVFIFMTYWHLLNAFTVTVPKDLYVVEYGSNMTIECKFPVEKQ<br>LDLAALIVYWEMEDKNIIQFVHGEEDLKVQHSSYRQRARLLKDQLS<br>LGNAALQITDVKLQDAGVYRCMISYGGADYKRITVKVNAPYNKINQ<br>RILVVDPVTSEHELTCQAEGYPKAEVIWTSSDHQVLSGKTTTTNSK<br>REEKLFNVTSTLRINTTTNEIFYCTFRRLDPEENHTAELVIPELPLAH<br>PPNERTAAATSITAYKSEGESAEFSFPLNLGEESLQGELRWKAEKA<br>PSSQSWITFSLKNQKVSVQKSTSNPKFQLSETLPLTLQIPQVSLQFA<br>GSGNLTLTLDRGILYQEVNLVVMKVTQPDSNTLTCEVMGPTSPKM<br>RLILKQENQEARVSRQEKVIQVQAPEAGVWQCLLSEGEEVKMDSKI<br>QVLSKGLNGSHHHHHH |
| Mouse (SEQ ID NO: 81) | MRIFAGIIFTACCHLLRAFTITAPKDLYVVEYGSNVTMECRFPVEREL<br>DLLALVVYWEKEDEQVIQFVAGEEDLKPQHSNFRGRASLPKDQLL<br>KGNAALQITDVKLQDAGVYCCIISYGGADYKRITLKVNAPYRKINQRI<br>SVDPATSEHELICQAEGYPEAEVIWTNSDHQPVSGKRSVTTSRTE<br>GMLLNVTSSLRVNATANDVFYCTFWRSQPGQNHTAELIIPELPATH<br>PPQNRTAAATSITAYKSEGESAEFSFPLNLGEESLQGELRWKAEK<br>APSSQSWITFSLKNQKVSVQKSTSNPKFQLSETLPLTLQIPQVSLQF<br>AGSGNLTLTLDRGILYQEVNLVVMKVTQPDSNTLTCEVMGPTSPK<br>MRLILKQENQEARVSRQEKVIQVQAPEAGVWQCLLSEGEEVKMDS<br>KIQVLSKGLNGSHHHHHH |

| PD-L1-rCd4-His | |
|---|---|
| Cyno<br>(SEQ ID NO: 184) | <u>MRIFAVFIFTIYWHLLNAFT</u>VTVPKDLYVVEYGSNMTIECKFPVEKQL<br>DLTSLIVYWEMEDKNIIQFVHGEEDLKVQHSNYRQRAQLLKDQLSL<br>GNAALRITDVKLQDAGVYRCMISYGGADYKRITVKVNAPYNKINQRI<br>LVVDPVTSEHELTCQAEGYPKAEVIWTSSDHQVLSGKTTTTNSKRE<br>EKLLNVTSTLRINTTANEIFYCIFRRLDPEENHTAELVIPELPLA-<br>LPPN<br>ERT<u>AAA</u>*TSITAYKSEGESAEFSFPLNLGEESLQGELRWKAEKAPSS<br>QSWITFSLKNQKVSVQKSTSNPKFQLSETLPLTLQIPQVSLQFAGS<br>GNLTLTLDRGILYQEVNLVVMKVTQPDSNTLTCEVMGPTSPKMRLI<br>LKQENQEARVSRQEKVIQVQAPEAGVWQCLLSEGEEVKMDSKIQV<br>LSKGLN*GS<u>HHHHHH</u> |

Signal peptide (underlined)
Extracellular domain of PD-L1 (regular font)
C-terminal rat CD4 (domains 3 and 4) (italics)
Junction between antigen and C-terminal fusion encoding a Notl restriction site (bold and underlined)
C-terminal hexahistidine tag (italics and underlined)

| PD-L1-Fc-His | |
|---|---|
| Human<br>(SEQ ID NO: 80) | <u>MRIFAVFIFMTYWHLLNAFT</u>VTVPKDLYVVEYGSNMTIECKFPVEKQ<br>LDLAALIVYWEMEDKNIIQFVHGEEDLKVQHSSYRQRARLLKDQLS<br>LGNAALQITDVKLQDAGVYRCMISYGGADYKRITVKVNAPYNKINQ<br>RILVVDPVTSEHELTCQAEGYPKAEVIWTSSDHQVLSGKTTTTNSK<br>REEKLFNVTSTLRINTTTNEIFYCTFRRLDPEENHTAELVIPELPLAH<br>PPNERT<u>AAA</u>*DKTHTCPPCPAPELLGGPSVFLFPPKPKDTLMISRTP<br>EVTCVV<u>V</u>*DVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYT<br>QKSLSLSPGKGS<u>HHHHHH</u> |
| Mouse<br>(SEQ ID NO: 82) | <u>MRIFAGIIFTACCHLLRAFT</u>ITAPKDLYVVEYGSNVTMECRFPVEREL<br>DLLALVVYWEKEDEQVIQFVAGEEDLKPQHSNFRGRASLPKDQLL<br>KGNAALQITDVKLQDAGVYCCIISYGGADYKRITLKVNAPYRKINQRI<br>SVDPATSEHELICQAEGYPEAEVIWTNSDHQPVSGKRSVTTSRTE<br>GMLLNVTSSLRVNATANDVFYCTFWRSQPGQNHTAELIIPELPATH<br>PPQNRT<u>AAA</u>*DKTHTCPPCPAPELLGGPSVFLFPPKPKDTLMISRTP<br>EVTCVV<u>V</u>*DVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYT<br>QKSLSLSPGKGS<u>HHHHHH</u> |

Signal peptide (underlined)
Extracellular domain of PD-L1 (regular font)
Human lgG1 Fc (italics)
Junction between antigen and C-terminal fusion encoding a Notl restriction site (bold and underlined)
C-terminal hexahistidine tag (italics and underlined)

| PD-L1 | |
|---|---|
| Human<br>(SEQ ID NO: 83) | *FTVTVPKDLYVVEYGSNMTIECKFPVEKQLDLAALIVYWEMEDKNII<br>QFVHGEEDLKVQHSSYRQRARLLKDQLSLGNAALQITDVKLQDAG<br>VYRCMISYGGADYKRITVKVNAPYNKINQRILVVDPVTSEHELTCQA<br>EGYPKAEVIWTSSDHQVLSGKTTTTNSKREEKLFNVTSTLRINTTTN<br>EIFYCTFRRLDPEENHTAELVIPELPLAHPPNER*THLVILGAILLCLG<br>VALTFIFRLRKGRMMDVKKCGIQDTNSKKQSDTHLEET |
| Mouse<br>(SEQ ID NO: 84) | *FTITAPKDLYVVEYGSNVTMECRFPVERELDLLALVVYWEKEDEQV<br>IQFVAGEEDLKPQHSNFRGRASLPKDQLLKGNAALQITDVKLQDAG<br>VYCCIISYGGADYKRITLKVNAPYRKINQRISVDPATSEHELICQAEG<br>YPEAEVIWTNSDHQPVSGKRSVTTSRTEGMLLNVTSSLRVNATAN<br>DVFYCTFWRSQPGQNHTAELIIPELPATHPPQNRT*WVLLGSILLF<br>LIVVSTVLLFLRKQVRMLDVEKCGVEDTSSKNRNDTQFEET |

Extracellular domain (italics)
Transmembrane and intracellular domains (bold)

The invention claimed is:
1. An antibody or antigen-binding fragment thereof, capable of binding specifically to PD-L1, comprising a variable heavy (VH) domain comprising heavy chain complementarity determining regions (CDRs) HCDR1, HCRD2 and HCDR3, and a variable light (VL) domain comprising light chain CDRs LCDR1, LCDR2 and LCDR3, wherein the antibody or antigen-binding fragment thereof comprises an antigen-binding site comprising HCDR1, HCRD2, HCDR3, LCDR1, LCDR2 and LCDR3;
  wherein the antigen-binding site comprises HCDR1, HCRD2, HCDR3, LCDR1, LCDR2 and LCDR3 of antibody:
   (a) G1AA/E12v2 of SEQ ID NO: 1, 18, 3, 15, 16 and 17;
   (b) G1AA/G12v2 of SEQ ID NO: 1, 18, 3, 19, 20, and 21;
   (c) G1AA/E05v2 of SEQ ID NO: 1, 18, 3, 19, 20 and 22;
   (d) G1/887_04_E12 of SEQ ID NO: 1, 23, 3, 15, 16 and 17;
   (e) G1/887_04_G12 of SEQ ID NO: 1, 23, 3, 19, 20 and 21;
   (f) G1/894_08_E05 of SEQ ID NO: 1, 23, 3, 19, 20 and 22;
   (g) G1/894_08_A05 of SEQ ID NO: 1, 23, 3, 19, 20 and 24;
   (h) G1AA/lambdav3 of SEQ ID NO: 1, 18, 3, 25, 13 and 14;
   (i) G1/280_02_G02_NS of SEQ ID NO: 1, 23, 3, 26, 13 and 14; or
   (j) G1/280_02_G02 of SEQ ID NO: 1, 78, 3, 26, 13 and 14;
  wherein the sequences are defined by Kabat nomenclature; and/or
  wherein the antigen-binding site comprises HCDR1, HCRD2, HCDR3, LCDR1, LCDR2 and LCDR3 of antibody:
   (a) G1AA/E12v2 of SEQ ID NO: 102, 111, 69, 103, 71 and 17;
   (b) G1AA/G12v2 of SEQ ID NO: 94, 111, 69, 100, 71, and 21;
   (c) G1AA/E05v2 of SEQ ID NO: 94, 111, 69, 100, 71 and 22;
   (d) G1/887_04_E12 of SEQ ID NO: 102, 98, 69, 103, 71 and 17;
   (e) G1/887_04_G12 of SEQ ID NO: 94, 98, 69, 100, 77 and 21;
   (f) G1/894_08_E05 of SEQ ID NO: 94, 98, 69, 100, 71 and 22;
   (g) G1/894_08_A05 of SEQ ID NO: 94, 98, 69, 100, 106 and 24;
   (h) G1AA/lambdav3 of SEQ ID NO: 94, 111, 69, 132, 77 and 14;
   (i) G1/280_02_G02 NS of SEQ ID NO: 94, 98, 69, 96, 77 and 14; or
   (j) G1/280_02_G02 of SEQ ID NO: 94, 95, 69, 96, 77 and 14;
  wherein the sequences are defined by ImMunoGeneTics (IMGT) nomenclature;
  and wherein:
   when the antigen-binding site of the antibody or antigen-binding fragment thereof comprises HCDR1, HCRD2, HCDR3, LCDR1, LCDR2 and LCDR3 of antibody G1AA/E12v2 of SEQ ID NO: 1, 18, 3, 15, 16 and 17, antibody G1AA/G12v2 of SEQ ID NO: 1, 18, 3, 19, 20, and 21, or antibody G1AA/E05v2 of SEQ ID NO: 1, 18, 3, 19, 20 and 22, and/or HCDR1, HCRD2, HCDR3, LCDR1, LCDR2 and LCDR3 of antibody G1AA/E12v2 of SEQ ID NO: 102, 111, 69, 103, 71 and 17, antibody G1AA/G12v2 of SEQ ID NO: 94, 111, 69, 100, 71, and 21, or antibody G1AA/E05v2 of SEQ ID NO: 94, 111, 69, 100, 71 and 22,
   the antibody or antigen-binding fragment thereof does not comprise a CD137 antigen-binding site comprising a first amino acid sequence and a second amino acid sequence located in the AB structural loop and the EF structural loop, respectively, of a CH3 domain of the antibody or antigen-binding fragment thereof, wherein the first amino acid sequence and the second amino acid sequence are PYIIPPY and GADRWLE, NPPYLFS and DYWRWLE, or NPPYLFS and YHWRWLE, respectively.

2. An antibody or antigen-binding fragment thereof according to claim 1, wherein the antigen-binding site comprises the VH domain and/or the VL domain of antibody:
   (a) G1AA/E12v2 of SEQ ID NO: 27 and 28, respectively;
   (b) G1AA/G12v2 of SEQ ID NO: 29 and 30, respectively;
   (c) G1AA/E05v2 of SEQ ID NO: 31 and 32, respectively;
   (d) G1/887_04_E12 of SEQ ID NO: 33 and 34, respectively;
   (e) G1/887_04_G12 of SEQ ID NO: 35 and 36, respectively;
   (f) G1/894_08_E05 of SEQ ID NO: 37 and 38, respectively;
   (g) G1/894_08_A05 of SEQ ID NO: 39 and 40, respectively;
   (h) G1AA/lambdav3 of SEQ ID Nos: 41 and 42, respectively;
   (i) G1/280_02_G02_NS of SEQ ID NO: 43 and 44, respectively; or
   (j) G1/280_02_G02 of SEQ ID NO: 45 and 46, respectively.

3. An antibody according to claim 1, wherein the antibody comprises the heavy chain and/or the light chain of antibody:
   (a) G1AA/E12v2 of SEQ ID NO: 47 and 48, respectively;
   (b) G1AA/G12v2 of SEQ ID NO: 49 and 50, respectively;
   (c) G1AA/E05v2 of SEQ ID NO: 51 and 52, respectively;
   (d) G1/887_04_E12 of SEQ ID NO: 53 and 54, respectively; or
   (e) G1/887_04_G12 of SEQ ID NO: 55 and 56, respectively;
   (f) G1/894_08_E05 of SEQ ID NO: 57 and 58, respectively;
   (g) G1/894_08_A05 of SEQ ID NO: 59 and 60, respectively;
   (h) G1AA/lambdav3 of SEQ ID NO: 61 and 62, respectively;
   (i) G1/280_02_G02_NS of SEQ ID NO: 63 and 64, respectively; or
   (j) G1/280_02_G02 of SEQ ID NO: 65 and 66, respectively.

4. An antibody or antigen-binding fragment thereof according to claim 1, comprising HCDR1, HCDR2, HCDR3, LCDR1, LCDR2 and LCDR3; the VH domain and/or the VL domain; the Fab; and/or the light chain and/or the heavy chain of antibody G1AA/E12v2, G1AA/G12v2 or G1AA/E05v2.

5. An antibody or antigen-binding fragment thereof, according to claim 1, comprising HCDR1, HCDR2, HCDR3 LCDR1, LCDR2 and LCDR3; the VH domain and/or the VL domain, the Fab; and/or the light chain and/or the heavy chain of antibody G1AA/E12v2 or G1/E12v2.

6. An antibody or antigen-binding fragment thereof, according to claim 1, wherein the antibody or antigen-binding fragment thereof is a multispecific molecule comprising at least a second antigen-binding site.

7. An antibody or antigen-binding fragment thereof, according to claim 6, wherein the antibody or antigen-binding fragment thereof comprises a second antigen-binding site located in a constant domain of the antibody or antigen-binding fragment.

8. An antibody or antigen-binding fragment thereof, according to claim 7, wherein the constant domain is a CH3 domain.

9. An antibody or antigen-binding fragment thereof according to claim 1, wherein the antibody is an IgG1 or fragment thereof with a modified Fc region with reduced immune effector function.

10. An antibody or antigen-binding fragment thereof according to claim 6, wherein the second antigen-binding site binds to an inhibitory checkpoint molecule, costimulatory molecule or tumour-associated antigen.

11. A nucleic acid molecule or set of nucleic acid molecules encoding an antibody or antigen-binding fragment thereof according to claim 1.

12. A composition comprising the antibody or antigen-binding fragment thereof according to claim 1 and an excipient.

13. A method for treatment of a disease or disorder in a patient comprising administering to the patient a therapeutically-effective amount of an antibody, or antigen-binding fragment thereof, according to claim 1.

14. A method of detecting a disease or disorder in a patient, the method comprising the use of an antibody, or antigen-binding fragment thereof, according to claim 1.

15. An antibody or antigen-binding fragment thereof according to claim 6, wherein the antibody or antigen-binding fragment thereof is a bispecific molecule comprising at least a second antigen-binding site.

16. An antibody or antigen-binding fragment thereof according to claim 15, wherein the antibody or antigen-binding fragment thereof comprises a second antigen-binding site located in a constant domain of the antibody or antigen-binding fragment.

17. An antibody or antigen-binding fragment thereof according to claim 16, wherein the constant domain is a CH3 domain.

18. An antibody or antigen-binding fragment thereof according to claim 15, wherein the second antigen-binding site binds to an inhibitory checkpoint molecule, costimulatory molecule or tumour-associated antigen.

19. A composition according to claim 12, wherein the composition is a pharmaceutical composition comprising the antibody or antigen-binding fragment thereof according to claim 1 and a pharmaceutically-acceptable excipient.

20. An antibody according to claim 3, wherein the heavy chain comprises an additional lysine residue (K) at the C-terminus of the heavy chain CH3 domain sequence.

21. An antibody according to claim 8, wherein the heavy chain comprises an additional lysine residue (K) at the C-terminus of the heavy chain CH3 domain sequence.

* * * * *

UNITED STATES PATENT AND TRADEMARK OFFICE
CERTIFICATE OF CORRECTION

PATENT NO. : 12,247,074 B2
APPLICATION NO. : 17/259642
DATED : March 11, 2025
INVENTOR(S) : Francisca Wollerton et al.

Page 1 of 2

It is certified that error appears in the above-identified patent and that said Letters Patent is hereby corrected as shown below:

In the Claims

At Column 325, Claim 1, Line 6:
HCRD2 and HCDR3, and a variable light (VL) domain
Should be:
HCDR2 and HCDR3, and a variable light (VL) domain At Column 325, Claim 1, Line 10:
HCRD2, HCDR3, LCDR1, LCDR2 and LCDR3;
Should be:
HCDR2, HCDR3, LCDR1, LCDR2 and LCDR3;

At Column 325, Claim 1, Line 12:
HCRD2, HCDR3, LCDR1, LCDR2 and LCDR3 of
Should be:
HCDR2, HCDR3, LCDR1, LCDR2 and LCDR3 of At Column 325, Claim 1, Line 34:
HCRD2, HCDR3, LCDR1, LCDR2 and LCDR3 of
Should be:
HCDR2, HCDR3, LCDR1, LCDR2 and LCDR3 of At Column 325, Claim 1, Line 60:
binding fragment thereof comprises HCDR1, HCRD2,
Should be:
binding fragment thereof comprises HCDR1, HCDR2, Signed and Sealed this
Twenty-second Day of July, 2025

Coke Morgan Stewart
*Acting Director of the United States Patent and Trademark Office*

At Column 325, Claim 1, Line 65:
18, 3, 19, 20 and 22, and/or HCDR1, HCRD2, HCDR3,
Should be:
18, 3, 19, 20 and 22, and/or HCDR1, HCDR2, HCDR3,